US009260530B2

(12) United States Patent
Tedder et al.

(10) Patent No.: US 9,260,530 B2
(45) Date of Patent: Feb. 16, 2016

(54) ANTI-CD19 ANTIBODIES AND USES IN B CELL DISORDERS

(71) Applicant: Duke University, Durham, NC (US)

(72) Inventors: Thomas F. Tedder, Durham, NC (US); Yasuhito Hamaguchi, Kanazawa (JP); Hanne Gron, Durham, NC (US); Norihito Yazawa, Tokyo (JP)

(73) Assignee: Duke University, Durham, NC (US)

( * ) Notice: Subject to any disclaimer, the term of this patent is extended or adjusted under 35 U.S.C. 154(b) by 154 days.

(21) Appl. No.: 13/957,055

(22) Filed: Aug. 1, 2013

(65) Prior Publication Data

US 2014/0056896 A1 Feb. 27, 2014

Related U.S. Application Data

(63) Continuation of application No. 13/603,154, filed on Sep. 4, 2012, now abandoned, which is a continuation of application No. 12/885,341, filed on Sep. 17, 2010, now Pat. No. 8,444,973, which is a continuation-in-part of application No. 12/275,545, filed on Nov. 21, 2008, now abandoned, which is a continuation of application No. 11/450,931, filed on Jun. 8, 2006, now abandoned, said application No. 12/885,341 is a continuation-in-part of application No. 12/325,426, filed on Dec. 1, 2008, now abandoned, which is a continuation of application No. 11/429,545, filed on May 5, 2006, now abandoned, said application No. 12/885,341 is a continuation-in-part of application No. 12/401,310, filed on Mar. 10, 2009, now abandoned, which is a continuation of application No. 11/355,905, filed on Feb. 15, 2006, now abandoned.

(60) Provisional application No. 60/689,033, filed on Jun. 8, 2005, provisional application No. 60/701,365, filed on Jul. 20, 2005, provisional application No. 60/679,095, filed on May 5, 2005, provisional application No. 60/653,587, filed on Feb. 15, 2005, provisional application No. 60/702,063, filed on Jul. 22, 2005.

(51) Int. Cl.
| | | |
|---|---|---|
| *C07K 16/28* | (2006.01) | |
| *A61K 39/395* | (2006.01) | |
| *A61K 38/13* | (2006.01) | |
| *A61K 45/06* | (2006.01) | |
| *A61K 39/00* | (2006.01) | |

(52) U.S. Cl.
CPC ............ *C07K 16/2896* (2013.01); *A61K 38/13* (2013.01); *A61K 39/3955* (2013.01); *A61K 39/39541* (2013.01); *A61K 45/06* (2013.01); *C07K 16/2803* (2013.01); *C07K 16/2887* (2013.01); *A61K 2039/505* (2013.01); *A61K 2039/507* (2013.01); *A61K 2039/54* (2013.01); *C07K 2317/73* (2013.01); *C07K 2317/732* (2013.01); *C07K 2317/77* (2013.01)

(58) Field of Classification Search
None
See application file for complete search history.

(56) References Cited

U.S. PATENT DOCUMENTS

| | | |
|---|---|---|
| 5,417,972 A | 5/1995 | Bhat et al. |
| 5,530,101 A | 6/1996 | Queen et al. |
| 5,593,676 A | 1/1997 | Bhat et al. |
| 5,618,920 A | 4/1997 | Robinson et al. |
| 5,675,062 A | 10/1997 | Haber et al. |
| 5,686,072 A | 11/1997 | Uhr et al. |
| 6,111,093 A | 8/2000 | Seed et al. |
| 6,134,982 A | 10/2000 | Takabatake et al. |
| 6,306,393 B1 | 10/2001 | Goldenberg et al. |
| 6,632,927 B2 | 10/2003 | Adair et al. |
| 7,109,304 B2 | 9/2006 | Hansen et al. |
| 2002/0041847 A1 | 4/2002 | Goldenberg |
| 2002/0155604 A1 | 10/2002 | Ledbetter et al. |
| 2003/0133930 A1 | 7/2003 | Goldenberg et al. |
| 2003/0148409 A1 | 8/2003 | Rossi et al. |
| 2004/0202658 A1 | 10/2004 | Benyunes |
| 2004/0228857 A1 | 11/2004 | Page et al. |
| 2006/0233791 A1 | 10/2006 | Tedder et al. |
| 2006/0263357 A1 | 11/2006 | Tedder et al. |
| 2006/0280738 A1 | 12/2006 | Tedder |
| 2007/0166306 A1 | 7/2007 | Fey et al. |
| 2007/0237779 A1 | 10/2007 | Ledbetter et al. |

FOREIGN PATENT DOCUMENTS

| | | |
|---|---|---|
| EP | 0481790 | 4/1992 |
| EP | 1247865 | 10/2002 |

(Continued)

OTHER PUBLICATIONS

Ho et al. (J. Biol. Chem. 2005, 280: 607-617).*

(Continued)

*Primary Examiner* — Ilia Ouspenski
(74) *Attorney, Agent, or Firm* — Ropes & Gray LLP

(57) ABSTRACT

The invention relates to immunotherapeutic compositions and methods for the treatment of B cell diseases and disorders in human subjects, such as, but not limited to, B cell malignancies and autoimmune diseases and disorders, using therapeutic antibodies that bind to the human CD19 antigen and that preferably mediate human ADCC. The present invention relates to pharmaceutical compositions comprising human or humanized anti-CD19 antibodies of the IgG1 or IgG3 human isotype. The present invention relates to pharmaceutical compositions comprising human or humanized anti-CD19 antibodies of the IgG2 or IgG4 human isotype that preferably mediate human ADCC. The present invention also relates to pharmaceutical compositions comprising chimerized anti-CD19 antibodies of the IgG1, IgG2, IgG3, or IgG4 isotype that mediate human ADCC. In preferred embodiments, the present invention relates to pharmaceutical compositions comprising monoclonal human, humanized, or chimeric anti-CD19 antibodies.

21 Claims, 40 Drawing Sheets

(56) References Cited

FOREIGN PATENT DOCUMENTS

| | | |
|---|---|---|
| JP | 2001 058956 | 3/2001 |
| WO | WO-90/04413 | 5/1990 |
| WO | WO-91/13974 | 9/1991 |
| WO | WO-94/09363 | 4/1994 |
| WO | WO-95/03770 | 2/1995 |
| WO | WO-96/36360 | 11/1996 |
| WO | WO-00/42072 | 7/2000 |
| WO | WO-00/67795 | 11/2000 |
| WO | WO-00/67796 | 11/2000 |
| WO | WO-00/74718 | 12/2000 |
| WO | WO-01/13945 | 3/2001 |
| WO | WO-01/80884 | 11/2001 |
| WO | WO-01/97843 | 12/2001 |
| WO | WO-01/97844 | 12/2001 |
| WO | WO-02/04021 | 1/2002 |
| WO | WO-02/50118 | 6/2002 |
| WO | WO-03/092597 | 11/2003 |
| WO | WO-2005/000901 | 1/2005 |
| WO | WO-2005/012493 | 2/2005 |
| WO | WO-2005/051307 | 6/2005 |
| WO | WO-2005/090406 | 9/2005 |
| WO | WO-2006/089133 | 8/2006 |

OTHER PUBLICATIONS

Anderson et al., Expression of human B cell-associated antigens on leukemias and lymphomas: a model of human B cell differentiation, Blood 63:1424-1433 (1984).
Anderson et al., Targeted anti-cancer therapy using rituximab, a chimaeric anti-CD20 antibody (IDEC-C2B8) in the treatment of non-Hodgkin's B-cell lymphoma, Biochem. Soc. Transac. 25:705-708 (1997).
Barfield et al., A one-step large-scale method for T- and B-cell depletion of mobilized PBSC for allogeneic transplantation, Cytotherapy 6:1-6 (2004).
Becker et al., Rituximab as treatment for refractory kidney transplant rejection, Am. J. Transplant 4:996-1001 (2004).
Bradbury et al., The CD19/CD21 Signal Transducing Complex of Human B Lymphocytes Includes the Target of Antiproliferative Antibody-1 and Leu-13 Molecules, J. Immunol. 149(9): 2841-2850 (1992).
Casset et al., A peptide mimetic of an anti-CD4 monoclonal antibody by rational design, Biochem. Biophys. Res. Comm. 307:198-205 (2003).
Colman, Effects of amino acid sequence changes on antibody-antigen interactions, Res. in Immun. 145:33-36 (1994).
Conry et al., Phase I trial of an anti-CD19 deglycosylated ricin A chain immunotoxin in non-Hodgkin's lymphoma: effect of an intensive schedule of administration, J. Immun. 18(4): 231-241 (1995).
De Gast et al., Clinical experience with CD3 × CD19 bispecific antibodies in patients with B cell malignancies, J. Hematother. 4(5): 433-437 (1995).
De Vita et al., Efficacy of selective B cell blockade in the treatment of rheumatoid arthritis: evidence for a pathogenetic role of B cells, Arthritis Rheumatism 46:2029-2033 (2002).
Dorken et al., Production of Monoclonal Antibodies for the Diagnosis of Minimal Infiltration of Leukemic Cells into the Bone Marrow: B Cell Specific Antibodies, Vehr. Dtsch. Ges. Path. 67:65-69 (1983).
Edwards et al., Sustained improvement in rheumatoid arthritis following a protocol designed to deplete B lymphocytes, Rheumatology,40: 205-211 (2001).
Grossbard et al., A Phase II study of adjuvant therapy with anti-B4-blocked ricin after autologous bone marrow transplantation for patients with relapsed B-cell non-Hodgkin's lymphoma, Clinical Cancer Res. 5:2392-2398 (1999).
Grossbard et al., Adjuvant immunotoxin therapy with anti-B4-blocked ricin after autologous bone marrow transplantation for patients with B-cell non-Hodgkin's lymphoma, Blood 81(9): 2263-2271 (1993).
Grossbard et al., Anti-B4-blocked ricin: A phase I trial of 7-day continuous infusion in patients with B-cell neoplasms, J. Clin. Oncol. 11(4):726-737 (1993).
Grossbard et al., Anti-B4-blocked ricin: a phase II trial of 7 day continuous infusion in patients with multiple myeloma, Br. J. of Haematology 102:509-515(1998).
Grossbard et al., Serotherapy of B-cell neoplasms with anti-B4-blocked ricin: a phase I trial of daily bolus infusion, Blood 79:576-585 (1992).
Hekman et al., Initial experience with treatment of human B cell lymphoma with anti-CD19 monoclonal antibody, Cancer Immunol. Immunotherapy 32:364-372 (1991).
Hooijberg et al., Enhanced antitumor effects of CD20 over CD19 monoclonal antibodies in a nude mouse xenograft model, Cancer Res. 55:840-846 (1995).
Hooijberg et al., Eradication of large human B cell tumors in nude mice with unconjugated CD20 monoclonal antibodies and interleukin 2, Cancer Res. 55:2627-2634 (1995).
Kaminski et al., Radioimmunotherapy of B-cell lymphoma with anti-B1 (anti-CD20) antibody, N. Engl. J. Med. 329:459-465 (1993).
Kansas et al., Transmembrane signals generated through MHC Class II, CD19, CD20, CD39, and CD40 antigens induce LFA-1-dependent and independent adhesion in human B cells through a tyrosine kinase-dependent pathway, J. Immunol. 147(12):4094-4102 (1991).
Kiesel et al., Removal of Cells from a Malignant B-Cell line from Bone Marrow with Immunomagnetic Beads and with Complement and Immunoglobulin Switch Variant Mediated Cytolysis, Leukemia Research 11(12):1119-1125 (1987).
Kipps et al., Importance of immunoglobulin isotype in human antibody-dependent, cell-mediated cytotoxicity directed by murine monoclonal antibodies, J. Exp. Med. 161(1):1-17 (1985).
Krop et al., Self Renewal of B-1 Lymphocytes is Dependent on CD19, Eur. J. Immunol. 26(1): 238-42 (1996).
Lang et al., Chimeric CD19 antibody mediates cytotoxic activity against leukemic blasts with effector cells from pediatric patients who received T-cell-depleted allografts, Blood 103(10):3982-3985 (2004).
Leandro et al., An open study of B lymphocyte depletion in systemic lupus erythematosus, Arthritis Rheum. 46:2673-2677 (2002).
Leandro et al., Clinical outcome in 22 patients with rheumatoid arthritis treated with B lymphocyte depletion, Ann. Rheum. Dis. 61:883-888 (2002).
Levasseur et al., Lymphocyte subsets may discern treatment effects in children and young adults with post-transplant lymphoproliferative disorder, Pediatr. Transplant. 7:370-75 (2003).
Li et al., Three-dimensional structures of the free and antigen-bound Fab from monoclonal antilysozyme antibody HyHEL-63, Biochemistry 39:6296-6309 (2000).
Loken et al., Flow cytometric analysis of human bone marrow. II. Normal B lymphocyte development, Blood 70:1316-1324 (1987).
MacCallum et al., Antibody-antigen interactions: contact analysis and binding site topography, J. Mol. Biol. 262:732-645 (1996).
Maloney et al., IDEC-C2B8 (Rituximab) anti-CD20 monoclonal antibody therapy in patients with relapsed low-grade non-Hodgkin's lymphoma, Blood 90:2188-2195 (1997).
Maloney et al., IDEC-C2B8: results of a phase I multiple-dose trial in patients with relapsed non-Hodgkin's lymphoma, J. Clin. Oncol. 15:3266-3274 (1997).
Manzke, et al., Locoregional treatment of low-grade B-cell lymphoma with CD3×CD19 bispecific antibodies and CD28 costimulation. I. Clinical phase I evaluation, Int. J. Cancer 91(4): 508-515 (2001).
Manzke, et al., Locoregional treatment of low-grade B-cell lymphoma with CD3×CD19 bispecific antibodies and CD28 costimulation. II. Assessment of cellular immune responses, Int. J. Cancer 91(4): 516-522 (2001).
McLaughlin et al., Clinical status and optimal use of rituximab for B-cell lymphomas, Oncology 12:1763-1769 (1998).
Meeker et al., A unique human B lymphocyte antigen defined by a monoclonal antibody, Hybridoma 3:305-320 (1984).
Messman et al., A phase I study of combination therapy with immunotoxins IgG-HD37- deglycosylated ricin A chain (dgA) and

(56) References Cited

OTHER PUBLICATIONS

IgG-RFB4-dgA (Combotox) in patients with refractory CD19(+), CD22(+) B cell lymphoma, Clin. Cancer Res. 6(4): 1302-1313 (2000).
Monoclonal Antibody Therapy in Treating Patients with Lymphoma or Leukemia. ClinicalTrials.gov Identifier: NCT00003874. [retrieved on Jan. 8, 2008] Retrieved from the Internet: <URL: http://www.clinicaltrials.gov/ct/show/NCT00003874?order=1>.
Multani et al., Phase II clinical trial of bolus infusion anti-B4 blocked ricin immunoconjugate in patients with relapsed B-cell non-Hodgkin's lymphoma, Clin. Cancer Res. 4(11): 2599-2604 (1998).
Nadler et al., B4, a human B lymphocyte-associated antigen expressed on normal, mitogen-activated, and malignant B lymphocytes, J. Immunol. 131:244-250 (1983).
Nicholson et al., Construction and characterisation of a functional CD19 specific single chain Fv fragment for immunotherapy of B lineage leukaemia, Mol. Immunol., 34:1157-1165 (1997).
Onrust et al., Rituximab, Drugs 58:79-88 (1999).
Padlan et al., Identification of specificity-determining residues in antibodies, Faseb J. 134(9):133-139 (1995).
Panka et al., Variable region framework differences result in decreased or increased affinity of variant anti-digoxin antibodies, Proc. Natl. Acad. Sci. USA 85:3080-3084 (1988).
Paul, Chapter B: Immunogenicity and antigen structure, Fundamental Immunology, Raven Press, 3rd ed., pp. 242 and 292-295 (1993).
Pezzutto et al., CD19 Monoclonal Antibody HD37 Inhibits Anti-Immunoglobulin-Induced B Cell Activation and Proliferation, J. Immunol. 138(9): 2793-2799 (1987).
Phase I/II Study of Enriched CD34+ Cells with Depleted B-cells in Patients with B Lymphoid Malignancies. [retrieved on Jan. 8, 2008] Retrieved from the Internet: <URL: http://www.cancer.gov/search/viewclinicaltrials.aspx?cdrid=67039&version=healthprofessional&print=1>.
Pietersz et al., In vitro and in vivo antitumor activity of a chimeric anti-CD19 antibody, Cancer Immunol. Immunother. 41:53-60 (1995).
Press et al., Immunotherapy of non-Hodgkin's lymphomas, Amer. Soc. Hematology 221-240 (2001).
Reff al., Depletion of B cells in vivo by a chimeric mouse human monoclonal antibody to CD20, Blood 83:435-445 (1994).
Reilley et al., Open-label, dose escalation study of the safety and pharmacokinetic profile of tefibazumab in healthy volunteers, Antimicrob. Agents Chem. 49(3):959-962 (2005).
Rifle et al., Donor-specific antibodies in allograft rejection: clinical and experimental data, Transplantation 79:S14-S18 (2005).
Rudikoff et al., Single amino acid substitution altering antigen-binding specificity, Proc. Natl. Acad. Sci. USA 79:1979-1983 (1982).
Schaar et al. Successful outcome with a "quintuple approach" of posttransplant lymphoproliferative disorder, Transplantation 71:47-52 (2001).
Scheuermann and Racila, CD19 antigen in leukemia and lymphoma diagnosis and immunotherapy, Leuk. Lymphoma 18:385-397(1995).
Sidner et al. In vivo human B-cell subset recovery after in vivo depletion with rituximab, anti-human CD20 monoclonal antibody, Hum. Antibodies 13:55-62 (2004).
Silverman et al, Rituximab therapy and autoimmune disorders: prospects for anti-B cell therapy, Arthritis Rheum. 48:1484-1492 (2003).
Smith, Rituximab (monoclonal anti-CD20 antibody): mechanisms of action and resistance, Oncogene 22:7359-7368 (2003).
Snanoudj et al., Immunological strategies targeting B cells in organ grafting, Transplantation 79:S33-35 (2005).
Sonnenday, Plasmapheresis, CMV hyperimmune globulin, and anti-CD20 allow ABO-incompatible renal transplantation without splenectomy, Am. J. Transplant. 4:1315-1322 (2004).
Stone et al., A phase I study of bolus versus continuous infusion of the anti-CD19 immunotoxin, IgG-HD37-dgA, in patients with B-cell lymphoma, Blood 88(4): 1188-1197 (1996).
Tedder et al., CD20: a regulator of cell-cycle progression of B lymphocytes, Immunol. Today 15:450-454 (1994).
Treon et al., Expression of serotherapy target antigens in Waldenstrom's macroglobulinemia: therapeutic applications and considerations, Semin. Oncol. 30:248-52(2003).
Tsimberidou et al., Anti-B4-blocked ricin post chemotherapy in patients with chronic lymphocytic leukemia—long-term follow-up of a monoclonal antibody-based approach to residual disease, Leuk. Lymphoma 44(10): 1719-1725 (2003).
Tyden et al. Successful ABO-incompatible kidney transplantations without splenectomy using antigen-specific immunoadsorption and rituximab, Transplantation 76:730-743 (2003).
Uckun et al., Detailed studies on expression and function of CD19 surface determinant using B43 monoclonal antibody and the clinical potential of anti-CD 19 immunotoxins, Blood 71: 13-29 (1988).
Uckun et al., Treatment of therapy-refractory B-lineage acute lymphoblastic leukemia with an apoptosis-inducing CD19-directed tyrosine kinase inhibitor, Clin. Can. Res. 5:3906-3913 (1999).
Viera et al., Rituximab for reduction of anti-HLA antibodies in patients awaiting renal transplantation: 1. Safety, pharmacodynamics, and pharmacokinetics, Transplantation 77:542-548 (2004).
Vuist et al., Potentiation by interleukin 2 of Burkitt's lymphoma therapy with anti-pan B (anti-CD19) monoclonal antibodies in a mouse xenotransplantation model, Cancer Res. 49(14):3783-3788 (1989).
Wang et al., The role of pathogenic B-cell clones in antibody mediated autoimmune disorders, J. Derm. Sci. 36:141-148 (2004).
Weiner, Monoclonal antibody therapy of cancer, Semin. Oncol. 26:43-51 (1999).
Wiemels, Perspectives on the causes of childhood leukemia, Chemico-Biol. Interactions 196:59-67 (2012).
Yazawa et al., Immunotherapy using unconjugated CD19 monoclonal antibodies in animal models for B lymphocyte malignancies and autoimmune disease, Proc. Natl. Acad. Sci. USA 102(42):15178-151823 (2005).
Zhou et al., Tissue-specific expression of the human CD19 gene in transgenic mice inhibits antigen-independent B-lymphocyte development., Mol. Cel. Biol. 14(6):3884-3894 (1994).
Zola et al., Preparation and characterization of a chimeric CD19 monoclonal antibody, Imm. Cell Biol. 69:411-422 (1991).

* cited by examiner

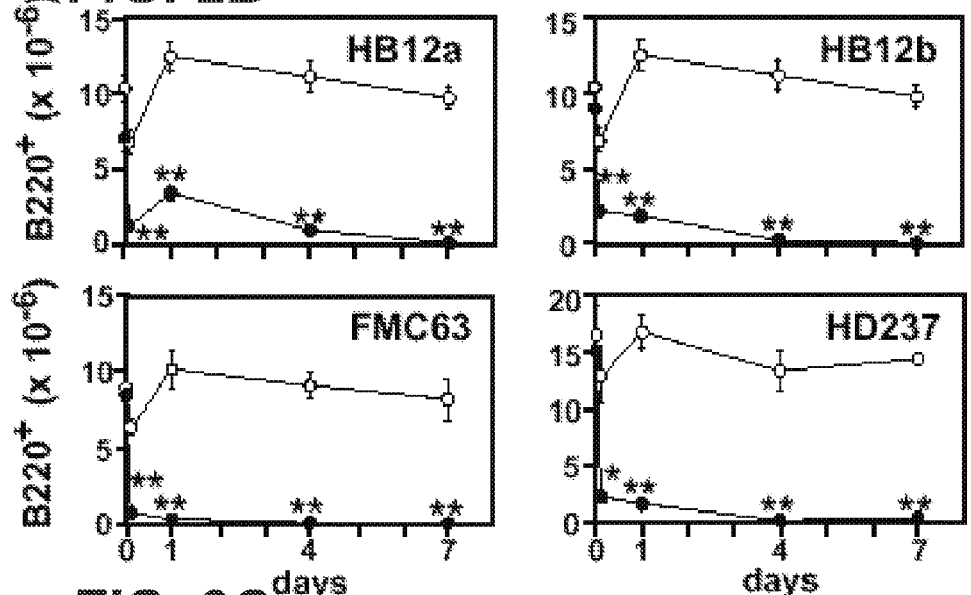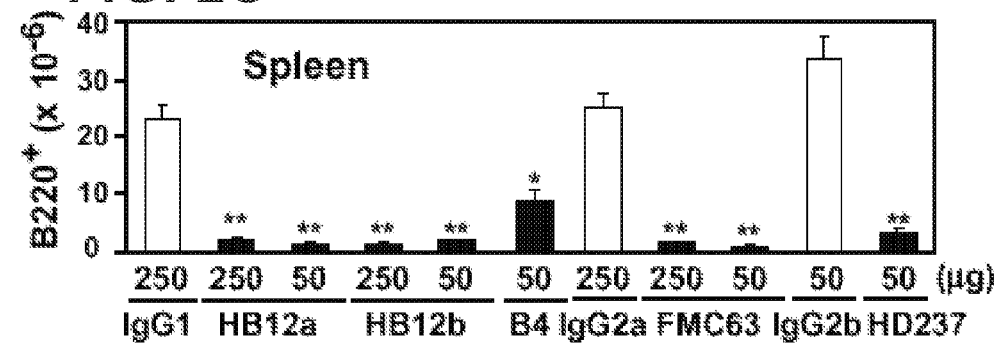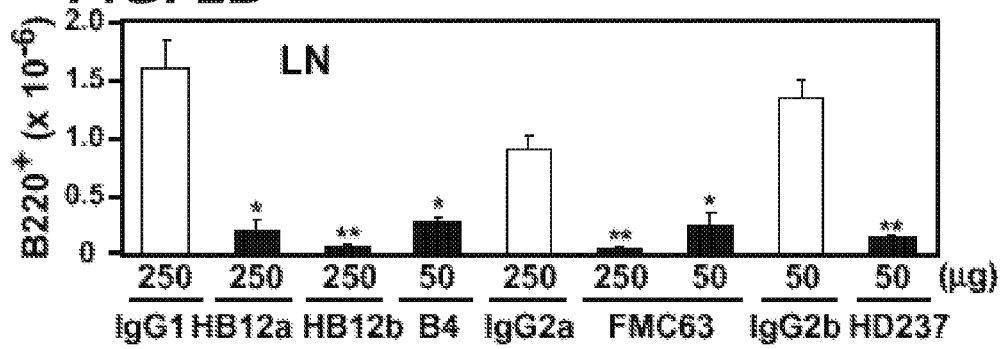

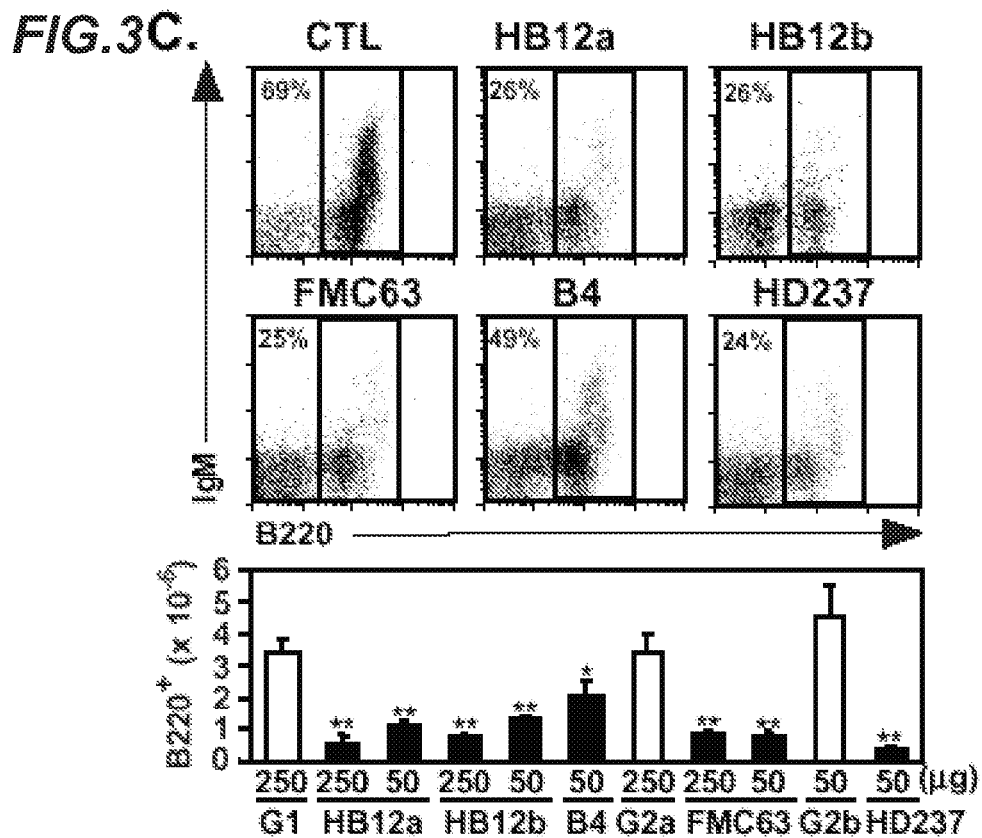
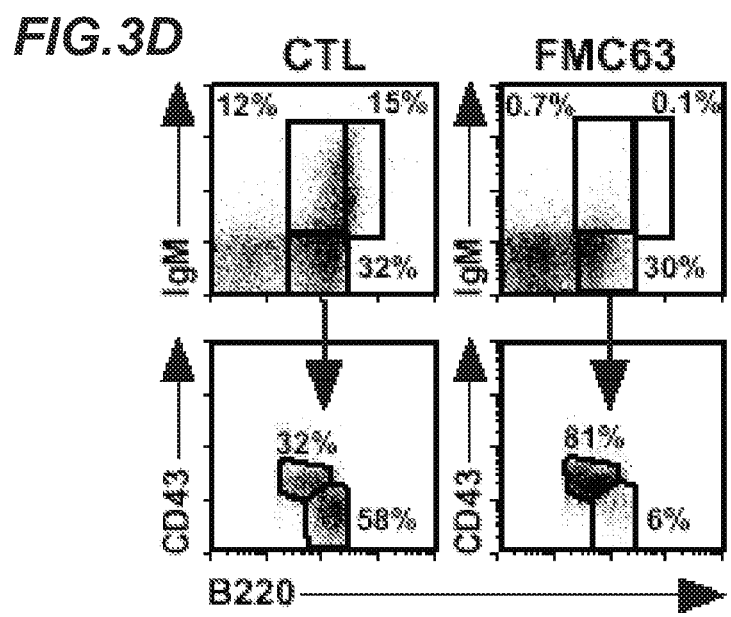

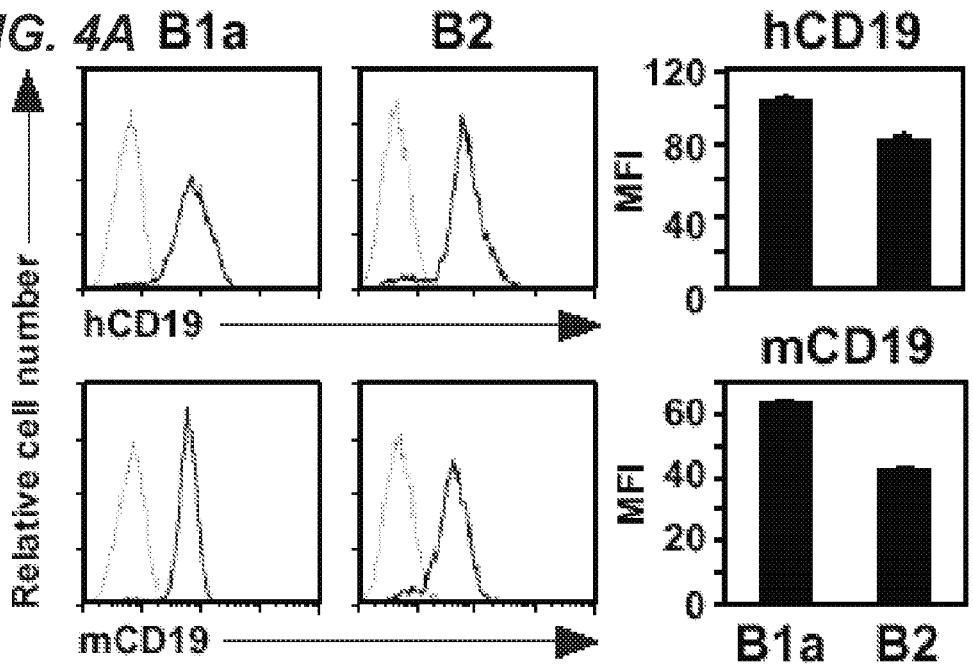
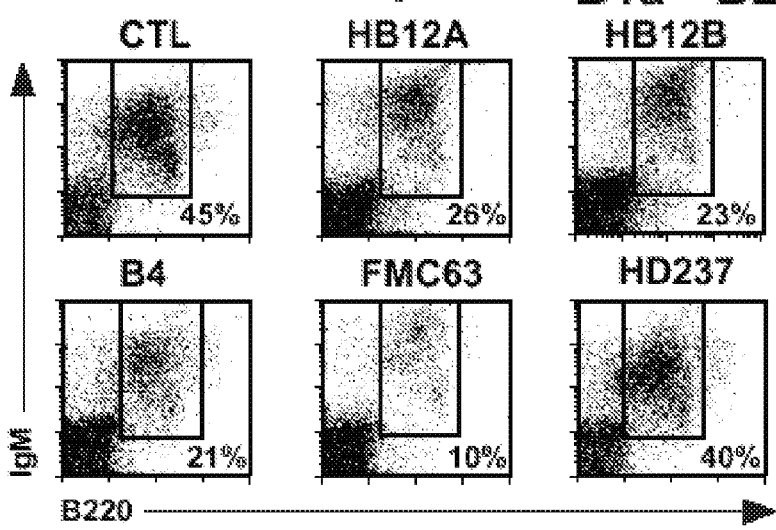
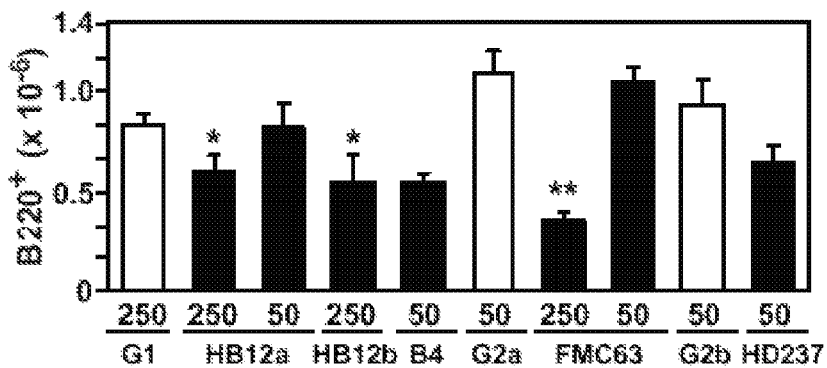

```
      1                     10                      18
    E   F   E   V   Q   L   Q   E   S   G   P   E   L   V   K   P   G   A   S   V    60
    GAA TTC GAG GTG CAG CTG CAG GAG TCT GGA CCT GAG CTG GTA AAG CCT GGG GCT TCA GTG 21                    30                      38
    K   M   S   C   K   A   S   G   Y   T   F   T   S   Y   V   M   H   W   V   K   120
    AAG ATG TCC TGC AAG GCT TCT GGA TAC ACA TTC ACT AGC TAT GTT ATG CAC TGG GTG AAG 41                    50                      58
    Q   K   P   G   Q   G   L   E   W   I   G   Y   F   N   P   Y   N   D   G   T   180
    CAG AAG CCT GGG CAG GGC CTT GAG TGG ATT GGA TAT TTT AAT CCT TAC AAT GAT GGT ACT 61                    70                      78
    D   Y   N   E   K   F   K   G   K   A   T   L   T   S   D   K   S   S   S   T   240
    GAT TAC AAT GAG AAG TTC AAA GGC AAG GCC ACA CTG ACT TCA GAC AAA TCC TCC AGC ACA 81                    90                      98
    A   Y   M   A   L   S   S   L   T   S   E   D   S   A   V   Y   Y   C   A   R   300
    GCC TAC ATG GCG CTC AGC AGC CTG ACC TCT GAG GAC TCT GCG GTC TAT TAC TGT GCA AGA 101                    110                     118
    G   T   Y   Y   Y   G   S   S   Y   P   F   D   Y   W   G   Q   G   T   T   L   360
    GGG ACC TAT TAC TAC GGT AGC TAC CCC TTT GAC TAC TGG GGC CAA GGC ACC ACT CTC

122
    T   V   S   S                                                                    373
    ACA GTC TCC TCA G
```

```
       1                                            10                           18
       E   F   E   V   Q   L   Q   E   S   G   P   E   L   V   K   P   G   A   S   V    60
       GAA TTC GAG GTG CAG CTG CAG GAG TCT GGA CCT GAG CTG GTG AAG CCT GGG GCC TCA GTG 21                                           30                           38
       K   I   S   C   K   A   S   G   Y   A   F   S   S   Y   W   M   N   W   V   I   120
       AAG ATT TCC TGC AAA GCT TCT GGC TAC GCA TTC AGT AGC TCT TGG ATG AAC TGG GTG ATA 41                                           50                           58
       Q   R   P   G   Q   G   L   E   W   I   G   R   I   Y   P   G   D   G   D   T   180
       CAG AGG CCT GGA CAG GGT CTT GAG TGG ATT GGA CGG ATT TAT CCT GGA GAT GGA GAT ACT 61                                           70                           78
       N   Y   N   G   K   F   K   G   K   A   T   L   T   A   D   K   S   S   S   T   240
       AAC TAC AAT GGG AAG TTC AAG GGC AAG GCC ACT CTG ACT GCA GAC AAA TCC TCC AGT ACA 81                                           90                           98
       A   Y   M   Q   L   S   S   L   T   S   V   D   S   A   V   Y   F   C   A   R   300
       GCC TAC ATG CAG CTC AGC AGC CTG ACC TCT GTG GAC TCT GCG GTC TAT TTC TGT GCA AGA 101                                         110                          118
       S   G   F   I   T   T   T   V   L   D   F   D   Y   W   G   H   G   T   L   T   360
       TCA GGA TTT ATT ACT ACG GTT TTA GAC TTT GAC TAC TGG GGC CAC GGC ACC ACT CTC ACA

121
       V   S   S                                                                         370
       GTC TCC TCA G
```

```
                    CATGGACTGAAGGAGTAGAAAACTGATCACTCCTATGTTTATTCCTCAAAATG         56
  M   S   P   A   Q   F   L   F   L   L   V   L   W   I   Q   E   T   N   G
 ATG AGT CCT GCC CAG TTC CTG TTT CTG TTA GTG CTC TGG ATT CAG GAA ACC AAC GGT      113
                                             10                      20
  1                                           T                       S
  D   V   G   M   T   Q   T   P   L   T   L   S   V   T   I   G   Q   P   A   S
 GAT GTT GGG ATG ACC CAG ACT CCA CTC TCC TTG TCG GTC ACC ATT GGA CAA CCA GCC TCT  173
                          30                                          40
                          L                                           W
  F   S   C   K   S   S   Q   S   L   Y   S   N   G   K   T   Y   L   N   W
 TTC TCT TGC AAG TCA AGT CAG AGC CTC TTA TAT AGT AAT GGA AAA ACC TAT TTG AAT TGG  233
                          50                                          60
                                                                      D
  L   Q   R   P   G   Q   S   P   K   R   L   I   H   L   V   S   K   L   D
 TTA CAG AGG CCA GGC CAG TCT CCA AAG CGC CTA ATC CAT CTG GTG TCT AAA CTG GAC      293
                          70                                          80
                          S                                           I
  S   G   V   P   D   R   F   T   G   S   G   S   G   T   D   F   T   L   K   I
 TCT GGA GTC CCT GAC AGG TTC ACT GGC AGT GGA TCA GGA ACA GAT TTT ACA CTG AAA ATC  353
                          90                                         100
                          V                                           P
  G   R   V   E   A   E   D   L   G   V   Y   Y   C   V   Q   G   T   H   F   P
 GGC AGA GTG GAG GCT GAG GAT TTG GGA GTT TAT TAC TGC GTG CAA GGT ACA CAT TTT CCG  413
  101                    110                                         120
  Y   T   F   G   G   G   T   K   L   E   I   K   R   A   D   A   A   P   T   V
 TA|C ACG TTC GGA GGG GGG ACC AAA CTA GAA ATA AAA C|GG GCT GAT GCT GCA CCA ACT GTA  473
                         127
                           S
  S   I   F   P   P   S
 TCC ATC TTC CCA CCA TCC AGT                                                      494
```

```
                                    CATGGACTGAAGGAGTAGAAAAGCATTCTCTCTTCCAGTTCTCAGAG         47
    M   E   K   D   T   L   L   L   W   V   L   L   L   W   V   P   G   S   T   G
    ATG GAG AAA GAC ACA CTC CTG CTA TGG GTC CTC CTG CTC TGG GTT CCA GGT TCC ACA GGT       107
        1                               10                                      20
        D   I   V   L   T   Q   S   P   T   S   L   A   V   S   L   G   Q   R   A   T
        GAC ATT GTG CTG ACG CAG TCT CCA ACC TCT TTG GCT GTG TCT CTA GGG CAG AGG GCC ACC   167
       21                              30                                      40
        I   S   C   R   A   S   E   S   V   D   T   F   G   I   S   F   M   N   W   F
        ATC TCC TGC AGA GCC AGT GAA AGT GTT GAT ACT TTT GGC ATT AGT TTT ATG AAC TGG TTC   227
       41                              50                                      60
        Q   Q   K   P   G   Q   P   P   K   L   L   I   H   A   A   S   N   Q   G   S
        CAA CAG AAA CCA GGA CAG CCA CCC AAA CTC CTC ATC CAT GCT GCA TCC AAT CAA GGA TCC   287
       61                              70                                      80
        G   V   P   A   R   F   S   G   S   G   S   T   D   F   S   L   N   I   H   H
        GGG GTC CCT GCC AGG TTT AGT GGC AGT GGG TCT GGG ACG GAC TTC AGC CTC AAC ATC CAT   347
       81                              90                                     100
        P   M   E   E   D   D   S   A   M   Y   F   C   Q   Q   S   K   E   V   P   F
        CCT ATG GAG GAG GAT GAT AGT GCA ATG TAT TTC TGT CAG CAA AGT AAG GAG GTT CCA TT|C   407
      101                             110                                     120
        T   F   G   S   G   T   K   L   E   I   K | R   A   D   A   A   P   T   V   S
        ACG TTC GGC TCG GGG ACA AAG TTG GAA ATA AAA| CGG GCT GAT GCT GCA CCA ACT GTA TCC   467
      121                    126
        I   F   P   P   S   S
        ATC TTC CCA CCA TCC AGT                                                          485
```

```
                   1         10        20        30CDR1     40          50  CDR2 60        70        80
Conse.    EVQLQESGPELVKPGASVKMSCKASGYTFTSYVMHWVKQKPGQGLEWIGYINPYNDGTDYNEKFKGKATLTSDKSSSTAYM
HB12a     ................Q..I.........................F............Y...................
4G7       .................I..........A.S.SW.N..I.R...R.Y.GDGD.N..G..........A.E.........
HB12b     .Q...Q...A...R.S..I..........A.S..W.N....R...Q.WGDGD.N..G..........A.E.........
HD37      .Q...A...R.S.................A.S..W.N....R...Q.WGDGD.N..G..........A.E.........
B43       ..K........G.A.SQ.LSVT.TV..VSLPD.GVS...IR.P.RK....L.V.WGSEGT.Y..SAL.SRL.IIK.N.K.QVFL
FMC63

90        100 CDR3              
Conse.    ALSSLTSEDSAVYYCARGTYYYGSSYYYPFDYWGQGTTLTVSS   124  (SEQ ID NO:5)
HB12a     .E..................R---V................    122  (SEQ ID NO:2)
4G7       .Q...V...........F..SGFITTVLDF.........H..    121  (SEQ ID NO:6)
HB12b     .Q...A...........F..RETTTVGR...AM....SV...    124  (SEQ ID NO:4)
HD37      .Q...R...........S..RETTTTVGR..AM....V....    121  (SEQ ID NO:7)
B43       .....................................SV...    121  (SEQ ID NO:8)
FMC63     KMN..QTD.T.I......K-H..G.--.AM............    120  (SEQ ID NO:9)
```

FIG. 7A

Light chain sequences

```
          1            10           20      CDR1  30              40           50    CDR2    60
Conse.  DIVMTQTPASLAVSLGQRATISCKASQSVDY-NGDSYLNWYQQRPGQPPKLLIYDASNLVSG
HB12a    .VG......LT.S.TI..P.SF....S...LL.S..KT.......LL......S..R..HLV.K.D.
4G7      .....AAP.IP.TP.ESVS....RS.K.LLNS..NT..Y.FL....S..Q.....RM...A..
B43      EL.L..S...................-D........I...................
HD37     ...LL..........................-D........I...................
HB12b    ....L..S.T...........R..E..T-F.I.FM..F..K.....F..K......HA...QG.
FMC63    ..Q....TS..SA...D.V...R...DI-----SK........K.DGTV.....HT.R.H..

70           80           90    CDR3  100          110
Conse.  VPDRFSGSGSGTDFTLNIHPVEKEDAATYYCQQSTEDPYTFGGGTKLEIKRAD    (SEQ ID NO:10)
HB12a    ......T........K.GR..A..LGV....V.G.HF............        (SEQ ID NO:16)
4G7      .....A...R.SR..A..VGV...M.HL.Y.F...A......L.....RS      (SEQ ID NO:14)
B43      I.P...........V....H.........W...................        (SEQ ID NO:12)
HD37     I.P...........V....H.........W..................---     (SEQ ID NO:11)
HB12b    ..A......S....M.ED.S.M.F....K.V.F..S.............        (SEQ ID NO:18)
FMC63    .S......YS.T.SNL.Q..I..F....GNTL...............T---      (SEQ ID NO:13)
```

FIG. 7B

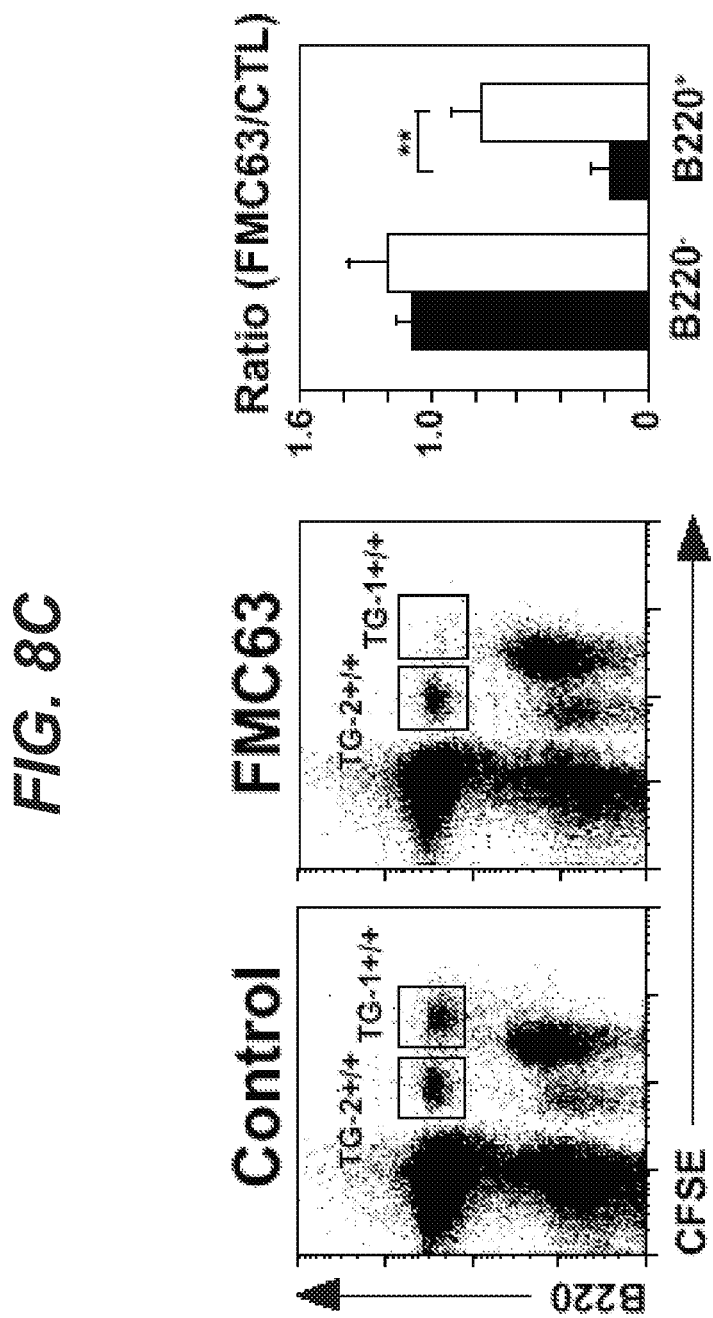

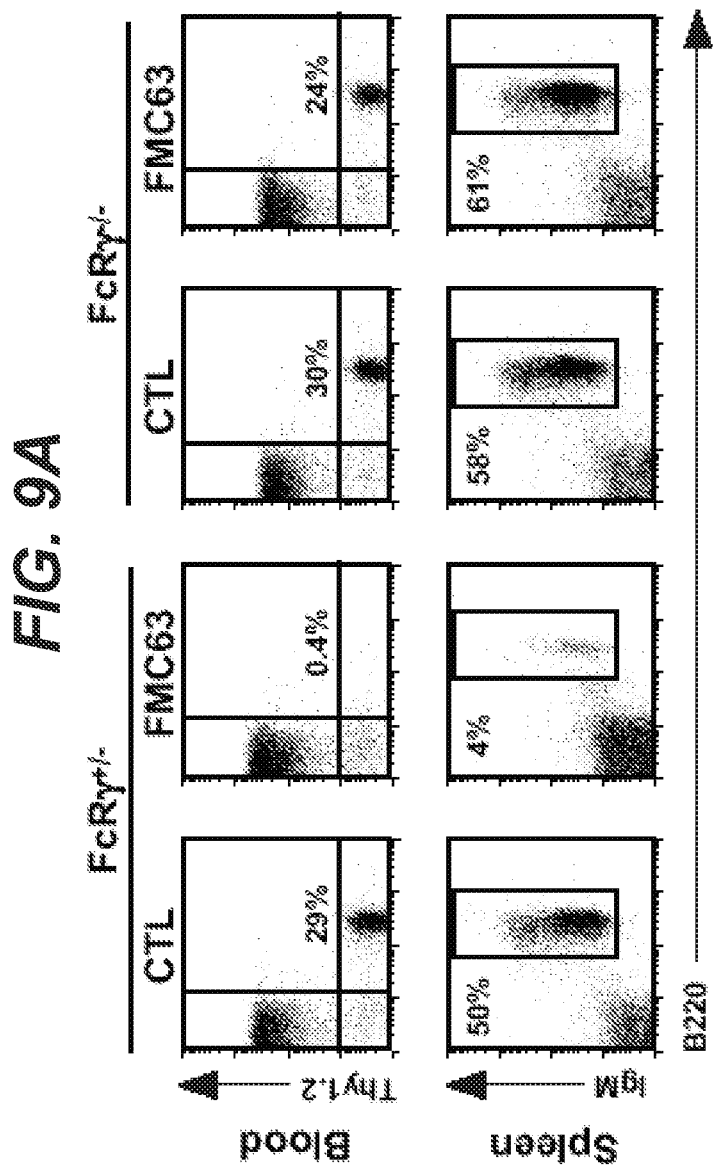

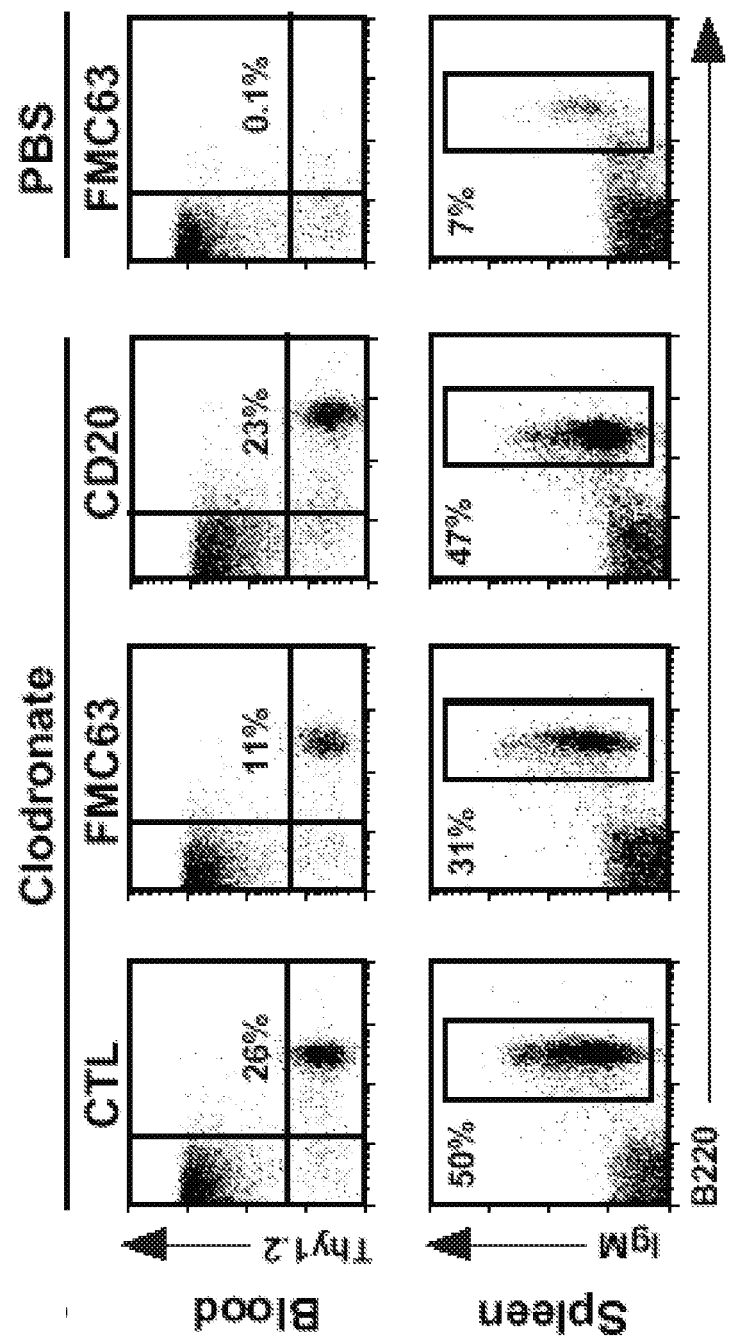

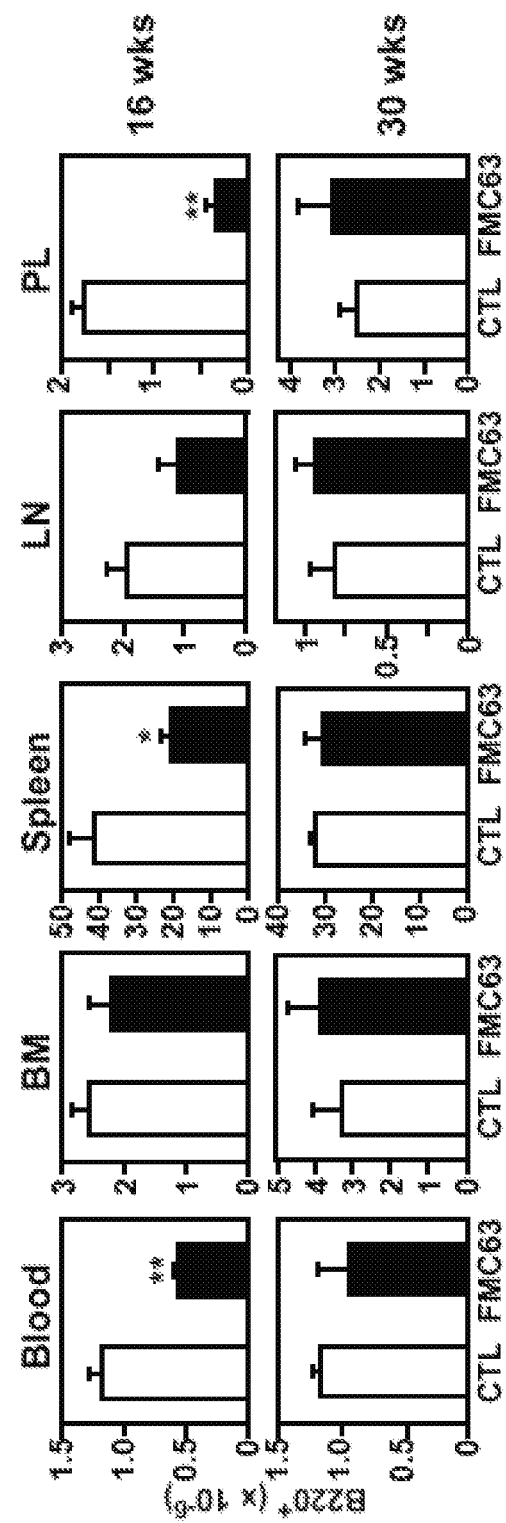

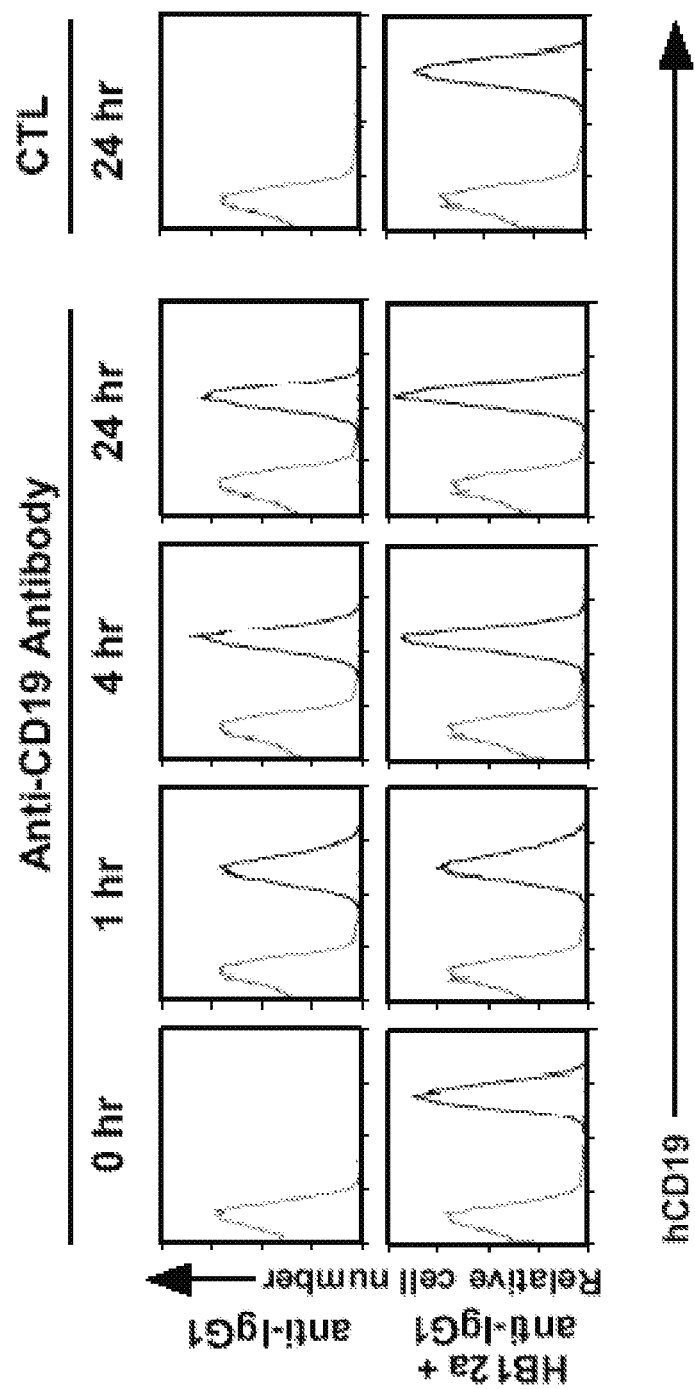

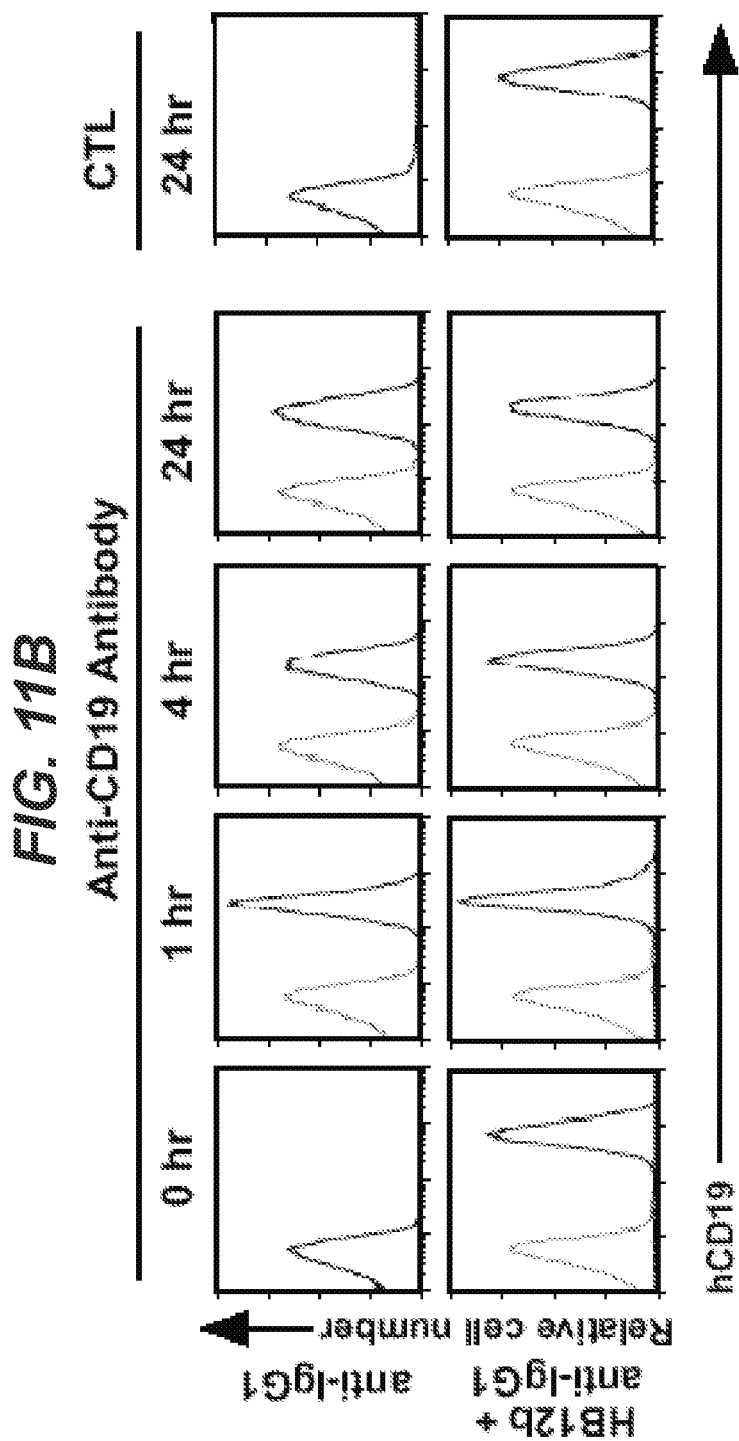

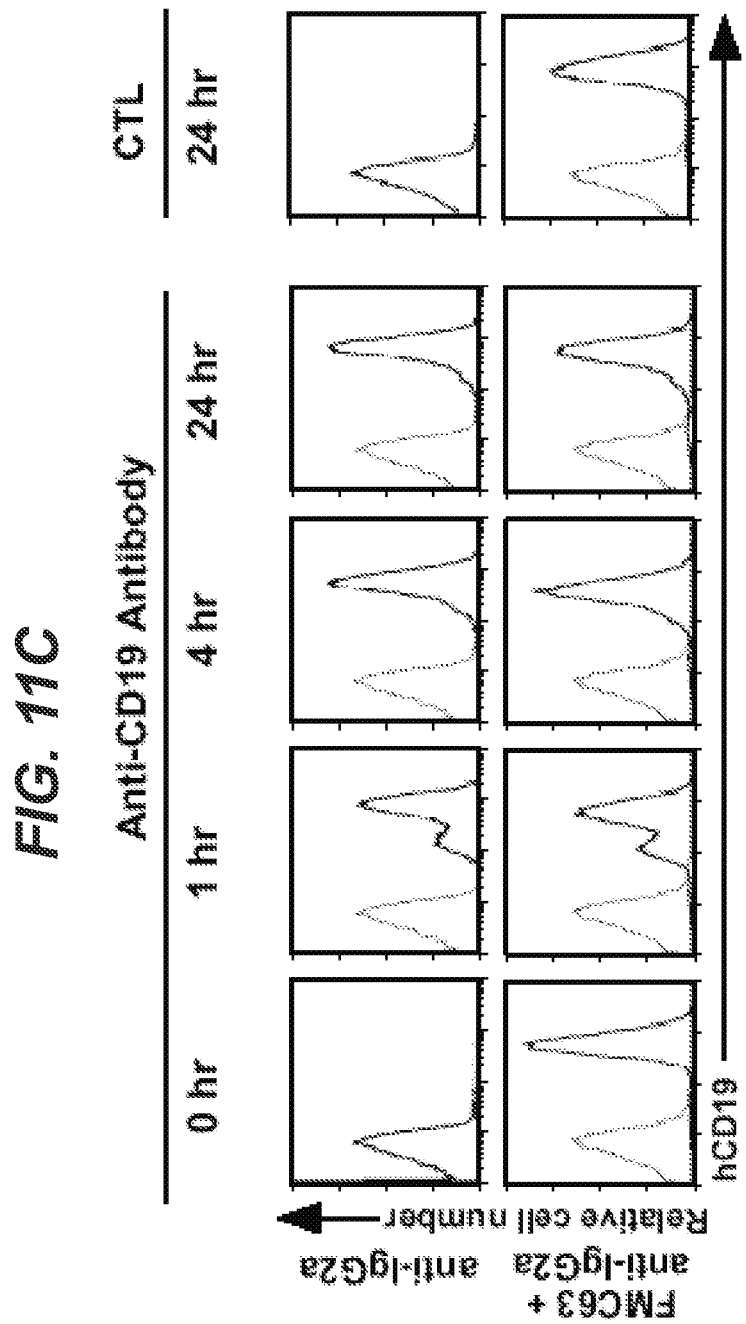

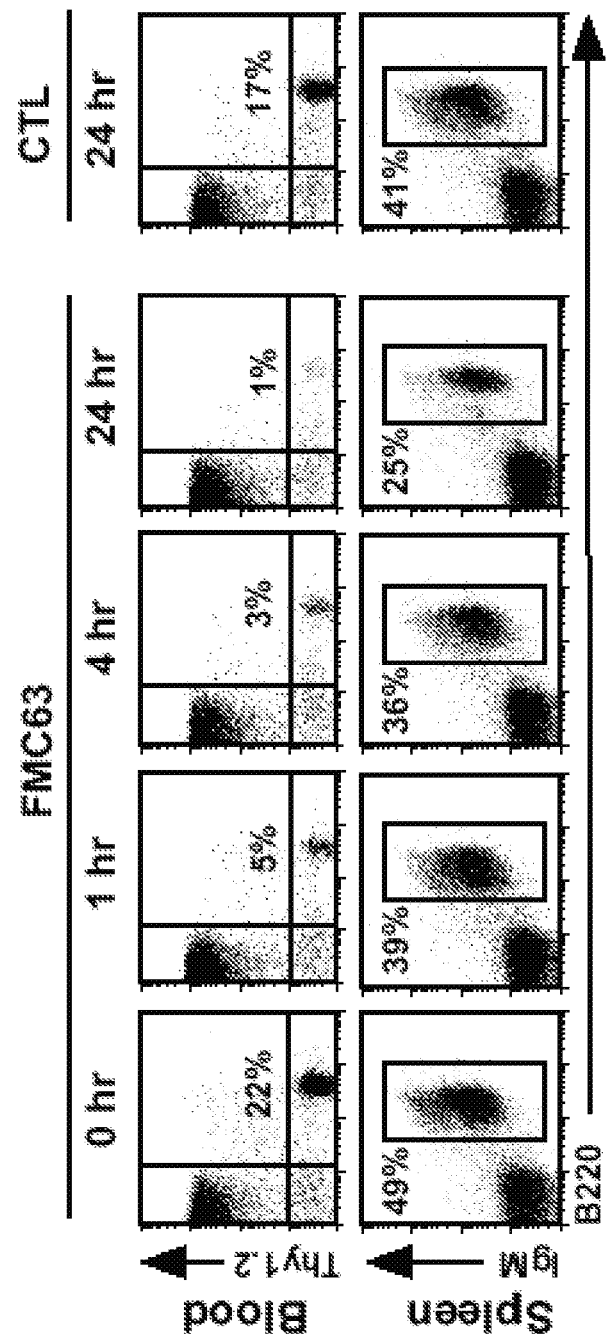

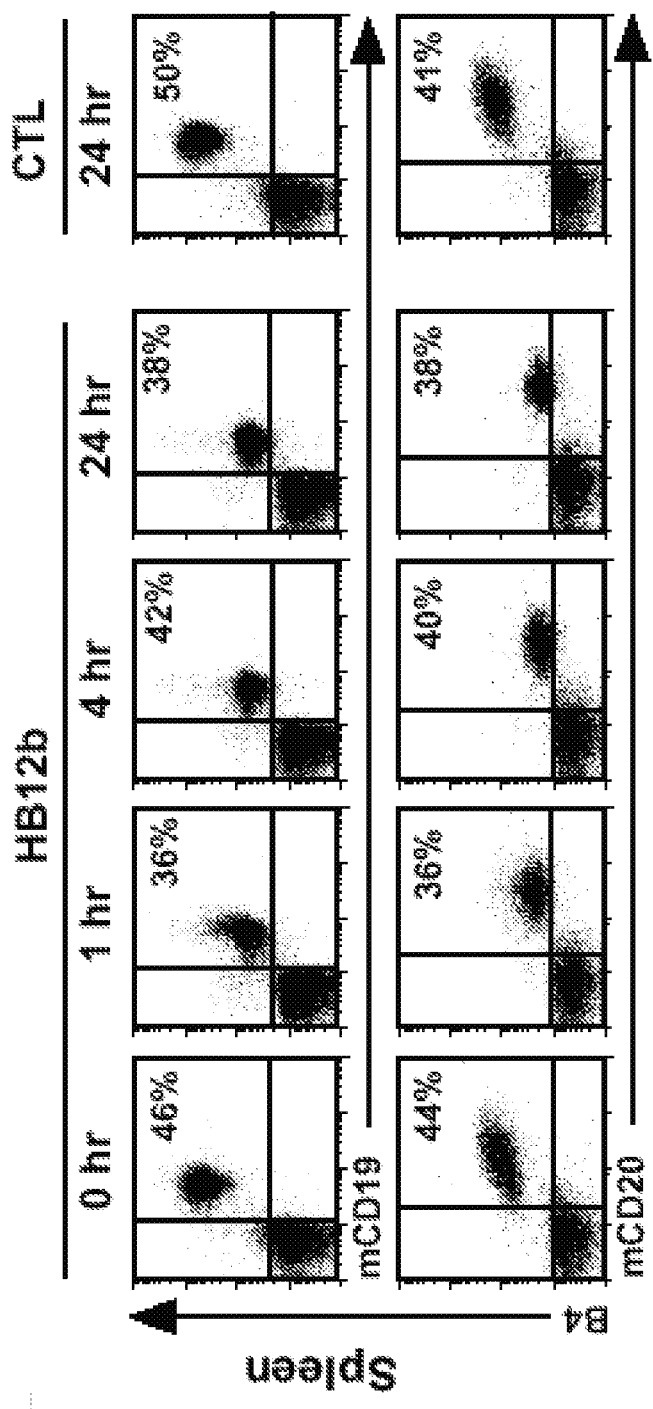

ABmt-CD19 ANTIBODIES AND USES IN B
CELL DISORDERS

RELATED APPLICATIONS

This application is a continuation of U.S. patent application Ser. No. 13/603,154 (filed Sep. 4, 2012), which is a continuation of U.S. patent application Ser. No. 12/885,341 (filed Sep. 17, 2010), which is a continuation-in-part of U.S. patent application Ser. No. 12/401,310 (filed Mar. 10, 2009), U.S. patent application Ser. No. 12/325,426 (filed Dec. 1, 2008), and U.S. patent application Ser. No. 12/275,545 (filed Nov. 21, 2008). U.S. patent application Ser. No. 12/401,310 is a continuation of U.S. patent application Ser. No. 11/355,905 (filed Feb. 15, 2006), which claims the benefit of U.S. Provisional Application Nos. 60/653,587 (filed Feb. 15, 2005) and U.S. 60/702,063 (filed on Jul. 22, 2005). U.S. patent application Ser. No. 12/325,426 is a continuation of U.S. patent application Ser. No. 11/429,545 (filed May 5, 2006), which claims the benefit of U.S. Provisional Application No. 60/679,095 (filed May 5, 2005). U.S. patent application Ser. No. 12/275,545 is a continuation of U.S. patent application Ser. No. 11/450,931 (filed Jun. 8, 2006), which claims the benefit of U.S. Provisional Application Nos. 60/689,033 (filed Jun. 8, 2005) and 60/701,365 (filed Jul. 20, 2005). The entire teachings of the referenced applications are expressly incorporated herein by reference.

This invention was made in part with government support under grant numbers CA1776, CA105001, and CA96547 awarded by the National Cancer Institute of the National Institutes of Health and under grant number AI56363 awarded by the National Institute of Allergy and Infectious Disease of the National Institutes of Health. The United States Government has certain rights in the invention.

1. INTRODUCTION

The present invention is directed to methods for the treatment and/or prevention of diseases and disorders, using therapeutic antibodies that bind to the human CD19 antigen. Diseases and disorders include B cell disorders or diseases in human subjects, including B cell malignancies, and autoimmune conditions. The present invention is also directed to methods for treatment and prevention of graft versus host disease (GVHD), humoral rejection, and post-transplantation lymphoproliferative disorder in human transplant recipients. In a preferred embodiment, the therapeutic anti-CD19 antibodies of the compositions and methods of the invention mediate human antibody-dependent-cell-mediated-cytotoxicity (ADCC). The present invention is further directed to compositions comprising human, humanized, or chimeric anti-CD19 antibodies of the IgG1 and/or IgG3 human isotype. The present invention is further directed to compositions comprising human, humanized, or chimeric anti-CD19 antibodies of the IgG2 and/or IgG4 human isotype that preferably mediate human ADCC. The present invention also encompasses monoclonal human, humanized, or chimeric anti-CD19 antibodies.

2. BACKGROUND OF THE INVENTION

B cell surface markers have been generally suggested as targets for the treatment of B cell disorders or diseases, autoimmune disease, and transplantation rejection. Examples of B cell surface markers include CD10, CD19, CD20, CD21, CD22, CD23, CD24, CD37, CD53, CD72, CD74, CD75, CD77, CD79a, CD79b, CD80, CD81, CD82, CD83, CD84, CD85, and CD86 leukocyte surface markers. Antibodies that specifically bind these markers have been developed, and some have been tested for the treatment of diseases and disorders.

For example, chimeric or radiolabeled monoclonal antibody (mAb)-based therapies directed against the CD20 cell surface molecule specific for mature B cells and their malignant counterparts have been shown to be an effective in vivo treatment for non-Hodgkin's lymphoma (Tedder et al., *Immunol. Today*, 15:450-454 (1994); Press et al., *Hematology*, 221-240 (2001); Kaminski et al., *N. Engl. J. Med.*, 329:459-465 (1993); Weiner, *Semin. Oncol.*, 26:43-51 (1999); Onrust et al., *Drugs*, 58:79-88 (1999); McLaughlin et al., *Oncology*, 12:1763-1769 (1998); Reff et al., *Blood*, 83:435-445 (1994); Maloney et al., *Blood*, 90:2188-2195 (1997); Maloney et al., *J. Clin. Oncol.*, 15:3266-3274 (1997); Anderson et al., *Biochem. Soc. Transac.*, 25:705-708 (1997)). Anti-CD20 monoclonal antibody therapy has also been found to ameliorate the manifestations of rheumatoid arthritis, systemic lupus erythematosus, idiopathic thrombocytopenic purpura and hemolytic anemia, as well as other immune-mediated diseases (Silverman et al., *Arthritis Rheum.*, 48:1484-1492 (2002); Edwards et al., *Rheumatology*, 40:1-7 (2001); DeVita et al., *Arthritis Rheumatism*, 46:2029-2033 (2002); Leandro et al., *Ann. Rheum. Dis.*, 61:883-888 (2002); Leandro et al., *Arthritis Rheum.*, 46:2673-2677 (2001)). The anti-CD22 monoclonal antibody LL-2 was shown to be effective in treating aggressive and relapsed lymphoma patients undergoing chemotherapeutic treatment (Goldenberg U.S. Pat. Nos. 6,134,982 and 6,306,393). The anti-CD20 (IgG1) antibody, RITUXAN™, has successfully been used in the treatment of certain diseases such as adult immune thrombocytopenic purpura, rheumatoid arthritis, and autoimmune hemolytic anemia (Cured et al., WO 00/67796). Despite the effectiveness of this therapy, most acute lymphoblastic leukemias (ALL) and many other B cell malignancies either do not express CD20, express CD20 at low levels, or have lost CD20 expression following CD20 immunotherapy (Smith et al., *Oncogene*, 22:7359-7368 (2003)). Moreover, the expression of CD20 is not predictive of response to anti-CD20 therapy as only half of non-Hodgkin's lymphoma patients respond to CD20-directed immunotherapy.

The human CD19 molecule is a structurally distinct cell surface receptor that is expressed on the surface of human B cells, including, but not limited to, pre-B cells, B cells in early development (i.e., immature B cells), mature B cells through terminal differentiation into plasma cells, and malignant B cells. Unlike CD20, the CD19 antigen was thought to be expressed at higher levels and internalized by cells when bound by an anti-CD19 antibody. The CD19 antigen has been one of the many proposed targets for immunotherapy. However, the perceived unavailability as a target due to cellular internalization, was thought to have presented obstacles to the development of therapeutic protocols that could be successfully used in human subjects.

CD19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al., *J. Immunol.*, 131:244-250 (1983), Loken et al., *Blood*, 70:1316-1324 (1987), Uckun et al., *Blood*, 71:13-29 (1988), Anderson et al., 1984. *Blood*, 63:1424-1433 (1984), Scheuermann, *Leuk. Lymphoma*, 18:385-397 (1995)). The expression of CD19 on plasma cells further suggests it may be expressed on differentiated B cell tumors such as multiple myeloma, plasmacytomas, Waldenstrom's tumors (Grossbard et al., *Br.*

J. Haematol., 102:509-15 (1998); Treon et al., Semin. Oncol., 30:248-52 (2003)). The CLB-CD19 antibody (anti-CD19 murine IgG2a mAb) was shown to inhibit growth of human tumors implanted in athymic mice (Hooijberg et al., Cancer Research, 55:840-846 (1995)). In another study, the monoclonal murine antibody FMC63 (IgG2a) was chimerized using a human IgG1 Fc region. Administration of this chimeric antibody to SCID mice bearing a human B cell lymphoma (xenotransplantation model) did not induce complement-mediated cytotoxicity or ADCC, but resulted in significant killing of the transplanted tumor cells (Geoffrey et al., Cancer Immunol. Immunother., 41:53-60 (1995)) In addition to favorable internalization and greater efficiency in depleting B cells, anti-CD19 antibody therapy was not recognized for the depletion of serum immunoglobulin levels.

The results obtained using xenotransplantation mouse models of tumor implantation led to studies using murine anti-CD19 antibodies in human patients. The murine CLB-CD19 antibody was administered to six patients diagnosed with a progressive non-Hodgkin's lymphoma who had failed previous conventional therapy (chemotherapy or radiotherapy). These patients were given total antibody doses ranging from 225 to 1,000 mg (Hekman et al., Cancer Immunol. Immunotherapy, 32:364-372 (1991)). Although circulating tumor cells were temporarily reduced in two patients after antibody infusion, only one patient achieved partial remission after two periods of antibody treatment. No conclusions regarding therapeutic efficacy could be drawn from this small group of refractory patients.

Subsequently, these investigators showed that the anti-tumor effects of unconjugated CD20 mAbs are far superior to those of CD19 mAbs in transplantation models (Hooijberg et al., Cancer Res., 55:840-846 (1995); and Hooijberg et al., Cancer Res., 55:2627-2634 (1995)). Moreover, they did not observe additive or synergistic effects on tumor incidence when using CD19 and CD20 mAbs in combination (Hooijberg et al., Cancer Res., 55:840-846 (1995)). Although the xenotransplantation animal models were recognized to be poor prognostic indicators for efficacy in human subjects, the negative results achieved in these animal studies discouraged interest in therapy with naked anti-CD19 antibodies.

The use of anti-CD19 antibody-based immunotoxins produced equally discouraging results. In early clinical trials, the B4 anti-CD19 antibody (murine IgG1 mAb) was conjugated to the plant toxin ricin and administered to human patients having multiple myeloma who had failed previous conventional therapy (Grossbard et al., British Journal of Haematology, 102:509-515 (1998)), advanced non-Hodgkin's lymphoma (Grossbard et al., Clinical Cancer Research, 5:2392-2398 (1999)), and refractory B cell malignancies (Grossbard et al., Blood, 79:576-585 (1992)). These trials generally demonstrated the safety of administering the B4-ricin conjugate to humans; however, results were mixed and response rates were discouraging in comparison to clinical trials with RITUXAN™ (Grossbard et al., Clinical Cancer Research, 5:2392-2398 (1999)). In addition, a significant portion of the patients developed a human anti-mouse antibody (HAMA) response or a human anti-ricin antibody (HARA) response.

In another trial, seven low-grade non-Hodgkin's lymphoma patients previously treated with conventional therapy were treated with the murine CLB-CD19 antibody in combination with continuous infusion of low-dose interleukin-2 (Vlasveld et al., Cancer Immunol. Immunotherapy, 40:37-47 (1995)). A partial remission occurred in one leukemic patient, and a greater than 50% reduction of circulating B cells was observed. Circulating B cell numbers were not changed in 4 of 5 remaining patients assessed. Thus, the therapeutic evaluation of murine anti-CD19 antibodies and anti-CD19 antibody-based immunotoxins in humans, generated anecdotal data that could not be evaluated for efficacy.

Due to the relatively recent appreciation of the role of humoral immunity in acute and chronic graft rejection, current therapeutic agents and strategies for targeting humoral immunity are less well developed than those for targeting cellular immunity.

Both cellular (T cell-mediated) and humoral (antibody, B cell-mediated) immunity are now known to play significant roles in graft rejection. While the importance of T cell-mediated immunity in graft rejection is well established, the critical role of humoral immunity in acute and chronic rejection has only recently become evident. Consequently, most of the advances in the treatment and prevention of graft rejection have developed from therapeutic agents that target T cell activation. The first therapeutic monoclonal antibody that was FDA approved for the treatment of graft rejection was the murine monoclonal antibody ORTHOCLONE-OKT3™ (muromonab-CD3), directed against the CD3 receptor of T cells. OKT3 has been joined by a number of other anti-lymphocyte directed antibodies, including the monoclonal anti-CD52 CAMPATH™ antibodies, CAMPATH-1G, CAMPATH-1H (alemtuzumab), and CAMPATH-1M), and polyclonal anti-thymocyte antibody preparations (referred to as anti-thymocyte globulin, or "ATG," also called "thymoglobin" or "thymoglobulin"). Other T cell antibodies approved for the prevention of transplant rejection include the chimeric monoclonal antibody SIMULECT™ (basiliximab) and the humanized monoclonal antibody ZENAPAX™ (daclizumab), both of which target the high-affinity IL-2 receptor of activated T cells.

The importance of humoral immunity in graft rejection was initially thought to be limited to hyperacute rejection, in which the graft recipient possesses anti-donor HLA antibodies prior to transplantation, resulting in rapid destruction of the graft in the absence of an effective therapeutic regimen of antibody suppression. Recently, it has become evident that humoral immunity is also an important factor mediating both acute and chronic rejection. For example, clinical observations demonstrated that graft survival in patients capable of developing class I or class II anti-HLA alloantibodies (also referred to as "anti-MHC alloantibodies") was reduced compared to graft survival in patients that could not develop such antibodies. Clinical and experimental data also indicate that other donor-specific alloantibodies and autoantibodies are critical mediators of rejection. For a current review of the evidence supporting a role for donor-specific antibodies in allograft rejection, see Rifle et al., Transplantation, 2005 79:S14-S18.

The available strategies for targeting humoral immunity include antibody depletion regimens and anti-B lymphocyte directed antibodies. For a recent review of immunological strategies for targeting humoral immunity, see Snanoudj et al., Transplantation, 2005 79:S33-35. Examples of antibody depletion regimens include treatment of the recipient with intravenous immunoglobulin, the removal of donor-reactive antibodies by immunoadsorption, and plasmapheresis. Most reports of anti-B lymphocyte directed antibodies have focused on anti-CD20 antibodies, and particularly the chimeric mouse-human anti-CD20 monoclonal antibody, RITUXAN™ (rituximab), which is FDA approved for the treatment of some B cell malignancies. More recently, rituximab has been evaluated for use in transplantation-related therapeutic regimens. For example, rituximab has been reported for use in a pre-transplant conditioning regimen, in a treatment regimen for acute rejection, and to reduce the anti-ABO antibody titer for ABO-incompatible kidney transplantation, with mixed results. Sinder et al. (*Hum. Antibodies,* 2004 13:55-62) reported a single-dose, dose-escalation phase 1 trial using rituximab for conditioning of dialysis patients awaiting transplantation. The results indicated that rituximab, as a single agent, partially depleted a subpopulation of B cells and reduced panel reactive alloantibodies. However, Viera et al. (*Transplantation,* 2004 77:542) reported only modest reductions in panel reactive alloantibodies using a single-dose of rituximab in patients awaiting renal transplantation. Becker et al. (*Am. J. Transplant,* 2004 4:996) reported the use of rituximab to treat acute rejection which had previously failed to respond to steroid treatment or to combination therapy with anti-thymocyte globulin and plasmapheresis. Rituximab conditioning in combination with other strategies such as immunoadsorption, plasmaphoresis, and intravenous immunoglobulins, without the need for splenectomy, was also reported in connection with ABO-incompatible kidney transplantations (see Tyden et al. *Transplantation,* 2003 76:730; Sonnenday *Am. J. Transplant.,* 2004 4:1315).

Anti-CD19 antibodies may offer advantages over anti-CD20 antibodies in being able to target a wider repertoire of B cells, but their use in transplantation immunotherapy has been limited primarily to the identification and monitoring of B cells. An additional use of anti-CD19 directed antibodies in transplantation was reported by Barfield et al., *Cytotherapy,* 2004 6:1-6. Barfield reported anti-CD3 antibodies and anti-CD19 antibodies conjugated to magnetic microbeads used as affinity reagents to capture T and B lymphocytes from donor peripheral stem cell grafts, ex vivo, to reduce allogeneic lymphocytes in the graft prior to transplantation.

In addition to the treatment and prevention of graft rejection, B cell directed antibodies have been used to treat post-transplant lymphoproliferative disorder (PTLD) (see LeVasseur et al. *Pediatr. Transplant.,* 2003 7:370-75). PTLD is characterized by hyperproliferative B cells and is associated with Epstein-Barr virus infected B cells, either originating from the graft or latent in the recipient. Schaar et al. reported a five-step protocol for the treatment of PTLD in patients at high risk following solid organ transplants of the pancreas-kidney, liver, heart, and kidney (*Transplantation,* 2001 71:47-52). The regimen included a murine anti-CD19 monoclonal antibody of isotype IgG2a in combination with a reduction in the amount of immunosuppressive agents and the addition of anti-viral agents, interferon-alpha, and gamma-globulins.

3. SUMMARY OF THE INVENTION

The invention relates to immunotherapeutic compositions and methods for the treatment of diseases, disorders, and other conditions of the immune system in human subjects, using therapeutic antibodies that bind to the human CD19 antigen and that preferably mediate human ADCC. In a particular embodiment, the anti-CD19 antibodies of the present invention mediate ADCC, complement dependent cellular cytotoxicity (CDC), or apoptosis of B cells. Diseases and disorders treatable with the compositions and methods of the present application include but are not limited to B cell diseases and disorders such as B cell malignanacies, and autoimmune diseases and disorders. The compositions and methods may also be used for the prophylaxis and treatment of GVHD, humoral rejection, and post-transplantation lymphoproliferative disorders in human subjects.

The present invention relates to pharmaceutical compositions comprising human or humanized anti-CD19 antibodies of the IgG1 or IgG3 human isotype. The present invention relates to pharmaceutical compositions comprising human or humanized anti-CD19 antibodies of the IgG2 or IgG4 human isotype that preferably mediate human ADCC. The present invention relates to pharmaceutical compositions comprising chimerized anti-CD19 antibodies of the IgG1, IgG2, IgG3, or IgG4 isotype that mediate human ADCC. In preferred embodiments, the present invention relates to pharmaceutical compositions comprising monoclonal human, humanized, or chimeric anti-CD19 antibodies.

The methods of the invention are demonstrated by way of example, using a transgenic mouse model for evaluating CD19-directed immunotherapies in human subjects.

In one embodiment, the invention provides for a pharmaceutical composition comprising a monoclonal human or humanized anti-CD19 antibody of the IgG1 or IgG3 human isotype in a pharmaceutically acceptable carrier. In another embodiment, the invention provides for a pharmaceutical composition comprising a therapeutically effective amount of a monoclonal chimerized anti-CD19 antibody of the IgG1 or IgG3 human isotype in a pharmaceutically acceptable carrier. In related embodiments, a therapeutically effective amount of a monoclonal chimerized anti-CD19 antibody of the IgG1 or IgG3 human isotype is less than 1 mg/kg of patient body weight. In other related embodiments, a therapeutically effective amount of a monoclonal chimerized anti-CD19 antibody of the IgG1 or IgG3 human isotype is greater than 2 mg/kg of patient body weight.

According to one aspect, the invention provides for a pharmaceutical composition comprising a therapeutically effective amount of monoclonal human or humanized anti-CD19 antibody that mediates human antibody-dependent cellular cytotoxicity (ADCC), in a pharmaceutically acceptable carrier. According to another aspect, the invention provides for a pharmaceutical composition comprising a monoclonal chimerized anti-CD19 antibody that mediates human antibody-dependent cellular cytotoxicity (ADCC), and/or complement dependent cytotoxicty (CDC) and/or apoptotic activity in a pharmaceutically acceptable carrier.

In some embodiments, therapeutic formulations and regimens are described for treating human subjects diagnosed with B cell malignancies that derive from B cells and their precursors, including but not limited to, acute lymphoblastic leukemias (ALL), Hodgkin's lymphomas, non-Hodgkin's lymphomas, B cell chronic lymphocytic leukemias (CLL), multiple myeloma, follicular lymphoma, mantle cell lymphoma, pro-lymphocytic leukemias, hairy cell leukemias, common acute lymphocytic leukemias and some Null-acute lymphoblastic leukemias.

In certain embodiments, the present invention concerns a method of treating a B cell malignancy in a human comprising administering to a human in need thereof a monoclonal human or humanized anti-CD19 antibody of the IgG1 or IgG3 human isotype in an amount sufficient to deplete circulating B cells. The present invention also concerns a method of treating a B cell malignancy in a human comprising administering to a human in need thereof a monoclonal human or humanized anti-CD19 antibody that mediates human antibody-dependent cellular cytotoxicity (ADCC) in an amount sufficient to deplete circulating B cells. ADCC The present invention also concerns a method of treating a B cell malignancy in a human patient comprising the administration of a therapeutically effective regimen of a monoclonal human or humanized anti-CD19 antibody of the IgG1 or IgG3 human isotype to a human patient in need of such treatment.

In one embodiment, the present invention provides a method of treating a B cell malignancy in a human patient comprising the administration of a therapeutically effective regimen of a monoclonal human or humanized anti-CD19 antibody that mediates human antibody-dependent cellular cytotoxicity (ADCC), to a human patient in need of such treatment. In another embodiment, the present invention provides a method of treating an early stage disease resulting from a B cell malignancy in a human patient comprising administration of a therapeutically effective regimen of a monoclonal anti-CD19 antibody that mediates human antibody-dependent cellular cytotoxicity (ADCC), to a human in need of such treatment. In a further embodiment, the present invention provides a method of treating a B cell malignancy in a human patient comprising administration of a therapeutically effective regimen of a monoclonal anti-CD19 antibody that mediates human antibody-dependent cellular cytotoxicity (ADCC), to a human subject in need thereof, wherein the human subject has not previously received treatment for the malignancy. Yet another embodiment of the present invention provides a method of treating a B cell malignancy in a human patient comprising administration of a therapeutically effective regimen of a monoclonal anti-CD19 antibody that mediates human antibody-dependent cellular cytotoxicity (ADCC), to a human patient in need of such treatment, wherein the B cell malignancy is CD19 positive. In a further embodiment, the present invention provides a method of treating a B cell malignancy in a human patient comprising administration of a therapeutically effective regimen of a monoclonal anti-CD19 antibody that mediates human antibody-dependent cellular cytotoxicity (ADCC), to a human patient in need of such treatment, wherein the human patient has a monocyte count of at least 1 per dL of circulating blood.

In other embodiments, therapeutic formulations and regimens are described for treating human subjects diagnosed with or at risk for development of autoimmune diseases or disorders, including but not limited to, rheumatoid arthritis, Systemic Lupus Erythematosis (SLE), Idiopathic/Autoimmune Thrombocytopenia Purpura (ITP), pemphigus-related disorders, diabetes, or scleroderma.

In certain embodiments, the present invention concerns a method of treating an autoimmune disease or disorder in a human comprising administering to a human in need thereof a monoclonal human or humanized anti-CD19 antibody of the IgG1 or IgG3 human isotype in an amount sufficient to deplete circulating B cells. The present invention also concerns a method of treating an autoimmune disease or disorder in a human patient comprising the administration of a therapeutically effective regimen of an anti-CD19 antibody that mediates human ADCC to a human patient in need of such treatment. The present invention also concerns methods of treating autoimmune disorders comprising the administration of a therapeutically effective regimen of a monoclonal human or humanized anti-CD19 antibody of the IgG1 or IgG3 human isotype.

In one embodiment, the present invention provides a method of treating an autoimmune disorder in a human patient comprising the administration of a therapeutically effective regimen of a monoclonal human or humanized anti-CD19 antibody that mediates ADCC, to a human patient in need of such treatment. In another embodiment, the present invention provides a method of treating an early stage autoimmune disorder comprising administration of a therapeutically effective regimen of a monoclonal anti-CD19 antibody that mediates ADCC, to a human in need of such treatment. In a further embodiment, the present invention provides a method of treating an autoimmune disorder in a human patient comprising administration of a therapeutically effective regimen of a monoclonal anti-CD19 antibody that mediates ADCC, to a human subject in need thereof, wherein the human subject has not previously received treatment for the disorder. Yet another embodiment of the present invention provides a method of treating an autoimmune disease or disorder in a human patient comprising administration of a therapeutically effective regimen of a monoclonal anti-CD19 antibody that mediates ADCC, to a human patient in need of such treatment, wherein the autoimmune disease or disorder is CD19 positive. In a further embodiment, the present invention provides a method of treating an autoimmune disease or disorder in a human patient comprising administration of a therapeutically effective regimen of a monoclonal anti-CD19 antibody that mediates human ADCC, to a human patient in need of such treatment, wherein the human patient has a monocyte count of at least 1 per dL of circulating blood. The present invention provides methods of treatment of an autoimmune disease or disorder, wherein the autoimmune disease or disorder is rheumatoid arthritis, systemic lupus erythematosis, idiopathic/autoimmune thrombocytopenia purpura, a pemphigus-related disorder, diabetes, or scleroderma.

In certain embodiments, the present invention provides methods for treating or preventing humoral rejection in a human transplant recipient in need thereof comprising administering to the recipient an anti-CD19 antibody in an amount sufficient to deplete circulating B cells, or circulating immunoglobulin, or both, wherein the anti-CD19 antibody is administered alone or in combination with one or more other therapeutic agents. In one embodiment, the transplant recipient in need of prophylaxis against humoral rejection is identified as a patient or patient population who has detectable circulating anti-HLA alloantibodies prior to transplantation. In another embodiment, the patient or patient population is identified as having panel reactive alloantibodies prior to transplantation. In another embodiment, the transplant recipient in need of treatment for humoral rejection is identified as a patient or patient population who has detectable circulating anti-HLA alloantibodies post-transplantation. In another embodiment, the patient or patient population is identified as having panel reactive alloantibodies post-transplantation. In another embodiment, the patient or patient population is identified as in need of transplant from an ABO blood type incompatible donor.

In certain embodiments, the invention provides methods for preventing humoral rejection in a human transplant recipient in need thereof comprising administering to the recipient prior to transplantation an anti-CD19 antibody in an amount sufficient to deplete circulating B cells, or circulating immunoglobulin, or both, wherein the anti-CD19 antibody is administered alone or in combination with one or more other therapeutic agents. In other embodiments, the invention provides methods for preventing graft rejection or graft versus host disease in a human transplant recipient in need thereof comprising contacting a graft prior to transplantation with an amount of an anti-CD19 antibody sufficient to deplete B cells from the graft. In one embodiment, the graft is contacted with the anti-CD19 antibody ex vivo. In another embodiment, the method further comprises contacting the graft with one or more of an anti-T lymphocyte antibody or anti-thymocyte globulin.

In certain embodiments, the invention provides methods for treating humoral rejection in a human transplant recipient in need thereof comprising administering to the recipient an anti-CD19 antibody in an amount sufficient to deplete circulating B cells, or circulating immunoglobulin, or both, wherein the anti-CD19 antibody is administered alone or in combination with one or more other therapeutic agents. In one embodiment, the rejection is an acute or a chronic humoral rejection. In one embodiment, the transplant recipient in need of treatment for humoral rejection is identified as a patient or patient population in an early stage of rejection, such as a latent humoral response characterized by circulating anti-donor alloantibodies, a silent reaction characterized by circulating anti-donor alloantibodies and C4d deposition, or a subclinical rejection characterized by circulating anti-donor alloantibodies, C4d deposition, and tissue pathology. In another embodiment, the transplant recipient in need of treatment for humoral rejection is identified as a patient or patient population is in a stage of rejection characterized by circulating anti-donor alloantibodies, C4d deposition, tissue pathology, and graft dysfunction.

In certain embodiments, the present invention also concerns methods for treating or preventing humoral rejection in a human transplant recipient in need thereof comprising administering a therapeutically effective regimen of an anti-CD19 antibody to the recipient. In one embodiment, the regimen further comprises administering a compound that enhances monocyte or macrophage function. In one embodiment, the regimen comprises a single administration of the anti-CD19 antibody to the recipient. In another embodiment, the regimen comprises more than one administration of the anti-CD19 antibody to the recipient. In one embodiment, the regimen comprises the administration of the antibody as a single therapeutic agent. In one embodiment, the regimen comprises the administration of the antibody in combination with one or more other therapeutic agents.

In certain embodiments, wherein the invention provides for the administration of an anti-CD19 antibody in combination with one or more other therapeutic agents, the therapeutic agents are selected from the group consisting of adriamycin, azathiopurine, busulfan, cyclophosphamide, cyclosporin A, cytoxin, fludarabine, 5-fluorouracil, methotrexate, mycophenolate mofetil, a nonsteroidal anti-inflammatory, rapamycin, sirolimus, and tacrolimus. In related embodiments, the one or more other therapeutic agents is an antibody selected from the group consisting of OKT3™ (muromonab-CD3), CAMPATH™-1H (alemtuzumab), CAMPATH™-1G, CAMPATH™-1M, SIMULECT™ (basiliximab), ZENAPAX™ (daclizumab), RITUXAN™ (rituximab), and anti-thymocyte globulin.

According to one aspect, the invention provides methods for the treatment and prevention of GVHD and rejection in transplant recipients who are characterized as being at risk for developing a humoral response to an allograft. In a related embodiment, the recipient has detectable levels of circulating anti-HLA alloantibodies.

In particular embodiments of the invention, the transplant recipient is a recipient of an allogeneic solid organ transplant selected from the group consisting of a heart transplant, a kidney-pancreas transplant, a kidney transplant, a liver transplant, a lung transplant, and a pancreas transplant. In one embodiment, the recipient is a recipient of an allogeneic transplant of pancreatic islet cells. In another embodiment, the recipient is a recipient of a hematopoietic cell transplant, for example, a bone marrow transplant and/or a transplant of peripheral blood stem cells.

The invention also provides for the administration of an anti-CD19 antibody as part of a therapeutic regimen for the treatment or prevention of graft rejection. In one embodiment, the therapeutic regimen further comprises one or more immunosuppression therapy, anti-lymphocyte therapy, immunoadsorption, or plasmapheresis. In particular embodiments, the immunosuppression therapy comprises administering to the transplant recipient one or more compounds selected from the group consisting of a steroid, an inhibitor of cytokine transcription, an inhibitor of nucleotide synthesis, an inhibitor of growth factor signal transduction, and an inhibitor of a T cell interleukin 2 receptor. In particular embodiments, the anti-lymphocyte therapy comprises administering to the recipient one or more antibodies selected from the group consisting of OKT3™ (muromonab-CD3), CAMPATH™-1H (alemtuzumab), CAMPATH™-1G, CAMPATH™-1M, SIMULECT™ (basiliximab), ZENAPAX™ (daclizumab), RITUXAN™ (rituximab), and anti-thymocyte globulin.

In certain embodiments of the methods of the present invention, the anti-CD19 antibody is a monoclonal antibody selected from the group consisting of a human antibody, a humanized antibody, and a chimeric antibody. Preferably, the anti-CD19 antibody mediates human antibody-dependent cellular cytotoxicity (ADCC). In certain embodiments, the anti-CD19 antibody is an IgG1 or IgG3 human isotype antibody. In other embodiments, the anti-CD19 antibody is an IgG2 or IgG4 human isotype antibody. In one embodiment, the anti-CD19 antibody has a half-life that is at least 4 to 7 days.

In particular embodiments of the invention, the anti-CD19 antibody is administered by a parenteral, intraperitoneal, or intramuscular route. In other embodiments, the anti-CD19 antibody is administered by an intravenous or subcutaneous route, preferably by a subcutaneous route in a dose of 37.5 mg/m$^2$ or less or in a dose of 1.5 mg/m$^2$ or less.

In a preferred embodiment of the methods provided by the invention, the anti-CD19 antibody is administered in an amount effective to reduce or deplete circulating B cells, to reduce or deplete circulating immunoglobulin (Ig), or to reduce or deplete both circulating B cells and circulating Ig in a transplant recipient. In one embodiment, the anti-CD19 antibody is administered in an amount effective to reduce or deplete B cells, to reduce or deplete immunoglobulin (Ig), or to reduce or deplete both B cells and Ig in a graft prior to transplantation of the graft to a recipient. In one embodiment, the methods provided by the invention achieve at least a 50% or at least a 75% depletion in circulating B cells. In related embodiments, the depletion in circulating B cells is observed for a period of at least 7 days, at least 30 days, or at least 6 months. In another preferred embodiment, the methods of the invention are effective to reduce panel reactive alloantibodies in the transplant recipient by at least 50%, at least 70%, at least 80%, at least 90%, or at least 95%.

The present invention also concerns methods for treating or preventing a post-transplant lymphoproliferative disorder in a human transplant recipient in need thereof comprising administering to the transplant recipient a human or humanized anti-CD19 antibody in an amount sufficient to deplete circulating B cells. In one embodiment, the invention further provides for the administration of an anti-viral agent to the transplant recipient.

3.1 Definitions

As used herein, the terms "antibody" and "antibodies" (immunoglobulins) refer to monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. Such antibodies may be derived from any mammal, including, but not limited to, humans, monkeys, pigs, horses, rabbits, dogs, cats, mice, etc.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see, Kabat et al., *Sequences of Proteins of Immunological Interest*, 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC.

The term "hypervariable region" when used herein refers to the amino acid residues of an antibody which are responsible for binding to its antigen. The hypervariable region comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.*, 196:901-917 (1987)). "Framework" or "FR" residues are those variable domain residues other than the hypervariable region residues as herein defined, and include chimeric, humanized, human, domain antibodies, diabodies, vaccibodies, linear antibodies, and bispecific antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma cells, uncontaminated by other immunoglobulin producing cells. Alternatively, the monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., *Nature*, 256:495 (1975), or may be made by any recombinant DNA method (see, e.g., U.S. Pat. No. 4,816,567), including isolation from phage antibody libraries using the techniques described in Clackson et al., *Nature*, 352:624-628 (1991) and Marks et al., *J. Mol. Biol.*, 222:581-597 (1991), for example. These methods can be used to produce monoclonal mammalian, chimeric, humanized, human, domain antibodies, diabodies, vaccibodies, linear antibodies, and bispecific antibodies.

The term "chimeric" antibodies includes antibodies in which at least one portion of the heavy and/or light chain is identical with or homologous to corresponding sequences in antibodies derived from a particular species or belonging to a particular antibody class or subclass, and at least one other portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

"Humanized" forms of nonhuman (e.g., murine) antibodies are chimeric antibodies that contain minimal sequence derived from nonhuman immunoglobulin. For the most part, humanized antibodies are human immunoglobulins (recipient antibody) in which residues from a hypervariable region of the recipient are replaced by residues from a hypervariable region of a nonhuman species (donor antibody) such as mouse, rat, rabbit or nonhuman primate having the desired specificity, affinity, and capacity. In some instances, framework region (FR) residues of the human immunoglobulin are replaced by corresponding nonhuman residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., *Nature*, 321:522-525 (1986); Riechmann et al., *Nature*, 332: 323-329 (1988); and Presta, *Curr. Op. Struct. Biol.*, 2:593-596 (1992).

A "human antibody" can be an antibody derived from a human or an antibody obtained from a transgenic organism that has been "engineered" to produce specific human antibodies in response to antigenic challenge and can be produced by any method known in the art. According to preferred techniques, elements of the human heavy and light chain loci are introduced into strains of the organism derived from embryonic stem cell lines that contain targeted disruptions of the endogenous heavy chain and light chain loci. The transgenic organism can synthesize human antibodies specific for human antigens, and the organism can be used to produce human antibody-secreting hybridomas. A human antibody can also be an antibody wherein the heavy and light chains are encoded by a nucleotide sequence derived from one or more sources of human DNA. A fully human antibody also can be constructed by genetic or chromosomal transfection methods, as well as phage display technology, or in vitro activated B cells, all of which are known in the art.

The "CD19" antigen refers to an antigen of about 90 kDa identified, for example, by the HD237 or B4 antibody (Kiesel et al., *Leukemia Research II*, 12:1119 (1987)). CD19 is found on cells throughout differentiation of B-lineage cells from the stem cell stage through terminal differentiation into plasma cells, including but not limited to, pre-B cells, B cells (including naïve B cells, antigen-stimulated B cells, memory B cells, plasma cells, and B lymphocytes) and follicular dendritic cells. CD19 is also found on B cells in human fetal tissue. In preferred embodiments, the CD19 antigen targeted by the antibodies of the invention is the human CD19 antigen.

"Antibody-dependent cell-mediated cytotoxicity" and "ADCC" refer to a cell-mediated reaction in which nonspecific cytotoxic cells (e.g., Natural Killer (NK) cells, neutrophils, and macrophages) recognize bound antibody on a target cell and subsequently cause lysis of the target cell. In preferred embodiments, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, *Annu. Rev. Immunol.*, 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., *PNAS (USA)*, 95:652-656 (1998).

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., *J. Immunol. Methods*, 202:163 (1996), may be performed.

"Effector cells" are leukocytes which express one or more FcRs and perform effector functions. Preferably, the cells express at least FcγRI, FcγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. In preferred embodiments the effector cells are human cells.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, Daëron, *Annu. Rev. Immunol.*, 15:203-234 (1997)). FcRs are reviewed in Ravetech and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *Immunol.*, 117:587 (1976) and Kim et al., *J. Immunol.*, 24:249 (1994)).

"Fv" is the minimum antibody fragment which contains a complete antigen-recognition and binding site. This region consists of a dimer of one heavy and one light chain variable domain in tight, non-covalent or covalent association. In the Fv configuration, the three CDRs of each variable domain interact to define an antigen-binding site on the surface of the $V_H$-$V_L$ dimer. Collectively, these six CDRs confer antigen-binding specificity to the Fv fragment. However, even a single variable domain (or half of a Fv comprising only three CDRs specific for an antigen) has the ability to recognize and bind antigen, although at a lower affinity than the entire binding site.

"Affinity" of an antibody for an epitope to be used in the treatment(s) described herein is a term well understood in the art and means the extent, or strength, of binding of antibody to epitope. Affinity may be measured and/or expressed in a number of ways known in the art, including, but not limited to, equilibrium dissociation constant (KD or Kd), apparent equilibrium dissociation constant (KD' or Kd'), and IC50 (amount needed to effect 50% inhibition in a competition assay). It is understood that, for purposes of this invention, an affinity is an average affinity for a given population of antibodies which bind to an epitope. Values of KD' reported herein in terms of mg IgG per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

An "epitope" is a term well understood in the art and means any chemical moiety that exhibits specific binding to an antibody. An "epitope" can also comprise an antigen, which is a moiety or molecule that contains an epitope, and, as such, also specifically binds to antibody.

A "B cell surface marker" as used herein is an antigen expressed on the surface of a B cell which can be targeted with an agent which binds thereto. Exemplary B cell surface markers include the CD10, CD19, CD20, CD21, CD22, CD23, CD24, CD25, CD37, CD53, CD72, CD73, CD74, CD75, CD77, CD79a, CD79b, CD80, CD81, CD82, CD83, CD84, CD85, and CD86 leukocyte surface markers. The B cell surface marker of particular interest is preferentially expressed on B cells compared to other non-B cell tissues of a mammal and may be expressed on both precursor B cells and mature B cells. In one embodiment, the preferred marker is CD19, which is found on B cells throughout differentiation of the lineage from the pro/pre-B cell stage through the terminally differentiated plasma cell stage.

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody. The constant domains of antibodies are not involved in binding to antigen, but may exhibit various effector functions. Depending on the amino acid sequence of the heavy chain constant region, a given antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called $\alpha$, $\delta$, $\epsilon$, $\gamma$, and $\mu$, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, the term "immunogenicity" means that a compound is capable of provoking an immune response (stimulating production of specific antibodies and/or proliferation of specific T cells).

As used herein, the term "antigenicity" means that a compound is recognized by an antibody or may bind to an antibody and induce an immune response.

As used herein, the term "avidity" is a measure of the overall binding strength (i.e., both antibody arms) with which an antibody binds an antigen. Antibody avidity can be determined by measuring the dissociation of the antigen-antibody bond in antigen excess using any means known in the art, such as, but not limited to, by the modification of indirect fluorescent antibody as described by Gray et al., *J. Virol. Meth.*, 44:11-24. (1993).

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. The terms "treat," "treating" or "treatment of" also means managing an autoimmune disease or disorder. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to an amount of an antibody or composition of the invention that is effective to produce a desired effect, which is optionally a therapeutic effect (i.e., by administration of a therapeutically effective amount). For example, a "sufficient amount" or "an amount sufficient to" can be an amount that is effective to deplete B cells.

A "therapeutically effective" amount as used herein is an amount that provides some improvement or benefit to the subject. Alternatively stated, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

4. BRIEF DESCRIPTION OF THE DRAWINGS

FIGS. 1A-1E illustrate CD19 expression by hCD19TG mouse lines. FIG. 1A shows human and mouse CD19 expression by B cells from hCD19TG (TG-1$^{+/-}$) mice. FIG. 1B shows the relative mean densities of human and mouse CD19 expression by CD19$^+$ blood B cells from hCD19TG mice. FIG. 1C shows the relative densities of hCD19 and mCD19 expression by CD19$^+$ B cells from TG-1$^{+/-}$ mouse tissues. FIG. 1D shows CD19 antibody binding density on mouse blood and spleen B220$^+$ B cells from TG-1$^{+/-}$ mice. FIG. 1E shows anti-CD19 antibody binding to hCD19 cDNA-transfected 300.19 cells.

FIGS. 2A-2D show blood, spleen, and lymph node B cell depletion in hCD19TG mice. FIG. 2A demonstrates representative B cell depletion from blood, spleen, and lymph node 7 days following anti-CD19 or isotype-matched control (CTL) antibody treatment of TG-1$^{+/-}$ mice. FIG. 2B shows a time course of circulating B cell depletion by anti-CD19 antibodies. FIG. 2C and FIG. 2D show spleen and lymph node B cell numbers (±SEM), respectively, after treatment of TG-1$^{+/-}$ mice with anti-CD19 (filled bars) or control (open bars) antibody at the indicated doses.

FIGS. 3A-3F depict bone marrow B cell depletion following anti-CD19 antibody treatment. FIG. 3A shows representative hCD19 and mCD19 expression by TG-1$^{+/-}$ bone marrow B cell subpopulations assessed by four-color immunofluorescence staining with flow cytometry analysis. FIG. 3B shows depletion of hCD19$^+$ cells in the bone marrow of hCD19TG mice seven days following FMC63 or isotype-matched control antibody (250 µg) treatment assessed by two-color immunofluorescence staining with flow cytometry analysis. FIG. 3C shows representative B220$^+$ B cell depletion in the bone marrow seven days following CD19 or isotype-matched control antibody (250 µg) treatment of TG-1$^{+/-}$ mice. FIG. 3D shows representative B cell subset depletion seven days following FMC63 or isotype-matched control antibody (250 µg) treatment of TG-1$^{+/-}$ mice as assessed by three-color immunofluorescence staining IgM$^-$B220$^{lo}$ pro-/pre-B cells were further subdivided based on CD43 expression (lower panels). FIG. 3E shows representative depletion of CD25+B220$^{lo}$ pre-B cells seven days following FMC63 or isotype-matched control antibody (250 µg) treatment of hCD19TG mouse lines as assessed by two-color immunofluorescence staining FIG. 3F shows bar graphs indicating numbers (±SEM) of pro-B, pre-B, immature, and mature B cells within bilateral femurs seven days following FMC63 (closed bars) or control (open bars) antibody treatment of ≥3 littermate pairs.

FIGS. 4A-4C demonstrate that peritoneal cavity B cells are sensitive to anti-CD19 antibody treatment. FIG. 4A shows human and mouse CD19 expression by peritoneal cavity CD5+B220+ B1a and CD5−B220$^{hi}$ B2 (conventional) B cells. FIG. 4B shows depletion of peritoneal cavity B220+ cells from TG-1+/− mice treated with CD19 (HB12a, HB12b, and FMC63 at 250 µg; B4 and HD237 at 50 µg) antibodies or control antibody (250 µg). FIG. 4C shows representative depletion of CD5+B220+ B1a and CD5−B220$^{hi}$ B2 B cells seven days following anti-CD19 or control antibody treatment of hCD19TG mice.

FIG. 5A depicts the nucleotide (SEQ ID NO:1) and predicted amino acid (SEQ ID NO:2) sequences for heavy chain $V_H$-D-$J_H$ junctional sequences of the HB12a anti-CD19 antibody. FIG. 5B depicts the nucleotide (SEQ ID NO:3) and predicted amino acid (SEQ ID NO:4) sequences for heavy chain $V_H$-D-$J_H$ junctional sequences of the HB12b anti-CD19 antibody.

FIG. 6A depicts the nucleotide (SEQ ID NO:15) and predicted amino acid (SEQ ID NO:16) sequences for light chain sequences of the HB12a anti-CD19 antibody. FIG. 6B depicts the nucleotide (SEQ ID NO:17) and predicted amino acid (SEQ ID NO:18) sequences for light chain sequences of the HB12b anti-CD19 antibody.

FIGS. 7A-7B depict the amino acid sequence alignment of published mouse anti-(human) CD19 antibodies. FIG. 7A shows a sequence alignment for heavy chain $V_H$-D-$J_H$ junctional sequences including a consensus sequence (SEQ ID NO:5), HB12a (SEQ ID NO:2), 4G7 (SEQ ID NO:6), HB12b (SEQ ID NO:4), HD37 (SEQ ID NO:7), B43 (SEQ ID NO:8), and FMC63 (SEQ ID NO:9). FIG. 7B shows light chain Vκ amino acid sequence analysis of anti-CD19 antibodies. Consensus sequence (SEQ ID NO:10), HB12a (SEQ ID NO:16), HB12b (SEQ ID NO:18), HD37 (SEQ ID NO:11), B43 (SEQ ID NO:12), FMC63 (SEQ ID NO:13), and 4G7 (SEQ ID NO:14) are aligned.

Figure 8A:
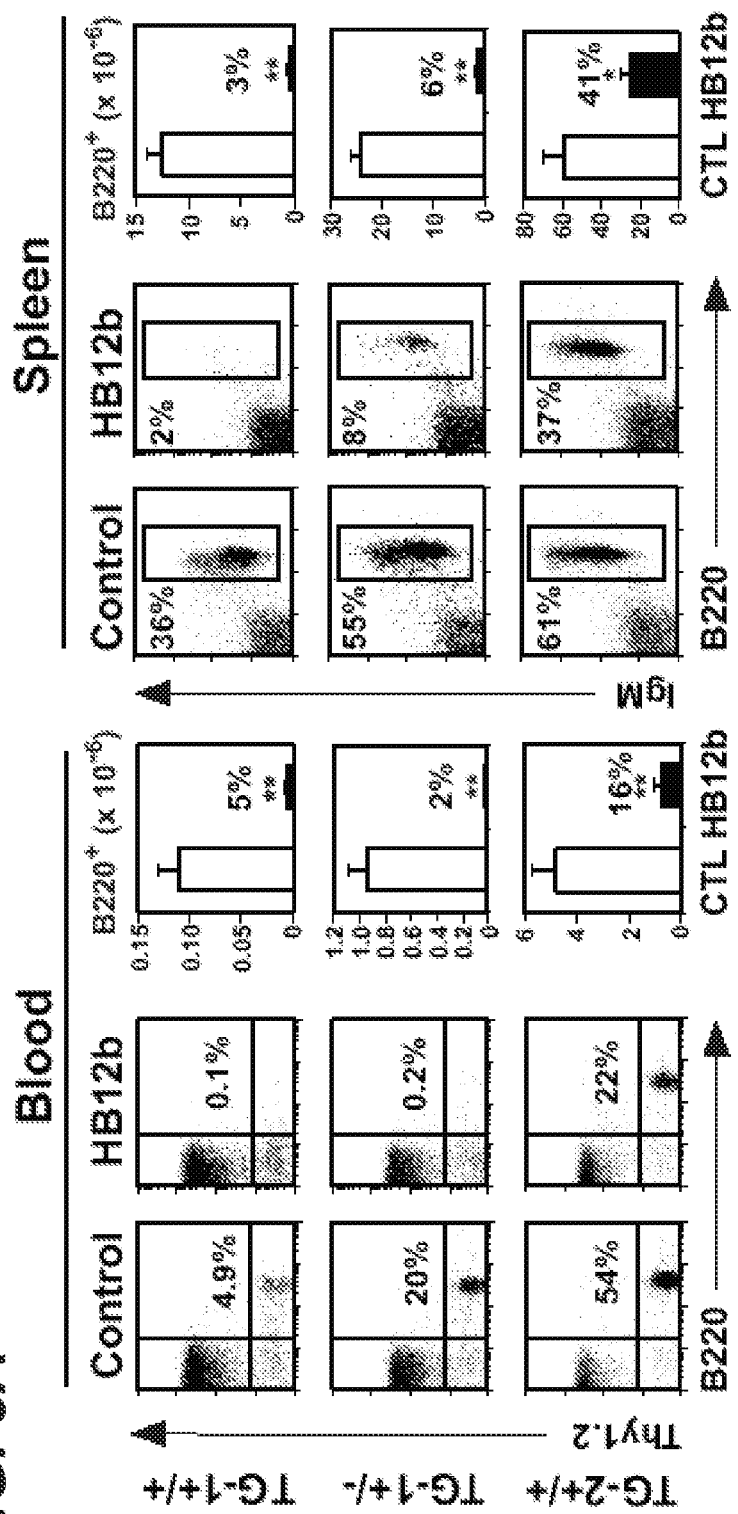
Figure 8B:
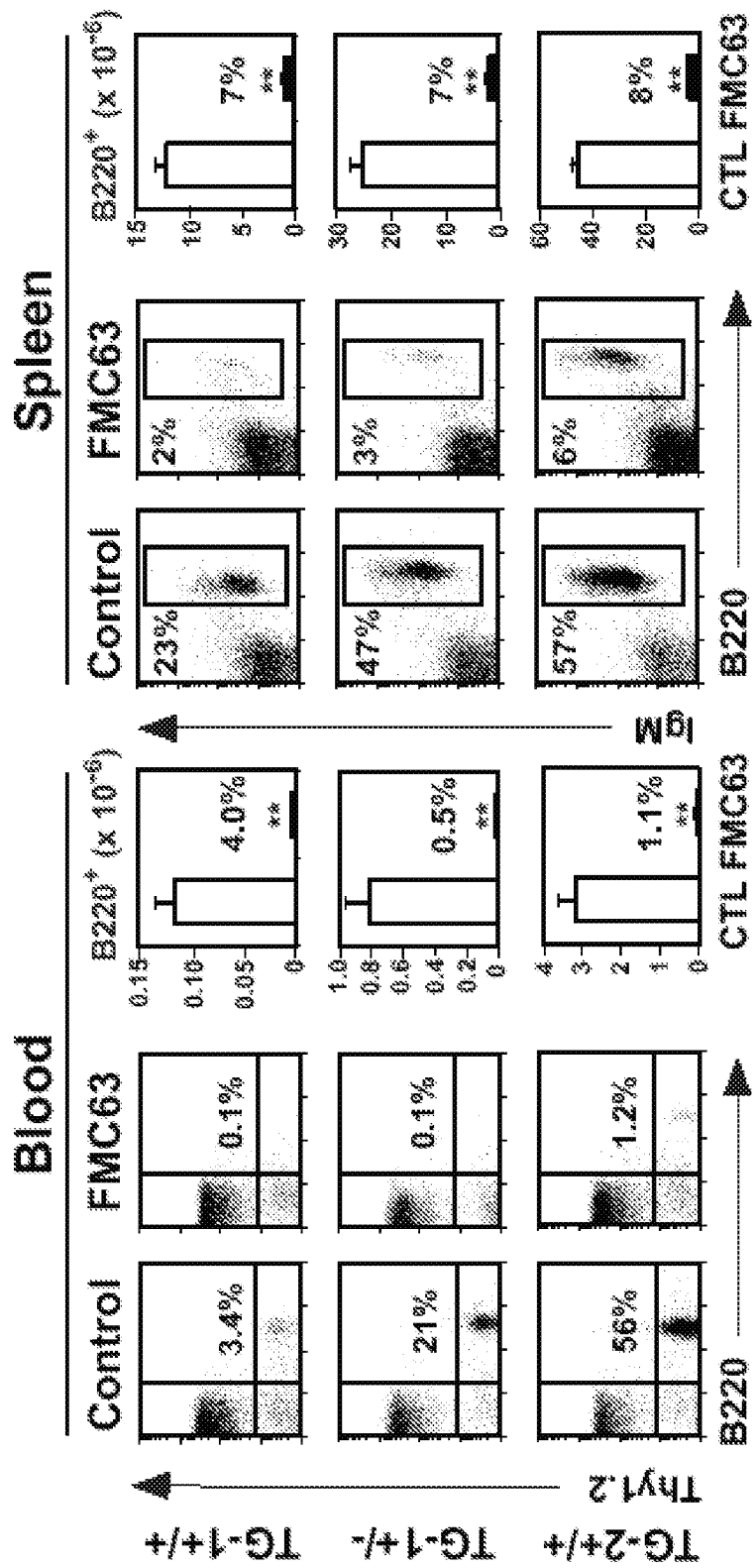
Figure 8D:
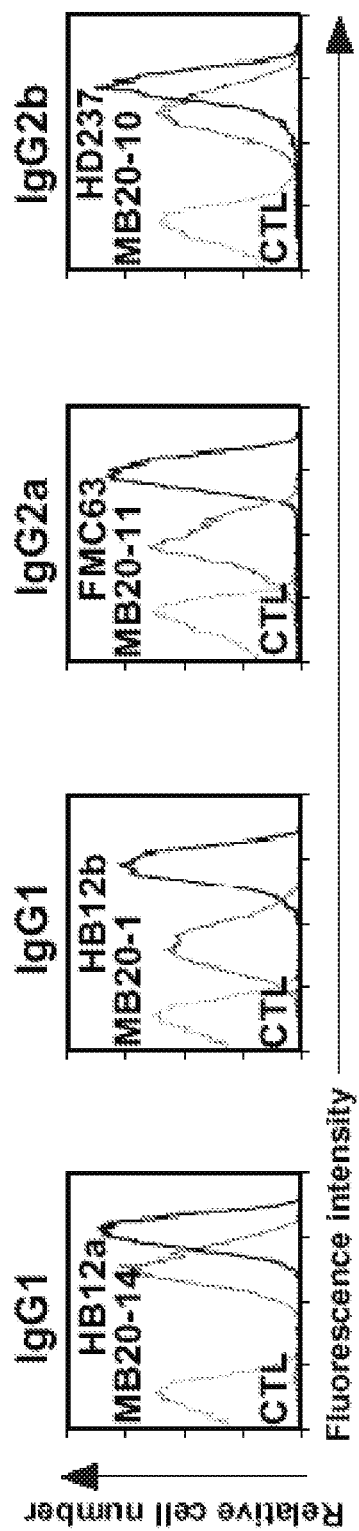

FIGS. 8A-8C demonstrate that CD19 density influences the efficiency of B cell depletion by anti-CD19 antibodies in vivo. Representative blood and spleen B cell depletion in hCD19TG mice are shown following HB12b (FIG. 8A) or FMC63 (FIG. 8B) antibody treatment (seven days, 250 µg/mouse). FIG. 8C shows the relative anti-CD19 antibody-binding densities on blood B220+ B cells from TG-1+/− mice. FIG. 8D shows the relative anti-CD19 antibody-binding densities on spleen B220+ B cells from hCD19TG-1+/− mice.

Figure 9B:
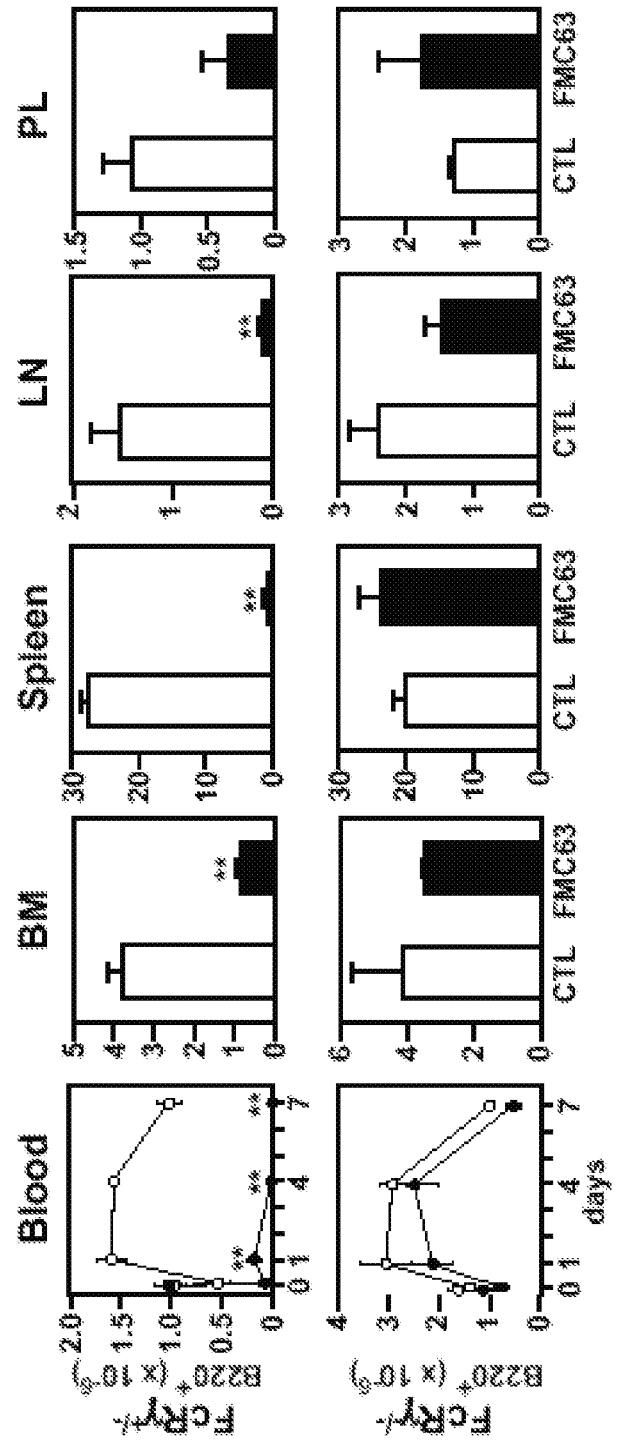
Figure 9D:
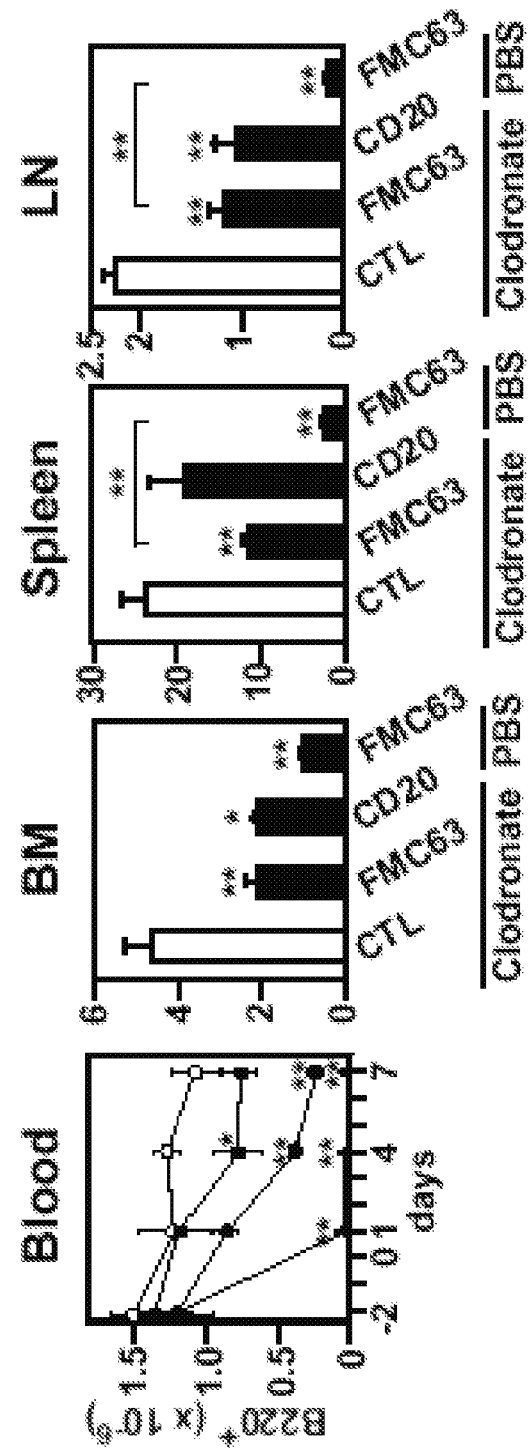

FIGS. 9A-9D demonstrate B cell depletion following anti-CD19 antibody treatment is FcRγ- and monocyte-dependent. FIG. 9A Representative blood and spleen B cell depletion 7 days after CD19 or isotype-control antibody treatment of hCD19 TG-1+/− FcRγ+/− or TG-1+/− FcRγ−/− littermates. FIG. 9B Blood and tissue B cell depletion seven days after antibody treatment of FcRγ−/− littermates on day zero. FIG. 9C Representative B cell numbers in monocyte-depleted hCD19TG-1+/− mice. FIG. 9D Blood and tissue B cell depletion seven days after antibody treatment.

Figure 10A:
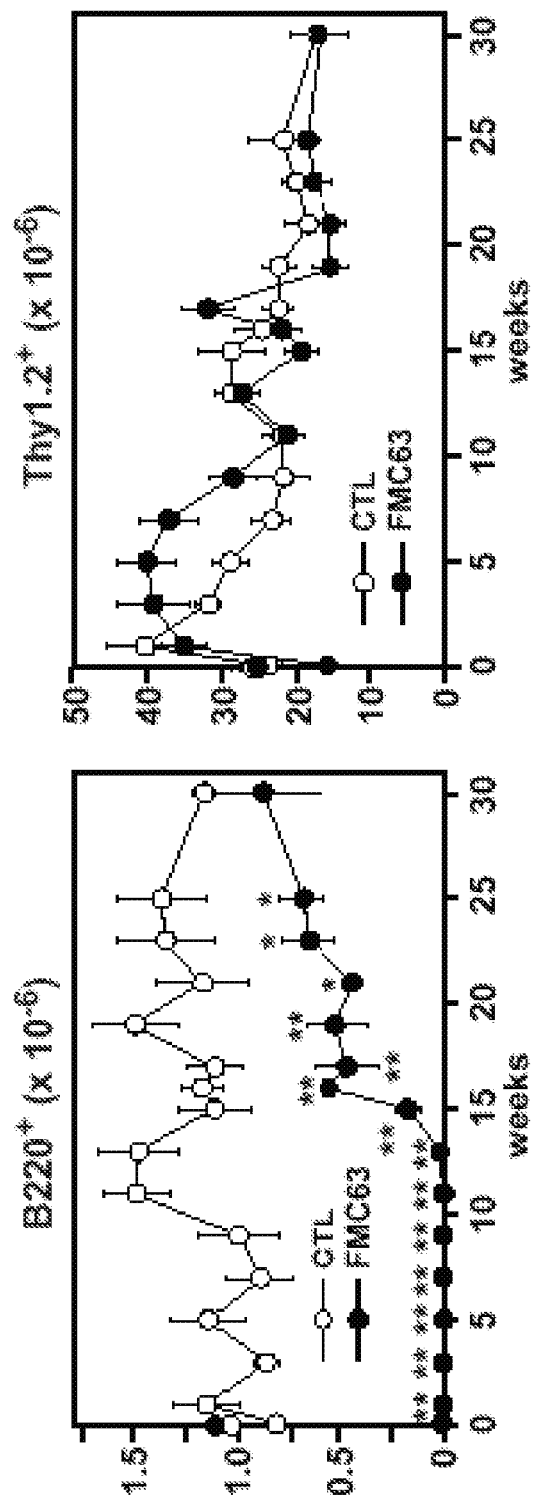
Figure 10B:
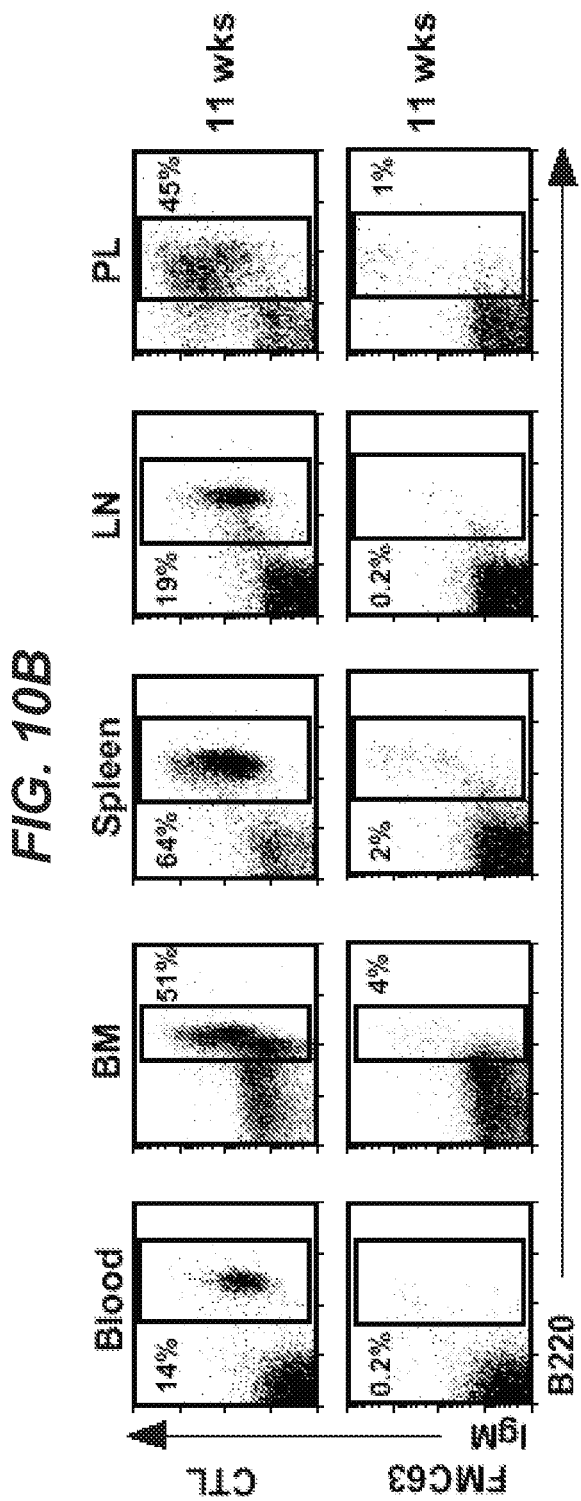
Figure 10D:
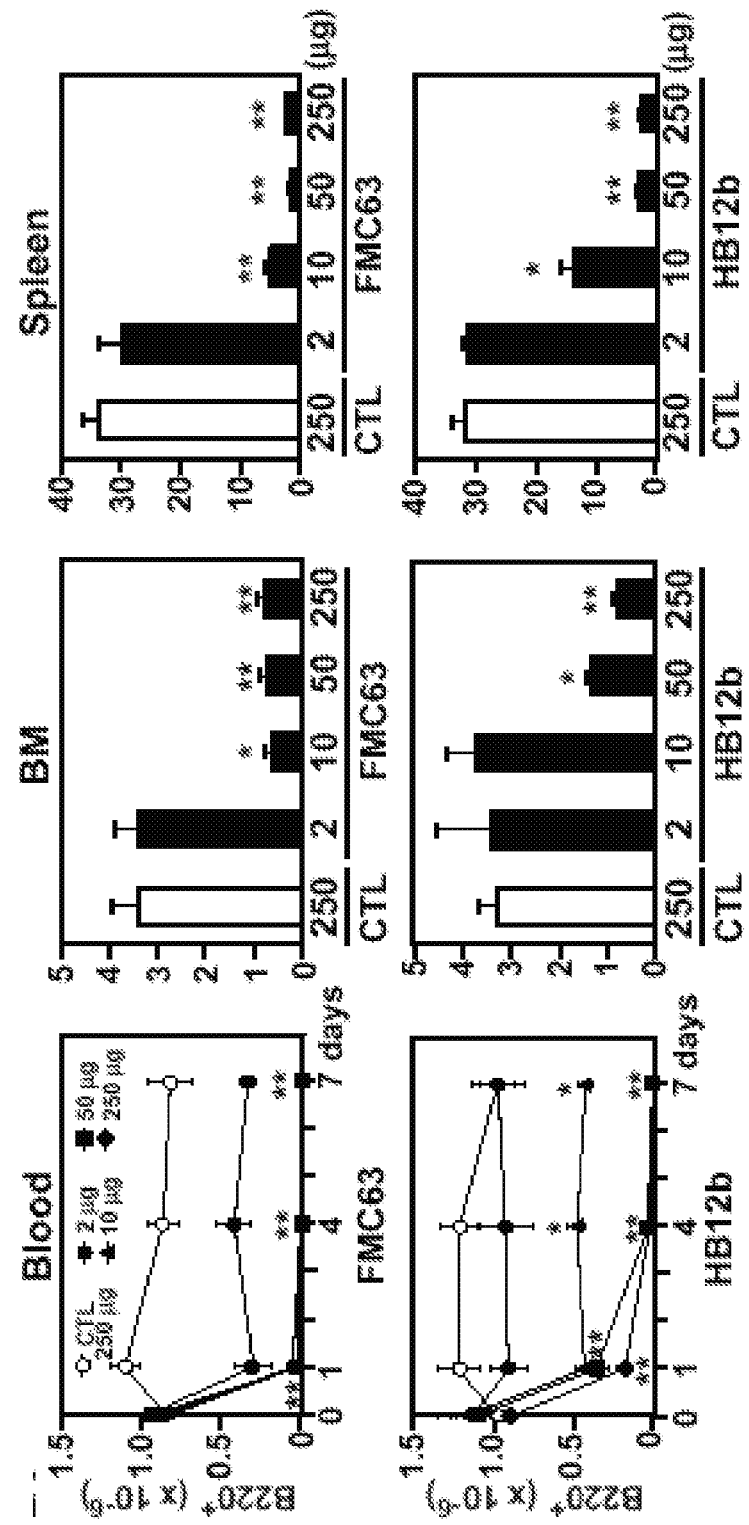

FIGS. 10A-10D demonstrate duration and dose response of B cell depletion following anti-CD19 antibody treatment. FIG. 10A shows numbers of blood B220+ B cells and Thy-1+ T cells following FMC63 or isotype-control antibody treatment of TG-1+/− mice on day zero. FIGS. 10B-C show representative tissue B cell depletion in mice shown in FIG. 10A at 11, 16, and 30 weeks following antibody treatment. FIG. 10D shows anti-CD19 antibody dose responses for blood, bone marrow, and spleen B cell depletion.

FIGS. 11A-11C demonstrate that CD19 is not internalized following antibody binding in vivo. Cell surface CD19 expression and B cell clearance in TG-1+/− mice treated with HB12a (FIG. 11A), HB12b (FIG. 11B), FMC63 (FIG. 11C) or isotype-matched control antibody (250 µg) in vivo.

Figure 12B:
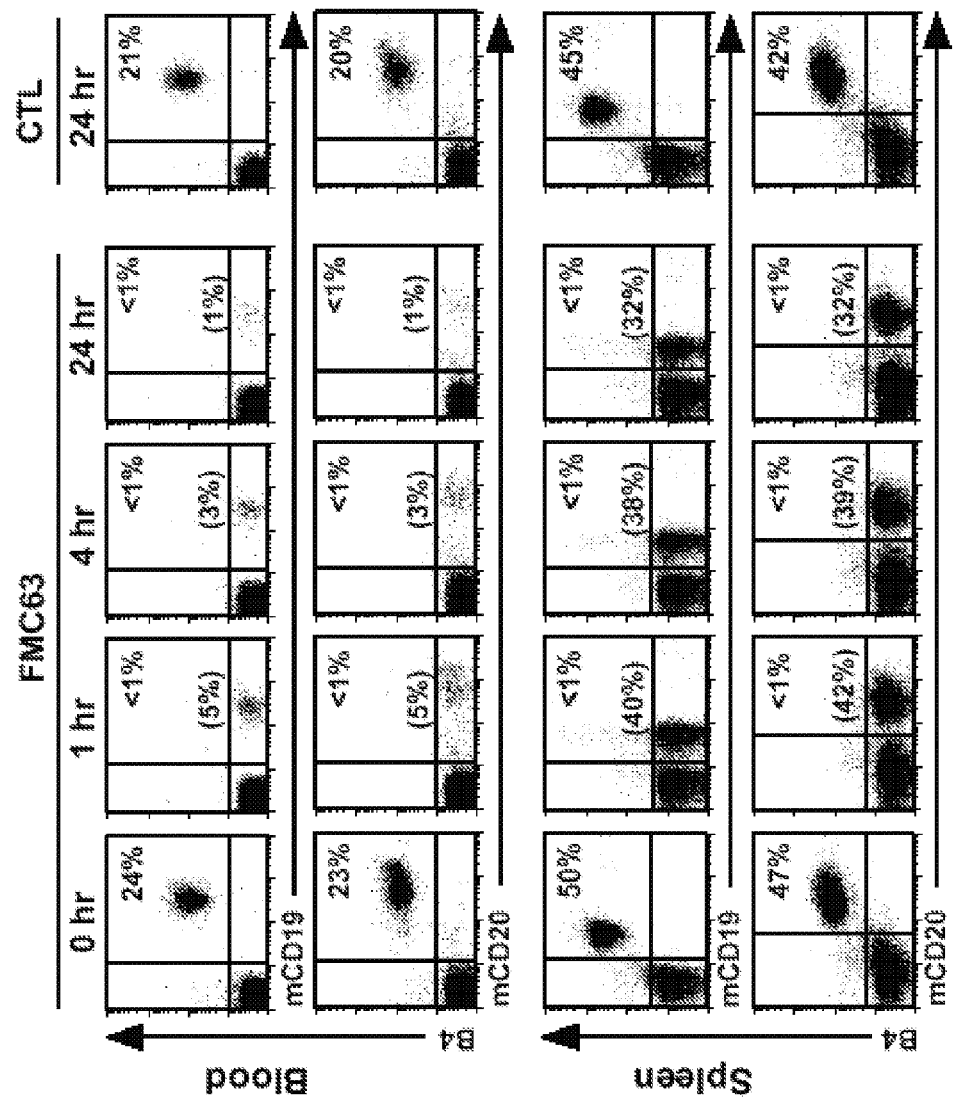

FIGS. 12A-12C demonstrate CD19 saturation following anti-CD19 antibody binding in vivo. FIG. 12A shows B cell clearance in TG-1+/− mice treated with FMC63 or isotype-matched control antibody (250 µg) in vivo. FIG. 12B shows FMC63 antibody treatment (250 µg) saturates antibody-binding sites on hCD19 within 1 hour of administration. FIG. 12C shows HB12b anti-CD19 antibody treatment (250 µg) saturates antibody-binding sites on hCD19 within 1 hour of administration as assessed in FIG. 12B.

Figure 13A:
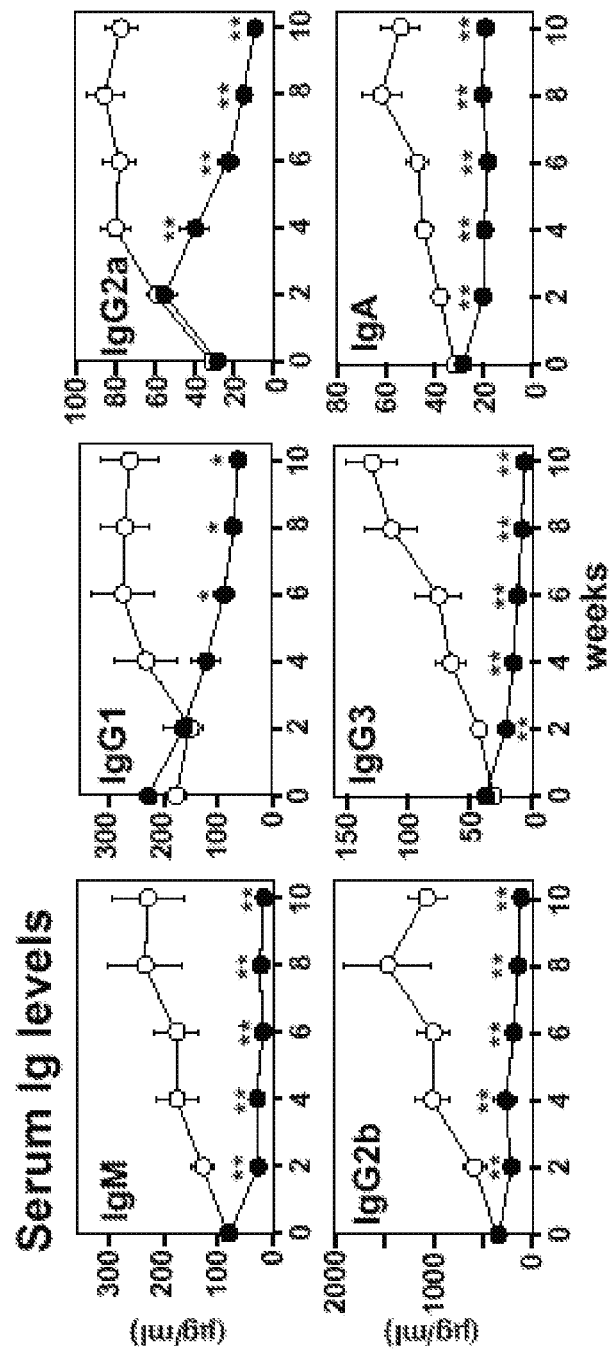
Figure 13B:
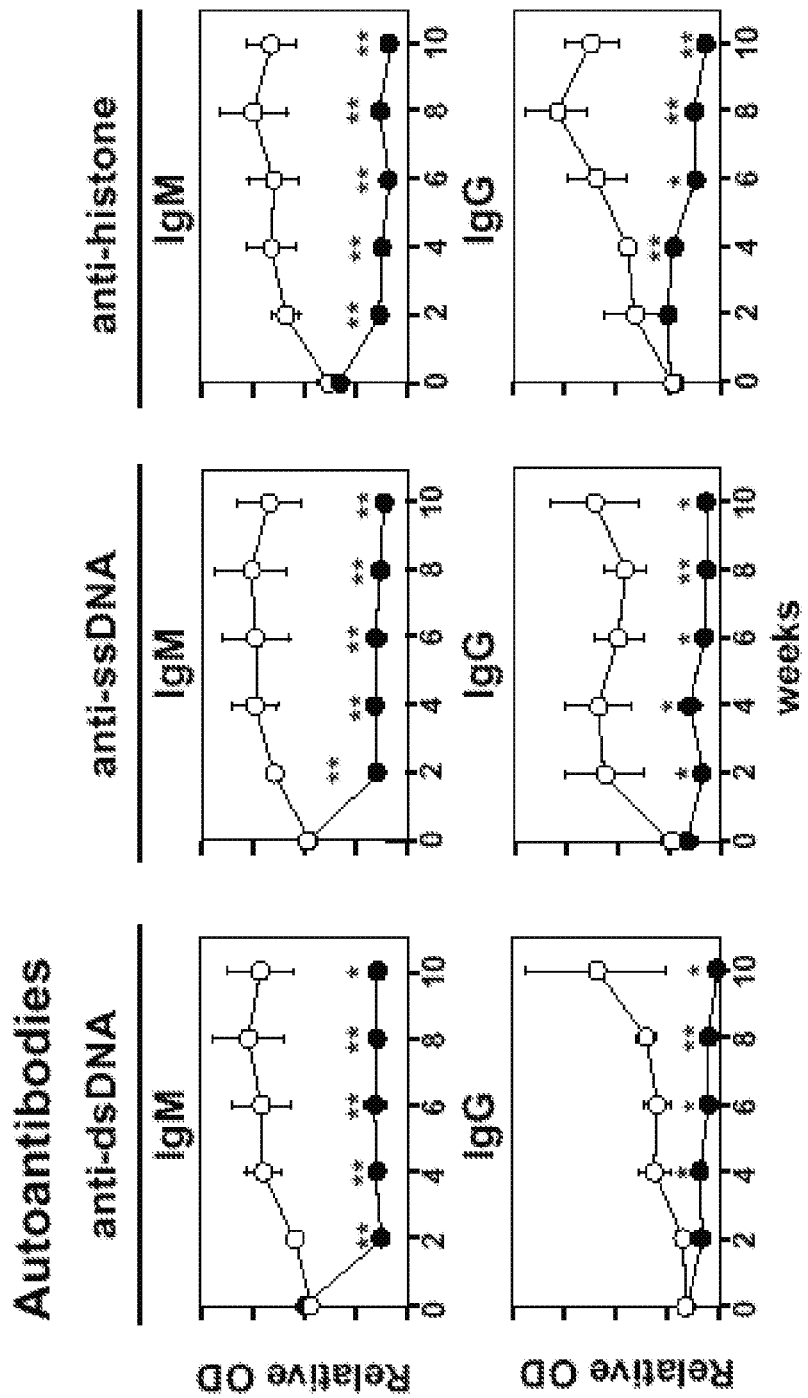

FIGS. 13A-13B demonstrate anti-CD19 antibody treatment reduces serum immunoglobulin and autoantibody levels in TG-1+/− mice. FIG. 13A depicts serum immunoglobulin levels and FIG. 13B anti-dsDNA, anti-ssDNA and anti-histone autoantibody levels after anti-CD19 antibody treatment.

Figure 14A:
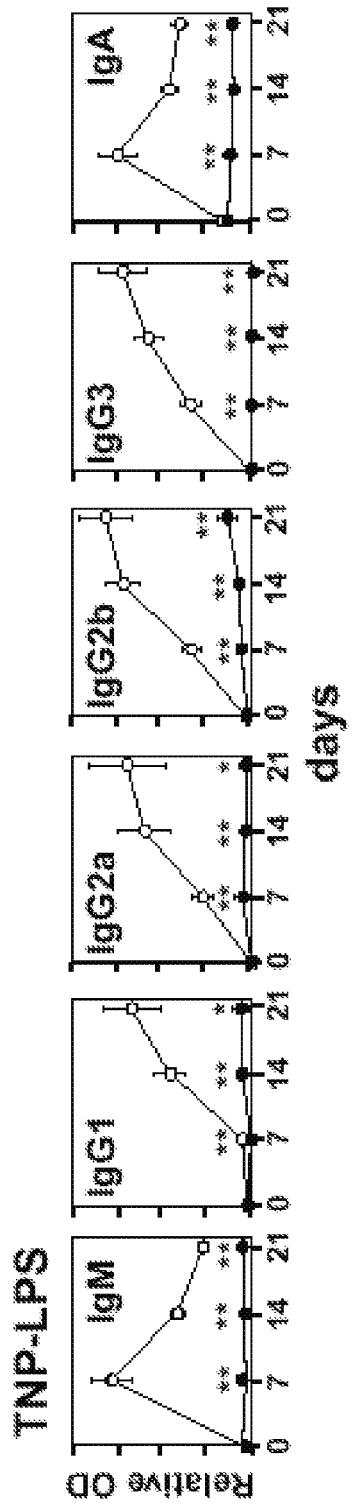
Figure 14B:
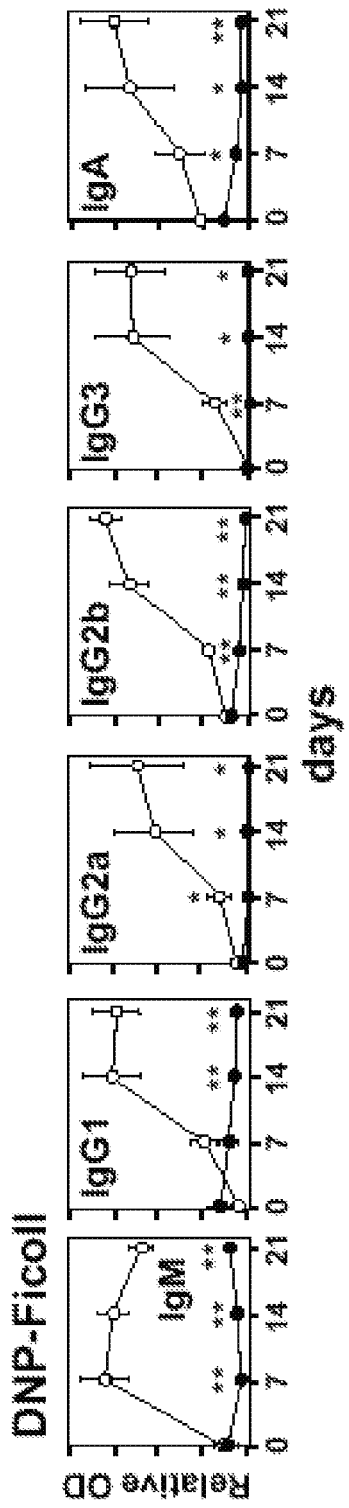

FIGS. 14A-14B demonstrate anti-CD19 antibody treatment blocks humoral immune responses in TG-1+/− mice. Antibody-treated mice were immunized with FIG. 14A TNP-LPS, FIG. 14B DNP-Ficoll and FIGS. 14C-14D DNP-KLH. Littermates were treated with FMC63 (closed circles) or control (open circles) antibody (250 µg) either (A-C) 7 days before or (D) 14 days after primary immunizations on day 0.

Figure 15:
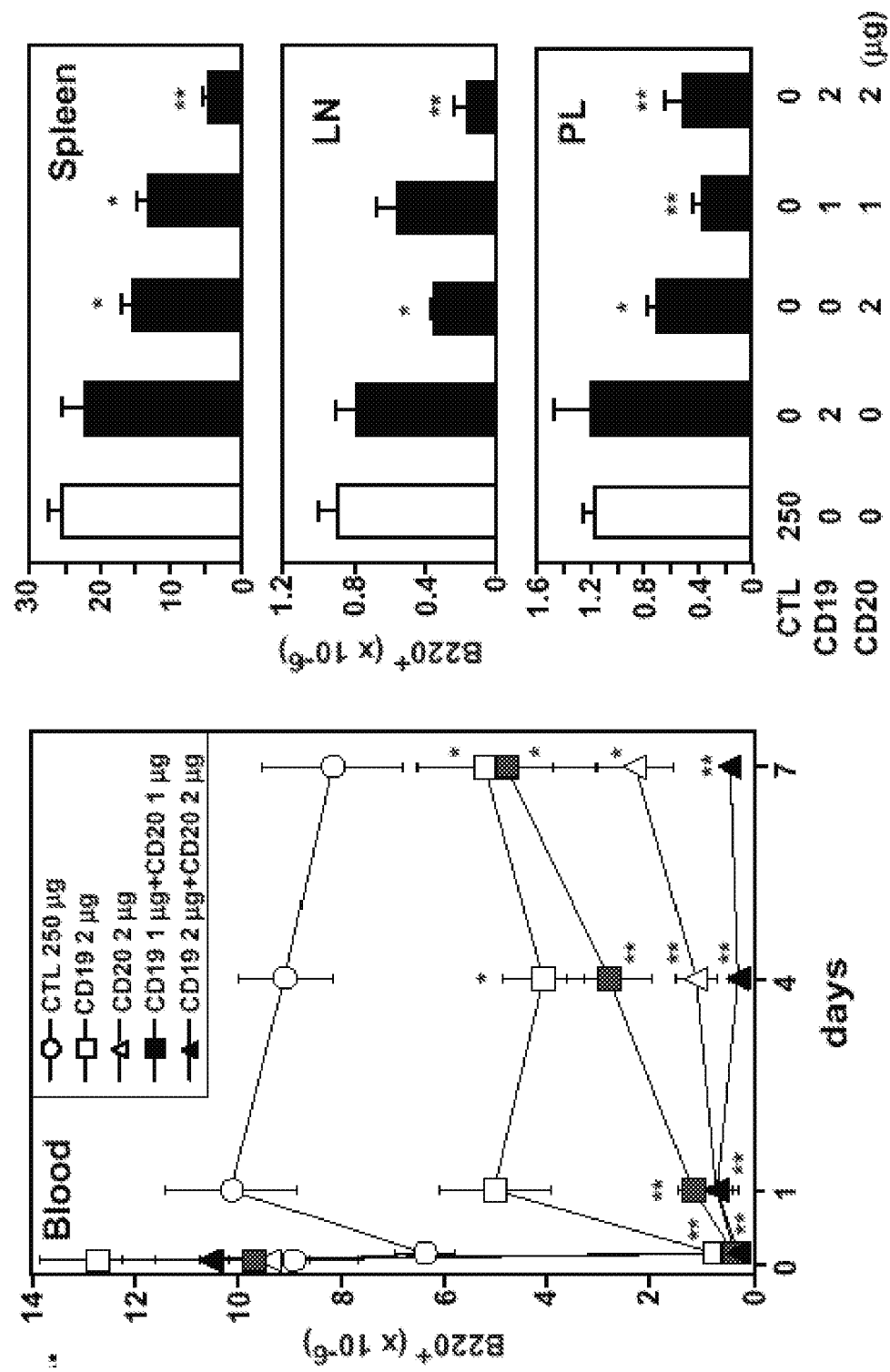

FIG. 15 demonstrates that simultaneous anti-CD19 and anti-CD20 antibody treatments are additive.

Figure 16:
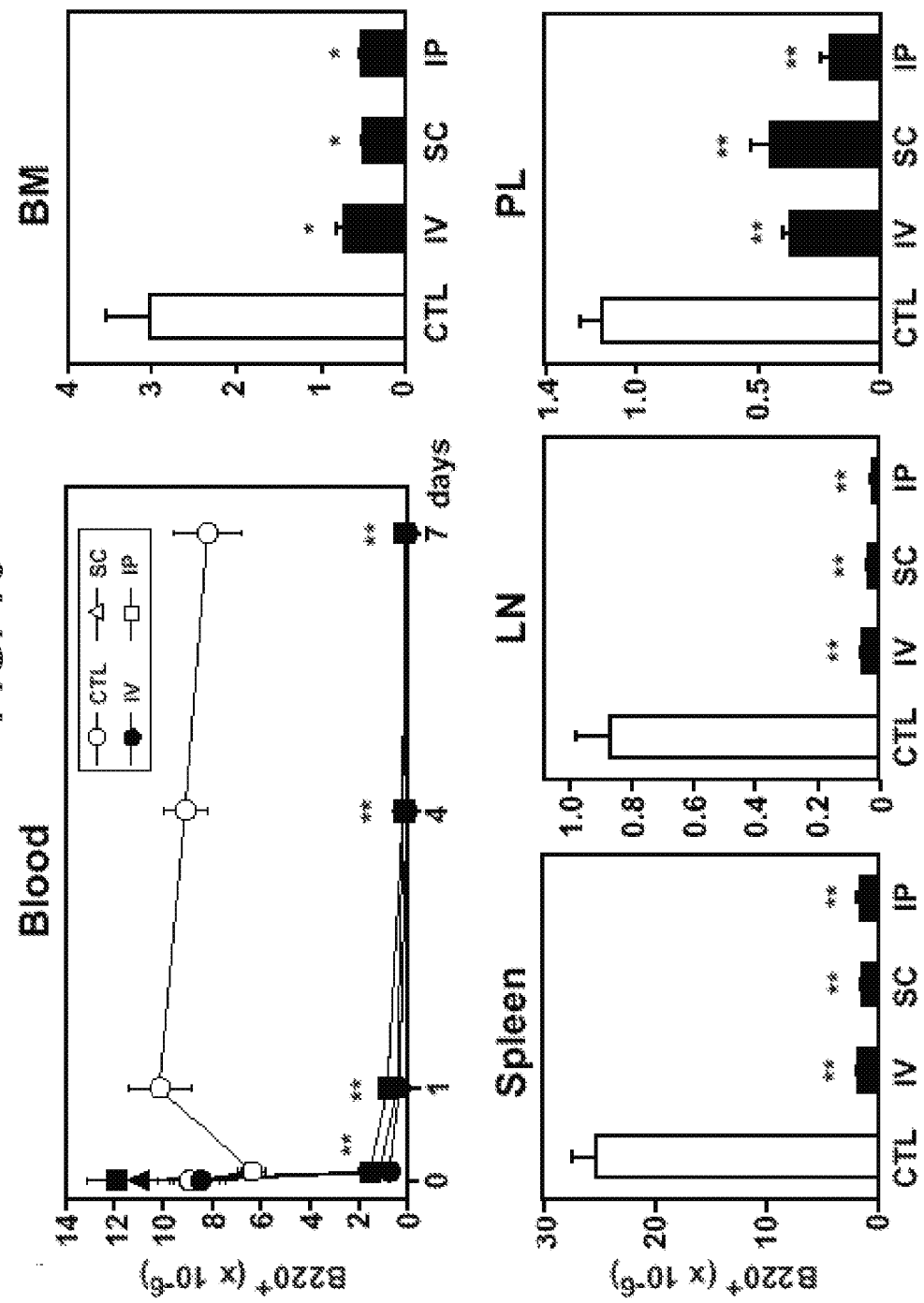

FIG. 16 demonstrates that subcutaneous (s.c.), intraperitoneal (i.p.) and i.v. administration of anti-CD19 antibody effectively depletes circulating and tissue B cells in vivo.

FIG. 17A-17B. Anti-CD19 antibody treatment prevents hCD19+ lymphoma growth in vivo (FIG. 17A) and increases survival rate (FIG. 17B).

5. DETAILED DESCRIPTION OF THE INVENTION

The present invention relates to pharmaceutical compositions comprising human, humanized, or chimeric anti-CD19 antibodies of the IgG1 or IgG3 human isotype. The present invention also relates to pharmaceutical compositions comprising human or humanized anti-CD19 antibodies of the IgG2 or IgG4 human isotype that preferably mediate human ADCC. In certain embodiments, the present invention also relates to pharmaceutical compositions comprising monoclonal human, humanized, or chimerized anti-CD19 antibodies that can be produced by means known in the art.

In certain embodiments, the invention relates to immunotherapeutic compositions and methods for the treatment of B cell diseases and disorders in human subjects, such as, but not limited to, B cell malignancies, using therapeutic antibodies that bind to the CD19 antigen and preferably mediate human ADCC. Therapeutic formulations and regimens are described for treating human subjects diagnosed with B cell malignancies that derive from B cells and their precursors, including but not limited to, acute lymphoblastic leukemias (ALL), Hodgkin's lymphomas, non-Hodgkin's lymphomas, B cell chronic lymphocytic leukemias (CLL), multiple myeloma, follicular lymphoma, mantle cell lymphoma, pro-lymphocytic leukemias, hairy cell leukemias, common acute lymphocytic leukemias and some Null-acute lymphoblastic leukemias In certain embodiments, the invention relates to immunotherapeutic compositions and methods for the treatment of autoimmune diseases and disorders in human subjects using therapeutic antibodies that bind to the CD19 antigen and preferably mediate human ADCC. Therapeutic formulations and regimens are described for treating human subjects diagnosed with autoimmune diseases or disorders, including but not limited to, rheumatoid arthritis, SLE, ITP, pemphigus-related disorders, diabetes, and scleroderma.

In certain embodiments, the invention relates to immunotherapeutic compositions and methods for the treatment and prevention of GVHD, graft rejection, and post-transplant lymphocyte proliferative disorder in human transplant recipients using therapeutic antibodies that bind to the CD19 antigen and preferably mediate human ADCC. In particular embodiments, the anti-CD19 antibodies of the invention mediate ADCC, complement dependent cellular cytotoxicity, or apoptosis. The compositions and methods of the invention have the advantage of specifically targeting B cells, leaving intact other functional elements and cell types of the immune system. Accordingly, in one aspect the invention provides compositions and methods for the treatment and prevention of GVHD, graft rejection, and post-transplantation lymphoproliferative disorder which are associated with fewer and/or less severe complications than less targeted therapeutic agents and regimens. In one embodiment, the compositions and methods of the invention are used in combination with lower doses of traditional therapeutic agents than would be possible in the absence of the methods and compositions of the invention. In another embodiment, the compositions and methods of the invention obviate the need for a more severe form of therapy, such as radiation therapy, high-dose chemotherapy, or splenectomy.

The compositions and methods of the invention also have the advantage of targeting a wider population of B cells than other B-cell directed immunotherapies. For example, the anti-CD19 antibodies of the present invention are effective to target bone marrow B cells, circulating B cells, and mature, antibody-secreting B cells. Accordingly, the methods and compositions of the invention are effective to reduce or deplete circulating B cells as well as circulating immunoglobulin (see, for example, FIGS. 13 and 14).

In certain embodiments, the anti-CD19 antibodies and compositions of the invention may be administered to a transplant recipient prior to or following transplantation, alone or in combination with other therapeutic agents or regimens for the treatment or prevention of GVHD and graft rejection. For example, the anti-CD19 antibodies and compositions of the invention may be used to deplete alloantibodies from a transplant recipient prior to or following transplantation of an allogeneic graft. The anti-CD19 antibodies and compositions of the invention may also be used to deplete antibody producing cells from the graft ex vivo, prior to transplantation, or in the donor, as prophylaxis against GVHD and graft rejection.

The transplant recipient in need of prophylaxis or treatment for humoral rejection is identified according to the knowledge and skill in the art. For example, a transplant recipient in need of prophylaxis against graft rejection may be identified as a patient or patient population having detectable circulating anti-HLA alloantibodies prior to transplantation. In another example, the patient or patient population is identified as having panel reactive alloantibodies prior to transplantation. The presence of detectable circulating anti-HLA alloantibodies in a transplant recipient post-transplantation can also be used to identify the patient or patient population in need of treatment for humoral rejection according to the invention. The patient or patient population in need of treatment for humoral rejection can also be identified according to other clinical criteria which indicate that a transplant recipient is at risk for developing a humoral rejection or has already developed a humoral rejection. For example, a transplant recipient in need of treatment for humoral rejection may be identified as a patient or patient population in an early stage of humoral rejection, such as a latent humoral response characterized by circulating anti-donor alloantibodies. An early stage of humoral rejection may also be a silent reaction characterized by circulating anti-donor alloantibodies and C4d deposition, or a subclinical rejection characterized by circulating anti-donor alloantibodies, C4d deposition, and tissue pathology. In later stages, the recipient is identified as a patient or patient population presenting with clinical indications of humoral rejection characterized according to the knowledge and skill in the art, for example, by circulating anti-donor alloantibodies, C4d deposition, tissue pathology, and graft dysfunction.

The present invention provides compositions and methods effective to reduce the incidence, severity, or duration of GVHD, a rejection episode, or post-transplant lymphoproliferative disorder. In certain embodiments, the compositions and methods of the invention are effective to attenuate the host response to ischemic reperfusion injury of a solid tissue or organ graft. In a preferred embodiment, the anti-CD19 antibody compositions and methods of the invention are effective to prolong survival of a graft in a transplant recipient.

Therapeutic formulations and regimens are described for treating or preventing GVHD, humoral rejection, and post-transplant lymphoproliferative disorder. The present invention encompasses grafts that are autologous, allogeneic, or xenogeneic to the recipient. The types of grafts encompassed by the invention include tissue and organ grafts, including, but not limited to, bone marrow grafts, peripheral blood stem cell grafts, skin grafts, arterial and venous grafts, pancreatic islet cell grafts, and transplants of the kidney, liver, pancreas, thyroid, and heart. The terms "graft" and "transplant" are used interchangeably herein. In one embodiment, the autologous graft is a bone marrow graft, an arterial graft, a venous graft, or a skin graft. In one embodiment, the allograft is a bone marrow graft, a corneal graft, a kidney transplant, a heart transplant, a liver transplant, a lung transplant, a pancreatic transplant, a pancreatic islet cell transplant, or a combined transplant of a kidney and pancreas. In one embodiment, the graft is a xenograft, preferably wherein the donor is a pig. The compositions and methods of the present invention may also be used to suppress a deleterious immune response to a non-biological graft or implant, including, but not limited to, an artificial joint, a stent, or a pacemaker device.

The anti-CD19 antibodies, compositions and methods of the invention can be used to treat or prevent GVHD, humoral rejection, or post-transplant lymphoproliferative disorder without regard to the particular indications initially giving rise to the need for the transplant or to the particular type of tissue transplanted. However, the indications which gave rise to the need for a transplant and the type of tissue transplanted may provide the basis for a comprehensive therapeutic regimen for the treatment or prevention of GVHD, graft rejection, and post-transplant lymphoproliferative disorder, which comprehensive regimen comprises the anti-CD19 antibody compositions and methods of the invention. A more detailed description of diagnostic criteria and therapeutic regimens is provided below.

5.1. Generation of Anti-CD19 Antibodies

5.1.1. Polyclonal Anti-CD19 Antibodies

Polyclonal antibodies are preferably raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobertzoyl sulfosuccinimide ester (conjugation through cysteine residues), N-hydroxysuccinimide (through lysine residues), glutaraldehyde, succunic anhydride, $SOCl_2$.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's incomplete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

5.1.2. Monoclonal Anti-CD19 Antibodies

The monoclonal anti-CD19 antibodies of the invention exhibit binding specificity to human CD19 antigen and can preferably mediate human ADCC. These antibodies can be generated using a wide variety of techniques known in the art including the use of hybridoma, recombinant, and phage display technologies, or a combination thereof. Antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the human CD19 antigen. For example, the monoclonal antibodies to be used in accordance with the present invention may be made by the hybridoma method first described by Kohler et al., *Nature*, 256:495 (1975), which can be used to generate murine antibodies (or antibodies derived from other nonhuman mammals, e.g., rat, goat, sheep, cows, camels, etc.), or human antibodies derived from transgenic animals (see, U.S. Pat. Nos. 6,075,181, 6,114,598, 6,150,584, and 6,657,103). Alternatively, the monoclonal antibodies can be made by recombinant DNA methods (see, e.g., U.S. Pat. No. 4,816,567) and include chimeric and humanized antibodies. The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

An engineered anti-CD19 antibody can be produced by any means known in the art, including, but not limited to, those techniques described below and improvements to those techniques. Large-scale high-yield production typically involves culturing a host cell that produces the engineered anti-CD19 antibody and recovering the anti-CD19 antibody from the host cell culture.

5.1.3. Hybridoma Techniques

Monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in *Monoclonal Antibodies and T Cell Hybridomas*, 563-681 (Elsevier, NY, 1981) (said references incorporated by reference in their entireties). For example, in the hybridoma method, a mouse or other appropriate host animal, such as a hamster or macaque monkey, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., NY, 1987)).

Culture medium in which hybridoma cells are growing is assayed for production of monoclonal antibodies directed against the human CD19 antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

5.1.4. Recombinant DNA Techniques

DNA encoding the anti-CD19 antibodies of the invention is readily isolated and sequenced using conventional procedures (e.g., by using oligonucleotide probes that are capable of binding specifically to genes encoding the heavy and light chains of the anti-CD19 antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of anti-CD19 antibodies in the recombinant host cells.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen-binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods*, 182:41-50; Ames et al., 1995, *J. Immunol. Methods*, 184:177-186; Kettleborough et al., 1994, *Eur. J. Immunol.*, 24:952-958; Persic et al., 1997, *Gene*, 187:9-18; Burton et al., 1994, *Advances in Immunology*, 57:191-280; International Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108; each of which is incorporated herein by reference in its entirety.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT Publication No. WO 92/22324; Mullinax et al., 1992, *BioTechniques*, 12(6):864-869; Sawai et al., 1995, *AJRI*, 34:26-34; and Better et al., 1988, *Science*, 240:1041-1043 (said references incorporated by reference in their entireties).

In a further embodiment, antibodies may be isolated from antibody phage libraries generated using the techniques described in McCafferty et al., *Nature*, 348:552-554 (1990). Clackson et al., *Nature*, 352:624-628 (1991). Marks et al., *J. Mol. Biol.*, 222:581-597 (1991) describe the isolation of murine and human antibodies, respectively, using phage libraries. Chain shuffling can be used in the production of high affinity (nM range) human antibodies (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of anti-CD19 antibodies.

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones. Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_L$ constant region, e.g., human kappa or lambda constant regions. Preferably, the vectors for expressing the $V_H$ or $V_L$ domains comprise an EF-1α promoter, a secretion signal, a cloning site for the variable domain, constant domains, and a selection marker such as neomycin. The $V_H$ and $V_L$ domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA*, 81:6851 (1984)), or by covalently joining to the immunoglobulin coding sequence all or part of the coding sequence for a non-immunoglobulin polypeptide.

5.1.5. Chimeric Antibodies

The anti-CD19 antibodies herein specifically include chimeric antibodies (immunoglobulins) in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

5.1.6. Humanized Antibodies

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, *Molecular Immunology*, 28(4/5): 489-498; Studnicka et al., 1994, *Protein Engineering*, 7(6): 805-814; and Roguska et al., 1994, *PNAS*, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., *J. Immunol.*, 169:1119-25 (2002), Caldas et al., *Protein Eng.*, 13(5):353-60 (2000), Morea et al., *Methods*, 20(3):267-79 (2000), Baca et al., *J. Biol. Chem.*, 272(16):10678-84 (1997), Roguska et al., *Protein Eng.*, 9(10):895-904 (1996), Couto et al., *Cancer Res.*, 55 (23 Supp):5973s-5977s (1995), Couto et al., *Cancer Res.*, 55(8):1717-22 (1995), Sandhu J S, *Gene*, 150(2):409-10 (1994), and Pedersen et al., *J. Mol. Biol.*, 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature*, 332:323, which are incorporated herein by reference in their entireties.)

A humanized anti-CD19 antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Humanization of anti-CD19 antibodies can also be achieved by veneering or resurfacing (EP 592,106; EP 519,596; Padlan, 1991, *Molecular Immunology*, 28(4/5):489-498; Studnicka et al., *Protein Engineering*, 7(6):805-814 (1994); and Roguska et al., *PNAS*, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987), the contents of which are incorporated herein by reference herein in their entirety). Another method uses a particular framework derived from the consensus sequence of all human antibodies of a particular subgroup of light or heavy chains. The same framework may be used for several different humanized anti-CD19 antibodies (Carter et al., *Proc. Natl. Acad. Sci. USA*, 89:4285 (1992); Presta et al., *J. Immunol.*, 151:2623 (1993), the contents of which are incorporated herein by reference herein in their entirety).

Anti-CD19 antibodies can be humanized with retention of high affinity for CD19 and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind CD19. In this way, FR residues can be selected and combined from the recipient and import sequences so that the desired antibody characteristic, such as increased affinity for CD19, is achieved. In general, the CDR residues are directly and most substantially involved in influencing antigen binding.

A "humanized" antibody retains a similar antigenic specificity as the original antibody, i.e., in the present invention, the ability to bind human CD19 antigen. However, using certain methods of humanization, the affinity and/or specificity of binding of the antibody for human CD19 antigen may be increased using methods of "directed evolution," as described by Wu et al., *J. Mol. Biol.*, 294:151 (1999), the contents of which are incorporated herein by reference herein in their entirety.

5.1.7. Human Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods described above using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human anti-CD19 antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-CD19 antibodies directed against the human CD19 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (*Int. Rev. Immunol.*, 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413, 923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA*, 90:2551 (1993); Jakobovits et al., *Nature*, 362:255-258 (1993); Bruggermann et al., *Year in Immunol.*, 7:33 (1993); and Duchosal et al., *Nature*, 355:258 (1992).

Human antibodies can also be derived from phage-display libraries (Hoogenboom et al., *J. Mol. Biol.*, 227:381 (1991); Marks et al., *J. Mol. Biol.*, 222:581-597 (1991); Vaughan et al., *Nature Biotech.*, 14:309 (1996)). Phage display technology (McCafferty et al., *Nature*, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.*, 222:581-597 (1991), or Griffith et al., *EMBO J.*, 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (*Methods Enzymol.*, 121:140-167 (1986)).

5.1.8. Altered/Mutant Antibodies

The anti-CD19 antibodies of the compositions and methods of the invention can be mutant antibodies. As used herein, "antibody mutant" or "altered antibody" refers to an amino acid sequence variant of an anti-CD19 antibody wherein one or more of the amino acid residues of an anti-CD19 antibody have been modified. The modifications to the amino acid sequence of the anti-CD19 antibody, include modifications to the sequence to improve affinity or avidity of the antibody for its antigen, and/or modifications to the Fc portion of the antibody to improve effector function. The modifications may be made to any known anti-CD19 antibodies or anti-CD19 antibodies identified as described herein. Such altered antibodies necessarily have less than 100% sequence identity or similarity with a known anti-CD19 antibody. In a preferred embodiment, the altered antibody will have an amino acid sequence having at least 25%, 35%, 45%, 55%, 65%, or 75% amino acid sequence identity or similarity with the amino acid sequence of either the heavy or light chain variable domain of an anti-CD19 antibody, more preferably at least 80%, more preferably at least 85%, more preferably at least 90%, and most preferably at least 95%. In a preferred embodiment, the altered antibody will have an amino acid sequence having at least 25%, 35%, 45%, 55%, 65%, or 75% amino acid sequence identity or similarity with the amino acid sequence of the heavy chain CDR1, CDR2, or CDR3 of an anti-CD19 antibody, more preferably at least 80%, more preferably at least 85%, more preferably at least 90%, and most preferably at least 95%. In a preferred embodiment, the altered antibody will maintain human CD19 binding capability. In certain embodiments, the anti-CD19 antibody of the invention comprises a heavy chain that is about 10%, 15%, 20%, 25%, 30%, 35%, 40%, 45%, 50%, 55%, 60%, 65%, 70%, 75%, 80%, 85%, 90%, 95% or more identical to an amino acid sequence of SEQ ID NO:2 (FIG. 5A) corresponding to the heavy chain of HB12a. In certain embodiments, the anti-CD19 antibody of the invention comprises a heavy chain that is about 10%, 15%, 20%, 25%, 30%, 35%, 40%, 45%, 50%, 55%, 60%, 65%, 70%, 75%, 80%, 85%, 90%, 95% or more identical to an amino acid sequence of SEQ ID NO:4 (FIG. 5B) corresponding to the heavy chain of HB12b. In certain embodiments, the anti-CD19 antibody of the invention comprises a light chain that is about 10%, 15%, 20%, 25%, 30%, 35%, 40%, 45%, 50%, 55%, 60%, 65%, 70%, 75%, 80%, 85%, 90%, 95% or more identical to an amino acid sequence of SEQ ID NO:16 (FIG. 6A) corresponding to the light chain of HB12a. In certain embodiments, the anti-CD19 antibody of the invention comprises a light chain that is about 10%, 15%, 20%, 25%, 30%, 35%, 40%, 45%, 50%, 55%, 60%, 65%, 70%, 75%, 80%, 85%, 90%, 95% or more identical to an amino acid sequence of SEQ ID NO:18 (FIG. 6B) corresponding to the light chain of HB12b. In a preferred embodiment, the altered antibody will have an amino acid sequence having at least 25%, 35%, 45%, 55%, 65%, or 75% amino acid sequence identity or similarity with the amino acid sequence of light chain CDR1, CDR2, or CDR3 of an anti-CD19 antibody, more preferably at least 80%, more preferably at least 85%, more preferably at least 90%, and most preferably at least 95%. Hybridomas producing HB12a and HB12b anti-CD19 antibodies have been deposited under ATCC deposit nos. PTA-6580 and PTA-6581.

Identity or similarity with respect to this sequence is defined herein as the percentage of amino acid residues in the candidate sequence that are identical (i.e., same residue) or similar (i.e., amino acid residue from the same group based on common side-chain properties, see below) with anti-CD19 antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

"% identity" as known in the art, is a measure of the relationship between two polynucleotides or two polypeptides, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

For example, sequences can be aligned with the software clustalW under Unix which generates a file with an ".aln" extension, this file can then be imported into the Bioedit program (Hall, T. A. 1999, *BioEdit: a user-friendly biological sequence alignment editor and analysis program for Windows 95/98/NT. Nucl. Acids. Symp. Ser.*, 41:95-98) which opens the .aln file. In the Bioedit window, one can choose individual sequences (two at a time) and alignment them. This method allows for comparison of the entire sequence.

Methods for comparing the identity of two or more sequences are well-known in the art.

Thus for instance, programs are available in the Wisconsin Sequence Analysis Package, version 9.1 (Devereux J. et al., *Nucleic Acids Res.*, 12:387-395, 1984, available from Genetics Computer Group, Madison, Wis., USA). The determination of percent identity between two sequences can be accomplished using a mathematical algorithm. For example, the programs BESTFIT and GAP, may be used to determine the % identity between two polynucleotides and the % identity between two polypeptide sequences. BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (*J. Mol. Biol.*, 48:443-354, 1970). GAP is more suited to comparing sequences which are approximately the same length and an alignment is expected over the entire length. Preferably the parameters "Gap Weight" and "Length Weight" used in each program are 50 and 3 for polynucleotides and 12 and 4 for polypeptides, respectively. Preferably % identities and similarities are determined when the two sequences being compared are optimally aligned.

Other programs for determining identity and/or similarity between sequences are also known in the art, for instance the BLAST family of programs (Karlin & Altschul, 1990, *Proc. Natl. Acad. Sci. USA*, 87:2264-2268, modified as in Karlin & Altschul, 1993, *Proc. Natl. Acad. Sci. USA*, 90:5873-5877, available from the National Center for Biotechnology Information (NCB), Bethesda, Md., USA, and accessible through the home page of the NCBI at www.ncbi.nlm.nih.gov). These programs exemplify a preferred, non-limiting example of a mathematical algorithm utilized for the comparison of two sequences. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12 to obtain nucleotide sequences homologous to a nucleic acid molecule encoding all or a portion if an anti-CD19 antibody of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al., 1997, *Nucleic Acids Res.*, 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See, http://www.ncbi.nlm.nih.gov. Another preferred, non-limiting example of a mathematical algorithm utilized for the comparison of sequences is the algorithm of Myers and Miller, 1988, *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a program for determining identity and/or similarity between sequences known in the art is FASTA (Pearson W. R. and Lipman D. J., *Proc. Nat. Acad. Sci. USA*, 85:2444-2448, 1988, available as part of the Wisconsin Sequence Analysis Package). Preferably the BLOSUM62 amino acid substitution matrix (Henikoff S, and Henikoff J. G., *Proc. Nat. Acad. Sci. USA*, 89:10915-10919, 1992) is used in polypeptide sequence comparisons including where nucleotide sequences are first translated into amino acid sequences before comparison.

Yet another non-limiting example of a program known in the art for determining identity and/or similarity between amino acid sequences is SeqWeb Software (a web-based interface to the GCG Wisconsin Package: Gap program) which is utilized with the default algorithm and parameter settings of the program: blosum62, gap weight 8, length weight 2.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

To generate an altered antibody, one or more amino acid alterations (e.g., substitutions) are introduced in one or more of the hypervariable regions of the species-dependent antibody. Alternatively, or in addition, one or more alterations (e.g., substitutions) of framework region residues may be introduced in an anti-CD19 antibody where these result in an improvement in the binding affinity of the antibody mutant for the antigen from the second mammalian species. Examples of framework region residues to modify include those which non-covalently bind antigen directly (Amit et al., *Science*, 233:747-753 (1986)); interact with/effect the conformation of a CDR (Chothia et al., *J. Mol. Biol.*, 196:901-917 (1987)); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, an altered antibody will comprise additional hypervariable region alteration(s).

The hypervariable region residues which are altered may be changed randomly, especially where the starting binding affinity of an anti-CD19 antibody for the antigen from the second mammalian species is such that such randomly produced altered antibody can be readily screened.

One useful procedure for generating such an altered antibody is called "alanine scanning mutagenesis" (Cunningham and Wells, *Science*, 244:1081-1085 (1989)). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

Another procedure for generating such an altered antibody involves affinity maturation using phage display (Hawkins et al., *J. Mol. Biol.*, 254:889-896 (1992) and Lowman et al., *Biochemistry*, 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-CD19 antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In another embodiment, the sites selected for modification are affinity matured using phage display (see above).

Any technique for mutagenesis known in the art can be used to modify individual nucleotides in a DNA sequence, for purposes of making amino acid substitution(s) in the antibody sequence, or for creating/deleting restriction sites to facilitate further manipulations. Such techniques include, but are not limited to, chemical mutagenesis, in vitro site-directed mutagenesis (Kunkel, *Proc. Natl. Acad. Sci. USA*, 82:488 (1985); Hutchinson, C. et al., *J. Biol. Chem.*, 253:6551 (1978)), oligonucleotide-directed mutagenesis (Smith, *Ann. Rev. Genet.*, 19:423-463 (1985); Hill et al., *Methods Enzymol.*, 155:558-568 (1987)), PCR-based overlap extension (Ho et al., *Gene*, 77:51-59 (1989)), PCR-based megaprimer mutagenesis (Sarkar et al., *Biotechniques*, 8:404-407 (1990)), etc. Modifications can be confirmed by double-stranded dideoxy DNA sequencing.

In certain embodiments of the invention the anti-CD19 antibodies can be modified to produce fusion proteins; i.e., the antibody, or a fragment fused to a heterologous protein, polypeptide or peptide. In certain embodiments, the protein fused to the portion of an anti-CD19 antibody is an enzyme component of ADEPT. Examples of other proteins or polypeptides that can be engineered as a fusion protein with an anti-CD19 antibody include, but are not limited to toxins such as ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell*, 47:641 (1986), and Goldenberg et al., *Cancer Journal for Clinicians*, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of SYNAGIS® antibodies or fragments thereof (e.g., an antibody or a fragment thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.*, 8:724-33; Harayama, 1998, *Trends Biotechnol.*, 16(2):76-82; Hansson et al., 1999, *J. Mol. Biol.*, 287:265-76; and Lorenzo and Blasco, 1998, *Biotechniques*, 24(2):308-313 (each of these patents and publications are hereby incorporated by reference in its entirety). The antibody can further be a binding-domain immunoglobulin fusion protein as described in U.S. Publication 20030118592, U.S. Publication 200330133939, and PCT Publication WO 02/056910, all to Ledbetter et al., which are incorporated herein by reference in their entireties.

In certain embodiments of the invention, the anti-CD19 antibodies can be modified to alter their isoelectric point (pI). Antibodies like all polypeptides have a pI, which is generally defined as the pH at which a polypeptide carries no net charge. It is known in the art that protein solubility is typically lowest when the pH of the solution is equal to the isoelectric point (pI) of the protein. As used herein the pI value is defined as the pI of the predominant charge form. The pI of a protein may be determined by a variety of methods including but not limited to, isoelectric focusing and various computer algorithms (see, e.g., Bjellqvist et al., 1993, *Electrophoresis*, 14:1023). In addition, the thermal melting temperatures (Tm) of the Fab domain of an antibody, can be a good indicator of the thermal stability of an antibody and may further provide an indication of the shelf-life. A lower Tm indicates more aggregation/less stability, whereas a higher Tm indicates less aggregation/more stability. Thus, in certain embodiments antibodies having higher Tm are preferable. Tm of a protein domain (e.g., a Fab domain) can be measured using any standard method known in the art, for example, by differential scanning calorimetry (see, e.g., Vermeer et al., 2000, Biophys. J. 78:394-404; Vermeer et al., 2000, Biophys. J. 79: 2150-2154).

Accordingly, an additional nonexclusive embodiment of the present invention includes modified antibodies of the invention that have certain preferred biochemical characteristics such as a particular isoelectric point (pI) or melting temperature (Tm).

More specifically, in one embodiment, the modified antibodies of the present invention have a pI ranging from 5.5 to 9.5. In still another specific embodiment, the modified antibodies of the present invention have a pI that ranges from about 5.5 to about 6.0, or about 6.0 to about 6.5, or about 6.5 to about 7.0, or about 7.0 to about 7.5, or about 7.5 to about 8.0, or about 8.0 to about 8.5, or about 8.5 to about 9.0, or about 9.0 to about 9.5. In other specific embodiments, the modified antibodies of the present invention have a pI that ranges from 5.5-6.0, or 6.0 to 6.5, or 6.5 to 7.0, or 7.0-7.5, or 7.5-8.0, or 8.0-8.5, or 8.5-9.0, or 9.0-9.5. Even more specifically, the modified antibodies of the present invention have a pI of at least 5.5, or at least 6.0, or at least 6.3, or at least 6.5, or at least 6.7, or at least 6.9, or at least 7.1, or at least 7.3, or at least 7.5, or at least 7.7, or at least 7.9, or at least 8.1, or at least 8.3, or at least 8.5, or at least 8.7, or at least 8.9, or at least 9.1, or at least 9.3, or at least 9.5. In other specific embodiments, the modified antibodies of the present invention have a pI of at least about 5.5, or at least about 6.0, or at least about 6.3, or at least about 6.5, or at least about 6.7, or at least about 6.9, or at least about 7.1, or at least about 7.3, or at least about 7.5, or at least about 7.7, or at least about 7.9, or at least about 8.1, or at least about 8.3, or at least about 8.5, or at least about 8.7, or at least about 8.9, or at least about 9.1, or at least about 9.3, or at least about 9.5.

It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. In one embodiment, a substitution is generated in an antibody of the invention to alter the pI. It is specifically contemplated that the substitution(s) of the Fc region that result in altered binding to FcγR (described supra) may also result in a change in the pI. In another embodiment, substitution(s) of the Fc region are specifically chosen to effect both the desired alteration in FcγR binding and any desired change in pI.

In one embodiment, the modified antibodies of the present invention have a Tm ranging from 65° C. to 120° C. In specific embodiments, the modified antibodies of the present invention have a Tm ranging from about 75° C. to about 120° C., or about 75° C. to about 85° C., or about 85° C. to about 95° C., or about 95° C. to about 105° C., or about 105° C. to about 115° C., or about 115° C. to about 120° C. In other specific embodiments, the modified antibodies of the present invention have a Tm ranging from 75° C. to 120° C., or 75° C. to 85° C., or 85° C. to 95° C., or 95° C. to 105° C., or 105° C. to 115° C., or 115° C. to 120° C. In still other specific embodiments, the modified antibodies of the present invention have a Tm of at least about 65° C., or at least about 70° C., or at least about 75° C., or at least about 80° C., or at least about 85° C., or at least about 90° C., or at least about 95° C., or at least about 100° C., or at least about 105° C., or at least about 110° C., or at least about 115° C., or at least about 120° C. In yet other specific embodiments, the modified antibodies of the present invention have a Tm of at least 65° C., or at least 70° C., or at least 75° C., or at least 80° C., or at least 85° C., or at least 90° C., or at least 95° C., or at least 100° C., or at least 105° C., or at least 110° C., or at least 115° C., or at least 120° C.

5.1.9. Domain Antibodies

The anti-CD19 antibodies of the compositions and methods of the invention can be domain antibodies, e.g., antibodies containing the small functional binding units of antibodies, corresponding to the variable regions of the heavy ($V_H$) or light ($V_L$) chains of human antibodies. Examples of domain antibodies include, but are not limited to, those available from Domantis Limited (Cambridge, UK) and Domantis Inc. (Cambridge, Mass., USA) that are specific to therapeutic targets (see, for example, WO04/058821; WO04/003019; U.S. Pat. Nos. 6,291,158; 6,582,915; 6,696,245; and 6,593,081). Commercially available libraries of domain antibodies can be used to identify anti-CD19 domain antibodies. In certain embodiments, the anti-CD19 antibodies of the invention comprise a CD19 functional binding unit and a Fc gamma receptor functional binding unit.

5.1.10. Diabodies

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

5.1.11. Vaccibodies

In certain embodiments of the invention, the anti-CD19 antibodies are vaccibodies. Vaccibodies are dimeric polypeptides. Each monomer of a vaccibody consists of a scFv with specificity for a surface molecule on APC connected through a hinge region and a Cγ3 domain to a second scFv. In other embodiments of the invention, vaccibodies containing as one of the scFv's an anti-CD19 antibody fragment may be used to juxtapose those B cells to be destroyed and an effector cell that mediates ADCC. For example, see, Bogen et al., U.S. Patent Application Publication No. 20040253238.

5.1.12. Linear Antibodies

In certain embodiments of the invention, the anti-CD19 antibodies are linear antibodies. Linear antibodies comprise a pair of tandem Fd segments ($V_H$-$C_{H1}$-$V_H$-$C_{H1}$) which form a pair of antigen-binding regions. Linear antibodies can be bispecific or monospecific. See, Zapata et al., *Protein Eng.*, 8(10):1057-1062 (1995).

5.1.13. Parent Antibody

In certain embodiments of the invention, the anti-CD19 antibody is a parent antibody. A "parent antibody" is an antibody comprising an amino acid sequence which lacks, or is deficient in, one or more amino acid residues in or adjacent to one or more hypervariable regions thereof compared to an altered/mutant antibody as herein disclosed. Thus, the parent antibody has a shorter hypervariable region than the corresponding hypervariable region of an antibody mutant as herein disclosed. The parent polypeptide may comprise a native sequence (i.e., a naturally occurring) antibody (including a naturally occurring allelic variant) or an antibody with pre-existing amino acid sequence modifications (such as other insertions, deletions and/or substitutions) of a naturally occurring sequence. Preferably the parent antibody is a humanized antibody or a human antibody.

5.1.14. Antibody Fragments

"Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

Traditionally, these fragments were derived via proteolytic digestion of intact antibodies (see, e.g., Morimoto et al., *Journal of Biochemical and Biophysical Methods*, 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology*, 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See, for example, WO 93/16185. In certain embodiments, the antibody is not a Fab fragment.

5.1.15. Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T cell receptor molecule (e.g., CD2 or CD3), or Fc receptors for IgG (FcγR), so as to focus cellular defense mechanisms to the B cell. Bispecific antibodies may also be used to localize cytotoxic agents to the B cell. These antibodies possess a B cell marker-binding arm and an arm which binds the cytotoxic agent (e.g., saporin, anti-interferon-α, vinca alkaloid, ricin A chain, metholaexate or radioactive isotope hapten). Bispecific antibodies can be prepared as full-length antibodies or antibody fragments (e.g., F(ab'), bispecific antibodies).

Methods for making bispecific antibodies are known in the art. (See, for example, Millstein et al., *Nature*, 305:537-539 (1983); Traunecker et al., *EMBO J.*, 10:3655-3659 (1991); Suresh et al., *Methods in Enzymology*, 121:210 (1986); Kostelny et al., *J. Immunol.*, 148(5):1547-1553 (1992); Hollinger et al., *Proc. Natl. Acad. Sci. USA*, 90:6444-6448 (1993); Gruber et al., *J. Immunol.*, 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089).

In certain embodiments of the invention, the compositions and methods do not comprise a bispecific murine antibody with specificity for human CD19 and the CD3 epsilon chain of the T cell receptor such as the bispecific antibody described by Daniel et al., *Blood*, 92:4750-4757 (1998). In preferred embodiments, where the anti-CD19 antibody of the compositions and methods of the invention is bispecific, the anti-CD19 antibody is human or humanized and has specificity for human CD19 and an epitope on a T cell or is capable of binding to a human effector cell such as, for example, a monocyte/macrophage and/or a natural killer cell to effect cell death.

5.1.16. Engineering Effector Function

It may be desirable to modify the anti-CD19 antibody of the invention with respect to effector function, so as to enhance the effectiveness of the antibody in treating B cell malignancies, an autoimmune disease or disorder, or a GVHD or rejection, for example. For example, cysteine residue(s) may be introduced in the Fc region, thereby allowing interchain disulfide bond formation in this region. The homodimeric antibody thus generated may have improved internalization capability and/or increased complement-mediated cell killing and/or antibody-dependent cellular cytotoxicity (ADCC). See, Caron et al., *J. Exp Med.*, 176:1191-1195 (1992) and Shopes, B., *J. Immunol.*, 148:2918-2922 (1992). Homodimeric antibodies with enhanced anti-tumor activity may also be prepared using heterobifunctional cross-linkers as described in Wolff et al., *Cancer Research*, 53:2560-2565 (1993). Alternatively, an antibody can be engineered which has dual Fc regions and may thereby have enhanced complement lysis and ADCC capabilities. See, Stevenson et al., *Anti-Cancer Drug Design*, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wild type Fc region have also been described (e.g., PCT Publication Nos. WO 2004/063351, to Stavenhagen et al.; the disclosure of which is incorporated herein in its entirety).

In vitro assays known in the art can be used to determine whether the anti-CD19 antibodies used in the compositions and methods of the invention are capable of mediating ADCC, such as those described herein.

5.1.17. Variant Fc Regions

The present invention provides formulation of proteins comprising a variant Fc region. That is, a non-naturally occurring Fc region, for example an Fc region comprising one or more non-naturally occurring amino acid residues. Also encompassed by the variant Fc regions of the present invention are Fc regions which comprise amino acid deletions, additions and/or modifications.

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region. Particularly preferred are proteins comprising variant Fc regions, which are non-naturally occurring variants of an Fc. Note: Polymorphisms have been observed at a number of Fc positions, including but not limited to Kabat 270, 272, 312, 315, 356, and 358, and thus slight differences between the presented sequence and sequences in the prior art may exist.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($K_{off}$ and $K_{on}$ respectively), binding affinity and/or avidity. It is generally understood that a binding molecule (e.g., a Fc variant protein such as an antibody) with a low $K_D$ is preferable to a binding molecule with a high $K_D$. However, in some instances the value of the $K_{on}$ or $K_{off}$ may be more relevant than the value of the $K_D$. One skilled in the art can determine which kinetic parameter is most important for a given antibody application.

The affinities and binding properties of an Fc domain for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

For example a modification that enhances Fc binding to one or more positive regulators (e.g., FcγRIIIA) while leaving unchanged or even reducing Fc binding to the negative regulator FcγRIIB would be more preferable for enhancing ADCC activity. Alternatively, a modification that reduced binding to one or more positive regulator and/or enhanced binding to FcγRIIB would be preferable for reducing ADCC activity. Accordingly, the ratio of binding affinities (e.g., equilibrium dissociation constants ($K_D$)) can indicate if the ADCC activity of an Fc variant is enhanced or decreased. For example a decrease in the ratio of FcγRIIIA/FcγRIIB equilibrium dissociation constants ($K_D$), will correlate with improved ADCC activity, while an increase in the ratio will correlate with a decrease in ADCC activity. Additionally, modifications that enhanced binding to C1q would be preferable for enhancing CDC activity while modification that reduced binding to C1q would be preferable for reducing or eliminating CDC activity.

In one embodiment, the Fc variants of the invention bind FcγRIIIA with increased affinity relative to a comparable molecule. In another embodiment, the Fc variants of the invention bind FcγRIIIA with increased affinity and bind FcγRIIB with a binding affinity that is unchanged relative to a comparable molecule. In still another embodiment, the Fc variants of the invention bind FcγRIIIA with increased affinity and bind FcγRIIB with a decreased affinity relative to a comparable molecule. In yet another embodiment, the Fc variants of the invention have a ratio of FcγRIIIA/FcγRIIB equilibrium dissociation constants ($K_D$) that is decreased relative to a comparable molecule.

In one embodiment, the Fc variant protein has enhanced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the Fc variant protein has enhanced binding to an Fc receptor. In another specific embodiment, the Fc variant protein has enhanced binding to the Fc receptor FcγRIIIA. In still another specific embodiment, the Fc variant protein has enhanced binding to the Fc receptor FcRn. In yet another specific embodiment, the Fc variant protein has enhanced binding to C1q relative to a comparable molecule.

In one embodiment of the present invention, antibodies specifically bind CD19 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another embodiment, the antibody of the invention binds to CD19 and/or antigenic fragments thereof with a $K_{off}$ of less than $1\times10^{-3}$ s$^{-1}$, or less than $3\times10^{-3}$ s$^{-1}$. In other embodiments, the antibody binds to CD19 and antigenic fragments thereof with a $K_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In another embodiment, the antibody of the invention binds to CD19 and/or antigenic fragments thereof with an association rate constant or $k_{on}$ rate of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$, or at least $10^9$ M$^{-1}$ s$^{-1}$.

In another embodiment, an Fc variant of the invention has an equilibrium dissociation constant ($K_D$) that is decreased between about 2 fold and about 10 fold, or between about 5 fold and about 50 fold, or between about 25 fold and about 250 fold, or between about 100 fold and about 500 fold, or between about 250 fold and about 1000 fold relative to a comparable molecule. In another embodiment, an Fc variant of the invention has an equilibrium dissociation constant ($K_D$) that is decreased between 2 fold and 10 fold, or between 5 fold and 50 fold, or between 25 fold and 250 fold, or between 100 fold and 500 fold, or between 250 fold and 1000 fold relative to a comparable molecule. In a specific embodiment, said Fc variants have an equilibrium dissociation constants ($K_D$) for FcγRIIIA that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule.

The serum half-life of proteins comprising Fc regions may be increased by increasing the binding affinity of the Fc region for FcRn. In one embodiment, the Fc variant protein has enhanced serum half life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277-282; Bruggemann et al., 1987, J Exp Med, 166:1351-1361; Wilkinson et al., 2001, J Immunol Methods, 258:183-191; Patel et al., 1995, *J Immunol Methods,* 184:29-38. Alternatively, or additionally, ADCC activity of the Fc variant protein of interest may be assessed in vivo, e.g., in an animal model such as that disclosed in Clynes et al., 1998, PNAS USA, 95:652-656.

In one embodiment, an Fc variant protein has enhanced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed. In one embodiment, an Fc variant protein has enhanced CDC activity relative to a comparable molecule. In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the Fc variant protein has both enhanced CDC activity and enhanced serum half life relative to a comparable molecule.

In one embodiment, the present invention provides formulations, wherein the Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In a specific embodiment, the present invention provides an Fc variant protein formulation, wherein the Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241 R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In another embodiment, the present invention provides an Fc variant protein formulation, wherein the Fc region comprises at least a non-naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non-naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non-naturally occurring amino acid selected from the group consisting of 239D, 330L and 332E, as numbered by the EU index as set forth in Kabat and at least one non-naturally occurring amino acid at one or more positions are selected from the group consisting of 252Y, 254T and 256E, as numbered by the EU index as set forth in Kabat.

In one embodiment, the Fc variants of the present invention may be combined with other known Fc variants such as those disclosed in Ghetie et al., 1997, Nat. Biotech. 15:637-40; Duncan et al, 1988, Nature 332:563-564; Lund et al., 1991, J. Immunol., 147:2657-2662; Lund et al, 1992, Mol. Immunol., 29:53-59; Alegre et al, 1994, Transplantation 57:1537-1543; Hutchins et al., 1995, Proc Natl. Acad Sci USA, 92:11980-11984; Jefferis et al, 1995, Immunol Lett., 44:111-117; Lund et al., 1995, Faseb J., 9:115-119; Jefferis et al, 1996, Immunol Lett., 54:101-104; Lund et al, 1996, J. Immunol., 157:4963-4969; Armour et al., 1999, Eur J Immunol 29:2613-2624; Idusogie et al, 2000, J. Immunol., 164:4178-4184; Reddy et al, 2000, J. Immunol., 164:1925-1933; Xu et al., 2000, Cell Immunol., 200:16-26; Idusogie et al, 2001, J. Immunol., 166: 2571-2575; Shields et al., 2001, J Biol. Chem., 276:6591-6604; Jefferis et al, 2002, Immunol Lett., 82:57-65; Presta et al., 2002, Biochem Soc Trans., 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351. Also encompassed by the present invention are Fc regions which comprise deletions, additions and/or modifications. Still other modifications/substitutions/additions/deletions of the Fc domain will be readily apparent to one skilled in the art.

Methods for generating non-naturally occurring Fc regions are known in the art. For example, amino acid substitutions and/or deletions can be generated by mutagenesis methods, including, but not limited to, site-directed mutagenesis (Kunkel, Proc. Natl. Acad. Sci. USA, 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene, 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). Alternatively, the technique of overlap-extension PCR (Higuchi, ibid.) can be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol., 17:176-180; Davies et al., 20017 Biotechnol Bioeng., 74:288-294; Shields et al., 2002, J Biol. Chem., 277:26733-26740; Shinkawa et al., 2003, J Biol. Chem., 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc., Princeton, N.J.); GlycoMAb™ glycosylation engineering technology (GLYCART biotechnology AG, Zurich, Switzerland). See, e.g., WO 00/061739; EA01229125; US 20030115614; Okazaki et al., 2004, JMB, 336: 1239-49.

5.1.18. Glycosylation of Antibodies

In still another embodiment, the glycosylation of antibodies utilized in accordance with the invention is modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. Alternatively, one or more amino acid substitutions can be made that result in elimination of a glycosylation site present in the Fc region (e.g., Asparagine 297 of IgG). Furthermore, a glycosylated antibodies may be produced in bacterial cells which lack the necessary glycosylation machinery.

Additionally or alternatively, an antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al., (2002) J. Biol. Chem., 277:26733-26740; Umana et al., (1999) Nat. Biotech., 17:176-1, as well as, European Patent No: EP 1,176,195; PCT Publications WO 03/035835; WO 99/54342. See also Li et al., 2006, Nat. Biotech 24: 210-215; and published U.S. patent applications: US2006/0040353; US2006/034830; US2006/0034829; US2006/0034828; US2006/0029604 and US2006/0024304, which describe altered glycosylation of antibodies.

5.2. Manufacture/Production of Anti-CD19 Antibodies

Once a desired anti-CD19 antibody is engineered, the anti-CD19 antibody can be produced on a commercial scale using methods that are well-known in the art for large scale manufacturing of antibodies. For example, this can be accomplished using recombinant expressing systems such as, but not limited to, those described below.

5.2.1. Recombinant Expression Systems

Recombinant expression of an antibody of the invention or variant thereof, generally requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well-known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

In an alternate embodiment, the anti-CD19 antibodies of the compositions and methods of the invention can be made using targeted homologous recombination to produce all or portions of the anti-CD19 antibodies (see, U.S. Pat. Nos. 6,063,630, 6,187,305, and 6,692,737). In certain embodiments, the anti-CD19 antibodies of the compositions and methods of the invention can be made using random recombination techniques to produce all or portions of the anti-CD19 antibodies (see, U.S. Pat. Nos. 6,361,972, 6,524,818, 6,541,221, and 6,623,958). Anti-CD19 antibodies can also be produced in cells expressing an antibody from a genomic sequence of the cell comprising a modified immunoglobulin locus using Cre-mediated site-specific homologous recombination (see, U.S. Pat. No. 6,091,001). Where human antibody production is desired, the host cell should be a human cell line. These methods may advantageously be used to engineer stable cell lines which permanently express the antibody molecule.

Once the expression vector is transferred to a host cell by conventional techniques, the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the anti-CD19 antibodies of the invention or portions thereof that can be used in the engineering and generation of anti-CD19 antibodies (see, e.g., U.S. Pat. No. 5,807,715). For example, mammalian cells such as Chinese hamster ovary cells (CHO), in conjunction with a vector such as the major intermediate early gene promoter element from human cytomegalovirus is an effective expression system for antibodies (Foecking et al., Gene, 45:101 (1986); and Cockett et al., Bio/Technology, 8:2 (1990)). In addition, a host cell strain may be chosen which modulates the expression of inserted antibody sequences, or modifies and processes the antibody gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

In preferred embodiments, human cell lines developed by immortalizing human lymphocytes can be used to recombinantly produce monoclonal human anti-CD19 antibodies. In preferred embodiments, the human cell line PER.C6. (Crucell, Netherlands) can be used to recombinantly produce monoclonal human anti-CD19 antibodies.

In bacterial systems, a number of expression vectors may be advantageously selected depending upon the use intended for the antibody molecule being expressed. For example, when a large quantity of such an antibody is to be produced, for the generation of pharmaceutical compositions comprising an anti-CD19 antibody, vectors which direct the expression of high levels of fusion protein products that are readily purified may be desirable. Such vectors include, but are not limited to, the E. coli expression vector pUR278 (Ruther et al., EMBO, 12:1791 (1983)), in which the antibody coding sequence may be ligated individually into the vector in frame with the lac Z coding region so that a fusion protein is produced; pIN vectors (Inouye & Inouye, 1985, *Nucleic Acids Res.*, 13:3101-3109 (1985); Van Heeke & Schuster, 1989, *J. Biol. Chem.*, 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see, Logan & Shenk, *Proc. Natl. Acad. Sci. USA*, 81:355-359 (1984)). Specific initiation signals may also be required for efficient translation of inserted antibody coding sequences. These signals include the ATG initiation codon and adjacent sequences. Furthermore, the initiation codon should generally be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., *Methods in Enzymol.*, 153:51-544 (1987)).

For long-term, high-yield production of recombinant proteins, stable expression is preferred. For example, cell lines which stably express the antibody molecule may be engineered. Rather than transient expression systems that use replicating expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. Plasmids that encode the anti-CD19 antibody can be used to introduce the gene/cDNA into any cell line suitable for production in culture. Alternatively, plasmids called "targeting vectors" can be used to introduce expression control elements (e.g., promoters, enhancers, etc.) into appropriate chromosomal locations in the host cell to "activate" the endogenous gene for anti-CD19 antibodies.

A number of selection systems may be used, including, but not limited to, the herpes simplex virus thymidine kinase (Wigler et al., *Cell*, 11:223 (1977)), hypoxanthineguanine phosphoribosyltransferase (Szybalska & Szybalski, *Proc. Natl. Acad. Sci. USA*, 48:202 (1992)), and adenine phosphoribosyltransferase (Lowy et al., *Cell*, 22:8-17 (1980)) genes can be employed in tk$^-$, hgprt$^-$ or aprT$^-$ cells, respectively. Also, antimetabolite resistance can be used as the basis of selection for the following genes: dhfr, which confers resistance to methotrexate (Wigler et al., *Natl. Acad. Sci. USA*, 77:357 (1980); O'Hare et al., *Proc. Natl. Acad. Sci. USA*, 78:1527 (1981)); gpt, which confers resistance to mycophenolic acid (Mulligan & Berg, *Proc. Natl. Acad. Sci. USA*, 78:2072 (1981)); neo, which confers resistance to the aminoglycoside G-418 (Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, TIB TECH 11(5):155-215 (1993)); and hygro, which confers resistance to hygromycin (Santerre et al., *Gene*, 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds.), *Current Protocols in Human Genetics*, John Wiley & Sons, NY (1994); Colberre-Garapin et al., 1981, *J. Mol. Biol.*, 150:1, which are incorporated by reference herein in their entireties.

The expression levels of an antibody molecule can be increased by vector amplification (for a review, see, Bebbington and Hentschel, *The use of vectors based on gene amplification for the expression of cloned genes in mammalian cells in DNA cloning*, Vol. 3, Academic Press, New York (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.*, 3:257 (1983)). Antibody expression levels may be amplified through the use recombinant methods and tools known to those skilled in the art of recombinant protein production, including technologies that remodel surrounding chromatin and enhance transgene expression in the form of an active artificial transcriptional domain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:562-565 (1986); and Kohler, 1980, *Proc. Natl. Acad. Sci. USA*, 77:2197-2199 (1980)). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.2.2. Antibody Purification and Isolation

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody mutant. Protein A can be used to purify antibodies that are based on human γ1, γ2, or γ4 heavy chains (Lindmark et al., *J. Immunol. Methods*, 62:1-13 (1983)). Protein G is recommended for all mouse isotypes and for human γ3 (Guss et al., *EMBO J.*, 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

5.3 Therapeutic Anti-CD19 Antibodies

The anti-CD19 antibody used in the compositions and methods of the invention is preferably a human antibody or a humanized antibody that preferably mediates human ADCC, or is selected from known anti-CD19 antibodies that preferably mediate human ADCC. In certain embodiments, the anti-CD19 antibodies can be chimeric antibodies. In preferred embodiments, anti-CD19 antibody is a monoclonal human, humanized, or chimeric anti-CD19 antibody. The anti-CD19 antibody used in the compositions and methods of the invention is preferably a human antibody or a humanized antibody of the IgG1 or IgG3 human isotype. In other embodiments, the anti-CD19 antibody used in the compositions and methods of the invention is preferably a human antibody or a humanized antibody of the IgG2 or IgG4 human isotype that preferably mediates ADCC.

While such antibodies can be generated using the techniques described above, in other embodiments of the invention, the murine antibodies HB12a and HB12b as described herein or other commercially available anti-CD19 antibodies can be chimerized, humanized, or made into human antibodies.

For example, known anti-CD19 antibodies that can be used include, but are not limited to, HD37 (IgG1) (DAKO, Carpinteria, Calif.), BU12 (G.D. Johnson, University of Birmingham, Birmingham, United Kingdom), 4G7 (IgG1) (Becton-Dickinson, Heidelberg, Germany), J4.119 (Beckman Coulter, Krefeld, Germany), B43 (PharMingen, San Diego, Calif.), SJ25C1 (BD PharMingen, San Diego, Calif.), FMC63 (IgG2a) (Chemicon Int'l., Temecula, Calif.) (Nicholson et al., *Mol. Immunol.*, 34:1157-1165 (1997); Pietersz et al., *Cancer Immunol. Immunotherapy*, 41:53-60 (1995); and Zola et al., *Immunol. Cell Biol.*, 69:411-422 (1991)), B4 (IgG1) (Beckman Coulter, Miami, Fla.) Nadler et al., *J. Immunol.*, 131:244-250 (1983), and/or HD237 (IgG2b) (Fourth International Workshop on Human Leukocyte Differentiation Antigens, Vienna, Austria, 1989; and Pezzutto et al., *J. Immunol.*, 138:2793-2799 (1987)).

In certain embodiments, the anti-CD19 antibody of the invention comprises the heavy chain of HB12a comprising an amino acid sequence of SEQ ID NO:2 (FIG. 5A). In other embodiments, the anti-CD19 antibody of the invention comprises the heavy chain of HB12b comprising an amino acid sequence of SEQ ID NO:4 (FIG. 5B).

In certain embodiments, the anti-CD19 antibody of the invention comprises the light chain of HB12a comprising an amino acid sequence of SEQ ID NO:16 (FIG. 6A). In other embodiments, the anti-CD19 antibody of the invention comprises the light chain of HB12b comprising an amino acid sequence of SEQ ID NO:18 (FIG. 6B).

In certain embodiments, the antibody is an isotype switched variant of a known antibody (e.g., to an IgG1 or IgG3 human isotype) such as those described above (e.g., HB12a or HB12b).

The anti-CD19 antibodies used in the compositions and methods of the invention can be naked antibodies, immunoconjugates or fusion proteins. Preferably the anti-CD19 antibodies described above for use in the compositions and methods of the invention are able to reduce or deplete B cells and circulating immunoglobulin in a human treated therewith. Depletion of B cells can be in circulating B cells, or in particular tissues such as, but not limited to, bone marrow, spleen, gut-associated lymphoid tissues, and/or lymph nodes. Such depletion may be achieved via various mechanisms such as antibody-dependent cell-mediated cytotoxicity (ADCC) and/or complement dependent cytotoxicity (CDC), inhibition of B cell proliferation and/or induction of B cell death (e.g., via apoptosis). By "depletion" of B cells it is meant a reduction in circulating B cells and/or B cells in particular tissue(s) by at least about 25%, 40%, 50%, 65%, 75%, 80%, 85%, 90%, 95% or more as described herein. In particular embodiments, virtually all detectable B cells are depleted from the circulation and/or particular tissue(s). By "depletion" of circulating immunoglobulin (Ig) it is meant a reduction by at least about 25%, 40%, 50%, 65%, 75%, 80%, 85%, 90%, 95% or more as described herein. In particular embodiments, virtually all detectable Ig is depleted from the circulation.

5.3.1. Screening of Antibodies for Human CD19 Binding

Binding assays can be used to identify antibodies that bind the human CD19 antigen. Binding assays may be performed either as direct binding assays or as competition-binding assays. Binding can be detected using standard ELISA or standard Flow Cytometry assays. In a direct binding assay, a candidate antibody is tested for binding to human CD19 antigen. In certain embodiments, the screening assays comprise, in a second step, determining the ability to cause cell death or apoptosis of B cells expressing human CD19. Competition-binding assays, on the other hand, assess the ability of a candidate antibody to compete with a known anti-CD19 antibody or other compound that binds human CD19.

In a direct binding assay, the human CD19 antigen is contacted with a candidate antibody under conditions that allow binding of the candidate antibody to the human CD19 antigen. The binding may take place in solution or on a solid surface. Preferably, the candidate antibody is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a CD19-antibody complex is detected.

In a competition-binding assay, a candidate antibody is evaluated for its ability to inhibit or displace the binding of a known anti-CD19 antibody (or other compound) to the human CD19 antigen. A labeled known binder of CD19 may be mixed with the candidate antibody, and placed under conditions in which the interaction between them would normally occur, with and without the addition of the candidate antibody. The amount of labeled known binder of CD19 that binds the human CD19 may be compared to the amount bound in the presence or absence of the candidate antibody.

In a preferred embodiment, to facilitate antibody antigen complex formation and detection, the binding assay is carried out with one or more components immobilized on a solid surface. In various embodiments, the solid support could be, but is not restricted to, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of human CD19, or other component, can be achieved through covalent or non-covalent attachments. In one embodiment, the attachment may be indirect, i.e., through an attached antibody. In another embodiment, the human CD19 antigen and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the human CD19 antigen which is immobilized to a solid support. Typically, the non-mobilized component of the binding reaction, in this case the candidate anti-CD19 antibody, is labeled to enable detection. A variety of labeling methods are available and may be used, such as luminescent, chromophore, fluorescent, or radioactive isotope or group containing same, and nonisotopic labels, such as enzymes or dyes. In a preferred embodiment, the candidate anti-CD19 antibody is labeled with a fluorophore such as fluorescein isothiocyanate (FITC, available from Sigma Chemicals, St. Louis).

Finally, the label remaining on the solid surface may be detected by any detection method known in the art. For example, if the candidate anti-CD19 antibody is labeled with a fluorophore, a fluorimeter may be used to detect complexes.

Preferably, the human CD19 antigen is added to binding assays in the form of intact cells that express human CD19 antigen, or isolated membranes containing human CD19 antigen. Thus, direct binding to human CD19 antigen may be assayed in intact cells in culture or in animal models in the presence and absence of the candidate anti-CD19 antibody. A labeled candidate anti-CD19 antibody may be mixed with cells that express human CD19 antigen, or with crude extracts obtained from such cells, and the candidate anti-CD19 antibody may be added. Isolated membranes may be used to identify candidate anti-CD19 antibodies that interact with human CD19. For example, in a typical experiment using isolated membranes, cells may be genetically engineered to express human CD19 antigen. Membranes can be harvested by standard techniques and used in an in vitro binding assay. Labeled candidate anti-CD19 antibody (e.g., fluorescent labeled antibody) is bound to the membranes and assayed for specific activity; specific binding is determined by comparison with binding assays performed in the presence of excess unlabeled (cold) candidate anti-CD19 antibody. Alternatively, soluble human CD19 antigen may be recombinantly expressed and utilized in non-cell based assays to identify antibodies that bind to human CD19 antigen. The recombinantly expressed human CD19 polypeptides can be used in the non-cell based screening assays. Alternatively, peptides corresponding to one or more of the binding portions of human CD19 antigen, or fusion proteins containing one or more of the binding portions of human CD19 antigen can be used in non-cell based assay systems to identify antibodies that bind to portions of human CD19 antigen. In non-cell based assays the recombinantly expressed human CD19 is attached to a solid substrate such as a test tube, microtiter well or a column, by means well-known to those in the art (see, Ausubel et al., supra). The test antibodies are then assayed for their ability to bind to human CD19 antigen.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

In one embodiment, for example, a phage library can be screened by passing phage from a continuous phage display library through a column containing purified human CD19 antigen, or derivative, analog, fragment, or domain, thereof, linked to a solid phase, such as plastic beads. By altering the stringency of the washing buffer, it is possible to enrich for phage that express peptides with high affinity for human CD19 antigen. Phage isolated from the column can be cloned and affinities can be measured directly. Knowing which antibodies and their amino acid sequences confer the strongest binding to human CD19 antigen, computer models can be used to identify the molecular contacts between CD19 antigen and the candidate antibody.

In another specific embodiment of this aspect of the invention, the solid support is membrane containing human CD19 antigen attached to a microtiter dish. Candidate antibodies, for example, can bind cells that express library antibodies cultivated under conditions that allow expression of the library members in the microtiter dish. Library members that bind to the human CD19 are harvested. Such methods are generally described by way of example in Parmley and Smith, 1988, *Gene*, 73:305-318; Fowlkes et al., 1992, *BioTechniques*, 13:422-427; PCT Publication No. WO94/18318; and in references cited hereinabove. Antibodies identified as binding to human CD19 antigen can be of any of the types or modifications of antibodies described above.

In certain embodiments, the screening assays comprise, in a second step, determining the ability to cause cell death or apoptosis of B cells expressing human CD19. Assays utilizing viable dyes, methods of detecting and analyzing caspases, and assays measuring DNA breaks can be used to assess the apoptotic activity of cells cultured in vitro with an anti-CD19 antibody of interest. For example, Annexin V or TdT-mediated dUTP nick-end labeling (TUNEL) assays can be carried out as described in Decker et al., *Blood*, 103:2718-2725 (2004) to detect apoptotic activity. The TUNEL assay involves culturing the cells of interest with fluorescein-labeled dUTP for incorporation into DNA strand breaks. The cells are then processed for analysis by flow cytometry. The Annexin V assay detects the exposure of phosphatidylserine (PS) on the outside of the plasma membrane using a fluorescein-conjugated antibody that specifically recognizes the exposed PS on the surface of apoptotic cells. In conjunction, a viable dye such as propidium iodide can be used to exclude late apoptotic cells from early apoptotic cells. The cells of interest are stained with the antibody and are analyzed by flow cytometry. Moreover, techniques for assaying apoptotic activity of an antibody are well-known in the art. See, e.g., Chaouchi et al., *J. Immunol.*, 154(7): 3096-104 (1995); Pedersen et al., *Blood*, 99(4): 1314-1318 (2002); Alberts et al., *Molecular Biology of the Cell*; Steensma et al., *Methods Mol. Med.*, 85: 323-32, (2003)).

5.3.2. Screening of Antibodies for Human ADCC Effector Function

Antibodies of the human IgG class are preferred for use in the invention because they have functional characteristics such a long half-life in serum and can mediate various effector functions (*Monoclonal Antibodies: Principles and Applications*, Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC and apoptotic activity as effector functions of the IgG class antibody, and it has been reported that among antibodies of the human IgG class, the IgG1 subclass has the highest ADCC activity and CDC activity in humans (*Chemical Immunology*, 65, 88 (1997)).

Expression of ADCC activity and CDC activity and apoptotic activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

The anti-CD19 antibodies of the invention can be modified with respect to effector function, e.g., so as to enhance ADCC and/or complement dependent cytotoxicity (CDC) and/or apoptotic activity of the antibody. This may be achieved by introducing one or more amino acid substitutions in the Fc region of an antibody. Alternatively or additionally, cysteine residue(s) may be introduced in the Fc region, allowing for interchain disulfide bond formation in this region. In this way a homodimeric antibody can be generated that may have improved internalization capability and or increased complement-mediated cell killing and ADCC (Caron et al., *J. Exp. Med.*, 176:1191-1195 (1992) and Shopes, *J. Immunol.*, 148: 2918-2922 (1992)). Heterobifunctional cross-linkers can also be used to generate homodimeric antibodies with enhanced anti-tumor activity (Wolff et al., *Cancer Research*, 53:2560-2565 (1993)). Antibodies can also be engineered to have two or more Fc regions resulting in enhanced complement lysis and ADCC capabilities (Stevenson et al., *Anti-Cancer Drug Design*, (3)219-230 (1989)).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see also PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wild type Fc region have also been described (e.g., PCT Publication No. WO 2004/063351, to Stavenhagen et al.; the disclosure of which is incorporated herein in its entirety).

At least four different types of FcγR have been found, which are respectively called FcγRI (CD64), FcγRII (CD32), FcγRIII (CD16), and FcγRIV. In human, FcγRII and FcγRIII are further classified into FcγRIIa and FcγRIIb, and FcγRIIIa and FcγRIIIb, respectively. FcγR is a membrane protein belonging to the immunoglobulin superfamily, FcγRII, FcγRIII, and FcγRIV have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRIII have a γ chain or ζ chain as a constituting component which has a signal transduction function in association with the α chain (*Annu. Rev. Immunol.*, 18, 709 (2000), *Annu. Rev. Immunol.*, 19, 275 (2001)). FcγRIV has been described by Bruhns et al., *Clin. Invest. Med.*, (Canada) 27:3 D (2004).

To assess ADCC activity of an anti-CD19 antibody of interest, an in vitro ADCC assay can be used, such as that described in U.S. Pat. No. 5,500,362 or 5,821,337. Useful effector cells for such assays include peripheral blood mononuclear cells (PBMC) and Natural Killer (NK) cells. For example, the ability of any particular antibody to mediate lysis of the target cell by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis of the target cells is detected by the release of label from the lysed cells. In fact, antibodies can be screened using the patient's own serum as a source of complement and/or immune cells. The antibodies that are capable of mediating human ADCC in the in vitro test can then be used therapeutically in that particular patient. Alternatively, or additionally, ADCC activity of the molecule of interest may be assessed in vivo, e.g., in an animal model such as that disclosed in Clynes et al., *PNAS (USA)*, 95:652-656 (1998). Moreover, techniques for modulating (i.e., increasing or decreasing) the level of ADCC, and optionally CDC activity, and optionally apoptotic activity of an antibody are well-known in the art. See, e.g., U.S. Pat. No. 6,194,551. (see, e.g., Chaouchi et al., J. Immunol., 154(7): 3096-104 (1995); Pedersen et al., Blood, 99(4): 1314-1318 (2002); Alberts et al., Molecular Biology of the Cell; Steensma et al., Methods Mol. Med., 85: 323-32, (2003)). Antibodies of the present invention preferably are capable or have been modified to have the ability of inducing ADCC and/or CDC and/or an apoptotic response. Preferably, such assays to determined ADCC function are practiced using humans effector cells to assess human ADCC function.

5.3.3. Immunoconjugates and Fusion Proteins

According to certain aspects of the invention, therapeutic agents or toxins can be conjugated to chimerized, human, or humanized anti-CD19 antibodies for use in the compositions and methods of the invention. In certain embodiments, these conjugates can be generated as fusion proteins. Examples of therapeutic agents and toxins include, but are not limited to, members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include adriamycin, doxorubicin, 5-fluorouracil, cytosine arabinoside (ara-c), cyclophosphamide, thiotepa, taxotere (docetaxel), busulfan, cytoxin, taxol, methotrexate, cisplatin, melphalan, vinblastine, bleomycin, etoposide, ifosfamide, mitomycin c, mitoxantrone, vincreistine, vinorelbine, carboplatin, teniposide, daunomycin, caminomycin, aminopterin, dactinomycin, mitomycins, esperamicins (see, U.S. Pat. No. 4,675,187), melphalan, and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in the combination therapies of the invention. CVB is a regimen used to treat non-Hodgkin's lymphoma (Patti et al., *Eur. J. Haematol.*, 51: 18 (1993)). Other suitable combination chemotherapeutic regimens are well-known to those of skill in the art. See, for example, Freedman et al., "Non-Hodgkin's Lymphomas," in Cancer Medicine, Volume 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone, and leucovorin), while a suitable third generation regimen is MACOP-B (methotrexate, doxorubicin, cyclophosphamide, vincristine, prednisone, bleomycin, and leucovorin). Additional useful drugs include phenyl butyrate and brostatin-1.

Other toxins that can be used in the immunoconjugates of the invention include poisonous lectins, plant toxins such as ricin, abrin, modeccin, botulina, and diphtheria toxins. Of course, combinations of the various toxins could also be coupled to one antibody molecule thereby accommodating variable cytotoxicity. Illustrative of toxins which are suitably employed in the combination therapies of the invention are ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell*, 47:641 (1986), and Goldenberg et al., *Cancer Journal for Clinicians*, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in Remington's Pharmaceutical Sciences, 19th Ed. (Mack Publishing Co. 1995), and in Goodman and Gilman's the Pharmacological Basis of Therapeutics, 7th Ed. (MacMillan Publishing Co. 1985). Other suitable toxins and/or chemotherapeutic agents are known to those of skill in the art.

The anti-CD19 antibody of the present invention may also be used in ADEPT by conjugating the antibody to a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes,", can be used to convert the prodrugs of the invention into free active drugs (see, e.g., Massey, *Nature*, 328: 457-458 (1987)). Antibody-abzyme conjugates can be prepared as described herein for delivery of the abzyme as desired to portions of a human affected by a B cell malignancy or an autoimmune disease or disorder.

The enzymes of this invention can be covalently bound to the antibody by techniques well-known in the art such as the use of the heterobifunctional crosslinking reagents discussed above. Alternatively, fusion proteins comprising at least the antigen-binding region of an antibody of the invention linked to at least a functionally active portion of an enzyme of the invention can be constructed using recombinant DNA techniques well-known in the art (see, e.g., Neuberger et al., *Nature*, 312: 604-608 (1984)).

Covalent modifications of the anti-CD19 antibody of the invention are included within the scope of this invention. They may be made by chemical synthesis or by enzymatic or chemical cleavage of the antibody, if applicable. Other types of covalent modifications of the anti-CD19 antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing α-amino-containing residues and/or ε-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the ε-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC *Crit. Rev. Biochem.*, pp. 259-306 (1981).

5.4. Pharmaceutical Formulations, Administration and Dosing

The pharmaceutical formulations of the invention contain as the active ingredient human, humanized, or chimeric anti-CD19 antibodies. The formulations contain naked antibody, immunoconjugate, or fusion protein in an amount effective for producing the desired response in a unit of weight or volume suitable for administration to a human patient, and are preferably sterile. The response can, for example, be measured by determining the physiological effects of the anti-CD19 antibody composition, such as, but not limited to, circulating B cell depletion, tissue B cell depletion, regression of a B cell malignancy or an autoimmune disease or disorder, or decrease of disease symptoms. The response can also be measured by determining the physiological effects of the anti-CD19 antibody composition such as circulating immunoglobulin depletion, or a reduction in the incidence, severity, or duration of GVHD, a rejection episode, or a post-transplantation lymphoproliferative disorder. Other assays will be known to one of ordinary skill in the art and can be employed for measuring the level of the response.

5.4.1. Pharmaceutical Formulations

An anti-CD19 antibody composition may be formulated with a pharmaceutically-acceptable carrier. The term "pharmaceutically acceptable" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, boric, formic, malonic, succinic, and the like. Also, pharmaceutically-acceptable salts can be prepared as alkaline metal or alkaline earth salts, such as sodium, potassium or calcium salts. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

According to certain aspects of the invention, the anti-CD19 antibody compositions can be prepared for storage by mixing the antibody or immunoconjugate having the desired degree of purity with optional physiologically acceptable carriers, excipients or stabilizers (*Remington's Pharmaceutical Sciences,* 16th edition, Osol, A. Ed. (1999)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS™ or polyethylene glycol (PEG).

The anti-CD19 antibody compositions also may contain, optionally, suitable preservatives, such as: benzalkonium chloride; chlorobutanol; parabens and thimerosal.

The anti-CD19 antibody compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of anti-CD19 antibody, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administration can be found in *Remington's Pharmaceutical Sciences*, Mack Publishing Co., Easton, Pa. In certain embodiments, carrier formulation suitable for various routes of administration can be the same or similar to that described for RITUXAN™. See, Physicians' Desk Reference (Medical Economics Company, Inc., Montvale, N.J., 2005), pp. 958-960 and 1354-1357, which is incorporated herein by reference in its entirety. In certain embodiments of the invention, the anti-CD19 antibody compositions are formulated for intravenous administration with sodium chloride, sodium citrate dihydrate, polysorbate 80, and sterile water where the pH of the composition is adjusted to approximately 6.5. Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catheterization of lymphatic vessels, also provide a useful means of treating B cell lymphomas or autoimmune diseases or disorders. In preferred embodiments, anti-CD19 antibodies of the compositions and methods of the invention are self-administered subcutaneously. In such preferred embodiments, the composition is formulated as a lyophilized drug or in a liquid buffer (e.g., PBS and/or citrate) at about 50 mg/mL.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration are typically sterile. This is readily accomplished by filtration through sterile filtration membranes.

Sustained-release preparations may be prepared. Suitable examples of sustained-release preparations include semipermeable matrices of solid hydrophobic polymers containing the anti-CD19 antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. In certain embodiments, the pharmaceutically acceptable carriers used in the compositions of the invention do not affect human ADCC or CDC.

The anti-CD19 antibody compositions disclosed herein may also be formulated as immunoliposomes. A "liposome" is a small vesicle composed of various types of lipids, phospholipids and/or surfactant which is useful for delivery of a drug (such as the anti-CD19 antibodies disclosed herein) to a human. The components of the liposome are commonly arranged in a bilayer formation, similar to the lipid arrangement of biological membranes. Liposomes containing the antibodies of the invention are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. The antibody of the present invention can be conjugated to the liposomes as described in Martin et al., *J. Biol. Chem.*, 257: 286-288 (1982) via a disulfide interchange reaction. A therapeutic agent can also be contained within the liposome. See, Gabizon et al., *J. National Cancer Inst.*, (19)1484 (1989).

Some of the preferred pharmaceutical formulations include, but are not limited to:

(a) A sterile, preservative-free liquid concentrate for intravenous (i.v.) administration of anti-CD19 antibody, supplied at a concentration of 10 mg/ml in either 100 mg (10 mL) or 500 mg (50 mL) single-use vials. The product can be formulated for i.v. administration using sodium chloride, sodium citrate dihydrate, polysorbate and sterile water for injection. For example, the product can be formulated in 9.0 mg/mL sodium chloride, 7.35 mg/mL sodium citrate dihydrate, 0.7 mg/mL polysorbate 80, and sterile water for injection. The pH is adjusted to 6.5.

(b) A sterile, lyophilized powder in single-use glass vials for subcutaneous (s.c.) injection. The product can be formulated with sucrose, L-histidine hydrochloride monohydrate, L-histidine and polysorbate 20. For example, each single-use vial can contain 150 mg anti-CD19 antibody, 123.2 mg sucrose, 6.8 mg L-histidine hydrochloride monohydrate, 4.3 mg L-histidine, and 3 mg polysorbate 20. Reconstitution of the single-use vial with 1.3 ml sterile water for injection yields approximately 1.5 ml solution to deliver 125 mg per 1.25 ml (100 mg/ml) of antibody.

(c) A sterile, preservative-free lyophilized powder for intravenous (IV) administration. The product can be formulated with α-trehalose dihydrate, L-histidine HCl, histidine and polysorbate 20 USP. For example, each vial can contain 440 mg anti-CD19 antibody, 400 mg α,α-trehalose dihydrate, 9.9 mg L-histidine HCl, 6.4 mg L-histidine, and 1.8 mg polysorbate 20, USP. Reconstitution with 20 ml of bacteriostatic water for injection (BWFI), USP, containing 1.1% benzyl alcohol as a preservative, yields a multi-dose solution containing 21 mg/ml antibody at a pH of approximately 6.

(d) A sterile, lyophilized powder for intravenous infusion in which the anti-CD19 antibody is formulated with sucrose, polysorbate, monobasic sodium phosphate monohydrate, and dibasic sodium phosphate dihydrate. For example, each single-use vial can contain 100 mg antibody, 500 mg sucrose, 0.5 mg polysorbate 80, 2.2 mg monobasic sodium phosphate monohydrate, and 6.1 mg dibasic sodium phosphate dihydrate. No preservatives are present. Following reconstitution with 10 ml sterile water for injection, USP, the resulting pH is approximately 7.2.

(e) A sterile, preservative-free solution for subcutaneous administration supplied in a single-use, 1 ml pre-filled syringe. The product can be formulated with sodium chloride, monobasic sodium phosphate dihydrate, dibasic sodium phosphate dihydrate, sodium citrate, citric acid monohydrate, mannitol, polysorbate 80 and water for injection, USP. Sodium hydroxide may be added to adjust pH to about 5.2. For example, each syringe can be formulated to deliver 0.8 ml (40 mg) of drug product. Each 0.8 ml contains 40 mg anti-CD19 antibody, 4.93 mg sodium chloride, 0.69 mg monobasic sodium phosphate dihydrate, 1.22 mg dibasic sodium phosphate dihydrate, 0.24 mg sodium citrate, 1.04 citric acid monohydrate, 9.6 mg mannitol, 0.8 mg polysorbate 80 and water for injection, USP.

(f) A sterile, preservative-free, lyophilized powder contained in a single-use vial that is reconstituted with sterile water for injection (SWFI), USP, and administered as a subcutaneous (s.c.) injection. The product can be formulated with sucrose, histidine hydrochloride monohydrate, L-histidine, and polysorbate. For example, a 75 mg vial can contain 129.6 mg or 112.5 mg of the anti-CD19 antibody, 93.1 mg sucrose, 1.8 mg L-histidine hydrochloride monohydrate, 1.2 mg L-histidine, and 0.3 mg polysorbate 20, and is designed to deliver 75 mg of the antibody in 0.6 ml after reconstitution with 0.9 ml SWFI, USP. A 150 mg vial can contain 202.5 mg or 175 mg anti-CD19 antibody, 145.5 mg sucrose, 2.8 mg L-histidine hydrochloride monohydrate, 1.8 mg L-histidine, and 0.5 mg polysorbate 20, and is designed to deliver 150 mg of the antibody in 1.2 ml after reconstitution with 1.4 ml SWFI, USP.

(g) A sterile, hyophilized product for reconstitution with sterile water for injection. The product can be formulated as single-use vials for intramuscular (IM) injection using mannitol, histidine and glycine. For example, each single-use vial can contain 100 mg antibody, 67.5 mg of mannitol, 8.7 mg histidine and 0.3 mg glycine, and is designed to deliver 100 mg antibody in 1.0 ml when reconstituted with 1.0 ml sterile water for injection. Alternatively, each single-use vial can contain 50 mg antibody, 40.5 mg mannitol, 5.2 mg histidine and 0.2 mg glycine, and is designed to deliver 50 mg of antibody when reconstituted with 0.6 ml sterile water for injection.

(h) A sterile, preservative-free solution for intramuscular (IM) injection, supplied at a concentration of 100 mg/ml. The product can be formulated in single-use vials with histidine, glycine, and sterile water for injection. For example, each single-use vial can be formulated with 100 mg antibody, 4.7 mg histidine, and 0.1 mg glycine in a volume of 1.2 ml designed to deliver 100 mg of antibody in 1 ml. Alternatively, each single-use vial can be formulated with 50 mg antibody, 2.7 mg histidine and 0.08 mg glycine in a volume of 0.7 ml or 0.5 ml designed to deliver 50 mg of antibody in 0.5 ml.

In certain embodiments, the pharmaceutical composition of the invention is stable at 4° C. In certain embodiments, the pharmaceutical composition of the invention is stable at room temperature.

5.4.2. Antibody Half-Life

In certain embodiments, the half-life of an anti-CD19 antibody of the compositions and methods of the invention is at least about 4 to 7 days. In certain embodiments, the mean half-life of the anti-CD19 antibody of the compositions and methods of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments the half-life of an anti-CD19 antibody of the compositions and methods of the invention can be up to about 50 days. In certain embodiments, the half-lives of the antibodies of the compositions and methods of the invention can be prolonged by methods known in the art. Such prolongation can in turn reduce the amount and/or frequency of dosing of the antibody compositions of the invention. Antibodies with improved in vivo half-lives and methods for preparing them are disclosed in U.S. Pat. No. 6,277,375; and International Publication Nos. WO 98/23289 and WO 97/3461.

The serum circulation of the anti-CD19 antibodies of the invention in vivo may also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein.

Plasma half-life of the antibodies of the compositions may be prolonged by altering the amino acid sequence of the antibody by introducing one or more changes in the heavy and/or light chain gene nucleic acid sequence to produce the desired amino acid change. Such changes could include but are not limited to changes in the variable region framework regions and/or in the Fc constant region. The techniques for altering antibody gene sequences are well known in the art.

Further, the antibodies of the compositions and methods of the invention can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413, 622, all of which are incorporated herein by reference.

5.4.3. Administration and Dosing

In accordance with the present invention, each of the methods of administration and doses described herein can be used in the anti-CD19 immunotherapy protocols described below.

Administration of the compositions of the invention to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intrapleural, intracerebral, intra-arterial, intraperitoneal, oral, intralymphatic, intranasal, rectal or vaginal administration, by perfusion through a regional catheter, or by direct intralesional injection. In a preferred embodiment, the compositions of the invention are administered by intravenous push or intravenous infusion given over defined period (e.g., 0.5 to 2 hours). The compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection given in one or more sites (e.g. thigh, waist, buttocks, arm), optionally once or twice weekly. In one embodiment, the compositions, and/or methods of the invention are administered on an outpatient basis.

In certain embodiments, the dose of a composition comprising anti-CD19 antibody is measured in units of mg/kg of patient body weight. In other embodiments, the dose of a composition comprising anti-CD19 antibody is measured in units of mg/kg of patient lean body weight (i.e., body weight minus body fat content). In yet other embodiments, the dose of a composition comprising anti-CD19 antibody is measured in units of mg/m$^2$ of patient body surface area. In yet other embodiments, the dose of a composition comprising anti-CD19 antibody is measured in units of mg per dose administered to a patient. Any measurement of dose can be used in conjunction with the compositions and methods of the invention and dosage units can be converted by means standard in the art.

Those skilled in the art will appreciate that dosages can be selected based on a number of factors including the age, sex, species and condition of the subject (e.g., stage of B cell malignancy or activity of autoimmune disease or disorder), physical condition of the transplant recipient or donor, the desired degree of cellular or autoimmune antibody depletion, the disease to be treated and/or the particular antibody or antigen-binding fragment being used and can be determined by one of skill in the art.

In certain embodiments, the particular dosages will vary depending on whether the regimen is indicated for pre-transplant conditioning, post-transplant maintenance, or post-transplant treatment of an acute or chronic rejection. For example, a higher dose may be required for the treatment of an active rejection episode than that required for pre-transplant conditioning or post-transplant maintenance regimens. In certain embodiments, the particular dosages chosen for pre- or post-transplant prophylaxis may also be affected by factors such as whether the patient is assessed as being at a high, intermediate, or low risk of developing a humoral response. For example, a patient at high risk for developing a humoral immune response may require a higher prophylactic dose than a patient assessed as being at low risk. In other embodiments, additional factors affecting dose may include whether there are clinical indications of an early or a late stage humoral rejection. For example, a lower dose may be required for treatment of an early stage rejection, such as a latent, silent, or preclinical humoral response, while a higher dose may be required to treat a more advanced stage of rejection, such as one exhibiting indications of graft dysfunction. In certain embodiments, the particular dosages chosen will vary depending on whether the anti-CD19 antibody compositions of the invention comprise or are used in combination with a therapeutic regimen for the treatment or prevention of GVHD, graft rejection, or post-transplant lymphoproliferative disorder. In a particular embodiment, a lower dose is used when the anti-CD19 antibody compositions of the invention are used in combination with one or more other therapeutic agents. In a preferred embodiment, the dose of one or more other therapeutic agents used in combination with the antibodies and compositions of the invention is lower than the dose that would otherwise be required.

Effective amounts of the compositions of the invention may be extrapolated from dose-response curves derived from in vitro test systems or from animal model (e.g., the cotton rat or monkey or GVHD or rejection) test systems. Models and methods for evaluation of the effects of antibodies are known in the art (Wooldridge et al., *Blood,* 89(8): 2994-2998 (1997), Sato et al., *Mol Immunol.* 42(7):821-831 (2005), Liu et al., *Arthritis Rheum.* 50(6):1884-1896 (2004), Nanki et al., *J Immunol.* 173(11):7010-7016 (2004), incorporated by reference herein in its entirety). In certain embodiments, for a particular B cell malignancy or an autoimmune disease or disorder, therapeutic regimens standard in the art for antibody therapy can be used with the compositions and methods of the invention.

Similarly, for certain embodiments in which a particular regimen such as pre-transplant conditioning, post-transplant maintenance, or post-transplant treatment of an acute or chronic rejection, therapeutic regimens standard in the art for antibody therapy can be used with the compositions and methods of the invention. In one embodiment, the regimen is a pre-transplant conditioning regimen and the compositions and methods of the invention are used to condition the recipient or the graft, or both the graft and the recipient.

Examples of dosing regimens that can be used in the methods of the invention include, but are not limited to, daily, three times weekly (intermittent), weekly, or every 14 days. In certain embodiments, dosing regimens include, but are not limited to, monthly dosing or dosing every 6-8 weeks.

Those skilled in the art will appreciate that dosages are generally higher and/or frequency of administration greater for initial treatment as compared with maintenance regimens.

In embodiments of the invention, the anti-CD19 antibodies bind to B cells and, thus, can result in more efficient (i.e., at lower dosage) depletion of B cells (as described herein). Higher degrees of binding may be achieved where the density of human CD19 on the surface of a patient's B cells is high. In exemplary embodiments, dosages of the antibody (optionally in a pharmaceutically acceptable carrier as part of a pharmaceutical composition) are at least about 0.0005, 0.001, 0.05, 0.075, 0.1, 0.25, 0.375, 0.5, 1, 2.5, 5, 10, 20, 37.5, or 50 mg/m$^2$ and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.1, 0.075 or 0.01 mg/m$^2$. In certain embodiments, the dosage is between about 0.0005 to about 200 mg/m$^2$, between about 0.001 and 150 mg/m$^2$, between about 0.075 and 125 mg/m$^2$, between about 0.375 and 100 mg/m$^2$, between about 2.5 and 75 mg/m$^2$, between about 10 and 75 mg/m$^2$, and between about 20 and 50 mg/m$^2$. In related embodiments, the dosage of anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of anti-CD19 antibody used is at least about 1 to 20, 3 to 15, or 5 to 10 mg/kg of body weight of a patient. In preferred embodiments, the dose of anti-CD19 antibody used is at least about 5, 6, 7, 8, 9, or 10 mg/kg of body weight of a patient. In certain embodiments, a single dosage unit of the antibody (optionally in a pharmaceutically acceptable carrier as part of a pharmaceutical composition) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250, 300, 350, 375, or 1500 micrograms/m$^2$. In other embodiments, dose is up to 1 g per single dosage unit.

All of the above doses are exemplary and can be used in conjunction with the compositions and methods of the invention, however where an anti-CD19 antibody is used in conjunction with a toxin or radiotherapeutic agent the lower doses described above are preferred. In certain embodiments, where the patient has low levels of CD19 density, the lower doses described above are preferred.

Similarly, where an anti-CD19 antibody is used in conjunction with a toxin, a radiotherapeutic, an immunosuppressive agent or an antilymphocytic agent, the lower doses described above are preferred. In certain embodiments, where the patient has low levels of CD19 density, the lower doses described above are preferred. In a preferred embodiment, the inclusion of one or more anti-CD19 antibody compositions of the invention in a therapeutic regimen comprising one or more immunosuppressive agents requires a lower dose of the one or more immunosuppressive agents than the dose required in the absence of the anti-CD19 antibody compositions.

In certain embodiments of the invention where chimeric anti-CD19 antibodies are used, the dose or amount of the chimeric antibody is greater than about 2, 3, 4, 5, 6, 7, 8, 9, 10, 11, 12, 13, 14, 15, or 16 mg/kg of patient body weight. In other embodiments of the invention where chimeric anti-CD19 antibodies are used, the dose or amount of the chimeric antibody is less than about 1, 0.9, 0.8, 0.7, 0.6, 0.5, 0.4, 0.3, 0.2, or 0.1 mg/kg of patient body weight.

In some embodiments of the methods of this invention, antibodies and/or compositions of this invention can be administered at a dose lower than about 375 mg/m$^2$; at a dose lower than about 37.5 mg/m$^2$; at a dose lower than about 0.375 mg/m$^2$; and/or at a dose between about 0.075 mg/m$^2$ and about 125 mg/m$^2$. In preferred embodiments of the methods of the invention, dosage regimens comprise low doses, administered at repeated intervals. For example, in one embodiment, the compositions of the invention can be administered at a dose lower than about 375 mg/m$^2$ at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days.

The specified dosage can result in B cell depletion in the human treated using the compositions and methods of the invention for a period of at least about 1, 2, 3, 5, 7, 10, 14, 20, 30, 45, 60, 75, 90, 120, 150, or 180 days or longer. In certain embodiments, pre-B cells (not expressing surface immunoglobulin) are depleted. In certain embodiments, mature B cells (expressing surface immunoglobulin) are depleted. In other embodiments, all non-malignant types of B cells can exhibit depletion. Any of these types of B cells can be used to measure B cell depletion. B cell depletion can be measured in bodily fluids such as blood serum, or in tissues such as bone marrow. In preferred embodiments of the methods of the invention, B cells are depleted by at least 30%, 40%, 50%, 60%, 70%, 80%, 90%, or 100% in comparison to B cell levels in the patient being treated before use of the compositions and methods of the invention. In preferred embodiments of the methods of the invention, B cells are depleted by at least 30%, 40%, 50%, 60%, 70%, 80%, 90%, or 100% in comparison to typical standard B cell levels for humans. In related embodiments, the typical standard B cell levels for humans are determined using patients comparable to the patient being treated with respect to age, sex, weight, and other factors.

In certain embodiments of the invention, a dosage of about 125 mg/m$^2$ or less of an antibody or antigen-binding fragment results in B cell depletion for a period of at least about 7, 14, 21, 30, 45, 60, 90, 120, 150, or 200 days. In another representative embodiment, a dosage of about 37.5 mg/m$^2$ or less depletes B cells for a period of at least about 7, 14, 21, 30, 45, 60, 90, 120, 150, or 200 days. In still other embodiments, a dosage of about 0.375 mg/m$^2$ or less results in depletion of B cells for at least about 7, 14, 21, 30, 45 or 60 days. In another embodiment, a dosage of about 0.075 mg/m$^2$ or less results in depletion of B cells for a period of at least about 7, 14, 21, 30, 45, 60, 90, 120, 150, or 200 days. In yet other embodiments, a dosage of about 0.01 mg/m$^2$, 0.005 mg/m$^2$ or even 0.001 mg/m$^2$ or less results in depletion of B cells for at least about 3, 5, 7, 10, 14, 21, 30, 45, 60, 90, 120, 150, or 200 days. According to these embodiments, the dosage can be administered by any suitable route, but is optionally administered by a subcutaneous route.

As another aspect, the invention provides the discovery that B cell depletion and/or treatment of B cell disorders can be achieved at lower dosages of antibody or antibody fragments than employed in currently available methods. Thus, in another embodiment, the invention provides a method of depleting B cells and/or treating a B cell disorder, or preventing GVHD, humoral rejection, or post-transplant lymphoproliferative disorder, comprising administering to a human an effective amount of an antibody that specifically binds to CD19, wherein a dosage of about 500, 475, 450, 425, 400, 375, 350, 325, 300, 275, 250, 225, 200, 175, 150, 125, 100, 75, 60, 50, 37.5, 20, 10, 5, 2.5, 1, 0.5, 0.375, 0.25, 0.1, 0.075, 0.05, 0.001, 0.0005 mg/m$^2$ or less results in a depletion of B cells (circulating and/or tissue B cells) and/or a depletion of circulating immunoglobulin of at least 25%, 35%, 50%, 60%, 75%, 80%, 85%, 90%, 95%, 98% or more for a period at least about 3, 5, 7, 10, 14, 21, 30, 45, 60, 75, 90, 120, 150, 180, or 200 days or longer. In representative embodiments, a dosage of about 125 mg/m$^2$ or 75 mg/m$^2$ or less results in at least about 50%, 75%, 85% or 90% depletion of B cells and/or a depletion of circulating immunoglobulin for at least about 7, 14, 21, 30, 60, 75, 90, 120, 150 or 180 days. In other embodiments, a dosage of about 50, 37.5 or 10 mg/m$^2$ results in at least about a 50%, 75%, 85% or 90% depletion of B cells and/or a depletion of circulating immunoglobulin for at least about 7, 14, 21, 30, 60, 75, 90, 120 or 180 days. In still other embodiments, a dosage of about 0.375 or 0.1 mg/m$^2$ results in at least about a 50%, 75%, 85% or 90% depletion of B cells and/or a depletion of circulating immunoglobulin for at least about 7, 14, 21, 30, 60, 75 or 90 days. In further embodiments, a dosage of about 0.075, 0.01, 0.001, or 0.0005 mg/m$^2$ results in at least about a 50%, 75%, 85% or 90% depletion of B cells and/or a depletion of circulating immunoglobulin for at least about 7, 14, 21, 30, or 60 days.

In certain embodiments of the invention, the dose can be escalated or reduced to maintain a constant dose in the blood or in a tissue, such as, but not limited to, bone marrow. In related embodiments, the dose is escalated or reduced by about 2%, 5%, 8%, 10%, 15%, 20%, 30%, 40%, 50%, 60%, 70%, 80%, 90%, and 95% in order to maintain a desired level of the antibody of the compositions and methods of the invention.

In certain embodiments, the invention provides a method of depleting B cells and/or a method of depleting immunoglobulin (Ig) and/or treating or preventing GVHD or humoral rejection, comprising contacting a graft ex vivo with an amount of one or more of the anti-CD19 antibody compositions of the invention sufficient to deplete B cells and/or Ig from the graft.

In certain embodiments, the dosage can be adjusted and/or the infusion rate can be reduced based on patient's immunogenic response to the compositions and methods of the invention.

According to one aspect of the methods of the invention, a loading dose of the anti-CD19 antibody and/or composition of the invention can be administered first followed by a maintenance dose until the B cell malignancy or autoimmune disease or disorder being treated progresses or is followed by a defined treatment course (e.g., CAMPATH™, MYLOTARG™, or RITUXAN™, the latter of which allow patients to be treated for a defined number of doses that has increased as additional data have been generated).

In another aspect of the methods of the invention, a loading dose of the anti-CD19 antibody and/or composition of the invention can be administered first followed by a maintenance dose which is administered until the GVHD, rejection episode, or post-transplantation lymphoproliferative disorder being treated is ameliorated. In one embodiment, the loading dose and/or maintenance dose of the anti-CD19 antibody and/or composition of the invention is followed by a defined treatment course comprising one or more immunosuppressive agents or therapies.

According to another aspect of the methods of the invention, a patient may be pretreated with the compositions and methods of the invention to detect, minimize immunogenic response, or minimize adverse effects of the compositions and methods of the invention. In some embodiments, the patient is a transplant recipient who may be pretreated with the compositions and methods of the invention to desensitize, minimize immunogenic response, or minimize adverse effects of the compositions and methods of the invention.

5.4.4. Toxicity Testing

The tolerance, toxicity and/or efficacy of the compositions and/or treatment regimens of the present invention can be determined by standard pharmaceutical procedures in cell cultures or experimental animals, e.g., for determining the LD50 (the dose lethal to 50% of the population), the ED50 (the dose therapeutically effective in 50% of the population), and IC50 (the dose effective to achieve a 50% inhibition). In a preferred embodiment, the dose is a dose effective to achieve at least a 60%, 70%, 80%, 90%, 95%, or 99% depletion of circulating B cells or circulating immunoglobulin, or both. The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to CD19-expressing cells in order to minimize potential damage to CD19-negative cells and, thereby, reduce side effects.

Data obtained from the cell culture assays and animal studies can be used in formulating a range of dosages of the compositions and/or treatment regimens for use in humans. The dosage of such agents lies preferably within a range of circulating concentrations that include the ED50 with little or no toxicity. The dosage may vary within this range depending upon the dosage form employed and the route of administration utilized. For any therapy used in the methods of the invention, the therapeutically effective dose can be estimated by appropriate animal models. Depending on the species of the animal model, the dose is scaled for human use according to art-accepted formulas, for example, as provided by Freireich et al., Quantitative comparison of toxicity of anticancer agents in mouse, rat, monkey, dog, and human, *Cancer Chemotherapy Reports*, NCI-1966 40:219-244. Data obtained from cell culture assays can be useful for predicting potential toxicity. Animal studies can be used to formulate a specific dose to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma drug levels may be measured, for example, by high performance liquid chromatography, ELISA, or by cell-based assays.

5.5. Patient Diagnosis and Therapeutic Regimens

Oncology

According to certain aspects of the invention, the treatment regimen and dose used with the compositions and methods of the invention is chosen based on a number of factors including, but not limited to, the stage of the B cell disease or disorder being treated. Appropriate treatment regimens can be determined by one of skill in the art for particular stages of a B cell disease or disorder in a patient or patient population. Dose response curves can be generated using standard protocols in the art in order to determine the effective amount of the compositions of the invention for treating patients having different stages of a B cell or disease or disorder. In general, patients having more advanced stages of a B cell disease or disorder will require higher doses and/or more frequent doses which may be administered over longer periods of time in comparison to patients having an early stage B cell disease or disorder.

The anti-CD19 antibodies, compositions and methods of the invention can be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

The inventors have shown that the inventive antibodies and compositions can deplete mature B cells. Thus, as another aspect, the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include, but are not limited to, acute lymphoblastic leukemia. In other particular embodiments, the invention can be practiced to treat extranodal tumors.

Autoimmune Diseases or Disorders

In other aspects of the invention, the treatment regimen and dose used with the compositions and methods of the invention is chosen based on a number of factors including, but not limited to, the stage of the autoimmune disease or disorder being treated. Appropriate treatment regimens can be determined by one of skill in the art for particular stages of a autoimmune disease or disorder in a patient or patient population. Dose response curves can be generated using standard protocols in the art in order to determine the effective amount of the compositions of the invention for treating patients having different stages of a autoimmune disease or disorder. In general, patients having more activity of a autoimmune disease or disorder will require higher doses and/or more frequent doses which may be administered over longer periods of time in comparison to patients having less activity of an autoimmune disease or disorder.

The anti-CD19 antibodies, compositions and methods of the invention can be practiced to treat an autoimmune disease or disorder. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders include, but are not limited to: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, eosinophilic fascites, fibromyalgia-fibromyositis, glomerulonephritis, Graves' disease, Guillain-Barre, Hashimoto's thyroiditis, Henoch-Schönlein purpura, idiopathic pulmonary fibrosis, idiopathic/autoimmune thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiffman syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome and chronic inflammation resulting from chronic viral or bacteria infections.

CD19 is expressed on mature B cells as well as earlier in B cell development than, for example, CD20, and is therefore particularly suited for depleting pre-B cells and immature B cells (i.e., do not express Ig on the cell surface), for example, in the bone marrow.

Transplantation

According to certain aspects of the invention, the treatment regimen and dose used with the compositions and methods of the invention is chosen based on a number of factors including, for example, clinical manifestation that place a patient at risk for developing a humoral rejection, or clinical evidence that such a rejection is developing. The terms "humoral" and "antibody-mediated" are used interchangeably herein.

The criteria for assessing the risk that a patient will develop a humoral rejection are established according to the knowledge and skill in the art. In one embodiment, a positive complement dependent cytotoxicity or antiglobulin enhanced complement dependent cytotoxicity crossmatch indicates that a patient is at high risk for humoral rejection. In one embodiment, a positive crossmatch or a prior positive complement dependent cytotoxicity or anti-globulin enhanced complement dependent cytotoxicity crossmatch indicates that a patient is at an intermediate risk for humoral rejection. In one embodiment, a negative crossmatch indicates that a patient is at a low risk for humoral rejection.

Appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for an acute or a chronic rejection. In certain embodiments, the particular regimen is varied for a patient who is assessed as being at a high or intermediate risk of developing a humoral response, compared with the regimen for a patient who is assessed as being at a low risk of developing a humoral response.

In certain embodiments, the particular regimen is varied according to the stage of humoral rejection, with more aggressive therapy being indicated for patients at later stages of rejection. The stages of humoral rejection may be classified according to the knowledge and skill in the art. For example, the stages of humoral rejection may be classified as one of stages I to IV according to the following criteria: Stage I Latent Response, characterized by circulating anti-donor alloantibodies, especially anti-HLA antibodies; Stage II Silent Reaction, characterized by circulating anti-donor alloantibodies, especially anti-HLA antibodies, and C4d deposition, but without histologic changes or graft dysfunction; Stage III Subclinical Rejection: characterized by circulating anti-donor alloantibodies, especially anti-HLA antibodies, C4d deposition, and tissue pathology, but without graft dysfunction; Stage IV Humoral Rejection: characterized by circulating anti-donor alloantibodies, especially anti-HLA antibodies, C4d deposition, tissue pathology, and graft dysfunction.

Dose response curves can be generated using standard protocols in the art in order to determine the effective amount of the compositions of the invention for use in a particular regimen, for example, in conditioning regimens prior to transplantation, and in post-transplantation regimens for prophylaxis and treatment of GVHD, humoral rejection, or post-transplantation lymphoproliferative disorders. In general, patients at high risk for developing a humoral rejection and those already exhibiting one or more clinical indicators of rejection will require higher doses and/or more frequent doses which may be administered over longer periods of time in comparison to patients who are not at high risk or who do not exhibit any indications of active rejection.

The anti-CD19 antibodies, compositions and methods of the invention can be practiced to treat or prevent GVHD, humoral rejection, or post-transplantation lymphoproliferative disorders, either alone or in combination with other therapeutic agents or treatment regimens. Other therapeutic regimens for the treatment or prevention of GVHD, humoral rejection, or post-transplantation lymphoproliferative disorders may comprise, for example, one or more of anti-lymphocyte therapy, steroid therapy, antibody depletion therapy, immunosuppression therapy, and plasmapheresis.

Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell surface antigens. Examples of such antibodies include, without limitation, OKT3™ (muromonab-CD3), CAMPATH™-1H (alemtuzumab), CAMPATH™-1G, CAMPATH™-1M, SIMULECT™ (basiliximab), and ZENAPAX™ (daclizumab). In a specific embodiment, the anti-lymphocyte therapy comprises one or more additional antibodies directed against B cells, including, without limitation, RITUXAN™ (rituximab).

Steroid therapy may comprise administration to the transplant recipient of one or more steroids selected from the group consisting of cortisol, prednisone, methyl prednisolone, dexamethazone, and indomethacin. Preferably, one or more of the steroids are corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies, anti-CD19 antibodies, anti-CD20 antibodies, and anti-CD22 antibodies.

Immunosuppression therapy may comprise the administration of one or more immunosuppressive agents such as inhibitors of cytokine transcription (e.g., cyclosporin A, tacrolimus), nucleotide synthesis (e.g., azathioprine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with the compositions and methods of the invention includes one or more of the following: adriamycin, azathioprine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-05 antibody, or a small molecule inhibitor of C1s, for example as described in Buerke et al. (*J. Immunol.*, 2001 167:5375-80).

In one embodiment, the compositions and methods of the invention are used in combination with one or more therapeutic regimens for suppressing humoral rejection, including, without limitation, tacrolimus and mycophenolate mofetil therapy, immunoadsorption, intravenous immunoglobulin therapy, and plasmapheresis.

5.5.1. Diagnosis and Staging of B Cell Malignancies

The progression of cancer, such as a B cell disease or disorder capable of tumor formation (e.g., non-Hodgkin lymphoma, diffuse large B cell lymphoma, follicular lymphoma, and Burkitt lymphoma) is typically characterized by the degree to which the cancer has spread through the body and is often broken into the following four stages which are prognostic of outcome. Stage I: The cancer is localized to a particular tissue and has not spread to the lymph nodes. Stage II: The cancer has spread to the nearby lymph nodes, i.e., metastasis. Stage III: The cancer is found in the lymph nodes in regions of the body away from the tissue of origin and may comprise a mass or multiple tumors as opposed to one. Stage IV: The cancer has spread to a distant part of the body. The stage of a cancer can be determined by clinical observations and testing methods that are well known to those of skill in the art. The stages of cancer described above are traditionally used in conjunction with clinical diagnosis of cancers characterized by tumor formation, and can be used in conjunction with the compositions and methods of the present invention to treat B cell diseases and disorders. Typically early stage disease means that the disease remains localized to a portion of a patient's body or has not metastasized.

With respect to non-tumor forming B cell diseases and disorders such as but not limited to multiple myeloma, the criteria for determining the stage of disease differs. The Durie-Salmon Staging System has been widely used. In this staging system, clinical stage of disease (stage I, II, or III) is based on several measurements, including levels of M protein, the number of lytic bone lesions, hemoglobin values, and serum calcium levels. Stages are further divided according to renal (kidney) function (classified as A or B). According to the Durie-Salmon Staging System Stage I (low cell mass) is characterized by all of the following: Hemoglobin value >10 g/dL; Serum calcium value normal or ≤12 mg/dL; Bone x-ray, normal bone structure (scale 0) or solitary bone plasmacytoma only; and Low M-component production rate: IgG value <5 g/dL, IgA value <3 g/d, Bence Jones protein <4 g/24 h. Stage I patients typically have no related organ or tissue impairment or symptoms. Stage II (intermediate cell mass) is characterized by fitting neither stage I nor stage III. Stage III (high cell mass) is characterized by one or more of the following: Hemoglobin value <8.5 g/dL; Serum calcium value >12 mg/dL; Advanced lytic bone lesions (scale 3); High M-component production rate: IgG value >7 g/dL, IgA value >5 g/dL, Bence Jones protein >12 g/24 h Subclassification (either A or B), where A is Relatively normal renal function (serum creatinine value <2.0 mg/dL) and B is Abnormal renal function (serum creatinine value ≥2.0 mg/dL).

Another staging system for myeloma is the International Staging System (ISS) for myeloma. This system can more effectively discriminate between staging groups and is based on easily measured serum levels of beta 2-microglobulin ($\beta$2-M) and albumin. According to the ISS for myeloma, Stage I is characterized by $\beta$2-M <3.5 and Albumin ≥3.5, Stage II is characterized by $\beta$2-M <3.5 and albumin <3.5 or $\beta$2-M 3.5-5.5, and Stage III is characterized by $\beta$2-M >5.5 (Multiple Myeloma Research Foundation, New Canaan, Conn.).

The stage of a B cell malignancy in a patient is a clinical determination. As indicated above, with respect to solid tumors, the spread, location, and number of tumors are the primary factors in the clinical determination of stage. Determination of stage in patients with non-tumor forming B cell malignancies can be more complex requiring serum level measurements as described above.

The descriptions of stages of B cell diseases and disorders above are not limiting. Other characteristics known in the art for the diagnosis of B cell diseases and disorders can be used as criteria for patients to determine stages of B cell diseases or disorders.

5.5.2. Diagnosis of Autoimmune Diseases or Disorders

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of autoantibodies, elevated cytokine levels, specific organ dysfunction, skin rashes, joint swelling, pain, bone remodeling, and/or loss of movement as primarily indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using the compositions and methods of the invention.

5.5.3. Clinical Criteria for Diagnosing B Cell Malignancies

Diagnostic criteria for different B cell malignancies are known in the art. Historically, diagnosis is typically based on a combination of microscopic appearance and immunophenotype. More recently, molecular techniques such as gene-expression profiling have been applied to develop molecular definitions of B cell malignancies (see, e.g., Shaffer et al., *Nature* 2:920-932 (2002)). Exemplary methods for clinical diagnosis of particular B cell malignancies are provided below. Other suitable methods will be apparent to those skilled in the art.

5.5.3.1. Follicular NHL

In general, most NHL (with the exception of mantle-cell lymphoma) have highly mutated immunoglobulin genes that appear to be the result of somatic hypermutation (SHM). The most common genetic abnormalities in NHL are translocations and mutations of the BCL6 gene.

Follicular NHL is often an indolent B cell lymphoma with a follicular growth pattern. It is the second most common lymphoma in the United States and Western Europe. The median age at which this disease presents is 60 years and there is a slight female predominance. Painless lymphadenopathy is the most common symptom. Tests often indicate involvement of the blood marrow and sometimes the peripheral blood. Follicular NHL is divided into cytologic grades based on the proportion of large cells in the follicle with the grades forming a continuum from follicular small cleaved-cell to large-cell predominance. (See, S. Freedman, et al., *Follicular*

Lymphoma, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000)).

Most follicular NHL is characterized by a translocation between chromosomes 14 and 18 resulting in overexpression of BCL2. Follicular NHL is also characterized by both SHM and ongoing SHM and a gene expression profile similar to germinal center (GC) B cells (see, e.g., Shaffer et al., *Nature* 2:920-932 (2002)), which are the putative cells of origin for this malignancy. Heavy and light chain rearrangements are typical. The tumor cells of this disease express monoclonal surface immunoglobulin with most expressing IgM. Nearly all follicular NHL tumor cells express the antigens CD19, CD20, CD79a, CD21, CD35 and CD10 but lack expression of CD5 and CD43. Paratrabecular infiltration with small cleaved cells is observed in the bone marrow. (See, S. Freedman et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000)).

Diagnosis of follicular NHL generally relies on biopsy of an excised node in order to evaluate tissue architecture and cytological features. Fine-needle aspirations are usually not adequate since this procedure is less likely to provide tissue that can be evaluated and it fails to provide enough tissue for additional tests. Bilateral bone marrow biopsies are also indicated since involvement can be patchy. Additional diagnostic procedures include chest x-rays, chest, abdomen, neck and pelvis computed tomography (CT) scans, complete blood count, and chemistry profile. Flow cytometry and immunohistochemistry can be used to distinguish between follicular NHL and other mature B cell lymphomas. (See, S. Freedman et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000))

5.5.3.2. Mantle-Cell Lymphoma

Mantle-cell lymphoma localizes to the mantle region of secondary follicles and is characterized by a nodular and/or diffuse growth pattern. Mantle-cell lymphoma patients have median age of 60-65 years with the disease affecting predominantly males. For diagnostic purposes, the usual presenting feature is a generalized lymphadenopathy. Additionally, the spleen is often enlarged. This B cell lymphoma is associated with a t(11;14) between the IgH locus and cyclin D1 gene, which results in overexpression of cyclin D1. More than 50% of cases show additional chromosomal abnormalities. Mantle-cell lymphoma is typically not characterized by SHM. (See, W. Hiddemann et al., *Mantle Cell Lymphoma*, pp. 461-476, In *Non-Hodgkin's Lymphomas*, P. Mauch et al., eds., Lippincott Williams & Wilkins, Philadelphia, Pa. (2004); D. Weisenburger et al., *Mantle Cell Lymphoma*, pp. 28-41, In *Malignant Lymphoma*, B. Hancock et al., eds., Oxford University Press, New York, N.Y. (2000)).

Immunophenotyping (flow cytometry or frozen section) immunohistochemistry of mantle cell lymphoma cells shows them to nearly always be monoclonal, bearing surface IgM. Mantle cell lymphoma cells have also been noted to bear surface IgD. The cells express the antigens CD19, CD20, CD22 and CD24, but not CD23. They also express surface antigens CD5 but not for CD10, distinguishing them from true follicle center-cell lymphomas which are almost always CD5 negative. Frequently, extranodal involvement is found including bone marrow infiltration and tumors of the liver and gastrointestinal tract. Mild anemia and leukemic expression is not uncommon with mantle-cell lymphoma. (See, A. Lal et al., *Role of Fine Needle Aspiration in Lymphoma*, pp. 181-220, In W. Finn et al., eds., *Hematopathology in Oncology*, Kluwer Academic Publishers, Norwell, Mass. (2004); W. Hiddemann et al., *Mantle Cell Lymphoma*, pp. 461-476, In *Non-Hodgkin's Lymphomas*, P. Mauch et al., eds., Lippincott Williams & Wilkins, Philadelphia, Pa. (2004)).

Diagnosis of mantle-cell lymphoma involves examination of the peripheral blood as well as bone marrow and lymph node biopsies. In addition, cytogenetic studies and immunophenotyping are useful in differential diagnosis. (See, W. Hiddemann, et al., *Mantle Cell Lymphoma* pp. 461-476, In *Non-Hodgkin's Lymphomas*, P. Mauch, et al., eds., Lippincott Williams & Wilkins, Philadelphia, Pa. (2004); D. Weisenburger, et al., *Mantle Cell Lymphoma*, pp. 28-41, In *Malignant Lymphoma*, B. Hancock, et al., eds., Oxford University Press, New York, N.Y. (2000)).

5.5.3.3. Burkitt's Lymphoma

Burkitt's lymphoma is an aggressive B cell lymphoma typically observed in children and young adults and is usually associated with bulky disease of the jaw and/or abdomen. Approximately 20% of patients have bone marrow involvement. An endemic form of Burkitt's lymphoma involves Epstein-Barr virus (EBV) infection of malignant cells; the sporadic form is independent of EBV infection. A translocation of c-myc to immunoglobulin loci, which results in deregulation of the c-myc gene, is characteristic of this disease (t(8;14)(q24;q32)). Interestingly, deletions of the c-myc sequences appear to be involved in the sporadic form of the disease, while the endemic form usually involves point mutations or insertions. (See, V. Pappa, et al., *Molecular Biology*, pp. 133-157, In *Malignant Lymphoma*, B. Hancock, et al., eds., Oxford University Press, New York, N.Y. (2000)). Burkitt's lymphoma is also characterized by SHM, and the malignant cells have a gene expression profile similar to GC B cells, suggesting that this malignancy is derived from GC B cells.

Immunophenotype of Burkett's lymphoma shows the cells of this disease express CD19, CD20, CD22, and CD79a, but not CD5, CD23, cyclin D or terminal deoxynucleotidyl transferase. Frequently, these cells are positive for CD10 and BCL6 and usually negative for BCL2. (See, I. Magrath, et al., *Burkitt's Lymphoma*, pp. 477-501, In *Non-Hodgkin's Lymphomas*, P. Mauch, et al., eds., Lippincott Williams & Wilkins, Philadelphia, Pa. (2004)).

High grade B cell Burkitt's-like lymphoma is a lymphoma borderline between Burkitt's lymphoma and large B cell lymphoma. The cells of this lymphoma express CD19 and CD20 but expression of CD10, which is nearly always present in true Burkitt's lymphoma, is frequently absent. Because of this and other characteristics, some believe this lymphoma should be classified as a diffuse large B cell lymphoma. (See, K. Maclennan, *Diffuse Aggressive B cell Lymphoma*, pp. 49-54, In *Malignant Lymphoma*, B. Hancock, et al., eds., Oxford University Press, New York, N.Y. (2000)).

Diagnosis of Burkitt's lymphoma generally relies on detection of the translocation associated with this lymphoma; thus, conventional cytogenetic analysis is usually performed. Long distance polymerase chain reaction techniques and fluorescent in situ hybridization (FISH) have been used to detect Ig-myc junctions in the translocations and other genetic alterations associated with this disease. (See, R. Siebert, et al., *Blood* 91:984-990 (1998); T. Denyssevych, et al., *Leukemia*, 16:276-283 (2002)).

5.5.3.4. Diffuse Large B Cell Lymphoma (DLBCL)

DLBCL is the most common non-Hodgkin's lymphoma and can arise from small B cell lymphoma, follicular lymphoma or marginal zone lymphoma. Typically, patients present with lymphadenopathy; however, a large percent of patients present in extranodal sites as well, with gastrointestinal involvement being the most common. Bone marrow involvement is observed in about 15% of patients. (See, Armitage, et al., *Diffuse Large B cell Lymphoma*, pp. 427-453, In *Non-Hodgkin's Lymphomas*, P. Mauch, et al., eds., Lippincott Williams & Wilkins, Philadelphia, Pa. (2004)). Heterogeneity in clinical, biological and morphological characteristics makes this group of lymphomas difficult to subclassify. However, two distinct subgroups have been identified with one expressing genes characteristic of germinal center B cells (GC-DLBCL) and the other overexpressing genes in peripheral blood B cells. Survival rates are significantly better for patients with GC-DLBCL than those with activated B cell type (ABC)-DLBCL. (See, W. Chan, *Archives of Pathology and Laboratory Medicine* 128(12): 1379-1384 (2004)).

DLBCLs express the cell surface antigens CD19, CD20, CD22, and CD79a. CD10 is expressed in the large majority of cases and CD5 expression is observed in about 10% of cases. (See, K. Maclennan, *Diffuse Aggressive B cell Lymphoma*, pp. 49-54, In *Malignant Lymphoma*, B. Hancock, et al., eds., Oxford University Press, New York, N.Y. (2000)). DLBCL is often marked by abnormalities of BCL6 and/or translocations of BCL2 to the IgH locus. GC B cell like (GC) DLBCL is characterized by SHM with highly mutated immunoglobulin genes and ongoing SHM in malignant clones with a GC B cell-like gene expression profile. Most GC DLBCL have undergone immunoglobulin class switching. ABC-DLBCL is characterized by high level expression of NF-κB target genes including BCL2, interferon regulatory factor 4, CD44, FLIP and cyclin D. SHM, but not ongoing SHM, is present, and ABC-DLBCL does not have a GC B cell gene expression profile. Almost all ABC-DLBCL express a high level of IgM.

5.5.3.5. Extranodal Marginal Zone Lymphoma

Extranodal marginal-zone lymphoma is an extranodal lymphoma that occurs in organs normally lacking organized lymphoid tissue (e.g., stomach, salivary glands, lungs and thyroid glands). It is largely a disease that affects older adults with a median age of over 60 years. Often, chronic inflammation or autoimmune processes precede development of the lymphoma. Gastric mucosal-associated lymphoid tissue (MALT) lymphoma, the most common type of marginal-zone lymphoma, is associated with *Helicobacter pylori* infection. Studies have shown a resolution of symptoms with eradication of the *H. pylori* infection following an antibiotic regimen. The presenting symptoms for gastric MALT lymphoma include nonspecific dyspepsia, epigastric pain, nausea, gastrointestinal bleeding and anemia. Systemic symptoms are uncommon, as are elevated levels of lactate acid dehydrogenase. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004); J. Radford, *Other Low-Grade Non-Hodgkin's Lymphomas*, pp. 325-330, In *Malignant Lymphoma*, B. Hancock, et al., eds., Oxford University Press, New York, N.Y. (2000). Systemic B symptoms include fevers greater than 38° C. for longer than 2 weeks without sign of infection, night sweats, extreme fatigue or unintentional weight loss of greater than or equal to 10% of body weight over the previous 6 months).

The immunophenotye of MALT lymphoma is characterized by expression of CD20, CD79a, CD21 and CD35 and lack of expression of CD5, CD23, and CD10. About half of MALT lymphomas express CD43. The immunoglobulin typically expressed in the tumor cells of this disease is IgM while IgD is not expressed. These features are critical in distinguishing this lymphoma from other small B cell lymphomas such as mantle cell lymphoma, lymphocytic lymphoma and follicular lymphoma. Trisomy 3 has been reported in 60% of MALT lymphoma cases. In 25-40% of gastric and pulmonary MALT lymphomas a t(11;18) is observed. This translocation is observed much less frequently in other MALT lymphomas. T(11;18) is associated with nuclear expression of BCL10. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004)). Marginal-zone lymphomas are generally characterized by SHM and ongoing SHM.

Diagnostic procedures include immunophenotyping or flow cytometry to determine the identity of the cell surface markers. In addition, molecular genetic analysis should be done to determine the presence of t(11;18) as this is an indicator that the disease will not respond to antibiotics. Histology can be used to determine the presence of *H. pylori*. Additional tests should include a complete blood count, basic biochemical tests including that for lactate acid dehydrogenase; CT scans of the abdomen, chest and pelvis and a bone marrow biopsy. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004)).

5.5.3.6. Nodal Marginal Zone B Cell Lymphoma

Nodal Marginal Zone B cell Lymphoma is a relatively newly classified lymphoma thus little has been published on it. It is a primary nodal B cell lymphoma sharing genetic and morphological characteristics with extranodal and splenic marginal zone lymphomas, but does not localize to the spleen or extranodally. Hepatitis C virus has been reported to be associated with this lymphoma as has Sjögren's syndrome. (See, F. Berger, et al., *Nodal Marginal Zone B cell Lymphoma*, pp. 361-365, In *Non-Hodgkin's Lymphomas*, P. Mauch, et al., eds., Lippincott Williams & Wilkins, Philadelphia, Pa. (2004)).

Nodal marginal zone lymphoma has a heterogeneous cytology and morphology. Due to its relatively high proportion of large cells this lymphoma, unlike the other marginal lymphomas (splenic and extranodal), cannot be classified as true low grade B cell lymphoma. The genetic and immunological phenotype of nodal marginal zone lymphoma includes expression of CD19, CD20, BCL2, sIgM and cytoplasmic IgG (cIg). These cells do not express CD5, CD10, CD23, CD43 or cyclin D1. The translocation characteristic of MALT lymphoma, t(11;18), is not observed for nodal marginal zone lymphoma. These characteristics aid in the differential diagnosis of this lymphoma from other small B cell lymphomas. (See, F. Berger, et al., *Nodal Marginal Zone B cell Lymphoma*, pp. 361-365, In *Non-Hodgkin's Lymphomas*, P. Mauch, et al., eds., Lippincott Williams & Wilkins, Philadelphia, Pa. (2004)).

5.5.3.7. Splenic Marginal Zone Lymphoma

Splenic Marginal Zone Lymphoma is an indolent micronodular B cell lymphoma with a characteristic clinical presentation of prominent splenomegaly and infiltration of the peripheral blood and the bone marrow. In addition, a relatively high level of liver involvement has been reported. A role for hepatitis C virus has been postulated for this lymphoma. The immunophenotype of splenic marginal zone lymphoma is typically CD20⁺, IgD⁺, BCL2⁺, p27⁺, CD3⁻, CD5⁻, CD10⁻, CD23⁻, CD38⁻, CD43⁻, BCL-6⁻, and cyclin D1⁻. Genetic characteristics include a 7q deletion, p53 alterations and SHM. (See, M. Piris, et al., *Splenic Marginal Zone Lymphoma*, pp. 275-282, In *Non-Hodgkin's Lymphomas*, P. Mauch, et al., eds., Lippincott Williams & Wilkins, Philadelphia, Pa. (2004)).

Diagnosis generally relies on immunophenotyping to determine the identity of the cell surface markers. Genetic and biochemical analysis, in combination with data on cell surface markers, help to differentiate this lymphoma from other small B cell lymphomas. (See, M. Piris, et al., *Splenic Marginal Zone Lymphoma*, pp. 275-282, In *Non-Hodgkin's Lymphomas*, P. Mauch, et al., eds., Lippincott Williams & Wilkins, Philadelphia, Pa. (2004)).

5.5.3.8. Acute (B Cell) Lymphocytic Leukemia (All)

ALL is a marrow-based neoplasm largely affecting children with the highest incidence between 1-5 years. Most common symptoms at presentation include fatigue, lethargy, fever and bone and joint pain. Fatigue and lethargy correlates with the degree of anemia present. An elevated white blood cell count is common at presentment. Radiographs of the chest often show skeletal lesions. Extramedullary spread is common and involves the central nervous system, testes, lymph nodes, liver, spleen and kidney. Anterior mediastinal masses are observed in only about 5-10% of newly diagnosed cases. (See, J. Whitlock, et al., *Acute Lymphocytic Leukemia*, pp. 2241-2271, In *Wintrobe's Clinical Hematology*, Tenth Edition, G. Lee, et al., eds. Williams & Wilkins, Baltimore, Md. (1999)).

The immunophenotype of ALL is CD10⁺, CD19⁺, CD20⁺, and CD24⁺. Pre-B cell ALL cells express cytoplasmic but not surface immunoglobulin, while mature B cell ALL (which accounts for only 1-2% of ALL cases) is distinguished from other leukemias of B cell lineage by the expression of surface immunoglobulin. Cytogenetic characteristics of ALL includes t(8;14), t(2;8) and t(8;22). Although rarely detected at the cytogenetic level t(12;21) may be the most common cytogenetic abnormality associated with childhood ALL (observed in about 25% of cases). (See, M. Kinney, et al., *Classification and Differentiation of the Acute Leukemias*, pp. 2209-2240, In *Wintrobe's Clinical Hematology*, Tenth Edition, G. Lee, et al., eds. Williams & Wilkins, Baltimore, Md. (1999); J Whitlock, et al., *Acute Lymphocytic Leukemia*, pp. 2241-2271; In *Wintrobe's Clinical Hematology*, Tenth Edition, G. Lee, et al., eds. Williams & Wilkins, Baltimore, Md., (1999)).

Precise diagnosis of acute leukemia usually relies on a bone aspirate and biopsy. Aspirate smears are used for morphological, immunological and cytological assessments. The demonstration of lymphoblasts in the bone marrow is diagnostic of ALL. The presence of greater than 5% leukemic lymphoblast cells in the bone marrow confirms ALL diagnosis but most require greater than 25% for a definitive diagnosis. Lumbar punctures are used to diagnose central nervous system involvement. Serum uric acids levels and serum lactate dehydrogenase levels have been found to be elevated in ALL. (See, M. Kinney, et al., *Classification and Differentiation of the Acute Leukemias*, pp. 2209-2240, In *Wintrobe's Clinical Hematology*, Tenth Edition, G. Lee, et al., eds. Williams & Wilkins, Baltimore, Md. (1999); J. Whitlock, et al., *Acute Lymphocytic Leukemia*, pp. 2241-2271; In *Wintrobe's Clinical Hematology*, Tenth Edition, G. Lee, et al., eds. Williams & Wilkins, Baltimore, Md., (1999)).

5.5.3.9. Chronic Lymphocytic Leukemia (CLL)/Small B Cell Lymphocytic Lymphoma (SLL)

CLL/SLL is the most common type of leukemia. When the disease involves the peripheral blood and bone marrow it is referred to as CLL. However, when the lymph nodes and other tissues are infiltrated by cells that are immunologically and morphologically identical to those in CLL, but where leukemic characteristics of the disease are absent, then the disease is referred to as SLL. This disease largely afflicts the elderly with a greater incidence of the disease occurring in men than women. Painless lymphadenopathy is the most common finding at presentation. Hypogammaglobulinemia is common with most cases of CLL/SLL exhibiting reduced levels of all immunoglobulins rather than any particular subclass of immunoglobulins. Asymptomatic patients are frequently diagnosed during routine blood counts (lymphocyte count of over 5000×10⁹/L). As many as 20% of CLL/SLL cases report B symptoms. An additional diagnostic feature is infiltration of the bone marrow by more than 30% by immature lymphocytes. Lymph node biopsies generally show infiltration of involved nodes with well-differentiated lymphocytes. Autoimmune phenomena are often associated with CLL/SLL including autoimmune hemolytic anemia and immune thrombocytopenia. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); *Clinical Oncology*, A. Neal, et al., Neal, Hoskin and Oxford University Press, co-publ., New York, N.Y. (2003))

In contrast with many of the low-grade B cell malignancies, nonrandom reciprocal translocations are rarely found in CLL/SLL. However, other cytogenetic abnormalities have been reported including deletions at 13q14, 11q22-23 and 17q13, with the latter two involving the p53 locus. Approximately 20% of cases exhibit trisomy 12. An elevated level of B-2 microglobulin, higher levels of CD38 expression and the production of tumor necrosis factor-alpha are all characteristic of CLL/SLL. The immunophenotype of CLL/SLL is very diagnostic and includes weak expression of surface immunoglobulin usually IgM, or IgM and IgG, as well as expression of the cell antigens CD19, CD20 and usually CD5 and CD23. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000)).

5.5.3.10. B Cell Prolymphocytic Leukemia (PLL)

PLL, once considered a variant of CLL, is now understood to be a distinct disease. PLL is generally a disease of elderly men and is characterized by a very high white blood cell count (greater than 200×10⁹/L) and splenomegaly. Additional symptoms include anemia and thrombocytopenia. Prolymphocytes in PLL comprise more than 55% of the cells in the blood and bone marrow. In contrast with CLL, autoimmune phenomena are rarely observed in PLL. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004)).

The immunophenotype of PLL is characterized by expression of CD19, CD21, CD22, CD24 and FMC7. The cells of PLL do not express CD23 and most do not express CD5. PLL cells exhibit complex chromosomal abnormalities, with deletions at 13q14 and 11q23 being some of the most frequent. The pattern of p53 mutation in PLL cells is different from that observed for CLL. Differential diagnosis usually relies on complete blood count, histological, immunophenotypic, and genetic analyses. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004)).

5.5.3.11. Hairy Cell Leukemia (HCL)

HCL is a rare, indolent chronic leukemia affecting more men than women and largely those of middle age. The typical symptoms include massive splenomegaly and pancytopenia. The peripheral blood and bone marrow contain the typical "hairy cells," which are B lymphocytes with cytoplasmic projections. Over 90% of HCL patients have bone marrow infiltration. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, In *Wintrobe's Clinical Hematology*, Tenth Edition, G. Lee et al., eds. Williams & Wilkins, Baltimore, Md. (1999)).

Cytogenetic analysis has shown that clonal abnormalities are present in 19% of cases and involve numerical and structural abnormalities of chromosomes 5, 7 and 14. The serum level of TNF-α is elevated in hairy cell leukemia and correlates with tumor burden. Hairy cell leukemia cells express surface immunoglobulins (IgG and IgM) and CD11 c, CD19, CD20, CD22 and typically CD25. In addition, FMC7, HC-2 and CD103 are expressed. HCL cells do not express CD5 or CD 10. Diagnosis generally involves the use of bone marrow aspirates, cytogenetics, blood smears and immunophenotyping. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, In *Wintrobe's Clinical Hematology*, Tenth Edition, G. Lee et al., eds. Williams & Wilkins, Baltimore, Md. (1999)).

5.5.3.12. Precursor B Cell Lymphoblastic Lymphoma/Pre-B Cell Acute Lymphoblastic Leukemia/Lymphoblastic Lymphoma Precursor B cell lymphoblastic lymphoma/pre-B cell acute lymphoblastic leukemia/Lymphoblastic lymphoma is a disease of precursor T or B cells. The T and B cell lymphoblastic lymphomas are morphologically identical, but clinical distinctions may be made based on degree of bone marrow infiltration or bone marrow involvement. 85-90% of lymphoblastic lymphomas are T-cell derived with the remainder being B cell derived. Lymphoblastic lymphoma has a median age of 20 years with a male predominance. Peripheral lymph node involvement is a common feature at presentation, occurring especially in the cervical, supraclavicular and axillary regions. This disease frequently presents with bone marrow involvement. Central nervous system is less common at presentment but often appears in cases of relapse. Other sites of involvement can include liver, spleen, bone, skin, pharynx and testes (See, J. Sweetenham, et al., *Precursor B- and T-Cell Lymphoblastic Lymphoma*, pp. 503-513, In *Non-Hodgkin's Lymphomas*, P. Mauch, et al., eds., Lippincott Williams & Wilkins, Philadelphia, Pa. (2004)).

Precursor B cell lymphoblastic lymphomas express immature markers B cell markers such as CD99, CD34 and terminal deoxynucleotidyl transferase. These cells also express CD79a, CD19, and sometimes CD20 and typically lack expression of CD45 and surface immunoglobulin. Translocations at 11q23, as well as t(9;22)(q34;q11.2) and t(12;21)(p13;q22), have been associated with poor prognosis. Good prognosis is associated with hyperdiploid karyotype, especially that associated with trisomy 4, 10, and 17 and t(12;21) (p13;q22). (See, J. Sweetenham, et al., *Precursor B- and T-Cell Lymphoblastic Lymphoma*, pp. 503-513, In *Non-Hodgkin's Lymphomas*, P. Mauch, et al., eds., Lippincott Williams & Wilkins, Philadelphia, Pa. (2004)).

Diagnostic tests include lymph node biopsies, blood tests, x-rays, CT scans, and lumbar punctures to examine the cerebralspinal fluid for malignant cells.

5.5.3.13. Primary Mediastinal Large B Cell Lymphoma

Primary mediastinal large B cell lymphoma is a diffuse large B cell lymphoma occurring predominantly in young women and characterized by a locally invasive anterior mediastinal mass originating in the thymus. Distant spread to peripheral nodes and bone marrow involvement is unusual. Systemic symptoms are common. While this disease resembles nodal large cell lymphomas, it has distinct genetic, immunological, and morphological characteristics.

The immunophenotype of tumor cells of primary mediastinal large B cell lymphoma are often surface immunoglobulin negative but do express such B cell associated antigens as CD19, CD20, CD22, and CD79a. CD10 and BCL6 are also commonly expressed. Expression of plasma cell associated markers CD 15, CD30, epithelial membrane antigen (EMA) is rare. BCL6 and c-myc gene arrangements are also uncommon. The presence of clonal immunoglobulin rearrangements, immunoglobulin variable region and gene hypermutation along with BCL6 hypermutation suggest that this lymphoma derives from a mature germinal center or post-germinal center B cell. The chromosomal translocations that seem to be associated with tumors of this disease are similar to those observed in other forms of diffuse large cell lymphoma. (See, P. Zinzani, et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

The diagnostic evaluation for primary mediastinal large B cell lymphoma generally includes a complete physical examination, complete hematological and biochemical analysis, total-body computerized tomography and bone marrow biopsy. Gallium-67 scanning is a useful test for staging, response to treatment and for assessment of relapse. (See, P. Zinzani et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

The immunophenotype of this disease shows expression of the B cell associated antigens CD19, CD20, CD22, and CD79a and a lack of expression of CD5, CD10, and CD23. Presence of strong surface immunoglobulin and CD20, the lack of expression of CD5, and CD23 and the presence of cytoplasmic immunoglobulin are characteristics that aid in distinguishing this disease from chronic lymphocytic leukemia. Also diagnostic of this disease is t(9;14)(p13;q32). (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); R. Chaganti, et al., *Cytogenetics of Lymphoma*, pp. 809-824, In *Non-Hodgkin's Lymphomas*, P. Mauch, et al., eds., Lippincott Williams & Wilkins, Philadelphia, Pa. (2004)).

Diagnostic tests typically include a complete blood count, renal and liver function tests, CT scans, biopsy and aspiration of the bone marrow, protein electrophoresis to quantify and characterize the paraprotein and serum viscosity. Measurement of $\beta_2$-microglobulin is used as a prognostic test. (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004)).

5.5.3.14. Lymphoplasmacytic Lymphoma (LPL)/Lymphoplasmacytic Immunocytoma/Waldström'S Macroglobulinemia LPL/Lymphoplasmacytic immunocytoma/Waldström's Macroglobulinemia is a nodal lymphoma that is usually indolent, and often involves bone marrow, lymph nodes and spleen. This is generally a disease of older adults with males slightly predominating. Most patients have monoclonal IgM paraprotein in their serum (>3 g/dL) resulting in hyperviscosity of the serum. Tumor cells have a plasmacytic morphology. A subset of LPL is characterized by recurrent translocations between chromosomes 9 and 14, which involves the PAX5 and immunoglobulin heavy-chain loci. LPL is characterized by SHM as well as ongoing SHM, and is believed to be derived from post-GC B cells. (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); A. Lal, et al., *Role of Fine Needle Aspiration in Lymphoma*, pp. 181-220, In W. Finn, et al., eds., *Hematopathology in Oncology*, Kluwer Academic Publishers, Norwell, Mass. (2004)).

5.5.3.15. Null-Acute Lymphoblastic Leukemia

Null-acute lymphoblastic leukemia is a subset of ALL which lacks B- or T-cell characteristics. Phenotypic analysis of leukemic blasts shows a typical null ALL pattern, i.e., CD10 (common ALL antigen)-negative, strongly HLA-DR-positive, and CD19 (B4)-positive (see Katz et al. (1988) Blood 71(5):1438-47)

5.5.3.16. Hodgkin'S Lymphoma

Hodgkin's lymphoma usually arises in the lymph nodes of young adults. It can be divided into classical subtype and a less common nodular lymphocytic predominant subtype.

The classical type exhibits SHM, but not ongoing SHM, and does not have a GC B cell gene expression profile. The nodular lymphocyte predominant type, in contrast, is characterized by SHM and ongoing SHM and a GC B cell gene expression profile. While the two types differ clinically and biologically, they do share certain features such as a lack of neoplastic cells within a background of benign inflammatory cells. B. Schnitzer et al., *Hodgkin Lymphoma*, pp. 259-290, In W. Finn and L. Peterson, eds., *Hematopathology in Oncology*, Kluwer Academic Publishers, Norwell, Mass. (2004)).

The most common features at presentation are painless enlargement of lymph nodes, usually in the neck, but occasionally in the inguinal region. Waxing and waning of nodes is also characteristic of this disease. B symptoms are observed in about one-third of patients. Isolated extranodal involvement is rare and in cases where dissemination has occurred extranodal involvement is observed about 10-20% of the time. (See, P. Johnson et al., *Hodgkin's Disease: Clinical Features*, pp. 181-204, In *Malignant Lymphoma*, B. Hancock, et al., eds., Oxford University Press, New York, N.Y. (2000)).

Reed-Sternberg (RS) cells are the malignant cells of Hodgkin's lymphoma. RS cells and their variants express CD15, CD25, CD30 and transferrin receptor. In addition these cells express polyclonal cytoplasmic immunoglobulin. In most cases of Hodgkin's lymphoma the RS cells do not express CD45, a feature that aids in distinguishing this disease from non-Hodgkin's Lymphomas. Epstein Barr virus has been demonstrated to be present in Reed-Sternberg cells in about one-half of Hodgkin's lymphoma cases but its role is unclear.

Diagnosis is most frequently made by lymph node biopsy. Additional diagnostic tests include a full blood count (often hematological tests are normal; white blood cell counts of less than $1.0 \times 10^9$/L are seen in about 20% of cases), erythrocyte sedimentation rate (often elevated in advanced stages of the disease), biochemical tests including electrolytes, urea, creatinine, urate, calcium (hypercalcemia is rare but when present is associated with extensive bone involvement), liver blood tests, lactate dehydrogenase (elevated levels often associated with advanced disease), albumin and beta$_2$-microglobulin ($\beta$2-M). Lymphanigiograms and chest x-rays and CT scans of the chest, abdomen and pelvis are important in identifying abnormal lymph nodes and the extent of extranodal involvement. Bone marrow biopsies are typically considered optional as bone marrow involvement is unusual and the results of such biopsies appear not to affect clinical management or prognosis. Splenechtomies are not usually performed today as it rarely influences management and CT or MRI imaging provides information on splenic status. Significantly elevated levels of p55, TNF and sICAM-1 are correlated to the stage of the disease, presence of symptoms and complete response rate. (See, P. Johnson, et al., *Hodgkin's Disease: Clinical Features*, pp. 181-204, In *Malignant Lymphoma*, B. Hancock, et al., eds., Oxford University Press, New York, N.Y. (2000); *Clinical Oncology*, A. Neal, et al., Neal, Hoskin and Oxford University Press, co-publ., New York, N.Y. (2003); R. Stein, *Hodgkin's Disease*, pp. 2538-2571, In *Wintrobe's Clinical Hematology*, Tenth Edition, G. Lee et al., eds. Williams & Wilkins, Baltimore, Md. (1999)).

5.5.3.17. Multiple Myeloma

Multiple myeloma is a malignancy of plasma cells. Neoplastic cells are located in the bone marrow, and osteolytic bone lesions are characteristic. Reciprocal chromosomal translocations between one of the immunoglobulin loci and a variety of other genes, e.g., cyclin D1, cyclin D3, c-MAF, MMSET (multiple myeloma SET-domain protein) or fibroblast growth factor receptor 3 are believed to be the primary oncogenic events. Multiple myeloma is characterized by SHM, and the putative cell of origin is a post-GC B cell. Multiple myeloma is typically first identified by symptoms such as recurrent infection, fatigue, pain, and kidney problems and is confirmed with clinical testing (see, for example, *Cancer: Principles and Practice of Oncology*. 6th edition. DeVita, V. T., Hellman, S, and Rosenberg, S. A. editors. 2001 Lippincott Williams and Wilkins Philadelphia, Pa. 19106 pp. 2465-2499).

In certain embodiments, patients who are candidates for treatment by the compositions and methods of the invention can undergo further diagnostic tests on blood and/or urine to confirm the diagnosis or suspicion of multiple myeloma including, but not limited to, complete blood count (CBC) tests to determine if the types of cells reported in a CBC are within their normal ranges which are well known in the art, blood chemistry profile to determine whether levels of various blood components, such as albumin, blood urea nitrogen (BUN), calcium, creatinine, and lactate dehydrogenase (LDH), deviate from standard values. Serum levels of beta$_2$-microglobulin ($\beta_2$-M) can also be examined and surrogate markers for IL-6, a growth factor for myeloma cells. Urinalysis can be used to measure the levels of protein in the urine. Electrophoresis can be used to measure the levels of various proteins, including M protein in the blood (called serum protein electrophoresis, or SPEP) or urine (called urine electrophoresis, or UEP). An additional test, called immunofixation electrophoresis (IFE) or immunoelectrophoresis, may also be performed to provide more specific information about the type of abnormal antibody proteins present. Assessing changes and proportions of various proteins, particularly M protein, can be used to track the progression of myeloma disease and response to treatment regimens. Multiple myeloma is characterized by a large increase in M protein which is secreted by the myeloma tumor cells.

Diagnostic tests on bone can also be conducted to confirm the diagnosis or suspicion of multiple myeloma including, but not limited to, X-rays and other imaging tests—including a bone (skeletal) survey, magnetic resonance imaging (MRI), and computerized axial tomography (CAT), also known as computed tomography (CT)—can assess changes in the bone structure and determine the number and size of tumors in the bone. Bone marrow aspiration or bone marrow biopsy can be used to detect an increase in the number of plasma cells in the bone marrow. Aspiration requires a sample of liquid bone marrow, and biopsy requires a sample of solid bone tissue. In both tests, samples are preferably taken from the pelvis (hip bone). The sturnum (breast bone) can also be used for aspiration of bone marrow.

Patients with multiple myeloma are typically categorized into the following three groups that help define effective treatment regimens. Monoclonal gammopathy of undetermined significance (MGUS) is typically characterized by a serum M protein level of less than 3 g/dL, bone marrow clonal plasma cells of less than 10%, no evidence of other B cell disorders, and no related organ or tissue impairment, such as hypercalcemia (increased serum calcium levels), impaired kidney function noted by increased serum creatinine, anemia, or bone lesions. Asymptomatic myelomas are typically stage I and includes smoldering multiple myeloma (SMM) and indolent multiple myeloma (IMM). SMM is characterized by serum M protein greater than or equal to 3 g/dL and IMM is characterized by bone marrow clonal plasma cells greater than or equal to 10% of the bone marrow cells. Symptomatic myeloma is characterized by M protein in serum and/or urine and includes Stage II multiple myeloma characterized by the presence of bone marrow clonal plasma cells or plasmacytoma and Stage III multiple myeloma characterized by related organ or tissue impairment.

Osteosclerotic myeloma is a component of the rare POEMS syndrome (polyneuropathy, organomegaly, endocrinopathy, monoclonal gammopathy and skin lesions). Peak incidence is at 40 to 50 years of age. Systemic features include skeletal lesions, marrow-plasma cells <5%, a normal CBC, increased platelets, and organomegaly. The CSF has a high protein with no cells present. The M-protein levels are low (<3 g/dl, median=1.1 g/dl); heavy chain class—usually α or γ; light chain class—usually λ; rare urine monoclonal and occasional cryoglobulinemia. Neuropathy occurs in 50% of the patients with weakness both proximal and distal, sensory loss is greater in larger than small fibers; and demyelination and long distal latency.

Smoldering multiple myeloma patients generally present with stable disease for months/years; no anemia, bone lesions, renal insufficiency or hypercalcemia; have >10% plasma cells in bone marrow and monoclonal serum protein. The criteria for smoldering multiple myeloma is compatible with the diagnosis of multiple myeloma; however, there is no evidence of progressive course. These are cases with a slow progression, the tumor cell mass is low at diagnosis and the percentage of bone marrow plasma cells in S phase is low (<0.5%). Characteristic clinical features include: serum M protein levels >3 g/dL and/or bone marrow plasma cells ≥10%; absence of anemia, renal failure, hypercalcemia, lytic bone lesions.

Indolent (or asymptomatic) multiple myeloma is a multiple myeloma diagnosed by chance in the absence of symptoms, usually after screening laboratory studies. Indolent multiple myeloma is similar to smoldering myeloma but with few bone lesions and mild anemia. Most cases of indolent multiple myeloma develop overt multiple myeloma within 3 years. Diagnostic criteria are the same as for multiple myeloma except: no bone lesions or one asymptomatic lytic lesion (X-ray survey); M component level <3 g/dL for IgG, 2 g/dL for IgA urine light chain <4 g/24 h; hemoglobin >10 g/dl, serum calcium normal, serum creatinine <2 mg/dL, and no infections.

5.5.3.18. Solitary Plasmacytoma

Solitary plasmacytoma is one of a spectrum of plasma cell neoplasms which range from benign monoclonal gammopathy to solitary plasmacytoma to multiple myeloma. Approximately seventy percent of all solitary plasmacytoma cases eventually result in multiple myeloma. These diseases are characterized by a proliferation of B cells which produce the characteristic paraprotein. Solitary plasmacytoma results in a proliferation of clonal plasma cells in a solitary site, usually a single bone or extramedullary tissue site. Diagnostic criteria of solitary plasmacytoma include a histologically confirmed single lesion, normal bone biopsy, negative skeletal survey, no anemia, normal calcium and renal function. Most cases exhibit minimally elevated serum M-protein (paraprotein). The median age at diagnosis is 50-55, about 5-10 years younger than the median age for multiple myeloma. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004), S. Chaganti, et al., *Cytogenetics of Lymphoma*, pp. 809-824, In *Non-Hodgkin's Lymphomas*, P. Mauch, et al., eds., Lippincott Williams & Wilkins, Philadelphia, Pa., (2004)).

The immunophenotypic and genetic features of plasmacytoma appear to be similar to multiple myeloma.

5.5.3.19. Light Chain Disease/Light Chain Deposition Disease (LCDD)

LCDD is a plasma cell dycrasias disorder caused by the over-synthesis of immunoglobulin light chains (usually kappa light chains) that are deposited in tissues. Patients commonly present with organ dysfunction, weakness, fatigue and weight loss. In approximately 80% of cases of LCDD a monoclonal immunoglobulin is detected. Detection of monoclonal kappa light chains using immunofluorescent techniques is limited by the tendency of light chains to give excess background staining, therefore, ultrastructural immunogold labeling may be necessary. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004)).

5.5.3.20. Plasma Cell Leukemia (PCL),

PCL, a plasma cell dycrasias, is a rare aggressive variant of multiple myeloma. The criteria for plasma cell leukemia is a peripheral blood absolute plasma cell count of greater than $2 \times 10^9$/L or plasma cells greater than 20% of white blood cells. Determination of the presence of a $CD138^+$ population with cytoplasmic light chain restriction by flow cytometry will distinguish PCL from lymphoid neoplasm with plasmacytic features. PCL cells are also characterized by the lack of surface light chain and CD19 expression, and either no or weak expression of CD45. About 50% of cases of PCL express CD20 and about 50% lack expression of CD56. The genetic abnormalities observed in PCL patients are the same as those observed for multiple myeloma patients but they are found at higher frequency in PCL. (See, C. Wilson, *The Plasma Cell Dycrasias*, pp. 113-144, In W. Finn and L. Peterson, eds., *Hematopathology in Oncology*, Kluwer Academic Publishers, Norwell, Mass., (2004)).

Plasma cell leukemia has two forms: if initial diagnosis is based on leukemic phase of myeloma then the primary form is present, otherwise it is secondary. Primary plasma cell leukemia is associated with a younger age, hepatosplenomegaly, lymphadenopathy, and fewer lytic bone lesions but poorer prognosis than the secondary form. The peripheral blood of plasma cell leukemic patients has greater than 20% plasma cells with absolute count of 2000/ml or more.

5.5.3.21. Monoclonal Gammopathy of Unknown Significance (MGUS)

MGUS is a relatively common condition characterized by the presence of electrophoretically homogeneous immunoglobulins or benign M-components. The occurrence of this condition appears to increase with age. Most individuals carrying the M-components never develop malignant plasma cell dycrasias, such as multiple myeloma. However, some individuals with this condition have associated malignant conditions. When symptomatic, patients can have enlarged liver or spleen and pleuroneuropathy. (See, J. Foerster, *Plasma Cell Dycrasias: General Considerations*, pp. 2612-2630, In *Wintrobe's Clinical Hematology*, Tenth Edition, G. Lee et al., eds. Williams & Wilkins, Baltimore, Md. (1999)).

MGUS can be differentiated from multiple myeloma by the presence of increased number of monoclonal plasma cells circulating in the peripheral blood. The serological characteristics of M-components are identical to other plasma cell dycrasias conditions, however, the total concentration of M-component is usually less than 30 g/L. The paraprotein is usually IgG; however multiple paraproteins may be present including IgG, IgA, IgM. The relative amount of each of the individual immunoglobulin classes is typically proportional to that found in normal serum. Proteinemia or proteinuria is rare. Serial measurements of M-protein levels in the blood and urine, and continued monitoring of the clinical and laboratory features (including protein electrophoresis) is the most reliable method of differentiating MGUS from early stage plasma cell dycrasias. In *Wintrobe's Clinical Hematology*, Tenth Edition, G. Lee et al., eds. Williams & Wilkins, Baltimore, Md. (1999)).

5.5.3.22. Mature B Cell Malignancies

The inventors have shown that the inventive anti-CD19 compositions can deplete mature B cells. Thus, as another aspect, the invention can be practiced to treat mature B cell malignancies including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

5.5.3.23. Pre-B Cell Malignancies:

Further, CD19 is expressed earlier in B cell development than, for example, CD20, and is therefore particularly suited for treating pre-B cell and immature B cell malignancies, e.g., in the bone marrow. Representative pre-B cell and immature B cell malignancies include but are not limited to mantle cell lymphoma, pre-B cell acute lymphoblastic leukemia, precursor B cell lymphoblastic lymphoma, and other malignancies characterized by CD19 expression.

5.5.4. Diagnosis and Clinical Criteria for Autoimmune Diseases or Disorders

Diagnostic criteria for different autoimmune diseases or disorders are also known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art. In certain embodiments of the invention, patients with low levels of autoimmune disease activity or patients with an early stage of an autoimmune disease (for diseases where stages are recognized) can be identified for treatment using the anti-CD19 antibody compositions and methods of the invention. The early diagnosis of autoimmune disease is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

5.5.4.1. Rheumatoid Arthritis

Rheumatoid arthritis is a chronic disease, mainly characterized by inflammation of the lining, or synovium, of the joints. It can lead to long-term joint damage, resulting in chronic pain, loss of function and disability. Identifying patients or patient populations in need of treatment for rheumatoid arthritis is a process. There is no definitive test that provides a positive or negative diagnosis of rheumatoid arthritis. Clinicians rely on a number of tools including, medical histories, physical exams, lab tests, and X-rays.

Physical symptoms vary widely among patients and commonly include, but are not limited to, joint swelling, joint tenderness, loss of motion in joints, joint malalignment, bone remodeling, fatigue, stiffness (particularly in the morning and when sitting for long periods of time), weakness, flu-like symptoms (including a low-grade fever), pain associated with prolonged sitting, the occurrence of flares of disease activity followed by remission or disease inactivity, rheumatoid nodules or lumps of tissue under the skin (typically found on the elbows, they can indicate more severe disease activity), muscle pain, loss of appetite, depression, weight loss, anemia, cold and/or sweaty hands and feet, and involvement of the glands around the eyes and mouth, causing decreased production of tears and saliva (Sjögren's syndrome). For Sjogren's specifically, the following references may be used, Fox et al., Arthritis Rheum., (1986) 29:577-586, and Vitali et al., Ann. Rheum. Dis., (2002). 61:554-558.

Apart form physical symptoms, clinicians commonly use tests, such as, but not limited to, complete blood count, erythrocyte sedimentation rate (ESR or sed rate), C-reactive protein, rheumatoid factor, anti-DNA antibodies, antinuclear antibodies (ANA), anti-cardiolipin antibodies, imaging studies, radiographs (X-rays), magnetic resonance imaging (MRI) of joints or organs, joint ultrasound, bone scans, and bone densitometry (DEXA). These tests are examples of tests that can be used in conjunction with the compositions and methods of the invention to check for abnormalities that might exist (i.e., identify patients or patient populations in need of treatment) or to monitor side effects of drugs and check progress.

Early symptoms of rheumatoid arthritis commonly are found in the smaller joints of the fingers, hands and wrists. Joint involvement is usually symmetrical, meaning that if a joint hurts on the left hand, the same joint will hurt on the right hand. In general, more joint erosion indicates more severe disease activity.

Symptoms of more advanced disease activity include damage to cartilage, tendons, ligaments and bone, which causes deformity and instability in the joints. The damage can lead to limited range of motion, resulting in daily tasks (grasping a fork, combing hair, buttoning a shirt) becoming more difficult. Skin ulcers, greater susceptibility to infection, and a general decline in health are also indicators of more advanced disease activity.

Progression of rheumatoid arthritis is commonly divided into three stages. The first stage is the swelling of the synovial lining, causing pain, warmth, stiffness, redness and swelling around the joint. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement.

Molecular techniques can also be used to identify patients or patient populations in need of treatment. For example, rheumatoid arthritis has been shown to be associated with allelic polymorphisms of the human leukocyte antigen (HLA)-DR4 and HLA-DRB1 genes (Ollier and Winchester, 1999, Genes and Genetics of Autoimmunity. Basel, Switzerland; Stastny, 1978, N. Engl J Med 298:869-871; and Gregersen et al., 1987, Arthritis Rheum 30:1205-1213). Rheumatoid arthritis patients frequently express two disease-associated HLA-DRB1*04 alleles (Weyand et al., 1992 Ann Intern Med 117:801-806). Patients can be tested for allelic polymorphisms using methods standard in the art. MHC genes are not the only germline-encoded genes influencing susceptibility to RA that can be used to diagnose or identify patients or patient populations in need of treatment. Female sex clearly increases the risk, and female patients develop a different phenotype of the disease than do male patients. Any molecular indicators of rheumatoid arthritis can be used to identify patients or patient populations in need of treatment with the anti-CD19 antibody compositions and methods of the invention.

Methods for determining activity of rheumatoid arthritis in a patient in relation to a scale of activity are well known in the art and can be used in connection with the pharmaceutical compositions and methods of the invention. For example, the American College of Rheumatologists Score (ACR score) can be used to determine the activity of rheumatoid arthritis of a patient or a patient population. According to this method, patients are given a score that correlates to improvement. For example, patients with a 20% improvement in factors defined by the ACR would be given an ACR20 score.

Initially, a patient exhibiting the symptoms of rheumatoid arthritis may be treated with an analgesic. In other embodiments, a patient diagnosed with or exhibiting the symptoms of rheumatoid arthritis is initially treated with nonsteroidal anti-inflammatory (NSAID) compounds. As the disease progresses and/or the symptoms increase in severity, rheumatoid arthritis may be treated by the administration of steroids such as but not limited to dexamethasone and prednisone. In more severe cases, a chemotherapeutic agent, such as but not limited to methotrexate or cytoxin may be administered to relieve the symptoms of rheumatoid arthritis.

In certain instances, rheumatoid arthritis may be treated by administration of gold, while in other instances a biologic, such as an antibody or a receptor (or receptor analog) may be administered. Examples of such therapeutic antibodies are Rituxin and Remicade. An illustrative example of a soluble receptor that can be administered to treat rheumatoid arthritis is Enbrel.

In extremely severe cases of rheumatoid arthritis, surgery may be indicated. Surgical approaches may include, but not be limited to: synovectomy to reduce the amount of inflammatory tissue by removing the diseased synovium or lining of the joint; arthroscopic surgery to take tissue samples, remove loose cartilage, repair tears, smooth a rough surface or remove diseased synovial tissue; osteotomy, meaning "to cut bone," this procedure is used to increase stability by redistributing the weight on the joint; joint replacement surgery or arthroplasty for the surgical reconstruction or replacement of a joint; or arthrodesis or fusion to fuse two bones together.

In certain embodiments of the methods of invention, a patient can be treated with an anti-CD19 antibody prior, concurrent, or subsequent to any of the therapies disclosed above. Moreover, the anti-CD19 antibodies of the present invention may be administered in combination with any of the analgesic, NSAID, steroid, or chemotherapeutic agents noted above, as well as in combination with a biologic administered for the treatment of rheumatoid arthritis.

5.5.4.2. Systemic Lupus Erythematosis (SLE)

Systemic lupus erythematosis (SLE) is a chronic (long-lasting) rheumatic disease which affects joints, muscles and other parts of the body. Patients or patient populations in need of treatment for SLE can be identified by examining physical symptoms and/or laboratory test results. Physical symptoms vary widely among patients. For example, in SLE, typically 4 of the following 11 symptoms exist before a patient is diagnosed with SLE: 1) malar rash: rash over the cheeks; 2) discoid rash: red raised patches; 3) photosensitivity: reaction to sunlight, resulting in the development of or increase in skin rash; 4) oral ulcers: ulcers in the nose or mouth, usually painless; 5) arthritis: nonerosive arthritis involving two or more peripheral joints (arthritis in which the bones around the joints do not become destroyed); 6) serositis pleuritis or pericarditis: (inflammation of the lining of the lung or heart); 7) renal disorder: excessive protein in the urine (greater than 0.5 gm/day or 3+ on test sticks) and/or cellular casts (abnormal elements the urine, derived from red and/or white cells and/or kidney tubule cells); 8) neurologic disorder: seizures (convulsions) and/or psychosis in the absence of drugs or metabolic disturbances which are known to cause such effects; 9) hematologic disorder: hemolytic anemia or leukopenia (white blood count below 4,000 cells per cubic millimeter) or lymphopenia (less than 1,500 lymphocytes per cubic millimeter) or thrombocytopenia (less than 100,000 platelets per cubic millimeter) (The leukopenia and lymphopenia must be detected on two or more occasions. The thrombocytopenia must be detected in the absence of drugs known to induce it); 10) antinuclear antibody: positive test for antinuclear antibodies (ana) in the absence of drugs known to induce it; and/or 11) immunologic disorder: positive anti-double stranded anti-DNA test, positive anti-sm test, positive antiphospholipid antibody such as anticardiolipin, or false positive syphilis test (vdrl).

Other physical symptoms that may be indicative of SLE include, but are not limited to, anemia, fatigue, fever, skin rash, muscle aches, nausea, vomiting and diarrhea, swollen glands, lack of appetite, sensitivity to cold (Raynaud's phenomenon), and weight loss.

Laboratory tests can also be used to identify patients or patient populations in need of treatment. For example, a blood test can be used to detect a autoantibodies found in the blood of almost all people with SLE. Such tests may include but are not limited to tests for antinuclear antibodies (ANA) in the absence of drugs known to induce it (Rahman, A. and Hiepe, F., *Lupus.* (2002), 11(12):770-773), anti-double stranded anti-DNA (Keren, D. F., *Clin. Lab. Med.*, (2002), 22(2):447-474.), anti-Sm, antiphospholipid antibody such as anticardiolipin (Gezer, S. *Dis. Mon.*, 2003, 49(12):696-741), or false positive syphilis tests (VDRL).

Other tests may include a complement test (C3, C4, CH50, CH100) can be used to measure the amount of complement proteins circulating in the blood (Manzi et al., *Lupus,* 2004, 13(5):298-303), a sedimentation rate (ESR) or C-reactive protein (CRP) may be used to measure inflammation levels, a urine analysis can be used to detect kidney problems, chest X-rays may be taken to detect lung damage, and an EKG can be used to detect heart problems.

Chronic SLE is associated with accumulating collateral damage to involved organ, particularly the kidney. Accordingly, early therapeutic intervention is desirable, i.e. prior to, for example, kidney failure. Available treatments for SLE are similar to those available for rheumatoid arthritis. These include initial treatments, either with an analgesic or a non-steroidal anti-inflammatory (NSAID) compound. As the disease progresses and/or the symptoms increase in severity, SLE may be treated by the administration of steroids such as but not limited to dexamethasone and prednisone.

In more severe cases, a chemotherapeutic agent, such as but not limited to methotrexate or cytoxin may be administered to relieve the symptoms of SLE. However, this approach is not preferred where the patient is a female of child-bearing age. In such instances, those therapeutic approaches that do not interfere with the reproductive capacity of the patient are strongly preferred.

In certain instances, SLE may be treated by administration of a biologic, such as an antibody or a receptor (or receptor analog). Examples of such therapeutic antibodies are Rituxin and Remicade. An illustrative example of a soluble receptor for an inflammatory cytokine that can be administered to treat SLE is Enbrel.

In certain embodiments of the methods of invention, a patient can be treated with an anti-CD19 antibody prior, concurrent, or subsequent to any of the therapies disclosed above that are used for the treatment of SLE. Moreover, the anti-CD19 antibodies of the present invention may be administered in combination with any of the analgesic, NSAID, steroid, or chemotherapeutic agents noted above, as well as in combination with a biologic administered for the treatment of SLE.

5.5.4.3. Idiopathic/Autoimmune Thrombocytopenia Purpura (ITP)

Idiopathic/autoimmune thrombocytopenia purpura (ITP) is a disorder of the blood characterized by immunoglobulin G (IgG) autoantibodies that interact with platelet cells and result in the destruction of those platelet cells. Typically, the antibodies are specific to platelet membrane glycoproteins. The disorder may be acute (temporary, lasting less than 2 months) or chronic (persisting for longer than 6 months). Patients or patient populations in need of treatment for ITP can be identified by examining a patient's medical history, physical symptoms, and/or laboratory test results. (Provan, D., and Newland, A., *Br. J. Haematol.* (2002), 118(4):933-944; George, J. N., *Curr. Hematol.* (2003), 2(5):381-387; Karpt-kin, S., *Autoimmunity.* (2004), 37(4):363-368; Cines, D. B., and Blanchette, V. S., N. Engl. *J. Med.* (2002), 346(13)995-1008).

Physical symptoms include purplish-looking areas of the skin and mucous membranes (such as the lining of the mouth) where bleeding has occurred as a result of a decrease in the number of platelet cells. The main symptom is bleeding, which can include bruising ("ecchymosis") and tiny red dots on the skin or mucous membranes ("petechiae"). In some instances bleeding from the nose, gums, digestive or urinary tracts may also occur. Rarely, bleeding within the brain occurs. Common signs, symptoms, and precipitating factors also include, but are not limited to, abrupt onset (childhood ITP), gradual onset (adult ITP), nonpalpable petechiae, purpura, menorrhagia, epistaxis, gingival bleeding, hemorrhagic bullae on mucous membranes, signs of GI bleeding, menometrorrhagia, evidence of intracranial hemorrhage, nonpalpable spleen, retinal hemorrhages, recent live virus immunization (childhood ITP), recent viral illness (childhood ITP), spontaneous bleeding when platelet count is less than 20,000/mm$^3$, and bruising tendency.

Laboratory test that can be used to diagnose ITP include, but are not limited to, a complete blood count test, or a bone marrow examination to verify that there are adequate platelet-forming cells (megakaryocyte) in the marrow and to rule out other diseases such as metastatic cancer and leukemia. Isolated thrombocytopenia is the key finding regarding laboratory evaluation. Giant platelets on peripheral smear are indicative of congenital thrombocytopenia. A CT scan of the head may be warranted if concern exists regarding intracranial hemorrhage.

The current treatments for ITP include, platelet transfusions and splenectomy. Other treatments include, the administration of glucocorticoids, administration of immunosuppressive agents, administration of agents that enhance platelet production, such as IL-11, and agents that activate megakaryocytes to produce platelets, such as thrombopoietin (TPO).

In more severe cases, a chemotherapeutic agent, such as but not limited to vincristine and vinblastine may be administered to relieve the symptoms of ITP. However, this approach is not preferred where the patient is a female of child-bearing age. In such instances, those therapeutic approaches that do not interfere with the reproductive capacity of the patient are strongly preferred.

In certain instances, ITP may be treated by administration of a biologic, such as an antibody or a receptor (or receptor analog). Examples of such therapeutic antibodies are anti-CD20 antibodies, such as, Rituximab.

In certain embodiments of the methods of invention, a patient can be treated with an anti-CD19 antibody prior, concurrent, or subsequent to any of the therapies disclosed above that are used for the treatment of ITP. Moreover, the anti-CD19 antibodies of the present invention may be administered in combination with any of the agents noted above, as well as in combination with a biologic administered for the treatment of ITP.

5.5.4.4. Pemphigus and Pemphigoid-Related Disorders

Both pemphigus- and pemphigoid-related disorders are a heterogenous group of autoimmune diseases characterized by a blistering condition of the skin and/or mucosal surfaces. In both diseases, the blistering is caused by autoimmune antibodies that recognize various proteins expressed on the surface of epithelial cells in the dermis and/or epidermis.

In patients with pemphigus-related disease, the blistering occurs within the epidermis and is due to the binding of autoantibodies specific for desmoglein 1 (Dsg1) and/or desmoglein 3 (Dsg3). The classic subtypes of pemphigus can be distinguished according to anti-desmoglein antibody specificities. Patients with pemphigus foliaceus (PF) produce anti-Dsg1 antibodies only. Patients with pemphigus vulgaris (PV) and paraneoplastic pemphigus (PNP) produce anti-Dsg3 antibodies if their lesions are restricted to mucosal tissues. In contrast, PV and PNP patients with lesions of the skin and mucosa produce both anti-Dsg1 and -Dsg3 autoantibodies. (Nagasaka, T. et al., *J. Clin. Invest.* 2004, 114:1484-1492; Seishema, M. et al., *Arch Dermatol.,* 2004. 140(12):1500-1503; Amagai, M., *j. Dermatol. Sci.,* 1999. 20(2):92-102)

In patients with pemphigoid-related disease including but not limited to, bulous phemphigoid, urticarial bulous pemphigoid, cicatricial pemphigoid, epidermolysis bullosa acquisita, and Linear IgA bullous dermatosis, the blistering occurs at the interface of the dermis with the epidermis. The most common form of pemphigoid disease is bulous pemphigoid (BP) which is characterized by the presence of autoantibodies that bind the bullous pemphigoid antigen 180 (BP180), bullous pemphigoid antigen 230 (BP230), laminin 5, and/or beta 4 integrin. (Fontao, L. et al., *Mol. Biol. Cell.* 2003), 14(5):1978-1992; Challacombe, S. J. et al, *Acta Odontol. Scand.* (2001), 59(4):226-234.)

Patients or patient populations in need of treatment for pemphigus- or pemphigoid-related disorders can be identified by examining a patient's medical history, physical symptoms, and/or laboratory test results (reviewed in: Mutasim, D. F., *Drugs Aging.* (2003), 20(9):663-681; Yeh, S. W. et al., *Dermatol. Ther.* (2003), 16(3):214-223; Rosenkrantz, W. S., *Vet. Dermatol.,* 15(2):90-98.).

Typically, diagnosis of these pemphigus- or pemphigoid-related disorders is made by skin biopsy. The biopsy skin sample is examined microscopically to determine the anatomical site of the blister (e.g. epidermis or between dermis and epidermis). These findings are correlated with direct or indirect immunohistochemical analyses to detect the presence of autoantibodies at the site of the lesion. Serum samples from patients may also be examined for the presence of circulating autoantibodies using an ELISA-based test for specific proteins. Several ELISA-based assays have been described for detection of desmoglein antibodies in human samples (Hashimoto, T., *Arch. Dermatol. Res.* (2003), 295 Suppl. 1:S2-11). The presence of these desmoglein autoantibodies in biopsy samples is diagnostic of pemphigus.

Clinically, pemphigus vulgaris can be diagnosed by the presence of blisters in the mouth. Inflammation or erosions may also be present in the lining of the eye and eyelids, and the membranes of the nose or genital tract. Half of the patients also develop blisters or erosions of the skin, often in the groin, underarm, face, scalp and chest areas. Pemphigus foliaceus is a superficial, relatively mild form of pemphigus. It usually manifests on the face and scalp, but also involves the back and chest. Lesions do not occur in the mouth. The blisters are more confined to the outermost surface and often itch. Paraneoplastic pemphigus is very rare and generally occurs in people who have cancer. The lesions are painful and affect the mouth, lips and esophagus (swallowing tube) as well as the skin. Due to involvement of the airways, signs of respiratory disease may occur and can be life-threatening.

The current treatments for pemphigus or pemphigoid-related disease includes the topical administration of creams and ointments to alleviate the discomfort associated with the skin condition, the administration of anti-inflammatory agents or the administration of immunosuppressive agents.

In certain embodiments of the methods of invention, a patient can be treated with an anti-CD19 antibody prior, concurrent, or subsequent to any of the therapies disclosed above that are used for the treatment of pemphigoid or pemphigoid related disease. Moreover, the anti-CD19 antibodies of the present invention may be administered in combination with any of the agents noted above.

5.5.4.5. Autoimmune Diabetes

According to certain aspects of the invention, a patient in need of treatment for autoimmune diabetes, also known as type 1A diabetes, can be treated with the anti-CD19 antibody compositions and methods of the invention. Type 1A diabetes is an autoimmune disease caused by the synergistic effects of genetic, environmental, and immunologic factors that ultimately destroy the pancreatic beta cells. The consequences of pancreatic beta cell destruction is a decrease in beta cell mass, insulin production/secretion declines and blood glucose levels gradually rise.

Patients or patient populations in need of treatment for type 1A diabetes can be identified by examining a patient's medical history, physical symptoms, and/or laboratory test results. Symptoms often come on suddenly and include, but are not limited to, low or non-existent blood insulin levels, increased thirst, increased urination, constant hunger, weight loss, blurred vision, and/or fatigue. Overt diabetes does not usually become evident until a majority of beta cells are destroyed (>80%). Typically, diabetes is clinically diagnosed if a patient has a random (without regard to time since last meal) blood glucose concentration ≥11.1 mmol/L (200 mg/dL) and/or a fasting (no caloric intake for at least 8 hours) plasma glucose ≥7.0 mmol/L (126 mg/dl) and/or a two-hour plasma glucose ≥11.1 mmol/L (200 mg/dL). Ideally, these tests should be repeated on different days with comparable results before diagnosis is confirmed. (Harrison's Principles of Internal Medicine, $16^{th}$ ed./editors, Dennis L. Kasper, et al. The McGraw-Hill Companies, Inc. 2005 New York, N.Y.).

Although the precise etiology of type 1A diabetes is unknown, there exists clear genetic linkage to specific HLA serotypes. In particular, autoimmune diabetes is associated with HLA DR3 and DR4 serotypes. The presence of both DR3 and DR4 confers the highest known genetic risk. Susceptibility to autoimmune diabetes is also linked to HLA class II (HLA-DQB1 *0302. In contrast, HLA haplotypes with DRB1-1501 and DQA1-0102-DQB1-0602 are associated with protection from type 1A diabetes (Redondo, M. J. et al., *J. Clin. Endocrinol. Metabolism* (2000), 10:3793-3797.)

The destruction of the insulin producing beta islet cells can be accompanied by islet cell autoantibodies, activated lymphocytic infiltrates in the pancreas and draining lymph nodes, T lymphocytes responsive to islet cell proteins, and release of inflammatory cytokines within the islets (Harrison's Principles of Internal Medicine, $16^{th}$ ed./editors, Dennis L. Kasper et al., The McGraw-Hill Companies, Inc. 2005, New York, N.Y.).

Autoantibodies associated with type 1A diabetes include but are not limited to antibodies that bind insulin, glutamic acid decarboxylase (GAD), ICA-512/IA-2, phogrin, islet ganglioside and carboxypeptidase H (Gianani, R. and Eisenbarth, G. S. *Immunol. Rev.* (2005), 204:232-249; Kelemen, K. et al, *J. Immunol.* (2004), 172(6):3955-3962); Falorni, A. and Borozzetti, A., *Best Pract. Res. Clin. Endocrinol. Metab.* 2005, 19(1):119-133.)

The current treatments for autoimmune diabetes include the administration of vitamin D, corticosteroids, agents which control blood pressure and agents that control glycemia (blood sugar levels).

In certain embodiments of the methods of invention, a patient can be treated with an anti-CD19 antibody prior, concurrent, or subsequent to any of the therapies disclosed above that are used for the treatment of autoimmune diabetes. Moreover, the anti-CD19 antibodies of the present invention may be administered in combination with any of the agents noted above.

5.5.4.6. Systemic Sclerosis (Scleroderma) and Related Disorders

Systemic sclerosis also known as Scleroderma encompasses a heterogeneous group of diseases including but not limited to, Limited cutaneous disease, Diffuse cutaneous disease, Sine scleroderma, Undifferentiated connective tissue disease, Overlap syndromes, Localized scleroderma, Morphea, Linear scleroderma, En coup de saber, Scleredema adultorum of Buschke, Scleromyxedema, Chronic graft-vs.-host disease, Eosinophilic fasciitis, Digital sclerosis in diabetes, and Primary anylooidosis and anyloidosis associated with multiple myeloma. (Reviewed in: Harrison's Principles of Internal Medicine, 16$^{th}$ ed./editors, Dennis L. Kasper, et al. The McGraw-Hill Companies, Inc. 2005 New York, N.Y.).

Clinical features associated with scleroderma can include Raynaud's phenomenon, skin thickening, subcutaneious calcinosis, telangiectasia, arthralgias/arthritis, myopathy, esophageal dysmotility. pulmonary fibrosis, isolated pulmonary arterial hypertension, congestive heart failure and renal crisis. The extent to which an patient displays one or more of these disease manifestations can influence the diagnosis and potential treatment plan.

Autoantibodies include: Anti-topioisomerase 1, anticentromere, anti-RNA polymerase I, II, and/or III, anti-Th RNP, anti-U, RNP (anti-fibrillarin), anti-PM/Sci, anti-nuclear antibodies (ANA).

Identification of patients and patient populations in need of treatment of scleroderma can be based on clinical history and physical findings. Patients or patient populations in need of treatment for scleroderma can be identified by examining a patient's medical history, physical symptoms, and/or laboratory test results. Diagnosis may be delayed in patients without significant skin thickening. Laboratory, X-ray, pulmonary function tests, and skin or renal (kidney) biopsies can be used to determine the extent and severity of internal organ involvement.

In the early months or years of disease onset, scleroderma may resemble many other connective tissue diseases, such as, but not limited to, Systemic Lupus Erythematosus, Polymyositis, and Rheumatoid Arthritis.

The most classic symptom of systemic sclerosis (scleroderma) is sclerodactyl). Initial symptoms include swollen hands, which sometimes progress to this tapering and claw-like deformity. Not everyone with scleroderma develops this degree of skin hardening. Other symptoms can include morphea, linear sclerodactyl) (hardened fingers), Raynaud's syndrome, calcinosis, and telangiectasia.

Blood tests such as antinuclear antibody (ANA) tests can be used in the diagnosis of both localized and systemic scleroderma. For example, anti-centromere antibodies (ACA) and anti-Scl-70 antibodies are indicative of patients in need of treatment for systemic sclerosis (Ho et al., 2003, Arthritis Res Ther., 5:80-93); anti-topo II alpha antibody are indicative of patients in need of treatment for local scleroderma; and anti-topo 1 alpha antibody are indicative of patients in need of treatment for systemic scleroderma. Several types of scleroderma and methods for diagnosing these types are recognized and well known in the art, including, but not limited to, juvenile scleroderma (Foeldvari, 2002, Curr Opin Rheumatol, 14:699-703; Cefle et al., 2004, Int J Clin Pract., 58:635-638); localized scleroderma; Nodular Scleroderma (Cannick, 2003, J. Rheumatol., 30:2500-2502); and Systemic scleroderma, including, but not limited to, Calcinosis, Raynaud's, Esophagus, Sclerodactyl), and Telangiectasia (CREST), limited systemic scleroderma, and diffuse systemic scleroderma. Systemic scleroderma is also known as systemic sclerosis (SSc). It may also be referred to as Progressive Systemic Sclerosis (PSSc), or Familial Progressive Systemic Sclerosis (FPSSc) (Nadashkevich et al., 2004, Med Sci Monit., 10:CR615-621; Frances et al., 2002, Rev Prat. 52:1884-90). Systemic sclerosis is a multisystem disorder characterized by the presence of connective tissue sclerosis, vascular abnormalities concerning small-sized arteries and the microcirculation, and autoimmune changes.

The type of systemic scleroderma known as CREST is not characterized by any skin tightening. CREST is characterized by Calcinosis (calcium deposits), usually in the fingers; Raynaud's; loss of muscle control of the Esophagus, which can cause difficulty swallowing; Sclerodactyl), a tapering deformity of the bones of the fingers; and Telangiectasia, small red spots on the skin of the fingers, face, or inside of the mouth. Typically two of these symptoms is sufficient for diagnosis of CREST. CREST may occur alone, or in combination with any other form of Scleroderma or with other autoimmune diseases.

Limited Scleroderma is characterized by tight skin limited to the fingers, along with either pitting digital ulcers (secondary to Raynaud's) and/or lung fibrosis. The skin of the face and neck may also be involved in limited scleroderma.

Diffuse Scleroderma is diagnosed whenever there is proximal tight skin. Proximal means located closest to the reference point. Proximal tight skin can be skin tightness above the wrists or above the elbows. Typically, a patient with skin tightness only between their elbows and their wrists will receive a diagnosis of either diffuse or limited systemic Scleroderma, depending on which meaning of proximal the diagnosing clinician uses.

The current therapies for scleroderma include extracorporeal photophoresis following 6-methoxypsoralen, and autologous stem cell transplant, The current treatments for scleroderma include the administration of the following agents, penicillamine, cholchicine, interferon alpha, interpheron gamma, chlorambucil, cyclosporine, 5-fluorouracil, cyclophosphamide, minocycline, thalidomide, etanercept, or methotrexate.

5.5.5. Diagnosis and Clinical Criteria for Transplantation

The present invention provides antibodies, compositions and methods for treating and preventing GVHD, humoral rejection, and post-transplant lymphoproliferative disorder in human transplant recipients. The compositions and methods of the invention can be used regardless of the particular indications which gave rise to the need for a transplant. Similarly, the use of the compositions and methods of the invention for the treatment and prevention of GVHD, humoral rejection, and post-transplant lymphoproliferative disorders is not limited by the particular type of tissue which is intended for transplantation or which has been transplanted.

In one embodiment, the invention provides compositions and methods for the prevention of humoral rejection in a human transplant recipient wherein the transplant recipient is identified as a patient or patient population at increased risk for developing a humoral rejection. Such patients may also be referred to as "sensitized." The criteria for the identification of sensitized patients is known to the skilled practitioner. Such criteria may include, for example, patients having detectable levels of circulating antibodies against HLA antigens, e.g., anti-HLA alloantibodies. Such criteria may also include patients who have undergone previous transplantations, a pregnancy, or multiple blood transfusions. Patients who are at an increased risk for humoral rejection also include those having imperfect donor-recipient HLA matching, and those transplantations which are ABO-incompatible. Sensitized individuals are preferred candidates for pretreatment or conditioning prior to transplantation. Sensitized individuals are also preferred candidates for post-transplantation maintenance regimens for the prevention of humoral rejection.

In one embodiment, the antibodies, compositions, and methods of the invention comprise or are used in combination with a therapeutic regimen for the treatment of an acute or chronic rejection. In particular embodiments, the rejection is characterized as a Stage I, a Stage II, a Stage III, or a Stage IV humoral rejection.

In one embodiment, the antibodies, compositions, and methods of the invention comprise or are used in combination with a therapeutic regimen for the treatment of an early stage humoral rejection. In particular embodiments, the early stage humoral rejection is a Stage I, II, or III rejection. Clinical indications of an early stage humoral rejection are determined according to the knowledge and skill in the art and may include, for example, the development in the patient of circulating donor-specific anti-HLA antibodies, the presence of complement markers of antibody activity such as C4d and C3d deposits in graft biopsies, and the presence of anti-HLA antibodies in graft biopsies. Other indicators of an early stage humoral rejection are known to the skilled practitioner and may include, for example, the development of antiendothelial antibodies, especially antivimentin antibodies, and the development of nonclassical MHC class I-related chain A (MICA) alloantibodies.

In one embodiment, the compositions and methods of the invention comprise or are used in combination with a therapeutic regimen for the treatment of humoral rejection characterized in part by graft dysfunction. In particular embodiments, the patient or patient population in need of treatment for humoral rejection is identified according to criteria known in the art for graft dysfunction. Examples of such criteria for particular types of grafts are provided in the sections that follow. In other embodiments, the patient or patient population in need of treatment for humoral rejection is identified according to other criteria that are particular to the type of tissue graft, such as histological criteria. Examples of such criteria are also provided in the sections that follow.

5.5.5.1. Bone Marrow Transplants

The compositions and methods of the invention are useful for treating or preventing GVHD, humoral rejection, and post-transplant lymphoproliferative disorder in a bone marrow transplant recipient. In one embodiment, the compositions and methods of the invention comprise or are used in combination with a pre-transplant conditioning regimen.

In one embodiment, the compositions and methods of the invention are used to deplete B cells from a bone marrow graft prior to transplantation. The graft may be from any suitable source, for example, cord blood stem cells, peripheral blood stem cells, or a bone marrow tap. Peripheral blood stem cells may be harvested from donor blood following a suitable conditioning regimen. Suitable regimens are known in the art and may include, for example, administration of one or more of the following to the donor prior to harvesting the donor blood: NEUPOGEN, cytokines such as GM-CSF, low dose chemotherapeutic regimens, and chemokine therapy. The graft may be either allogeneic or autologous to the transplant recipient. The graft may also be a xenograft.

The compositions and methods of the invention are useful in a number of contexts in which there is a hematopoietic indication for bone marrow transplantation. In one embodiment, an autologous bone marrow graft is indicated for a B cell leukemia or lymphoma, preferably acute lymphoblastic leukemia ("ALL") or non-Hodgkins lymphoma, and the compositions and methods of the invention are used for the depletion of residual malignant cells contaminating the graft. In one embodiment, an autologous bone marrow transplant is indicated for patients unable to clear a viral infection, for example a viral infection associated with Epstein Barr virus (EBV), human immunodeficiency virus (HIV), or cytomegalovirus (CMV), and the anti-CD19 antibody compositions and methods of the invention are used to deplete the graft of B cells which may harbor the virus. In another embodiment, the graft is an allogeneic graft and the anti-CD19 antibody compositions and methods of the invention are used for depleting donor B cells from the graft as prophylaxis against GVHD.

In one embodiment, the indication is a B cell associated autoimmune condition and the compositions and methods of the invention are used to deplete the deleterious B cells from the patient without the need for chemotherapy or radiation therapy conditioning regimens. In one embodiment, the compositions of the invention are administered in combination with a chemotherapy or radiation therapy regimen, which regimen comprises a lower dose of one or more chemotherapeutic agents, or a lower dose of radiation, than the dose that is administered in the absence of the compositions of the invention. In one embodiment, the patient receives an autologous bone marrow graft subsequent to chemotherapy or radiation therapy, wherein the graft is depleted of deleterious B cells prior to transplantation using the compositions and methods described herein.

A patient or patient population in need of, or likely to benefit from, a bone marrow transplant is identified according to the knowledge and skill in the art. Examples of patients that may be candidates for bone marrow transplantation include patients who have undergone chemotherapy or radiation therapy for the treatment of a cancer or an autoimmune disease or disorder, and patients who are unable to clear a viral infection residing in cells of the immune system.

5.5.5.2. Liver Transplants

The compositions and methods of the invention are useful for treating or preventing GVHD, humoral rejection, and post-transplant lymphoproliferative disorder in a liver transplant recipient. In particular embodiments, the rejection is an acute or a chronic rejection. In one embodiment, the compositions and methods of the invention are used for the prevention of GVHD, humoral rejection, and post-transplant lymphoproliferative disorder in a liver transplant recipient. In one embodiment, the compositions and methods of the invention comprise or are used in combination with a pre-transplant conditioning regimen. In one embodiment, the compositions of the invention are administered to the transplant recipient. In one embodiment, the compositions of the invention are contacted with the graft, ex vivo, prior to transplantation.

The liver transplant may be from any suitable source as determined according to the knowledge and skill in the art. In one embodiment, the liver is an HLA-matched allogeneic graft. In another embodiment, the liver is a xenograft, preferably from a pig donor. In one embodiment, the liver is used ex vivo to filter the patient's blood, e.g., extracorporeal perfusion. Extracorporeal perfusion is a form of liver dialysis in which the patient is surgically connected to a liver maintained outside the body. This procedure is sometimes referred to as "bioartificial liver." In accordance with this embodiment, the compositions and methods of the invention are used to prevent the development of antibodies against liver antigens which may contaminate the patient's blood.

In one embodiment, the compositions and methods of the invention comprise an improved therapeutic regimen for the treatment and prevention of GVHD, humoral rejection, and post-transplant lymphoproliferative disorder. In a particular embodiment, the compositions and methods of the invention comprise an improved therapeutic regimen, wherein the improvement lies in a decreased incidence and/or severity of complications associated with traditional immunosuppressive agents. In one embodiment, the incidence and/or severity of nephrotoxicity, hepatotoxicity, and hirsutism is reduced compared with traditional regimens relying on cyclosporin A or other calcineurin inhibitors. In one embodiment, the incidence and/or severity of obesity, osteodystrophy, diabetes mellitus and susceptibility to bacterial and viral infections is reduced compared with traditional regimens relying on corticosteroids.

In a preferred embodiment, the compositions and methods of the invention are used in combination with lower doses of one or more traditional immunosuppressive agents than the doses that are used in the absence of anti-lymphocyte antibody therapy. Preferably, the lower doses result in a decreased incidence and/or severity of one or more complications associated with the one or more traditional immunosuppressive agents.

A patient or patient population in need of, or likely to benefit from, a liver transplant is identified according to the knowledge and skill in the art. Examples of patients that may be candidates for liver transplantation include persons having one or more of the following conditions, diseases, or disorders: acute liver failure, amyloidosis, bilirubin excretion disorders, biliary atresia, Budd-Chiari syndrome, chronic active autoimmune hepatitis, cirrhosis (either associated with viral hepatitis including hepatitis B and hepatitis C, alcoholic cirrhosis, or primary biliary cirrhosis), cholangitis, congenital factor VIII or IX disorder, copper metabolism disorders, cystic fibrosis, glycogenesis, hypercholesterolemia, lipidoses, mucopolysaccharidosis, primary sclerosing cholangitis, porphyrin metabolism disorders, purine and pyrimidine metabolism disorders, and primary benign and malignant neoplasms, especially of the liver and intrahepatic bile ducts, biliary system, biliary passages, or digestive system.

The clinical criteria for the identification of a patient or patient population in need of, or likely to benefit from, a liver transplant can be determined according to the knowledge and skill in the art. Such criteria may include, for example, one or more of the following symptoms: fatigue, weight loss, upper abdominal pain, purities, jaundice, liver enlargement, discolored urine, elevated alkaline phosphatase, and gamma glutamylpeptidase activity, elevated bilirubin levels, decreased serum albumin, elevated liver-specific enzymes, low bile production, increased blood urea nitrogen, increased creatinine and/or presence of anti-neutrophil cytoplasmic antibodies (ANCA) titers, recurrent variceal hemorrhage, intractable ascites, spontaneous bacterial peritonitis, refractory encephalopathy, severe jaundice, exacerbated synthetic dysfunction, sudden physiologic deterioration, and fulminant hepatic failure.

5.5.5.3. Kidney (Renal) Transplants

The compositions and methods of the invention are useful for treating or preventing GVHD, humoral rejection, and post-transplant lymphoproliferative disorder in a renal transplant recipient. As used herein, the term "renal transplant" encompasses the transplant of a kidney and the combined transplant of a kidney and a pancreas. In particular embodiments, the rejection is characterized as an acute rejection or a chronic rejection.

In one embodiment, the compositions and methods of the invention comprise or are used in combination with a pre-transplant conditioning regimen. In one embodiment, a single dose of one or more of the compositions of the present invention is effective to reduce panel reactive antibodies and deplete B cells in the patient or patient population. In another embodiment, multiple doses of one or more of the compositions of the invention are effective to reduce panel reactive antibodies and deplete B cells in the patient or patient population. In one embodiment, a single dose of one or more of the compositions of the present invention is administered in combination with one or more immunosuppressive agents and is effective to reduce panel reactive antibodies and deplete B cells in the patient or patient population.

In certain embodiments, the compositions and methods of the invention are for treating or preventing GVHD and graft rejection in a patient having received a renal transplant. In one embodiment, the patient has not yet exhibited clinical signs of rejection. In a related embodiment, the compositions and methods of the invention comprise or are used in combination with a maintenance regimen for the prevention of graft rejection in the transplant recipient. In one embodiment, the compositions and methods of the invention are for the treatment of a subclinical humoral rejection. In a related embodiment, the patient or patient population in need of treatment for a subclinical humoral rejection is indicated by the detection of CD4 deposition in a biopsy from the graft or by the detection of circulating anti-HLA antibodies.

In one embodiment, the compositions and methods of the invention comprise or are used in combination with a therapeutic regimen for the treatment of an acute or chronic rejection episode in a transplant recipient. In one embodiment, the patient or patient population in need of treatment for an acute or chronic rejection episode is identified by the detection of one or more clinical indicators of rejection. In specific embodiments, the one or more clinical indicators of rejection are detected one to six weeks post-transplantation. In one embodiment, the one or more clinical indicators of rejection are detected 6, 12, 18, 24, 36, 48, or 60 months post-transplantation. In a preferred embodiment, the acute rejection is biopsy-confirmed acute humoral rejection.

In one embodiment, one or more of the compositions of the invention comprise a therapeutic regimen for the treatment of acute rejection. In a particular embodiment, the therapeutic regimen further comprises one or more of the following: plasmapheresis, tacrolimus/mycophenolate, intravenous immunoglobulin, immunoadsorption with protein A, and anti-CD20 antibody. In one embodiment, the patient has been on an immunosuppressive protocol prior to the development of the rejection. In a particular embodiment, the immunosuppressive protocol includes one or more of cyclosporine, azathioprine, and steroid therapy.

Clinical indicators of acute humoral rejection are known in the art and include, for example, a sudden severe deterioration of renal function, the development of oliguria, and compromised renal perfusion. Additional indicators include, for example, inflammatory cells in peritubular capillaries on biopsy and circulating donor-specific alloantibodies. In one embodiment, the patient presents with one or more of the following diagnostic criteria for a humoral rejection of a renal allograft: (1) morphological evidence of acute tissue injury; (2) evidence of antibody action, such as C4d deposits or immunoglobulin and complement in arterial fibrinoid necrosis; and (3) detectable circulating antibodies against donor HLA antigens or donor endothelial antigens. In one embodiment, the patient presents with all three of the above diagnostic criteria.

In one embodiment, the patient presents with one or more of the foregoing diagnostic criteria of acute humoral rejection and the compositions of the present invention are used in combination with one or more of the following immunosuppressive agents to treat the acute humoral rejection: intravenous immunoglobulin, anti-thymocyte globulins, anti-CD20 antibody, mycophenolate mofetil, or tacrolimus. In another embodiment, the compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of a chronic renal allograft rejection. In one embodiment, one or more of the compositions of the invention are used alone or in combination with one or more immunosuppressive agents, including for example, anti-CD154 (CD40L), tacrolimus, sirolimus, and mizoribin. In a preferred embodiment, one or more of the anti-CD19 antibodies of the invention are used in combination with tacrolimus and mycophenolate.

Clinical indicators of chronic rejection in the kidneys are known in the art and may include, for example, arterial intimal fibrosis with intimal mononuclear cells (chronic allograft vasculopathy), duplication of the glomerular basement membranes (chronic allograft glomerulopathy), lamination of the peritubular basement membrane, C4d in peritubular capillaries, and detectable circulating donor HLA-reactive antibodies. In a preferred embodiment, the compositions and methods of the invention comprise or are used in combination with a therapeutic regimen to treat chronic rejection before graft lesions develop.

In another embodiment, the patient or patient population in need of treatment is identified as having one or more clinical indicators of transplant glomerulopathy. In a related embodiment, the compositions of the invention comprise or are used in combination with a therapeutic regimen comprising one or more therapeutic agents. In a preferred embodiment, the therapeutic regimen is effective to stabilize renal function and inhibit graft rejection. In a particular embodiment, the one or more therapeutic agents include angiotensin converting enzyme (ACE) inhibitors and/or receptor antagonists, intravenous immunoglobulin, anti-thymocyte globulins, anti-CD20 antibody, mycophenolate mofetil, or tacrolimus. Preferably, the anti-CD19 antibodies of the invention are used in combination with mycophenolate mofetil and tacrolimus, with or without other therapeutic agents. Plasmapheresis may also be used as part of the therapeutic regimen.

A patient or patient population in need of, or likely to benefit from, a renal transplant is identified according to the knowledge and skill in the art. Examples of patients that may be candidates for renal transplantation include patients diagnosed with amyloidosis, diabetes (type I or type II), glomerular disease (e.g., glomerulonephritis), gout, hemolytic uremic syndrome, HIV, hereditary kidney disease (e.g., polycystic kidney disease, congenital obstructive uropathy, cystinosis, or prune bell syndrome), other kidney disease (e.g., acquired obstructive nephropathy, acute tubular necrosis, acute intersititial nephritis), rheumatoid arthritis, systemic lupus erythematosus, or sickle cell anemia. Other candidates for renal transplant include patients having insulin deficiency, high blood pressure, severe injury or burns, major surgery, heart disease or heart attack, liver disease or liver failure, vascular disease (e.g., progressive systemic sclerosis, renal artery thrombosis, scleroderma), vesicoureteral reflux, and certain cancers (e.g., incidental carcinoma, lymphoma, multiple myeloma, renal cell carcinoma, Wilms tumor). Other candidates for renal transplant may include, for example, heroin users, persons who have rejected a previous kidney or pancreas graft, and persons undergoing a therapeutic regimen comprising antibiotics, cyclosporin, or chemotherapy.

The compositions and methods of the invention are useful for treating or preventing GVHD, humoral rejection, and post-transplant lymphoproliferative disorder in a cardiac transplant recipient. In particular embodiments, the rejection is an acute or a chronic rejection. In one embodiment, the compositions and methods of the invention comprise or are used in combination with a pre-transplant conditioning regimen.

In certain embodiments, the compositions and methods of the invention comprise or are used in combination with a therapeutic regimen for the treatment of acute humoral rejection in a cardiac transplant recipient. In a particular embodiment, the therapeutic regimen further comprises one or more of the following: plasmapheresis, intravenous immunoglobulin, and anti-CD20 antibody therapy. The patient or patient population in need of treatment for an acute humoral rejection is identified by the detection of one or more of the clinical indications of acute humoral rejection. Examples of clinical indicators of acute humoral rejection may include one or more of the following: hemodynamic dysfunction, defined by shock, hypotension, decreased cardiac output, and a rise in capillary wedge or pulmonary artery pressure. In a particular embodiment, the acute humoral rejection is diagnosed within 6, 12, 18, 24, 36, 48, or 60 months post-transplantation.

In one embodiment, the compositions and methods of the invention comprise or are used in combination with a therapeutic regimen for the prevention of rejection in a cardiac transplant recipient. In one embodiment, the transplant recipient in need of prophylaxis against rejection is identified as a patient or patient population having one or more of the following risk factors: female sex, cytomegalovirus seropositivity, elevated response to panel reactive antibodies, positive pre- and/or post-transplant crossmatch, and presensitization with immunosuppressive agents.

In one embodiment, the compositions and methods of the invention are for the treatment or prevention of graft deterioration in a heart transplant recipient. In one embodiment, the transplant recipient in need of treatment for, or prophylaxis against, graft deterioration is identified as a patient or patient population having one or more of the following clinical indications of humoral rejection: deposition of immunoglobulin, C1q, C3, and/or C4d in capillaries, evidence of CD68-positive cells within capillaries, and evidence of infiltration of the graft by inflammatory cells upon biopsy. In one embodiment, the compositions of the present invention are used in combination with one or more of the following immunosuppressive agents to treat graft deterioration in a heart transplant recipient: intravenous immunoglobulin, anti-thymocyte globulins, anti-CD20 antibody, mycophenolate mofetil, or tacrolimus. In another embodiment, the anti-CD19 antibody compositions of the invention are used in combination with one or more immunosuppressive agents and a procedure for the removal of alloantibodies from the patient, such as plasmapheresis or immunoadsorption.

In one embodiment, the compositions and methods of the invention comprise or are used in combination with a therapeutic regimen for the treatment of chronic cardiac rejection, preferably chronic allograft vasculopathy, also referred to as transplant coronary artery disease. In another embodiment, the compositions and methods of the invention comprise or are used in combination with a therapeutic regimen for the prevention of transplant coronary artery disease in a patient or patient population at risk. The criteria for identifying a patient or patient population at risk of developing transplant coronary artery disease are known in the art and may include, for example, patients having poorly matched transplants, patients who develop circulating anti-HLA antibodies, and patients who develop one or more clinical indications of humoral rejection early after cardiac transplant.

A patient or patient population in need of, or likely to benefit from, a heart transplant is identified according to the knowledge and skill in the art. Examples of patients that may be candidates for heart transplantation include those who have been diagnosed with any of the following diseases and disorders: coronary artery disease, cardiomyopathy (noninflammatory disease of the heart), heart valve disease with congestive heart failure, life-threatening abnormal heart rhythms that do not respond to other therapy, idiopathic cardiomyopathy, ischemic cardiomyopathy, dilated cardiomyopathy, ischemic cardiomyopathy, and congenital heart disease for which no conventional therapy exists or for which conventional therapy has failed.

The clinical criteria for the identification of a patient or patient population in need of, or likely to benefit from, a heart transplant can be determined according to the knowledge and skill in the art. Such criteria may include, for example, one or more of the following: ejection fraction less than 25%, intractable angina or malignant cardiac arrhythmias unresponsive to conventional therapy, and pulmonary vascular resistance of less than 2 Wood units. In addition, the patient or patient population in need of a heart transplant may be identified by performing a series of tests according to the knowledge and skill in the art. Such tests include, for example, resting and stress echocardiograms, EKG, assay of blood creatinine levels, coronary arteriography, and cardiopulmonary evaluation including right- and left-heart catheterization.

5.5.5.4. Lung Transplants

The compositions and methods of the invention are useful for treating or preventing GVHD, humoral rejection, and post-transplant lymphoproliferative disorder in a lung transplant recipient. In particular embodiments, the rejection is characterized as an acute or a chronic rejection. In one embodiment, the compositions and methods of the invention comprise or are used in combination with a pre-transplant conditioning regimen.

A patient or patient population in need of, or likely to benefit from, a lung transplant is identified according to the knowledge and skill in the art. Examples of patients that may be candidates for lung transplantation include patients having one of the following diseases or conditions: bronchiectasis, chronic obstructive pulmonary disease, cystic fibrosis, Eisenmenger syndrome or congenital heart disease with Eisenmenger syndrome. emphysema, eosinophilic granuloma of the lung, or histiocytosis X, inhalation/burn trauma, lymphangioleiomyomatosis (LAM), primary pulmonary hypertension, pulmonary fibrosis (scarring of the lung), or sarcoidosis.

The clinical criteria for the identification of a patient or patient population in need of, or likely to benefit from, a lung transplant can be determined according to the knowledge and skill in the art. Such criteria may include, for example, one or more of the following: Chronic obstructive pulmonary disease (COPD) and alpha1-antitrypsin deficiency emphysema characterized by one or more of the following indicators: postbronchodilator FEV1 of less than 25% predicted, resting hypoxemia, i.e., $PaO_2$ of less than 55-60 mm Hg, hypercapnia. secondary pulmonary hypertension, a rapid rate of decline in FEV1, or life-threatening exacerbations; cystic fibrosis characterized by one or more of the following indicators: postbronchodilator FEV1 of less than 30% predicted, resting hypoxemia, hypercapnia, or increasing frequency and severity of exacerbations; idiopathic pulmonary fibrosis characterized by one or more of the following indicators: vital capacity (VC) and TLC of less than 60-65% predicted, and resting hypoxemia; secondary pulmonary hypertension characterized by clinical, radiographic, or physiologic progression while on medical therapy; primary pulmonary hypertension characterized by one or more of the following indicators: NYHA functional class III or IV, mean right atrial pressure of greater than 10 mm Hg, mean pulmonary arterial pressure of greater than 50 mm Hg, cardiac index of less than 2.5 L/min/$m^2$, and failure of therapy with long-term prostacyclin infusion.

5.5.5.5. Post-Transplant Lymphoproliferative Disorder

The immunosuppression necessary for successful transplantation can give rise to a post-transplant lymphoproliferative disorder of B cell origin. Generally, a post-transplant lymphoproliferative disorder is associated with Epstein-Barr virus infected cells. Post-transplant lymphoproliferative disorder (PTLD) can range in severity from a benign self-limiting mononucleosis-like syndrome to an aggressive non-Hodgkins lymphoma. The compositions and methods of the present invention may be used to treat PTLD arising from any transplant. Preferably, the transplant is a solid organ transplant, for example, a heart transplant, a liver transplant, a kidney transplant, or a combined kidney-pancreas transplant. In a preferred embodiment, the compositions and methods of the invention are used to treat PTLD as part of a therapeutic regimen that includes a temporary cessation or reduction of other immunosuppressive therapy.

In one embodiment, the anti-CD19 antibody compositions of the invention are administered as part of a therapeutic regimen including one or more of the following: high dose intravenous gamma globulin, a cytokine, an anti-viral agent, and an anti-CD20 monoclonal antibody. Preferably, the therapeutic regimen includes a temporary cessation or reduction of immunosuppression therapy. In a preferred embodiment, intravenous gamma globulin is administered at a daily dose of 0.4 g/kg for 1 to 5 days, preferably for 3 days, and the cytokine is interferon alpha administered for at least 7 days. In one embodiment, one or more cytokines is used in the regimen. In one embodiment, one or more anti-viral agents is used in the regimen. The anti-viral agent may be selected from any suitable anti-viral agent known to those of skill in the art. In one embodiment, the anti-viral agent is aciclovir or ganciclovir. Preferably the anti-viral agent is administered for at least one or two weeks. The anti-viral agent may also be administered for longer periods, for example, 1 month, 2 months, 3 months, 4 months, or 5 months.

5.5.6. Determining CD19 Density In a Sample or Subject

While not required, assays for CD19 density can be employed to further characterize the patient's diagnosis. Methods of determining the density of antibody binding to cells are known to those skilled in the art (See, e.g., Sato et al., *J. Immunology*, 165:6635-6643 (2000); which discloses a method of assessing cell surface density of specific CD antigens). Other standard methods include Scatchard analysis. For example, the antibody or fragment can be isolated, radiolabeled, and the specific activity of the radiolabeled antibody determined. The antibody is then contacted with a target cell expressing CD19. The radioactivity associated with the cell can be measured and, based on the specific activity, the amount of antibody or antibody fragment bound to the cell determined.

Alternatively, fluorescence activated cell sorting (FACS) analysis can be employed. Generally, the antibody or antibody fragment is bound to a target cell expressing CD19. A second reagent that binds to the antibody is then added, for example, a fluorochrome labeled anti-immunoglobulin antibody. Fluorochrome staining can then be measured and used to determine the density of antibody or antibody fragment binding to the cell.

As another suitable method, the antibody or antibody fragment can be directly labeled with a detectable label, such as a fluorophore, and bound to a target cell. The ratio of label to protein is determined and compared with standard beads with known amounts of label bound thereto. Comparison of the amount of label bound to the cell with the known standards can be used to calculate the amount of antibody bound to the cell.

In yet another aspect, the present invention provides a method for detecting in vitro or in vivo the presence and/or density of CD19 in a sample or individual. This can also be useful for monitoring disease and effect of treatment and for determining and adjusting the dose of the antibody to be administered. The in vivo method can be performed using imaging techniques such as PET (positron emission tomography) or SPECT (single photon emission computed tomography). Alternatively, one could label the anti-CD19 antibody with Indium using a covalently attached chelator. The resulting antibody can be imaged using standard gamma cameras the same way as ZEVALIN™ (Indium labeled anti-CD20 mAb) (Biogen Idec) is used to image CD20 antigen.

In one embodiment, the in vivo method can be performed by contacting a sample to be tested, optionally along with a control sample, with a human anti-CD19 antibody of the invention under conditions that allow for formation of a complex between an antibody of the invention and the human CD19 antigen. Complex formation is then detected (e.g., using an FACS analysis or Western blotting). When using a control sample along with the test sample, a complex is detected in both samples and any statistically significant difference in the formation of complexes between the samples is indicative of the presence of human CD19 in the test sample.

In other embodiments, mean fluorescence intensity can be used as a measure of CD19 density. In such embodiments, B cells are removed from a patient and stained with CD19 antibodies that have been labeled with a fluorescent label and the fluorescence intensity is measured using flow cytometry. Fluorescence intensities can be measured and expressed as an average of intensity per B cell. Using such methods, mean fluorescence intensities that are representative of CD19 density can be compared for a patient before and after treatment using the methods and compositions of the invention, or between patients and normal levels of hCD19 on B cells.

In patients where the density of CD19 expression on B cells has been determined, the density of CD19 may influence the determination and/or adjustment of the dosage and/or treatment regimen used with the anti-CD19 antibody of the compositions and methods of the invention. For example, where density of CD19 is high, it may be possible to use anti-CD19 antibodies that less efficiently mediate ADCC in humans. In certain embodiments, where the patient treated using the compositions and methods of the invention has a low CD19 density, a higher dosage of the anti-CD19 antibody of the compositions and methods of the invention may be used. In other embodiments, where the patient treated using the compositions and methods of the invention has a low CD19 density, a low dosage of the anti-CD19 antibody of the compositions and methods of the invention may be used. In certain embodiments, where the patient treated using the compositions and methods of the invention has a high CD19 density, a lower dosage of the anti-CD19 antibody of the compositions and methods of the invention may be used. In certain embodiments, CD19 density can be compared to CD20 density in a patient, CD19 density can be compared to an average CD19 density for humans or for a particular patient population, or CD19 density can be compared to CD19 levels in the patient prior to therapy or prior to onset of a B cell or an autoimmune disease or disorder. In certain embodiments, the patient treated using the compositions and methods of the invention has a B cell malignancy or an autoimmune disease or disorder where CD19 is present on the surface of B cells.

5.6 Immunotherapeutic Protocols

In accordance with the present invention, each of the immunotherapeutic protocols described herein can utilize the routes and methods of administration and doses described in any of the preceding sections.

The anti-CD19 antibody compositions used in the therapeutic regimen/protocols, referred to herein as "anti-CD19 immunotherapy" can be naked antibodies, immunoconjugates and/or fusion proteins. The compositions of the invention can be used as a single agent therapy or in combination with other therapeutic agents or regimens. The anti-CD19 antibodies or immunoconjugates can be administered prior to, concurrently with, or following the administration of one or more therapeutic agents. Therapeutic agents that can be used in combination therapeutic regimens with the compositions of the invention include any substance that inhibits or prevents the function of cells and/or causes destruction of cells. Examples, include, but are not limited to, radioactive isotopes, chemotherapeutic agents, and toxins such as enzymatically active toxins of bacterial, fungal, plant or animal origin, or fragments thereof.

The therapeutic regimens described herein, or any desired treatment regimen can be tested for efficacy using a transgenic animal model such as the mouse model described below, which expresses human CD19 antigen in addition to or in place of native CD19 antigen. Thus, an anti-CD19 antibody treatment regimen can be tested in an animal model to determine efficacy before administration to a human.

The anti-CD19 antibodies, compositions and methods of the invention can be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular, NHL, small lymphocytic (SL) NHL, intermediate grade/follicular NHL, intermediate grade diffuse NHL, high grade immunoblastic NHL, high grade lymphoblastic NHL, high grade small noncleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma The inventors have shown that the inventive antibodies and compositions can deplete mature B cells. Thus, as another aspect, the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include but are not limited to acute lymphoblastic leukemia In other particular embodiments, the invention can be practiced to treat extranodal tumors.

In some embodiments, the anti-CD19 antibodies, compositions and methods of the invention can be practiced to treat autoimmune diseases or disorders.

In other embodiments, therapeutic agents that can be used in combination therapeutic regimens with the compositions of the invention include any substance that inhibits or prevents the function of cells and/or causes destruction of cells. Preferably, the agent inhibits or prevents the function of lymphocytes and/or causes destruction of lymphocytes. Examples, include, but are not limited to, immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a preferred embodiment, the immunosuppressant agent includes one or more of the following: adriamycin, azathiopurine, busulfan, cyclophosphamide, cyclosporin A (CyA), cytoxin, fludarabine, 5-fluorouracil, methotrexate, mycophenolate mofetil (MOFETIL), nonsteroidal anti-inflammatories (NSAIDs), rapamycin, and tacrolimus (FK506). Other examples include radioactive isotopes, chemotherapeutic agents, and toxins such as enzymatically active toxins of bacterial, fungal, plant or animal origin, or fragments thereof.

5.6.1. Anti-CD19 Immunotherapy

In accordance with the present invention "anti-CD19 immunotherapy" encompasses the administration of any of the anti-CD19 antibodies of the invention in accordance with any of the therapeutic regimens described herein. The anti-CD19 antibodies can be administered as naked antibodies, or immunoconjugates or fusion proteins.

Anti-CD19 immunotherapy encompasses the administration of the anti-CD19 antibody as a single agent therapeutic for the treatment of a B cell malignancy, treatment of an autoimmune disease or disorder, or prevention of GVHD, humoral rejection, or post-transplant lymphoproliferative disorder. Anti-CD19 immunotherapy encompasses methods of treating an early stage disease resulting from a B cell malignancy, methods of treating a human patient with a low level of activity of an autoimmune disease or disorder, and/or methods of treating a human patient at increased risk for developing GVHD, humoral rejection, or post-transplant lymphoproliferative disorder.

According to certain aspects of the invention, the anti-CD19 antibody used in the compositions and methods of the invention, is a naked antibody. In related embodiments, the dose of naked anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of naked anti-CD19 antibody used is at least about 1 to 20, 3 to 15, or 5 to 10 mg/kg of body weight of a patient. In preferred embodiments, the dose of naked anti-CD19 antibody used is at least about 5, 6, 7, 8, 9, or 10 mg/kg of body weight of a patient.

In certain embodiments, the dose comprises about 375 mg/m$^2$ of anti-CD19 antibody administered weekly for 4 to 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for 4 to 8 consecutive weeks.

The exemplary doses of anti-CD19 antibody described above can be administered as described herein. In one embodiment, the above doses are single dose injections. In other embodiments, the doses are administered over a period of time. In other embodiments, the doses are administered multiple times over a period of time. The period of time may be measured in days, months or weeks. Multiple doses of the anti-CD19 antibody can be administered at intervals suitable to achieve a therapeutic benefit while balancing toxic side effects. For example, where multiple doses are used, it is preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, the compositions of the invention are administered to a human patient as long as the patient is responsive to therapy. In other embodiments, the compositions of the invention are administered to a human patient as long as the patient's disease does not progress. In related embodiments, the compositions of the invention are administered to a human patient until a patient's disease does not progress or has not progressed for a period of time, then the patient is not administered the compositions of the invention unless the disease reoccurs or begins to progress again.

In other embodiments, the compositions of the invention are administered to a human patient until the GVHD or rejection episode subsides. In another embodiment, the compositions of the invention are administered to a human patient until graft function is substantially restored, then the patient is not administered the compositions of the invention unless another rejection episode is indicated. In one embodiment, the compositions of the invention are administered to a human patient until the lymphoproliferative disorder has been ameliorated as indicated by a reduction in the number of circulating B-lymphocytes and/or a reduction in the level of circulating immunoglobulin.

For example, a patient can be treated with any of the above doses for about 4 to 8 weeks, during which time the patient is monitored for disease progression (i.e., activity of an autoimmune disease or disorder). If disease progression stops or reverses, then the patient will not be administered the compositions of the invention until that patient relapses, i.e., the disease being treated reoccurs or progresses. Upon this reoccurrence or progression, the patient can be treated again with the same dosing regimen initially used or using other doses described above.

In certain embodiments, the compositions of the invention can be administered as a loading dose followed by multiple lower doses (maintenance doses) over a period of time. In such embodiments, the doses may be timed and the amount adjusted to maintain effective B cell depletion. In preferred embodiments, the loading dose is about 10, 11, 12, 13, 14, 15, 16, 17, or 18 mg/kg of patient body weight and the maintenance dose is at least about 5 to 10 mg/kg of patient body weight. In preferred embodiments, the maintenance dose is administered at intervals of every 7, 10, 14 or 21 days. The maintenance doses can be continued indefinitely, until toxicity is present, until platelet count decreases, until there is no disease progression, until the patient generates an immune response to the drug, or until disease progresses to a terminal state. In yet other embodiments, the compositions of the invention are administered to a human patient until the disease progresses to a terminal stage.

In some embodiments, the maintenance doses can be continued indefinitely, until toxicity is present, until platelet count decreases, until there is no evidence of GVHD or rejection, until the patient generates an immune response against the anti-CD19 antibody compositions, or until disease progresses to a terminal state.

In embodiments of the invention where circulating monocyte levels of a patient are monitored as part of a treatment regimen, doses of anti-CD19 antibody administered may be spaced to allow for recovery of monocyte count. For example, a composition of the invention may be administered at intervals of every 8, 9, 10, 11, 12, 13, 14, 15, 16, 17, 18, 19, 20, 21, 22, 23, 24, 25, 26, 27, 28, 29, or 30 days.

In embodiments of the invention where an anti-CD19 antibody is conjugated to or administered in conjunction with a toxin, one skilled in the art will appreciate that the dose of anti-CD19 antibody can be adjusted based on the toxin dose and that the toxin dose will depend on the specific type of toxin being used. Typically, where a toxin is used, the dose of anti-CD19 antibody will be less than the dose used with a naked anti-CD19 antibody. The appropriate dose can be determined for a particular toxin using techniques well known in the art. For example, a dose ranging study can be conducted to determine the maximum tolerated dose of anti-CD19 antibody when administered with or conjugated to a toxin.

In embodiments of the invention where an anti-CD19 antibody is conjugated to or administered in conjunction with a radiotherapeutic agent, the dose of the anti-CD19 antibody will vary depending on the radiotherapeutic used. In certain preferred embodiments, a two step process is used. First, the human patient is administered a composition comprising a naked anti-CD19 antibody and about 6, 7, 8, 9, or 10 days later a small amount of the radiotherapeutic is administered. Second, once the tolerance, distribution, and clearance of the low dose therapy has been determined, the patient is administered a dose of the naked anti-CD19 antibody followed by a therapeutic amount of the radiotherapeutic is administered. Such treatment regimens are similar to those approved for treatment of Non-Hodgkin's lymphoma using ZEVALIN™ (Indium labeled anti-CD20 mAb) (Biogen Idec) or BEXXAR™ (GSK, Coulter Pharmaceutical).

5.6.1.1. Oncology

Anti-CD19 immunotherapy encompasses methods of treating a B cell malignancy wherein the anti-CD19 antibody mediates ADCC. Anti-CD19 immunotherapy encompasses methods of treating a B cell malignancy, wherein the anti-CD19 antibody is administered before the patient has received any treatment for the malignancy, whether that therapy is chemotherapy, radio chemical based therapy or surgical therapy.

In a preferred embodiment, a human subject having a B cell malignancy can be treated by administering a human or humanized antibody that preferably mediates human ADCC. In cases of early stage disease, or single agent therapies, any anti-CD19 antibody that preferably mediates ADCC can be used in the human subjects (including murine and chimeric antibodies); however, human and humanized antibodies are preferred.

Antibodies of the IgG1 or IgG3 human isotypes are preferred for therapy. However, the IgG2 or IgG4 human isotypes can be used, provided they mediate human ADCC. Such effector function can be assessed by measuring the ability of the antibody in question to mediate target cell lysis by effector cells in vitro or in vivo.

The dose of antibody used should be sufficient to deplete circulating B cells. Progress of the therapy can be monitored in the patient by analyzing blood samples. Other signs of clinical improvement can be used to monitor therapy.

Methods for measuring depletion of B cells that can be used in connection with the compositions and methods of the invention are well known in the art and include, but are not limited to the following embodiments. In one embodiment, circulating B cells depletion can be measured with flow cytometry using a reagent other than an anti-CD19 antibody that binds to B cells to define the amount of B cells. In other embodiments, antibody levels in the blood can be monitored using standard serum analysis. In such embodiments, B cell depletion is indirectly measured by defining the amount to an antibody known to be produced by B cells. The level of that antibody is then monitored to determine the depletion and/or functional depletion of B cells. In another embodiment, B cell depletion can be measured by immunochemical staining to identify B cells. In such embodiments, B cells extracted from patient tissues can be placed on microscope slides, labeled and examined for presence or absence. In related embodiments, a comparison is made between B cells extracted prior to therapy and after to determine differences in the presence of B cells.

Tumor burden can be measured and used in connection with the compositions and methods of the invention. Methods for measuring tumor burden are well known in the art and include, but are not limited to the following embodiments. In certain embodiments, PET scans can be used to measure metabolic activity and identify areas of higher activity which are indicative of tumors. CT scans and MRI can also be used to examine soft tissue for the presence and size of tumors. In other embodiments, bone scans can be used to measure tumor volume and location. In yet other embodiments, tumor burden can be measured by examining the blood flow into and out of a tumor using doppler technology (e.g., ultrasound). In such embodiments, changes in blood flow over time or deviations from normal blood flow in the appropriate tissue of a patient can be used to calculate an estimate to tumor burden. Such methods for measuring tumor burden can be used prior to and following the methods of treatment of the invention.

In preferred embodiments of the methods of the invention B cells are depleted and/or tumor burden is decreased while ADCC function is maintained.

In embodiments of the invention where the anti-CD19 antibody is administered as a single agent therapy, the invention contemplates use of different treatment regimens.

According to certain aspects of the invention, the anti-CD19 antibody used in the compositions and methods of the invention, is a naked antibody. In related embodiments, the dose of naked anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of naked anti-CD19 antibody used is at least about 1 to 20, 3 to 15, or 5 to 10 mg/kg of body weight of a patient. In preferred embodiments, the dose of naked anti-CD19 antibody used is at least about 5, 6, 7, 8, 9, or 10 mg/kg of body weight of a patient.

In certain embodiments, the dose comprises about 375 mg/m$^2$ of anti-CD19 antibody administered weekly for 4 to 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for 4 to 8 consecutive weeks.

The exemplary doses of anti-CD19 antibody described above can be administered as described in herein. In one embodiment, the above doses are single dose injections. In other embodiments, the doses are administered over a period of time. In other embodiments, the doses are administered multiple times over a period of time. The period of time may be measured in days, months or weeks. Multiple doses of the anti-CD19 antibody can be administered at intervals suitable to achieve a therapeutic benefit while balancing toxic side effects. For example, where multiple doses are used, it is preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, the compositions of the invention are administered to a human patient as long as the patient is responsive to therapy. In other embodiments, the compositions of the invention are administered to a human patient as long as the patient's disease does not progress. In related embodiments, the compositions of the invention are administered to a human patient until a patient's disease does not progress or has not progressed for a period of time, then the patient is not administered the compositions of the invention unless the disease reoccurs or begins to progress again. For example, a patient can be treated with any of the above doses for about 4 to 8 weeks, during which time the patient is monitored for disease progression. If disease progression stops or reverses, then the patient will not be administered the compositions of the invention until that patient relapses, i.e., the disease being treated reoccurs or progresses. Upon this reoccurrence or progression, the patient can be treated again with the same dosing regimen initially used or using other doses described above.

In certain embodiments, the compositions of the invention can be administered as a loading dose followed by multiple lower doses (maintenance doses) over a period of time. In such embodiments, the doses may be timed and the amount adjusted to maintain effective B cell depletion. In preferred embodiments, the loading dose is about 10, 11, 12, 13, 14, 15, 16, 17, or 18 mg/kg of patient body weight and the maintenance dose is at least about 5 to 10 mg/kg of patient body weight. In preferred embodiments, the maintenance dose is administered at intervals of every 7, 10, 14 or 21 days. The maintenance doses can be continued indefinitely, until toxicity is present, until platelet count decreases, until there is no disease progression, until the patient generates an immune response to the drug, or until disease progresses to a terminal state. In yet other embodiments, the compositions of the invention are administered to a human patient until the disease progresses to a terminal stage.

In embodiments of the invention where circulating monocyte levels of a patient are monitored as part of a treatment regimen, doses of anti-CD19 antibody administered may be spaced to allow for recovery of monocyte count. For example, a composition of the invention may be administered at intervals of every 8, 9, 10, 11, 12, 13, 14, 15, 16, 17, 18, 19, 20, 21, 22, 23, 24, 25, 26, 27, 28, 29, or 30 days.

In embodiments of the invention where an anti-CD19 antibody is conjugated to or administered in conjunction with a toxin, one skilled in the art will appreciate that the dose of anti-CD19 antibody can be adjusted based on the toxin dose and that the toxin dose will depend on the specific type of toxin being used. Typically, where a toxin is used, the dose of anti-CD19 antibody will be less than the dose used with a naked anti-CD19 antibody. The appropriate dose can be determined for a particular toxin using techniques well known in the art. For example, a dose ranging study can be conducted to determine the maximum tolerated dose of anti-CD19 antibody when administered with or conjugated to a toxin.

In embodiments of the invention where an anti-CD19 antibody is conjugated to or administered in conjunction with a radiotherapeutic agent, the dose of the anti-CD19 antibody will vary depending on the radiotherapeutic used. In certain preferred embodiments, a two step process is used. First, the human patient is administered a composition comprising a naked anti-CD19 antibody and about 6, 7, 8, 9, or 10 days later a small amount of the radiotherapeutic is administered. Second, once the tolerance, distribution, and clearance of the low dose therapy has been determined, the patient is administered a dose of the naked anti-CD19 antibody followed by a therapeutic amount of the radiotherapeutic is administered. Such treatment regimens are similar to those approved for treatment of Non-Hodgkin's lymphoma using ZEVALIN™ (Indium labeled anti-CD20 mAb) (Biogen Idec) or BEXXAR™ (GSK, Coulter Pharmaceutical).

5.6.1.2. Autoimmune Diseases and Disorders

In other embodiments, Anti-CD19 immunotherapy encompasses methods of treating a human patient with a high level of activity of an autoimmune disease or disorder. Anti-CD19 immunotherapy encompasses methods of treating a human patient with an early stage of an autoimmune disease or disorder that has been characterized by stages. Anti-CD19 immunotherapy encompasses methods of treating a human patient with an late stage of an autoimmune disease or disorder that has been characterized by stages. Anti-CD19 immunotherapy encompasses methods of treating an autoimmune disease or disorder wherein the anti-CD19 antibody mediates ADCC, CDC, or apoptosis. Anti-CD19 immunotherapy encompasses methods of treating an autoimmune disease or disorder, wherein the anti-CD19 antibody is administered before the patient has received any treatment for the autoimmune disease or disorder.

In a preferred embodiment, a human subject having an autoimmune disease or disorder can be treated by administering an anti-CD19 antibody. In certain embodiments, the anti-CD19 antibody is a human or humanized antibody that preferably mediates human ADCC. In cases of early stage disease, or single agent therapies, any anti-CD19 antibody that preferably mediates ADCC can be used in the human subjects (including murine and chimeric antibodies); however, human and humanized antibodies are preferred.

Antibodies of the IgG1 or IgG3 human isotypes are preferred for therapy. However, the IgG2 or IgG4 human isotypes can be used, provided they mediate human ADCC. Such effector function can be assessed by measuring the ability of the antibody in question to mediate target cell lysis by effector cells in vitro or in vivo.

The dose of antibody used should be sufficient to deplete circulating B cells. Progress of the therapy can be monitored in the patient by analyzing blood samples. Other signs of clinical improvement can be used to monitor therapy.

Methods for measuring depletion of B cells that can be used in connection with the compositions and methods of the invention are well known in the art and include, but are not limited to the following embodiments. In one embodiment, circulating B cells depletion can be measured with flow cytometry using a reagent other than an anti-CD19 antibody that binds to B cells to define the amount of B cells. In other embodiments, antibody levels in the blood can be monitored using standard serum analysis. In such embodiments, B cell depletion is indirectly measured by defining the amount to an antibody known to be produced by B cells. The level of that antibody is then monitored to determine the depletion and/or functional depletion of B cells. In another embodiment, B cell depletion can be measured by immunochemical staining to identify B cells. In such embodiments, B cells extracted from patient tissues can be placed on microscope slides, labeled and examined for presence or absence. In related embodiments, a comparison is made between B cells extracted prior to therapy and after to determine differences in the presence of B cells.

In embodiments of the invention where the anti-CD19 antibody is administered as a single agent therapy, the invention contemplates use of different treatment regimens. The treatment regimens can comprise one or more treatment cycles depending on the activity of an autoimmune disease or disorder. Generally if disease activity is low, then fewer cycles of treatment are administered. If more than one cycle is needed, the time between any two treatment cycles may be fixed or variable to accommodate patient-specific differences in disease activity, disease responsiveness, drug tolerability, recovery times, pharmacokinetic (PK) parameters, and/or pharmacological response(s). For example, in certain embodiments, the time between any two treatment cycles can be about 2 months, 4 months, 8 months, 12 months, 18 months, or 24 months. In certain embodiments, the time between any two treatment cycles can be about 1 month, 3 months, 5 months, 9 months, 11 months, 17 months, 19 months, 21 months, or 25 months. In certain embodiments, the time between any two treatment cycles can be about 2 to 4, 3 to 5, 6 to 8, 7 to 9, 8 to 10, 9 to 11, 10 to 12, 11 to 13, 12 to 14, 13 to 15, 14 to 16, 15 to 17, 16 to 18, 17 to 19, 18 to 20, 19 to 21, 20 to 22, 21 to 23, or 22 to 24 months. In certain embodiments, the time between any two treatment cycles is about 24 months.

The number of injections of the anti-CD19 antibody compositions of the invention per cycle may be fixed or variable to allow for patient-specific differences in disease activity, disease responsiveness, drug tolerability, recovery times, PK parameters, and/or pharmacological response(s). In certain embodiments, the number of injections per cycle can be 1, 2, 3, 4, 5, or 6 injections. In certain embodiments, the number of injections per cycle is 1 injection.

For any injection, the administered dose of the anti-CD19 antibody compositions of the invention may be fixed or variable to allow for initial drug loading and/or to account for patient-specific differences in mass, body surface area, disease activity, disease responsiveness, drug tolerability, recovery times, PK parameters, and/or pharmacological response(s). In certain embodiments, the administered dose per injection of the anti-CD19 antibody compositions of the invention is about 0.1 mg/Kg of patient body weight, 0.3 mg/Kg of patient body weight, 1.0 mg/Kg of patient body weight, 2.0 mg/Kg of patient body weight, 4.0 mg/Kg of patient body weight, or 10 mg/Kg of patient body weight. In certain embodiments, the administered dose per injection of the anti-CD19 antibody compositions of the invention is about 0.1 to 0.3, 0.3 to 0.5, 0.5 to 0.7, 0.7 to 0.9, 0.9 to 1.1, 1.1 to 1.3, 1.3 to 1.5, 1.5 to 1.7, 1.7 to 1.9, 1.9 to 2.1, 2.1 to 2.3, 2.3 to 2.5, 2.5 to 2.7, 2.7 to 2.9, 2.9 to 3.1, 3.1 to 3.3, 3.3 to 3.5, 3.5 to 3.7, 3.7 to 3.9, 3.9 to 4.1, 4.1 to 4.3, 4.3 to 4.5, 4.5 to 4.7, 4.7 to 4.9, 4.9 to 5.1, 5.1 to 5.3, 5.3 to 5.5, 5.5 to 5.7, 5.7 to 5.9, 5.9 to 6.1, 6.1 to 6.3, 6.3 to 6.5, 6.5 to 6.7, 6.7 to 6.9, 6.9 to 7.1, 7.1 to 7.3, 7.3 to 7.5, 7.5 to 7.7, 7.7 to 7.9, 7.9 to 8.1, 8.1 to 8.3, 8.3 to 8.5, 8.5 to 8.7, 8.7 to 8.9, 8.9 to 9.1, 9.1 to 9.3, 9.3 to 9.5, 9.5 to 9.7, 9.7 to 9.9, or 9.9 to 10.1 mg/Kg of patient body weight. In certain embodiments, the administered dose per injection is about 0.3 mg/Kg of patient body weight.

If more than one injection is needed, the time between any two injections of the anti-CD19 antibody compositions of the invention may be fixed or variable to accommodate patient-specific differences in disease activity, disease responsiveness, drug tolerability, recovery times, PK parameters, and/or pharmacological response(s). In certain embodiments, the time between any two injections is about 1, 2, 3, 4, 5, 6, 7, 8, 9, 10, 11, 12, 13, 14, 15, 16, 17, 18, 19, 20, 21, 22, 23, 24, 25, 26, 27, 28 days, 29, 30, 32, 32, 33, 34, 35, 36, 37, 38, 39, 40, 41, 42, 43, 44, or 45 days. In certain embodiments, the time between any two injections is about 1 to 3, 1 to 5, 1 to 10, 1 to 15, 1 to 20, 1 to 25, 1 to 30, 1 to 35, 1 to 40, or 1 to 45 days. In certain embodiments, the time between any two injections is 1 day.

According to certain aspects of the invention, the anti-CD19 antibody used in the compositions and methods of the invention, is a naked antibody. In related embodiments, the dose of naked anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of naked anti-CD19 antibody used is at least about 1 to 20, 3 to 15, or 5 to 10 mg/kg of body weight of a patient. In preferred embodiments, the dose of naked anti-CD19 antibody used is at least about 5, 6, 7, 8, 9, or 10 mg/kg of body weight of a patient.

In certain embodiments, the dose comprises about 375 mg/m$^2$ of anti-CD19 antibody administered weekly for 4 to 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for 4 to 8 consecutive weeks.

The exemplary doses of anti-CD19 antibody described above can be administered as described herein. In one embodiment, the above doses are single dose injections. In other embodiments, the doses are administered over a period of time. In other embodiments, the doses are administered multiple times over a period of time. The period of time may be measured in days, months or weeks. Multiple doses of the anti-CD19 antibody can be administered at intervals suitable to achieve a therapeutic benefit while balancing toxic side effects. For example, where multiple doses are used, it is preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, the compositions of the invention are administered to a human patient as long as the patient is responsive to therapy. In other embodiments, the compositions of the invention are administered to a human patient as long as the patient's disease does not progress. In related embodiments, the compositions of the invention are administered to a human patient until a patient's disease does not progress or has not progressed for a period of time, then the patient is not administered the compositions of the invention unless the disease reoccurs or begins to progress again. For example, a patient can be treated with any of the above doses for about 4 to 8 weeks, during which time the patient is monitored for disease progression (i.e., activity of an autoimmune disease or disorder). If disease progression stops or reverses, then the patient will not be administered the compositions of the invention until that patient relapses, i.e., the disease being treated reoccurs or progresses. Upon this reoccurrence or progression, the patient can be treated again with the same dosing regimen initially used or using other doses described above.

In certain embodiments, the compositions of the invention can be administered as a loading dose followed by multiple lower doses (maintenance doses) over a period of time. In such embodiments, the doses may be timed and the amount adjusted to maintain effective B cell depletion. In preferred embodiments, the loading dose is about 10, 11, 12, 13, 14, 15, 16, 17, or 18 mg/kg of patient body weight and the maintenance dose is at least about 5 to 10 mg/kg of patient body weight. In preferred embodiments, the maintenance dose is administered at intervals of every 7, 10, 14 or 21 days. The maintenance doses can be continued indefinitely, until toxicity is present, until platelet count decreases, until there is no disease progression, until the patient generates an immune response to the drug, or until disease progresses to a terminal state. In yet other embodiments, the compositions of the invention are administered to a human patient until the disease progresses to a terminal stage.

In embodiments of the invention where circulating monocyte levels of a patient are monitored as part of a treatment regimen, doses of anti-CD19 antibody administered may be spaced to allow for recovery of monocyte count. For example, a composition of the invention may be administered at intervals of every 8, 9, 10, 11, 12, 13, 14, 15, 16, 17, 18, 19, 20, 21, 22, 23, 24, 25, 26, 27, 28, 29, or 30 days.

In embodiments of the invention where an anti-CD19 antibody is conjugated to or administered in conjunction with a toxin, one skilled in the art will appreciate that the dose of anti-CD19 antibody can be adjusted based on the toxin dose and that the toxin dose will depend on the specific type of toxin being used. Typically, where a toxin is used, the dose of anti-CD19 antibody will be less than the dose used with a naked anti-CD19 antibody. The appropriate dose can be determined for a particular toxin using techniques well known in the art. For example, a dose ranging study can be conducted to determine the maximum tolerated dose of anti-CD19 antibody when administered with or conjugated to a toxin.

In embodiments of the invention where an anti-CD19 antibody is conjugated to or administered in conjunction with a radiotherapeutic agent, the dose of the anti-CD19 antibody will vary depending on the radiotherapeutic used. In certain preferred embodiments, a two step process is used. First, the human patient is administered a composition comprising a naked anti-CD19 antibody and about 6, 7, 8, 9, or 10 days later a small amount of the radiotherapeutic is administered. Second, once the tolerance, distribution, and clearance of the low dose therapy has been determined, the patient is administered a dose of the naked anti-CD19 antibody followed by a therapeutic amount of the radiotherapeutic is administered. Such treatment regimens are similar to those approved for treatment of Non-Hodgkin's lymphoma using ZEVALIN™ (Indium labeled anti-CD20 mAb) (Biogen Idec) or BEXXAR™ (GSK, Coulter Pharmaceutical).

5.6.1.3. Transplantation

In further embodiments, Anti-CD19 immunotherapy encompasses methods of treating a human patient with an early stage of GVHD, humoral rejection, or post-transplant lymphoproliferative disorder that has been characterized by stages. Anti-CD19 immunotherapy encompasses methods of treating a human patient with an late stage of GVHD, humoral rejection, or post-transplant lymphoproliferative disorder that has been characterized by stages. Anti-CD19 immunotherapy encompasses methods of treating or preventing GVHD, humoral rejection, or post-transplant lymphoproliferative disorder wherein the anti-CD19 antibody mediates ADCC, CDC, or apoptosis. Anti-CD19 immunotherapy encompasses methods of treating GVHD, humoral rejection, or post-transplant lymphoproliferative disorder, wherein the anti-CD19 antibody is administered before the patient has received any other treatment for the GVHD, humoral rejection, or post-transplant lymphoproliferative disorder.

In a preferred embodiment, a human subject experiencing GVHD, humoral rejection, or post-transplant lymphoproliferative disorder can be treated by administering an anti-CD19 antibody. In certain embodiments, the anti-CD19 antibody is a human or humanized antibody that preferably mediates human ADCC. In cases of an early stage of GVHD, humoral rejection, or post-transplant lymphoproliferative disorder, any anti-CD19 antibody that preferably mediates ADCC can be used in the human subjects (including murine and chimeric antibodies); however, human and humanized antibodies are preferred.

Antibodies of the IgG1 or IgG3 human isotypes are preferred for therapy. However, the IgG2 or IgG4 human isotypes can be used, provided they mediate human ADCC. Such effector function can be assessed by measuring the ability of the antibody in question to mediate target cell lysis by effector cells in vitro or in vivo.

The dose of antibody used should be sufficient to deplete circulating B cells or to deplete B cells from a graft, or to deplete circulating immunoglobulin (Ig) in the recipient, or to deplete both circulating B cells and immunoglobulin in the recipient. Progress of the therapy can be monitored in the patient by analyzing blood samples. Other signs of clinical improvement can be used to monitor therapy.

Methods for measuring depletion of B cells and Ig that can be used in connection with the compositions and methods of the invention are well-known in the art and include, but are not limited to the following embodiments. In one embodiment, circulating B cell depletion can be measured with flow cytometry using a reagent other than an anti-CD19 antibody that specifically binds to B cells thereby allowing them to be identified and enumerated. In other embodiments, B cell and Ig levels in the blood can be monitored using standard serum analysis. In such embodiments, B cell depletion is indirectly measured by defining the amount to an antibody known to be produced by B cells. The level of that antibody is then monitored to determine the depletion and/or functional depletion of B cells. In another embodiment, B cell depletion can be measured by immunochemical staining to identify B cells. In such embodiments, B cells or tissues or serum comprising B cells extracted from a patient can be placed on microscope slides, labeled and examined for presence or absence. In related embodiments, a comparison is made between B cells extracted prior to therapy and after to determine differences in the presence of B cells.

In embodiments of the invention where the anti-CD19 antibody is administered as a single agent therapy, the invention contemplates use of different treatment regimens. The treatment regimens can comprise one or more treatment cycles depending on whether the regimen is indicated for pre-transplant conditioning, post-transplant maintenance, or post-transplant treatment of an acute or chronic rejection. The particular regimen may also depend on whether the patient is assessed as being at high, intermediate, or low risk of developing a humoral response. In the context of rejection, the apparent stage of the humoral response to the graft may influence the treatment regimen chosen. Preferably, for pre-transplant conditioning, a single cycle is administered. The single cycle may be administered to the recipient or to the graft, or to both the recipient and the graft. For post-transplant maintenance or prevention of GVHD, humoral rejection, or lymphoproliferative disorder, preferably multiple cycles are administered. For the treatment of a rejection episode, preferably a single high dose cycle is administered followed by one or more lower doses, either alone or in combination with other therapeutic regimens. The other therapeutic regimens may comprise, for example, one or more antibodies directed against T cells or B cells, antibiotics, anti-viral agents, antibody depletion therapies, or immunosuppressive agents. If more than one cycle is needed, the time between any two treatment cycles may be fixed or variable to accommodate patient-specific differences including the patient's risk assessment for developing GVHD, a humoral rejection, or a lymphoproliferative disorder; or the stage of humoral rejection in a patient already presenting with rejection. Other patient-specific differences include, for example, responsiveness to therapy, drug tolerability, recovery times, pharmacokinetic (PK) parameters, and/or pharmacological response(s). For example, in certain embodiments, the time between any two treatment cycles can be about 2, 4, 6, 8, or 10 days; 2 months, 4 months, 8 months, 12 months, 18 months, or 24 months. In certain embodiments, the time between any two treatment cycles can be about 1, 3, 5, 7, or 9 days; 1 month, 3 months, 5 months, 9 months, 11 months, 17 months, 19 months, 21 months, or 25 months. In certain embodiments, the time between any two treatment cycles can be about 2 to 4, 3 to 5, 6 to 8, 7 to 9, 8 to 10, 9 to 11, 10 to 12, 11 to 13, 12 to 14, 13 to 15, 14 to 16, 15 to 17, 16 to 18, 17 to 19, 18 to 20, 19 to 21, 20 to 22, 21 to 23, or 22 to 24 months. In certain embodiments, the time between any two treatment cycles is about 24 months.

The number of injections of the anti-CD19 antibody compositions of the invention per cycle may be fixed or variable to allow for patient-specific differences including the patient's risk assessment for developing GVHD, a humoral rejection, or a lymphoproliferative disorder; or the stage of humoral rejection in a patient already presenting with rejection. Other patient-specific differences include, for example, responsiveness to therapy, drug tolerability, recovery times, PK parameters, and/or pharmacological response(s). In certain embodiments, the number of injections per cycle can be 1, 2, 3, 4, 5, or 6 injections. In certain embodiments, the number of injections per cycle is 1 injection.

For any injection, the administered dose of the anti-CD19 antibody compositions of the invention may be fixed or variable to allow for initial drug loading and/or to account for patient-specific differences in mass, body surface area, disease activity, disease responsiveness, drug tolerability, recovery times, PK parameters, and/or pharmacological response(s). In certain embodiments, the administered dose per injection of the anti-CD19 antibody compositions of the invention is about 0.1 mg/kg of patient body weight, 0.3 mg/kg of patient body weight, 1.0 mg/kg of patient body weight, 2.0 mg/kg of patient body weight, 4.0 mg/kg of patient body weight, or 10 mg/kg of patient body weight. In certain embodiments, the administered dose per injection of the anti-CD19 antibody compositions of the invention is about 0.1 to 0.3, 0.3 to 0.5, 0.5 to 0.7, 0.7 to 0.9, 0.9 to 1.1, 1.1 to 1.3, 1.3 to 1.5, 1.5 to 1.7, 1.7 to 1.9, 1.9 to 2.1, 2.1 to 2.3, 2.3 to 2.5, 2.5 to 2.7, 2.7 to 2.9, 2.9 to 3.1, 3.1 to 3.3, 3.3 to 3.5, 3.5 to 3.7, 3.7 to 3.9, 3.9 to 4.1, 4.1 to 4.3, 4.3 to 4.5, 4.5 to 4.7, 4.7 to 4.9, 4.9 to 5.1, 5.1 to 5.3, 5.3 to 5.5, 5.5 to 5.7, 5.7 to 5.9, 5.9 to 6.1, 6.1 to 6.3, 6.3 to 6.5, 6.5 to 6.7, 6.7 to 6.9, 6.9 to 7.1, 7.1 to 7.3, 7.3 to 7.5, 7.5 to 7.7, 7.7 to 7.9, 7.9 to 8.1, 8.1 to 8.3, 8.3 to 8.5, 8.5 to 8.7, 8.7 to 8.9, 8.9 to 9.1, 9.1 to 9.3, 9.3 to 9.5, 9.5 to 9.7, 9.7 to 9.9, or 9.9 to 10.1 mg/kg of patient body weight. In certain embodiments, the administered dose per injection is about 0.3 mg/kg of patient body weight. If more than one injection is needed, the time between any two injections of the anti-CD19 antibody compositions of the invention may be fixed or variable to accommodate patient-specific differences including the patient's risk assessment for developing GVHD, a humoral rejection, or a lymphoproliferative disorder; or the stage of humoral rejection in a patient already presenting with rejection. Other patient-specific differences include, for example, disease activity, disease responsiveness to therapy, drug tolerability, recovery times, PK parameters, and/or pharmacological response(s). In certain embodiments, the time between any two injections is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 32, 33, 34, 35, 36, 37, 38, 39, 40, 41, 42, 43, 44, or 45 days. In certain embodiments, the time between any two injections is about 1 to 3, 1 to 5, 1 to 10, 1 to 15, 1 to 20, 1 to 25, 1 to 30, 1 to 35, 1 to 40, or 1 to 45 days. In certain embodiments, the time between any two injections is 1 day.

5.6.2. Combination Therapies 5.6.2.1. Combination with Immunoregulatory Agents

The anti-CD19 immunotherapy of the invention may also be used in conjunction with one or more immunoregulatory agents. In this approach, the use of chimerized antibodies is preferred; the use of human or humanized anti-CD19 antibody is most preferred. The term "immunoregulatory agent" as used herein for combination therapy refers to substances that act to suppress, mask, or enhance the immune system of the host.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab')$_2$ fragments or epitope binding fragments), nucleic acid molecules (e.g., antisense nucleic acid molecules, iRNA and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of immunosuppressants, include, but are not limited to, mycophenolate mofetil (CELLCEPT™), D-penicillamine (CUPRIMINE™, DEPEN™), methotrexate (RHEUMATREX™, TREX-ALL™), and hydroxychloroquine sulfate (PLAQUENIL™)

Immunomodulatory agents would also include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T cell antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T cell receptor (U.S. Pat. No. 5,114,721); T cell receptor fragments (Offner et al., *Science,* 251:430-432 (1991); WO 90/11294; and WO 91/01133); and T cell receptor antibodies (EP 340, 109) such as T10B9.

Examples of cytokines include, but are not limited to lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoiotin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, preferably a cytokine Preferred cytokines are selected from the group consisting of interleukin-1 (IL-1), IL-2, IL-3, IL-12, IL-15, IL-18, G-CSF, GM-CSF, thrombopoietin, and γ interferon.

In certain embodiments, the immunomodulatory agent is a cytokine receptor modulator. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies). In a specific embodiment, a cytokine receptor modulator is IL-4, IL-10, or a fragment thereof. In another embodiment, a cytokine receptor modulator is an anti-IL-1β antibody, anti-IL-6 antibody, anti-IL-12 receptor antibody, anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

In certain embodiments, the immunomodulatory agent is a T cell receptor modulator. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies, anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies, anti-CD52 antibodies (e.g., CAM-PATH™-1H (Ilex)), anti-CD2 monoclonal antibodies) and CTLA4-immunoglobulin.

In certain embodiments, the immunomodulatory agent is a TNF-α antagonist. Examples of TNF-α antagonists include, but are not limited to, antibodies (e.g., infliximab (REMICADE™; Centocor), D2E7 (Abbott Laboratories/Knoll Pharmaceuticals Co., Mt. Olive, N.J.), CDP571 which is also known as HUMIRA™ and CDP-870 (both of Celltech/Pharmacia, Slough, U.K.), and TN3-19.12 (Williams et al., 1994, *Proc. Natl. Acad. Sci. USA,* 91:2762-2766; Thorbecke et al., 1992, *Proc. Natl. Acad. Sci. USA,* 89:7375-7379)) soluble TNF-α receptors (e.g., sTNF-R1 (Amgen), etanercept (ENBREL™; Immunex) and its rat homolog RENBREL™, soluble inhibitors of TNF-α derived from TNFrI, TNFrII (Kohno et al., 1990, *Proc. Natl. Acad. Sci. USA,* 87:8331-8335), and TNF-α Inh (Seckinger et al., 1990, *Proc. Natl. Acad. Sci. USA,* 87:5188-5192)), IL-10, TNFR-IgG (Ashkenazi et al., 1991, *Proc. Natl. Acad. Sci. USA,* 88:10535-10539), the murine product TBP-1 (Serono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

These immunoregulatory agents are administered at the same time or at separate times from the anti-CD19 antibodies of the invention, and are used at the same or lesser dosages than as set forth in the art. The preferred immunoregulatory agent will depend on many factors, including, for example, type of autoimmune disease or disorder being treated, or whether the treatment is prophylactic or whether it is to treat an early or later stage of GVHD or graft rejection, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

5.6.2.2. Combination with Anti-Inflammatory Agents and Therapies

The anti-CD19 immunotherapy of the invention of the present invention may also be in conjunction with an anti-inflammatory agent. Anti-inflammatory agents have exhibited success in treatment of inflammatory and autoimmune disorders and are now a common and a standard treatment for such disorders. Any anti-inflammatory agent well-known to one of skill in the art can be used in the compositions and methods of the invention.

Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINET™), fenoprofen (NALFON™), indomethacin (INDOCINT™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ORUDIS™ and ACTRON™), nabumetone (RELAFEN™), diclofenac & misoprostol (ARTHROTEC™), ibuprofen (MOTRIN™, ADVIL™, NUPRIN™), ketorolac (TORADOL™), valdecoxib (BEXTRA™), meloxicam (MOBIC™), flurbiprofen (ANSAID™), and piroxicam (FELDENE™). Such NSAIDs function by inhibiting a cyclooxygenase enzyme (e.g., COX-1 and/or COX-2).

Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

Disease-Modifying Anti-Rheumatic Drugs (DMARDs) can also be used in conjunction with the anti-CD19 antibodies of the compositions and methods of the invention. DMARDs work by suppressing the immune system and decreasing inflammation, however DMARDs take time to show results in comparison to other drugs. Examples of DMARDs include, but are not limited to, hydroxychloroquine (PLAQUENIL™), chlorambucil (LEUKERAN™), cyclophosphamide (CYTOXAN™), leflunomide (ARAVA™), methotrexate, and cyclosporine (NEORAL™)

In certain embodiments, the anti-CD19 immunotherapy of the invention of the present invention may also be in conjunction with an anti-inflammatory therapy. A non-limiting example of such therapy is protein-A immuoadsorption therapy. According to this therapy, a patient's blood is filtered to remove antibodies and immune complexes that promote inflammation. This filtering can be achieved by methods well known to those of skill in the art.

These anti-inflammatory agents and therapies are administered at the same time or at separate times from the anti-CD19 antibodies of the invention, and are used at the same or lesser dosages than as set forth in the art. The preferred anti-inflammatory agent will depend on many factors, including the type of autoimmune disease or disorder being treated, as well as the patient's history.

In some embodiments, these anti-inflammatory agents and therapies are administered at the same time or at separate times from the anti-CD19 antibodies of the invention, and are used at the same or lesser dosages than as set forth in the art. The preferred anti-inflammatory agent will depend on many factors, including whether the treatment is prophylactic or whether it is to treat an early or later stage of GVHD or graft rejection, as well as the patient's history.

In other embodiments, these anti-inflammatory agents and therapies are administered at the same time or at separate times from the anti-CD19 antibodies of the invention, and are used at the same or lesser dosages than as set forth in the art. The preferred anti-inflammatory agent will depend on many factors, including whether the treatment is prophylactic or whether it is to treat an early or later stage of GVHD or graft rejection, as well as the patient's history.

5.6.2.3. Combination with Therapeutic Antibodies

The anti-CD19 antibodies, compositions, and methods of the invention may be administered in combination with one or more other antibodies, including, but not limited to, anti-CD19 antibodies, anti-CD20 antibodies, anti-CD52 antibodies, and anti-CD22 antibodies (as described, for example, in U.S. Patent Application Publication No. 2005/0070693, U.S. Pat. No. 5,484,892, U.S. Patent Application Publication No. 2004/0001828 of U.S. application Ser. No. 10/371,797, U.S. Patent Application Publication No. 2003/0202975 of U.S. application Ser. No. 10/372,481, and U.S. Provisional Application Ser. No. 60/420,472, the entire contents of each of which are incorporated by reference herein for their teachings of CD22 antigens and anti-CD22 antibodies). The antibodies are preferably monoclonal antibodies. In one embodiment, the anti-CD19 antibodies, compositions, and methods of the invention are administered in combination with anti-CD20 antibodies, such as RITUXAN™ (C2B8; RITUXIMAB™; IDEC Pharmaceuticals). Other examples of therapeutic antibodies that can be used in combination with the antibodies of the invention or used in the compositions of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™(Tositumomab; GlaxoSmithKline Corixa), ERBITUX™ (Cetuximab; Imclone), AVASTIN™ (Bevacizumab; Genentech), and LymphoStat™ (Human Genome Sciences).

In certain embodiments, the anti-CD19 and anti-CD20 and/or anti-CD22 antibodies can be administered, optionally in the same pharmaceutical composition, in any suitable ratio. To illustrate, the ratio of the anti-CD19 and anti-CD20 antibody can be a ratio of about 1000:1, 500:1, 250:1, 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500, or 1:1000 or more. Likewise, the ratio of the anti-CD19 and anti-CD22 antibody can be a ratio of about 1000:1, 500:1, 250:1, 100:1, 90:1, 80:1, 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500, or 1:1000 or more.

5.6.2.4. Combination with Compounds that Enhance Monocyte or Macrophage Function In certain embodiments of the methods of the invention, a compound that enhances monocyte or macrophage function (e.g., at least about 25%, 50%, 75%, 85%, 90%, 95% or more) can be used in conjunction with the anti-CD19 immunotherapy. Such compounds are known in the art and include, without limitation, cytokines such as interleukins (e.g., IL-12), and interferons (e.g., alpha or gamma interferon).

The compound that enhances monocyte or macrophage function or enhancement can be formulated in the same pharmaceutical composition as the antibody, immunoconjugate or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa). In such embodiments, the compound that enhances monocyte or macrophage function is administered to the human subject prior to, concurrently with, or following treatment with other therapeutic regimens and/or the compositions of the invention. In one embodiment, the human subject has a blood leukocyte, monocyte, neutrophil, lymphocyte, and/or basophil count that is within the normal range for humans. Normal ranges for human blood leukocytes (total) is about 3.5-about 10.5 ($10^9$/L). Normal ranges for human blood neutrophils is about 1.7-about 7.0 ($10^9$/L), monocytes is about 0.3-about 0.9 ($10^9$/L), lymphocytes is about 0.9-about 2.9 ($10^9$/L), basophils is about 0-about 0.3 ($10^9$/L), and eosinophils is about 0.05-about 0.5 ($10^9$/L). In other embodiments, the human subject has a blood leukocyte count that is less than the normal range for humans, for example, at least about 0.01, 0.05, 0.1, 0.2, 0.3, 0.4, 0.5, 0.6, 0.7, or 0.8 ($10^9$/L) leukocytes.

This embodiment of the invention can be practiced with the antibodies, immunoconjugates or antibody fragments of the invention or with other antibodies known in the art and is particularly suitable for subjects that are resistant to anti-CD19, anti-CD20 and/or anti-CD22 antibody therapy (for example, therapy with existing antibodies such as C2B8), subjects that are currently being or have previously been treated with chemotherapy, subjects that have had a relapse in a B cell disorder, subjects that are immunocompromised, or subjects that otherwise have an impairment in macrophage or monocyte function. The prevalence of patients that are resistant to therapy or have a relapse in an autoimmune disease or disorder may be attributable, at least in part, to an impairment in macrophage or monocyte function. Thus, the invention provides methods of enhancing ADCC and/or macrophage and/or monocyte function to be used in conjunction with the methods of administering anti-CD19 antibodies and antigen-binding fragments.

5.6.2.5. Combination with Chemotherapeutic Agents

Anti-CD19 immunotherapy (using naked antibody, immunoconjugates, or fusion proteins) can be used in conjunction with other therapies including but not limited to, chemotherapy, radioimmunotherapy (RIT), chemotherapy and external beam radiation (combined modality therapy, CMT), or combined modality radioimmunotherapy (CMRIT) alone or in combination, etc. In certain preferred embodiments, the anti-CD19 antibody therapy of the present invention can be administered in conjunction with CHOP (Cyclophosphamide-Hydroxydoxorubicin-Oncovin (vincristine)-Prednisolone). As used herein, the term "administered in conjunction with" means that the anti-CD19 immunotherapy can be administered before, during, or subsequent to the other therapy employed.

In certain embodiments, the anti-CD19 immunotherapy is in conjunction with a cytotoxic radionuclide or radiotherapeutic isotope. For example, an alpha-emitting isotope such as $^{225}$Ac, $^{224}$Ac, $^{211}$AT, $^{212}$Bi, $^{213}$Bi, $^{212}$Pb, $^{224}$Ra, or $^{223}$Ra. Alternatively, the cytotoxic radionuclide may a beta-emitting isotope such as $^{186}$Re, $^{188}$Re, $^{90}$Y, $^{131}$I, $^{67}$Cu, $^{177}$Lu, $^{153}$Sm, $^{166}$Ho, or $^{64}$Cu. Further, the cytotoxic radionuclide may emit Auger and low energy electrons and include the isotopes $^{125}$I, $^{123}$I or $^{77}$Br. In other embodiments the isotope may be $^{198}$Au, $^{32}$P, and the like. In certain embodiments, the amount of the radionuclide administered to the subject is between about 0.001 mCi/kg and about 10 mCi/kg.

In some preferred embodiments, the amount of the radionuclide administered to the subject is between about 0.1 mCi/kg and about 1.0 mCi/kg. In other preferred embodiments, the amount of the radionuclide administered to the subject is between about 0.005 mCi/kg and 0.1 mCi/kg.

In certain embodiments, the anti-CD19 immunotherapy is in conjunction with a chemical toxin or chemotherapeutic agent. Preferably the chemical toxin or chemotherapeutic agent is selected from the group consisting of an enediyne such as calicheamicin and esperamicin; duocarmycin, methotrexate, doxorubicin, melphalan, chlorambucil, ARA-C, vindesine, mitomycin C, cis-platinum, etoposide, bleomycin and 5-fluorouracil.

Suitable chemical toxins or chemotherapeutic agents that can be used in combination therapies with the anti-CD19 immunotherapy include members of the enediyne family of molecules, such as calicheamicin and esperamicin. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include adriamycin, doxorubicin, 5-fluorouracil, cytosine arabinoside (Ara-C), cyclophosphamide, thiotepa, taxotere (docetaxel), busulfan, cytoxin, taxol, methotrexate, cisplatin, melphalan, vinblastine, bleomycin, etoposide, ifosfamide, mitomycin c, mitoxantrone, vincreistine, vinorelbine, carboplatin, teniposide, daunomycin, caminomycin, aminopterin, dactinomycin, mitomycins, esperamicins (see, U.S. Pat. No. 4,675,187), melphalan and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in the combination therapies of the invention. CVB is a regimen used to treat non-Hodgkin's lymphoma. Patti et al., *Eur. J. Haematol.* 51:18 (1993). Other suitable combination chemotherapeutic regimens are well-known to those of skill in the art. See, for example, Freedman et al., "*Non-Hodgkin's Lymphomas*," in Cancer Medicine, Volume 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and, CHOP (cyclophosphamide, doxorubicin, vincristine, and prednisone). A useful second generation chemotherapeutic regimen is, m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody, immunoconjugate or fusion protein can be administered in any order, or together.

Other toxins that are preferred for use in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Illustrative of toxins which are suitably employed in the combination therapies of the invention are ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell*, 47:641 (1986), and Goldenberg et al., *Cancer Journal for Clinicians*, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in Remington's Pharmaceutical Sciences, 19th Ed. (Mack Publishing Co. 1995), and in Goodman and Gilman's The Pharmacological Basis of Therapeutics, 7th Ed. (MacMillan Publishing Co. 1985). Other suitable toxins and/or chemotherapeutic agents are known to those of skill in the art.

The anti-CD19 immunotherapy of the present invention may also be in conjunction with a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of such combinations includes any enzyme capable of acting on a prodrug in such a way so as to covert it into its more active, cytotoxic form. The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "*Prodrugs in Cancer Chemotherapy*" Biochemical Society Transactions, 14, pp. 375-382, 615th Meeting Belfast (1986) and Stella et al., "*Prodrugs: A Chemical Approach to Targeted Drug Delivery*," Directed Drug Delivery, Borchardt et al. (ed.), pp. 247-267, Humana Press (1985). Prodrugs that can be used in combination with the anti-CD19 antibodies of the invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, α-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

In certain embodiments, administration of the compositions and methods of the invention may enable the postponement of toxic therapy and may help avoid unnecessary side effects and the risks of complications associated with chemotherapy and delay development of resistance to chemotherapy. In certain embodiments, toxic therapies and/or resistance to toxic therapies is delayed in patients administered the compositions and methods of the invention delay for up to about 6 months, 1, 2, 3, 4, 5, 6, 7, 8, 9, or 10 years.

5.6.2.6. Combination with Therapeutic Antibodies

The anti-CD19 immunotherapy described herein may be administered in combination with other antibodies, including, but not limited to, anti-CD20 mAb, anti-CD52 mAb, anti-CD22 antibody (as described, for example, in U.S. Pat. No. 5,484,892, U.S. patent publication number 2004/0001828 of U.S. application Ser. No. 10/371,797, U.S. patent publication number 2003/0202975 of U.S. application Ser. No. 10/372,481 and U.S. provisional application Ser. No. 60/420,472, the entire contents of each of which are incorporated by reference herein for their teachings of CD22 antigens and anti-CD22 antibodies), and anti-CD20 antibodies, such as RITUXAN™ (C2B8; RITUXIMAB™; Biogen Idec). Other examples of therapeutic antibodies that can be used in combination with the antibodies of the invention or used in the compositions of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™ (Tositumomab; GlaxoSmithKline Corixa), ERBITUX™ (Cetuximab; Imclone), and AVASTIN™ (Bevacizumab; Genentech).

In certain embodiments, the anti-CD19 and anti-CD20 and/or anti-CD22 mAb can be administered, optionally in the same pharmaceutical composition, in any suitable ratio. To illustrate, the ratio of the anti-CD19 and anti-CD20 antibody can be a ratio of about 1000:1, 500:1, 250:1, 100:1, 90:1, 80:1, 70:1, 60;1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500 or 1:1000 or more. Likewise, the ratio of the anti-CD19 and anti-CD22 antibody can be a ratio of about 1000:1, 500:1, 250:1, 100:1, 90:1, 80:1, 70:1, 60;1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100, 1:250, 1:500 or 1:1000 or more.

5.6.2.7. Combination Compounds that Enhance Monocyte or Macrophage Function

In certain embodiments of the methods of the invention, a compound that enhances monocyte or macrophage number or function (e.g., at least about 25%, 50%, 75%, 85%, 90%, 95% or more) can be used in conjunction with the anti-CD19 immunotherapy. Such compounds are known in the art and include, without limitation, cytokines such as interleukins (e.g., IL-12), and interferons (e.g., alpha or gamma interferon).

The compound that enhances monocyte or macrophage function or enhancement can be formulated in the same pharmaceutical composition as the antibody, immunoconjugate or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa). In such embodiments, the compound that enhances monocyte or macrophage function is administered to the human subject prior to, concurrently with, or following treatment with other therapeutic regimens and/or the compositions of the invention. In one embodiment, the human subject has a blood leukocyte, monocyte, neutrophil, lymphocyte, and/or basophil count that is within the normal range for humans. Normal range for human blood leukocytes (total) is about 3.5-about 10.5 ($10^9$/L). Normal range for human blood neutrophils is about 1.7-about 7.0 ($10^9$/L), monocytes is about 0.3-about 0.9 ($10^9$/L), lymphocytes is about 0.9-about 2.9 ($10^9$/L), basophils is about 0-about 0.3 ($10^9$/L), and eosinophils is about 0.05-about 0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

This embodiment of the invention can be practiced with the antibodies, immunoconjugates or antibody fragments of the invention or with other antibodies known in the art and is particularly suitable for subjects that are resistant to anti-CD19, anti-CD20 and/or anti-CD22 antibody therapy (for example, therapy with existing antibodies such as C2B8), subjects that are currently being or have previously been treated with chemotherapy, subjects that have had a relapse in a B cell disorder, subjects that are immunocompromised, or subjects that otherwise have an impairment in macrophage or monocyte function. The prevalence of patients that are resistant to therapy or have a relapse in a B cell disorder may be attributable, at least in part, to an impairment in macrophage or monocyte function. Thus, the invention provides methods of enhancing ADCC and/or macrophage and/or monocyte function to be used in conjunction with the methods of administering anti-CD19 antibodies and antigen-binding fragments.

5.6.2.8. Combination with Immunoregulatory Agents

The anti-CD19 immunotherapy of the present invention may also be used in conjunction with an immunoregulatory agent. In this approach, the use of chimerized antibodies is preferred; the use of human or humanized anti-CD19 antibody is most preferred. The term "immunoregulatory agent" as used herein for combination therapy refers to substances that act to suppress, mask, or enhance the immune system of the host. This would include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-$\gamma$, -$\beta$, or -$\alpha$ antibodies; anti-tumor necrosis factor-$\alpha$ antibodies; anti-tumor necrosis factor-$\beta$ antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-$\beta$; streptodornase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T-cell receptor antibodies (EP 340,109) such as T10B9. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$; mullerian-inhibiting substance; mouse gonadotropin-associated peptide; inhibin; activin; vascular endothelial growth factor; integrin; thrombopoietin (TPO); nerve growth factors such as NGF-$\alpha$; platelet-growth factor; transforming growth factors (TGFs) such as TGF-$\alpha$ and TGF-$\alpha$; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, preferably a cytokine. Preferred cytokines are selected from the group consisting of interleukin-1 (IL-1), IL-2, IL-3, IL-12, IL-15, IL-18, G-CSF, GM-CSF, thrombopoietin, and $\gamma$ interferon.

These immunoregulatory agents are administered at the same time or at separate times from the anti-CD19 antibodies of the invention, and are used at the same or lesser dosages than as set forth in the art. The preferred immunoregulatory agent will depend on many factors, including the type of disorder being treated, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

5.6.2.9. Combination with Other Therapeutic Agents

Agents that act on the tumor neovasculature can also be used in conjunction with anti-CD19 immunotherapy and include tubulin-binding agents such as combrestatin A4 (Griggs et al., *Lancet Oncol.*, 2:82, (2001)) and angiostatin and endostatin (reviewed in Rosen, *Oncologist*, 5:20, 2000, incorporated by reference herein). Immunomodulators suitable for use in combination with anti-CD19 antibodies include, but are not limited to, of $\alpha$-interferon, $\gamma$-interferon, and tumor necrosis factor alpha (TNF$\alpha$). In certain embodiments, the therapeutic agents used in combination therapies using the compositions and methods of the invention are peptides.

In certain embodiments, the anti-CD19 immunotherapy is in conjunction with one or more calicheamicin molecules. The calicheamicin family of antibiotics are capable of producing double-stranded DNA breaks at sub-picomolar concentrations. Structural analogues of calicheamicin which may be used include, but are not limited to, $\gamma 1$, $\gamma 21$, $\gamma 31$, N-acetyl-$\gamma 11$, PSAG and 011 (Hinman et al., *Cancer Research*, 53:3336-3342 (1993) and Lode et al., *Cancer Research*, 58: 2925-2928 (1998)).

Alternatively, a fusion protein comprising an anti-CD19 antibody of the invention and a cytotoxic agent may be made, e.g., by recombinant techniques or peptide synthesis.

In yet another embodiment, an anti-CD19 antibody of the invention may be conjugated to a "receptor" (such as streptavidin) for utilization in tumor pretargeting wherein the antagonist-receptor conjugate is administered to the patient, followed by removal of unbound conjugate from the circulation using a clearing agent and then administration of a "ligand" (e.g., biotin) which is conjugated to a therapeutic agent (e.g., a radionucleotide).

In certain embodiments, a treatment regimen includes compounds that mitigate the cytotoxic effects of the anti-CD19 antibody compositions of the invention. Such compounds include analgesics (e.g., acetaminophen), bisphosphonates, antihistamines (e.g., chlorpheniramine maleate), and steroids (e.g., dexamethasone, retinoids, deltoids, betamethasone, cortisol, cortisone, prednisone, dehydrotestosterone, glucocorticoids, mineralocorticoids, estrogen, testosterone, progestins).

In certain embodiments, the therapeutic agent used in combination with the anti-CD19 immunotherapy of the invention is a small molecule (i.e., inorganic or organic compounds having a molecular weight of less than about 2500 daltons). For example, libraries of small molecules may be commercially obtained from Specs and BioSpecs B.V. (Rijswijk, The Netherlands), Chembridge Corporation (San Diego, Calif.), Comgenex USA Inc. (Princeton, N.J.), and Maybridge Chemicals Ltd. (Cornwall PL34 OHW, United Kingdom).

In certain embodiments the anti-CD19 immunotherapy can be administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In certain embodiments the anti-CD19 immunotherapy of the invention can be administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole (SPORANOX®)), polyene (e.g., nystatin, amphotericin B (FUNGIZONE®), amphotericin B lipid complex ("ABLC") (ABELCET®), amphotericin B colloidal dispersion ("ABCD") (AMPHOTEC®), liposomal amphotericin B (AMBISONE®)), potassium iodide (KI), pyrimidine (e.g., flucytosine (ANCOBON®)), and voriconazole (VFEND®). Administration of anti-bacterial and anti-fungal agents can mitigate the effects or escalation of infectious disease that may occur in the methods of the invention where a patient's B cells are significantly depleted.

In certain embodiments of the invention, the anti-CD19 immunotherapy of the invention can be administered in combination with one or more of the agents described above to mitigate the toxic side effects that may accompany administration of the compositions of the invention. In other embodiments, the anti-CD19 immunotherapy of the invention can be administered in combination with one or more agents that are well known in the art for use in mitigating the side effects of antibody administration, chemotherapy, toxins, or drugs.

In certain embodiments of the invention, where the anti-CD19 immunotherapy composition of the invention is administered to treat multiple myeloma or any other condition, the composition may be administered in combination with or in treatment regimens with calcium channel blockers, such as, but not limited to nifedipine (PROCARDIA®, ADALAT®), amlodopine (NORVASC®), isradipine (DYNACIRC®), diltiazem (CARDIZEM®, DILACOR XR®), nicardipine (CARDENE®), nisoldipine (SULAR®), and felodipine (PLENDIL®).

In certain embodiments of the invention, the compositions of the invention may be administered in combination with or in treatment regimens with angiotensin II receptor antagonists, such as, but not limited to, losartan (COZAAR®) and valsartan (DIOVAN®).

In certain embodiments of the invention, the compositions of the invention may be administered in combination with or in treatment regimens with prazosin (MINIPRESS®), doxazosin (CARDURA®), and pentoxifylline (TRENTAL®).

In certain embodiments of the invention, the compositions of the invention may be administered in combination with or in treatment regimens with high-dose chemotherapy (melphalan, melphalan/prednisone (MP), vincristine/doxorubicin/dexamethasone (VAD), liposomal doxorubicin/vincristine, dexamethasone (DVd), cyclophosphamide, etoposide/dexamethasone/cytarabine, cisplatin (EDAP)), stem cell transplants (e.g., autologous stem cell transplantation or allogeneic stem cell transplantation, and/or mini-allogeneic (non-myeloablative) stem cell transplantation), radiation therapy, steroids (e.g., corticosteroids, dexamethasone, thalidomide/dexamethasone, prednisone, melphalan/prednisone), supportive therapy (e.g., bisphosphonates, growth factors, antibiotics, intravenous immunoglobulin, low-dose radiotherapy, and/or orthopedic interventions), THALOMID™ (thalidomide, Celgene), and/or VELCADE™ (bortezomib, Millennium).

In embodiments of the invention where the anti-CD19 immunotherapy of the invention are administered in combination with another antibody or antibodies and/or agent, the additional antibody or antibodies and/or agents can be administered in any sequence relative to the administration of the antibody of this invention. For example, the additional antibody or antibodies can be administered before, concurrently with, and/or subsequent to administration of the anti-CD19 antibody or immunoconjugate of the invention to the human subject. The additional antibody or antibodies can be present in the same pharmaceutical composition as the antibody of the invention, and/or present in a different pharmaceutical composition. The dose and mode of administration of the antibody of this invention and the dose of the additional antibody or antibodies can be the same or different, in accordance with any of the teachings of dosage amounts and modes of administration as provided in this application and as are well known in the art.

5.7. Use of Anti-CD19 Antibodies in Diagnosing Disease or Monitoring Immune Recognition The present invention also encompasses anti-CD19 antibodies, and compositions thereof, that immunospecifically bind to the human CD19 antigen, which anti-CD19 antibodies are conjugated to a diagnostic or detectable agent. In preferred embodiments, the antibodies are human or humanized anti-CD19 antibodies. Such anti-CD19 antibodies can be useful for monitoring or prognosing the development or progression of a B cell malignancyor an autoimmune disease or disorder as part of a clinical testing procedure, such as determining the efficacy of a particular therapy. In addition, anti-CD19 antibodies can be useful for monitoring immune system reconstitution following immunosuppressive therapy or bone marrow transplantation. Such diagnosis, detection, and monitoring can be accomplished by coupling an anti-CD19 antibody that immunospecifically binds to the human CD19 antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I,), carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti) gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, nonradioactive paramagnetic metal ions, and molecules that are radiolabelled or conjugated to specific radioisotopes. Any detectable label that can be readily measured can be conjugated to an anti-CD19 antibody and used in diagnosing B cell malignancies or an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD19 antibody conjugated to a diagnostic or detectable agent.

5.8. Kits

The invention provides a pharmaceutical pack or kit comprising one or more containers filled with a composition of the invention for the prevention, treatment, management or amelioration of a B cell malignancy, or one or more symptoms thereof, potentiated by or potentiating a B cell malignancy. The invention provides a pharmaceutical pack or kit comprising one or more containers filled with a composition of the invention for the prevention, treatment, management or amelioration of an autoimmune disease or disorder, or one or more symptoms thereof, potentiated by or potentiating an autoimmune disease or disorder. The invention provides a pharmaceutical pack or kit comprising one or more containers filled with a composition of the invention for the prevention, treatment, management or amelioration of GVHD, humoral rejection, or a post-transplant lymphoproliferative disorder.

The present invention provides kits that can be used in the above-described methods. In one embodiment, a kit comprises a composition of the invention, in one or more containers. In another embodiment, a kit comprises a composition of the invention, in one or more containers, and one or more other prophylactic or therapeutic agents useful for the prevention, management or treatment of a B cell malignancy, or one or more symptoms thereof, potentiated by or potentiating a B cell malignancy. In yet another embodiment, the kit comprises a composition of the invention, in one or more containers, and one or more other prophylactic or therapeutic agents useful for the prevention, management or treatment of an autoimmune disease or disorder, or one or more symptoms thereof, potentiated by or potentiating an autoimmune disease or disorder in one or more other containers. In a further embodiment, the kit comprises a composition of the invention, in one or more containers, and one or more other prophylactic or therapeutic agents useful for the prevention, management or treatment of GVHD, graft rejection, or a post-transplant lymphoproliferative disorder in one or more other containers. Preferably, the kit further comprises instructions for preventing, treating, managing or ameliorating a B cell malignancy, an autoimmune disorder, or GVHD, graft rejection, or a post-transplant lymphoproliferative disorder, as well as side effects and dosage information for method of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLES

In the examples below, a transgenic mouse model was used for evaluating human CD19 directed immunotherapies. These data show that antibodies that both bind the CD19 antigen and mediate ADCC are effective at inducing B cell depletion in vivo, in subjects having effector cells that express FcγR, (preferably, FcγRIII or FcγRIV) and carry out ADCC. Such antibodies can be used to induce a durable depletion of B cells in vivo, and in certain embodiments can eliminate virtually all B cells from the circulation, spleen and lymph nodes. Surprisingly, bone marrow B cells and their precursors that express relatively low densities of the CD19 antigen are depleted as well. The effectiveness of B cell depletion is not dependent on which region of human CD19 an anti-CD19 antibody binds, but is influenced by CD19 density (in the patient sample). The efficiency of B cell clearance may correlate with the anti-CD19 antibody's ability to mediate ADCC. The efficiency of B cell clearance using anti-CD19 antibodies may also correlate with host effector FcγR expression/function.

Materials and Methods

The murine HB12a and HB12b anti-CD19 antibodies described herein are exemplary of antibodies that bind to human CD19. Such antibodies can be used to engineer human, humanized, or chimeric anti-CD19 antibodies using the techniques described above. Human, humanized, or chimeric anti-CD19 antibodies having the same specificity for human CD19 or portions thereof as the HB12a and HB12b antibodies are contemplated for use in the compositions and methods of the invention. In particular, human, humanized, or chimeric anti-CD19 antibodies having the same or similar heavy chain CDR1, CDR2, and/or CDR3 regions as the HB12a or HB12b are contemplated for use in the compositions and methods of the invention.

Antibody Generation and Sequence Analysis. The HB12a and HB12b antibodies were generated in Balb/c mice immunized with a mouse pre-B cell line that was transfected with cDNAs encoding human CD19 (Zhou et al., *Mol. Cell. Biol.*, 14:3884-94 (1994)). Both antibodies were submitted to the Fifth International Workshop and Conference on Human Leukocyte Differentiation Antigens that was held in Boston on Nov. 3-7, 1993.

Heavy chain gene utilization was determined using RNA extracted from 1–5×10$^6$ hybridoma cells using the RNEASY® Mini Kit (QIAGEN®, Valencia, Calif.). First strand cDNA was synthesized in a volume of 20 μL from 2 μg of total RNA using 200 units of SUPERSCRIPT III® reverse transcriptase and first strand cDNA synthesis buffer from INVITROGEN® (Carlsbad, Calif.), 20 ng random hexamer primers and 20 units of RNAse inhibitor from PROMEGA® (Madison, Wis.), and 80 nmoles of dNTP from Denville (Metuchen, N.J.). One μl of cDNA solution was used as template for PCR amplification of heavy chain ($V_H$) genes. PCR reactions were carried out in a 50-μl volume of a reaction mixture composed of 10 mM Tris-HCl (pH 8.3), 5 mM NH$_4$Cl, 50 mM KCl, 1.5 mM MgCl$_2$, 800 μM dNTP (Denville), 400 pmol of each primer, and 2.5 U of Taq DNA polymerase (Invitrogen) with 10% pfu proofreading polymerase (Stratagene, LaJolla, Calif.). For $V_L$, PCR reactions were carried out in a 50-μl volume of a reaction mixture composed of 20 mM Tris-HCl (pH 8.4), 50 mM KCl, 1.5 mM MgCl$_2$, 800 μM dNTP (Denville), 400 pmol of each primer, and 2.5 U of Taq DNA polymerase (Invitrogen) spiked with 10% pfu proofreading polymerase (Stratagene). After a 3 min denaturation step, amplification was for 32 cycles (94° C. for 1 min, 58° C. for 1 min, 72° C. for 1 min) followed by a 10 minute extension at 72° C. (Thermocycler, Perkin Elmer). Heavy chain cDNA was amplified using a promiscuous sense 5' V$_H$ primer (Ms-V$_H$E; 5' GGG AAT TCG AGG TGC AGC TGC AGG AGT CTG G 3') (SEQ ID NO:19) as previously described (Kantor et al., *J. Immunol.*, 158:1175-1186 (1997)) and an antisense primer complementary to the Cγ coding region (primer Cγ1; 5' GAG TTC CAG GTC ACT GTC ACT GGC TCA GGG A 3') (SEQ ID NO:20).

Light chain gene utilization was determined using cytoplasmic RNA extracted as described for heavy chain. The 5' variable region nucleotide sequence was obtained from cDNA that was generated using the GeneRacer™ kit (Invitrogen). Total RNA was dephosphorylated with calf intestinal phosphatase. The 5' cap structure was removed from intact, full-length mRNA with tobacco acid pyrophosphatase. A GeneRacer RNA oligo was ligated to the 5' end of the mRNA using T4 RNA ligase providing a known 5' priming site for GeneRacer PCR primers after the mRNA was transcribed into cDNA. The ligated mRNA was reverse transcribed with Superscript™ III RT and the GeneRacer random primer. The first strand cDNA was amplified using the GeneRacer 5' primer (homologous to the GeneRacer RNA oligo) and a constant region specific antisense 3' primer (GAC TGA GGC ACC TCC AGA TGT TAA CTG) (SEQ ID NO:21). Touchdown PCR amplifications were carried out in a 50-μL volume with buffers as recommended by Invitrogen, using 2.5 U of Taq DNA polymerase (Invitrogen) with 10% pfu proofreading polymerase (Stratagene) added. After a 2 min denaturation step, Taq and pfu was added and amplification was carried out in 3 steps: five cycles of 94° C. for 30 s, 72° C. for 60 s; 5 cycles of 94° C. for 30 s, 72° C. for 60 s; 20 cycles of 94° C. for 30 s, 65° C. for 30 s, 72° C. for 60 s, followed by 10 min extension at 72° C. 2.5 U of Taq was added and the extension allowed to proceed for another 10 min to ensure intact 3'A-overhangs. Amplified PCR products were cloned into the pCR4-TOPO vector for sequencing and transformed into OneShot® TOP10 competent cells. DNA inserts from 8 clones was sequenced for each mAb light chain using the pCR4-TOPO vector specific "M13 Forward" and "M13 Reverse" primers, as described for heavy chain.

The purified heavy and light chain PCR products were sequenced directly in both directions using an ABI 377 PRISM® DNA sequencer after amplification using the Perkin Elmer Dye Terminator Sequencing system with AmpliTaq® DNA polymerase and the same primers used for initial PCR amplification or pCR4-TOPO vector specific primers, as described for light chain. The HB12a and HB12b heavy and light chain regions were sequenced completely on both the sense and anti-sense DNA strands.

Antibodies and Immunofluorescence Analysis. Monoclonal mouse anti-CD19 antibodies that bind to the human CD19 antigen used herein included HB12a (IgG 1) and HB12b (IgG 1), FMC63 (IgG2a, Chemicon International, Temecula, Calif.), B4 (IgG1, Beckman Coulter, Miami, Fla.) (Nadler et al., *J. Immunol.*, 131:244-250 (1983)), and HD237 (IgG2b, Fourth International Workshop on Human Leukocyte Differentiation Antigens, Vienna, Austria, 1989), an isotype switch variant of the HD37 antibody (Pezzutto et al., *J. Immunol.*, 138:2793-2799 (1987)). Other antibodies included: monoclonal mouse anti-CD19 antibody which binds to mouse CD19, MB19-1 (IgA) (Sato et al., *J. Immunol.*, 157: 4371-4378 (1996)); monoclonal mouse CD20-specific antibodies (Uchida et al., *Intl. Immunol.*, 16:119-129 (2004)); B220 antibody RA3-6B2 (DNAX Corp., Palo Alto, Calif.); Thy1.2 antibody (CALTAG™ Laboratories, Burlingame, Calif.); and CD5, CD43 and CD25 antibodies (BD PHARMINGEN™, Franklin Lakes, N.J.). Isotype-specific and anti-mouse Ig or IgM antibodies were from Southern Biotechnology Associates, Inc. (Birmingham, Ala.).

The mouse pre-B cell line, 300.19 (Alt et al., *Cell*, 27:381-388 (1981)), transfected with hCD19 cDNA (Tedder and Isaacs, *J. Immunol.*, 143:712-717 (1989)), or single-cell leukocyte suspensions were stained on ice using predetermined optimal concentrations of each antibody for 20-30 minutes according to established methods (Zhou et al., *Mol. Cell. Biol.*, 14:3884-3894 (1994)). Cells with the forward and side light scatter properties of lymphocytes were analyzed on FACSCAN® or FACSCALIBUR® flow cytometers (Becton Dickinson, San Jose, Calif.). Background staining was determined using unreactive control antibodies (CALTAG™ Laboratories, Burlingame, Calif.) with gates positioned to exclude ≥98% of the cells. For each sample examined, ten-thousand cells with the forward and side light scatter properties of mononuclear cells were analyzed for each sample whenever possible, with fluorescence intensities shown on a four-decade log scale.

Mice. Transgenic mice expressing human CD19 (h19-1) and their wild-type (WT) littermates were produced as previously described (Zhou et al., *Mol. Cell. Biol.*, 14:3884-3894 (1994)). TG-1 mice were generated from the original h19-1 founders (C57BL/6×B6/SJL), and were crossed onto a C57BL/6 background for at least 7 generations. TG-2 mice were generated from the original h19-4 founders (C57BL/6× B6/SJL). After multiple generations of backcrossing, TG-1$^{+/+}$ mice were obtained the B cells of which expressed cell surface density of human CD19 at about the same density found on human B cells. Human CD19 expressing mice have been further described and used as a model in several studies (Engel et al., *Immunity*, 3:39-50 (1995); Sato et al., *Proc. Natl. Acad. Sci. USA*, 92:11558-11562 (1995); Sato et al., *J. Immunol.*, 157:4371-4378 (1996); Tedder et al., *Immunity*, 6:107-118 (1997); Sato et al., *J. Immunol.*, 158:4662-4669 (1997); Sato et al., *J. Immunol.*, 159:3278-3287 (1997); Sato et al., *Proc. Natl. Acad. Sci. USA*, 94:13158-13162 (1997); Inaoki et al., *J. Exp. Med.*, 186:1923-1931 (1997); Fujimoto et al., *J. Immunol.*, 162:7088-7094 (1999); Fujimoto et al., *Immunity*, 11:191-200 (1999); Satterthwaite et al., *Proc. Natl. Acad. Sci. USA*, 97:6687-6692 (2000); Fujimoto et al., *Immunity*, 13:47-57 (2000); Sato et al., *J. Immunol.*, 165:6635-6643 (2000); Zipfel et al., *J. Immunol.*, 165:6872-6879 (2000); Qian et al., *J. Immunol.*, 166:2412-2419 (2001); Hasegawa et al., *J. Immunol.*, 167:2469-2478 (2001); Hasegawa et al., *J. Immunol.*, 167:3190-3200 (2001); Fujimoto et al., *J. Biol. Chem.*, 276:44820-44827 (2001); Fujimoto et al., *J. Immunol.*, 168: 5465-5476 (2002); Saito et al., *J. Clin. Invest.*, 109:1453-1462 (2002); Yazawa et al., *Blood*, 102:1374-80 (2003); Shoham et al., *J. Immunol.*, 171:4062-4072 (2003)). CD19-deficient (CD19$^{-/-}$) mice and their WT littermates are also as previously described (Engel et al., *Immunity*, 3:39-50 (1995)). Expression of human CD19 in transgenic mice has been shown to lower endogenous mouse CD19 expression (Sato et al., *J. Immunol.*, 157:4371-4378 (1996); and Sato et al., *J. Immunol.*, 158:4662-4669 (1997)) and hypotheses regarding this lowering of endogenous mouse CD19 expression have also been assessed (Shoham et al., *J. Immunol.*, 171:4062-4072 (2003)). Densities of CD19 expression in transgenic mice expressing human CD19 have also been assessed (Sato et al., *J. Immunol.*, 165:6635-6643 (2000)).

TG-1$^{+/+}$ mice were bred with FcR (Fc receptor) common γ chain (FcRγ)-deficient mice (FcRγ$^{-/-}$, B6.129P2-Fcergr1$^{tm1}$) from Taconic Farms (Germantown, N.Y.) to generate hCD19$^{+/-}$ FcRγ$^{-/-}$ and WT littermates. Mice hemizygous for a c-Myc transgene (Eμu-cMycTG, C57Bl/6-J-TgN(Igh-Myc); The Jackson Laboratory, Bar Harbor, Me.) were as described (Harris et al., *J. Exp. Med.*, 167:353 (1988) and Adams et al., *Nature*, 318:533 (1985)). c-MycTG mice (B6/129 background) were crossed with hCD19TG-1$^{+/+}$ mice to generate hemizygous hCD19TG-1$^{+/-}$ cMycTG$^{+/-}$ offspring as determined by PCR screening. Rag1$^{-/-}$ (B6.129S7-Rag1$^{tm1Mom}$/J) mice were from The Jackson Laboratory. Macrophage-deficient mice were generated by tail vein injections of clodronate-encapsulated liposomes (0.1 mL/10 gram body weight; Sigma Chemical Co., St. Louis, Mo.) into C57BL/6 mice on day −2, 1 and 4 in accordance with standard methods (Van Rooijen and Sanders, *J. Immunol. Methods*, 174:83-93 (1994)). All mice were housed in a specific pathogen-free barrier facility and first used at 6-9 weeks of age.

ELISAs. Serum Ig concentrations were determined by ELISA using affinity-purified mouse IgM, IgG1, IgG2a, IgG2b, IgG3, and IgA (Southern Biotechnology Associates, Inc.) to generate standard curves as described (Engel et al., *Immunity*, 3:39 (1995)). Serum IgM and IgG autoantibody levels against dsDNA, ssDNA and histone were determined by ELISA using calf thymus double-stranded (ds) DNA (Sigma-Aldrich), boiled calf thymus DNA (which contains single-stranded (ss) DNA) or histone (Sigma-Aldrich) coated microtiter plates as described (Sato et al., *J. Immunol.*, 157: 4371 (1996)).

Immunotherapy. Sterile anti-CD19 and unreactive, isotype control antibodies (0.5-250 µg) in 200 µL phosphate-buffered saline (PBS) were injected through lateral tail veins. All experiments used 250 µg of antibody unless indicated otherwise. Blood leukocyte numbers were quantified by hemocytometer following red cell lysis, B220$^+$ B cell frequencies were determined by immunofluorescence staining with flow cytometry analysis. Antibody doses in humans and mice were compared using the Oncology Tool Dose Calculator (www.fda.gov/cder/cancer/animalframe.htm).

Immunizations. Two-month old WT mice were immunized i.p. with 50 µg of 2,4,6-trinitrophenyl (TNP)-conjugated lipopolysaccharide (LPS) (Sigma, St. Louis, Mo.) or 25 µg 2,4-dinitrophenol-conjugated (DNP)-FICOLL® (Biosearch Technologies, San Rafael, Calif.) in saline. Mice were also immunized i.p. with 100 µg of DNP-conjugated keyhole limpet hemocyanin (DNP-KLH, CALBIOCHEM®-NOVABIOCHEM® Corp., La Jolla, Calif.) in complete Freund's adjuvant and were boosted 21 days later with DNP-KLH in incomplete Freund's adjuvant. Mice were bled before and after immunizations as indicated. DNP- or TNP-specific antibody titers in individual serum samples were measured in duplicate using ELISA plates coated with DNP-BSA (CALBIOCHEM®-NOVABIOCHEM® Corp., La Jolla, Calif.) or TNP-BSA (Biosearch Technologies, San Rafael, Calif.) according to standard methods (Engel et al., *Immunity*, 3:39-50 (1995)). Sera from TNP-LPS immunized mice were diluted 1:400, with sera from DNP-FICOLL® and DNP-BSA immunized mice diluted 1:1000 for ELISA analysis.

Tumor Studies. Spontaneous lymph node tumor from a hCD19TG-1$^{+/-}$ c-mycTG$^{+/-}$ mouse was isolated and expanded in vivo. Tumor cells (10$^{-5}$/mouse) were administered i.v. to Rag$^{-/-}$ recipient mice on day 0, with FMC63 and isotype-matched control mAbs (250 µg/ml) given i.v. on days 1 and 7. Blood leukocytes from recipient mice were isolated weekly with the number of circulating mouse CD19$^+$ B220$^+$ cells quantified by immunofluorescent staining with flow cytometry analysis.

Statistical Analysis. All data are shown as means±SEM. The Student's t-test was used to determine the significance of differences between sample means.

Example 1

Human CD19 Expression in Transgenic Mice

The transgenic hCD19TG mice described herein or other transgenic animals expressing human CD19 can be used to assess different therapeutic regimens comprising human, humanized, or chimeric anti-CD19 antibodies, such as variations in dosing concentration, amount, or timing. The efficacy in human patients of different therapeutic regimens can be predicted using the two indicators described below, i.e., B cell depletion in certain bodily fluids and/or tissues and the ability of a monoclonal human or humanized anti-CD19 antibody to bind B cells. In particular embodiments, treatment regimens that are effective in human CD19 transgenic mice can be used with the compositions and methods of the invention to treat B cell malignancies in humans.

In order to determine whether human CD19 was expressed on B cells from transgenic mice (hemizygous TG-1$^{+/-}$) expressing the human CD19 transgene, B cells were extracted from the bone marrow, blood, spleen and peritoneal lavage of these mice. Human CD19 and mouse CD19 expression were assessed in these cells by contacting the cells with mouse monoclonal anti-CD19 antibodies that bind CD19. Binding of the antibody to the B lineage cells was detected using two-color immunofluorescence staining with flow cytometry analysis.

Figure 1A:
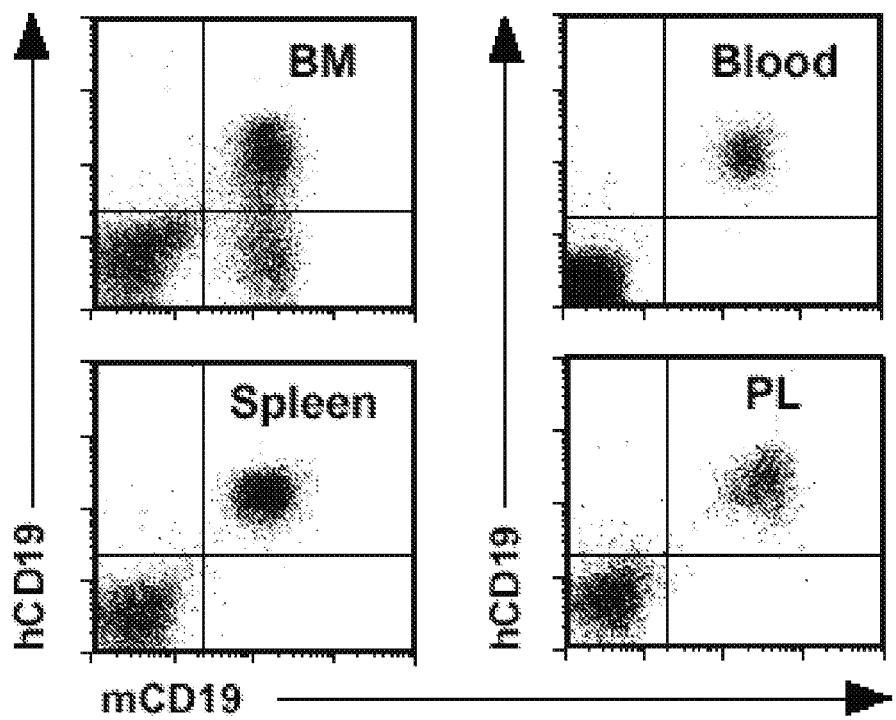

The results are shown in FIG. 1A in graphs of the detected expression of murine CD19 (mCD19) (x-axis) plotted against the detected expression of human CD19 (hCD19) (y-axis) for bone marrow (BM), blood, spleen and peritoneal lavage (PL). The units of the axis represent a four decade log scale beginning with 1 on the lower left. The B4 anti-CD19 antibody that binds to human CD19 (Beckman/Coulter) was used to visualize human CD19 expression and the 1D3 CD19 antibody that binds to mouse CD19 (PharMingen) was used to visualize mouse CD19 expression (also used for FIGS. 1B and 1C). While human CD19 expression increases incrementally during human B cell development, murine CD19 is expressed at high levels during mouse bone marrow B cell development. FIG. 1A shows that human CD19 expression parallels mouse CD19 expression on peripheral B cells found in blood, spleen and peritoneal lavage (PL) demonstrating that the mouse anti-hCD19 antibody (that binds human CD19) binds the peripheral B cell populations. In addition, a small population of bone marrow (BM) derived B cells express endogenous mouse CD19 but not human CD19 (monoclonal mouse anti-CD19 antibody that binds to human CD19). Thus, bone marrow B cells fall into two categories in hemizygous TG-1$^{+/-}$ mice, mature B lineage cells that are hCD19$^+$mCD19$^+$ and less mature B lineage cells that are only mCD19$^+$ (FIG. 1A). These results are consistent with the findings of Zhou et al. (*Mol. Cell. Biol.*, 14:3884-3894 (1994)) which indicated that human CD19 expression in these transgenic mice correlates with B cell maturation. All mature B cells within the blood, spleen, and peritoneal cavity were both hCD19$^+$ and mCD19$^+$.

Figure 1B:
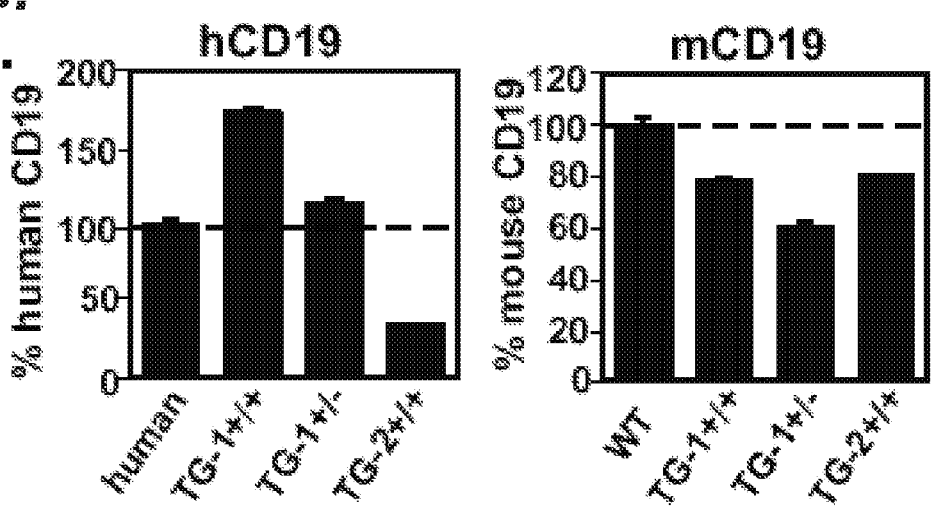

The relative expression levels of mCD19 and hCD19, as assessed by measuring mean fluorescence intensity (mouse anti-CD19 for hCD19 and mouse anti-CD19 for mCD19)

respectively, are shown in FIG. 1B. Among TG-1 mice homozygous for the hCD19 transgene (TG-1$^{+/-}$), hCD19 expression on blood borne B cells was comparable to hCD19 expression on human B cells. To compare the relative densities of hCD19 and mCD19 expression in TG-1$^{+/+}$ TG-1$^{+/-}$, and TG-2$^{+/+}$ transgenic mouse lines, blood derived B cells were extracted and assayed for CD19 expression as described above. The results are shown in FIG. 1B in histograms showing the percent human CD19 expression for human blood B cells, TG-1$^{+/+}$, TG-1$^{+/-}$ and TG-2$^{+/+}$ blood B cells from hCD19TG mice (left) and the percent mouse CD19 expression for wild type (WT) mouse blood B cells, TG-1$^{+/+}$, TG-1$^{+/-}$, and TG-2$^{+/+}$ CD19$^{+}$ blood B cells from hCD19TG mice (right). The values (linear values of mean fluorescent intensity) represent the mean relative densities of CD19 expression (±SEM) compared to blood B cells from humans or wild-type (WT) mice (shown as 100%). The results show that in homozygous TG-1$^{+/+}$ mice, blood B cells expressed hCD19 at densities as measured by mean fluorescence intensities about 72% higher than human blood B cells. Blood B cells in TG-1$^{+/-}$ mice expressed hCD19 at densities similar to human blood B cells, while blood B cells in TG-2$^{+/+}$ mice expressed hCD19 at densities 65% lower than human blood B cells.

Figure 1C:
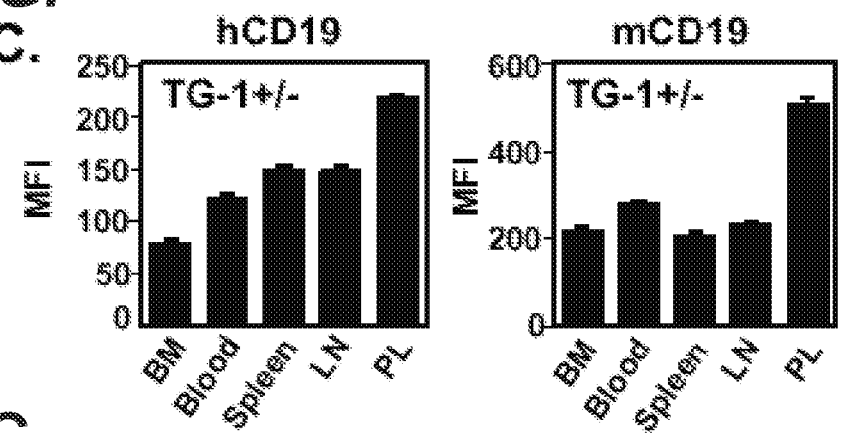

Further comparisons of the relative densities of hCD19 and mCD19 expression in B cells from TG-1$^{+/-}$ mouse tissues are shown in FIG. 1C in histograms showing the mean fluorescence intensities (MFI±SEM) of anti-CD19 antibody staining for B cells from bone marrow, blood, spleen, lymph node, and PL for hCD19 (left) and mCD19 (right). The results demonstrate that in TG-1$^{+/-}$ mice, hCD19 was expressed at increasing levels by B220$^{+}$ cells in the bone marrow (63% of human blood levels)<blood (100%)<spleen (121%)=lymph node (120%) and <peritoneal cavity (177%). Human CD19 expression had a small influence on mCD19 expression. Levels of mRNA for hCD19 and mCD19 did not change.

To determine whether mouse anti-hCD19 antibodies (that bind to human CD19) of the IgG1 (HB12a, HB12b, B4), IgG2a (FMC63) and IgG2b (HD237) isotypes react differently, blood and spleen B220$^{+}$ B cells were isolated from TG-1$^{+/-}$ mice. The isolated cells were contacted in vitro with the above-mentioned anti-CD19 antibodies and assessed for their ability to bind human CD19 expressing transgenic mouse (hCD19TG) B cells using monoclonal antibody staining which was visualized using isotype-specific PE-conjugated secondary antibodies with flow cytometry analysis.

Figure 1D:
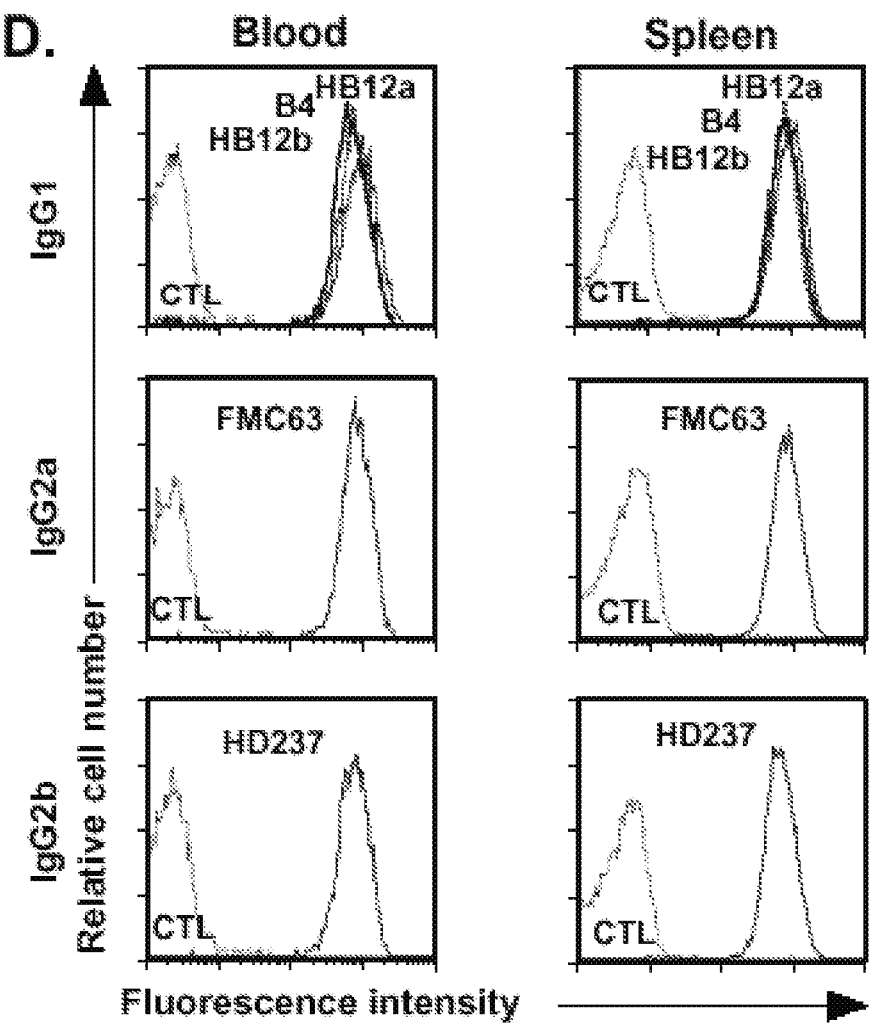

The results are shown in FIG. 1D in graphs of the fluorescence intensity (x-axis) versus the relative B cell number (y-axis) for IgG2b (murine isotype), IgG2a (murine isotype), and IgG1 (murine isotype) anti-CD19 antibodies at 5 µg/mL. The fluorescence intensity of B220$^{+}$ cells stained with anti-CD19 antibody are shown as solid lines and the fluorescence intensity of the isotype-matched control (CTL) is shown as a dashed line. Each antibody reached saturating levels of reactivity with spleen B cells at a concentration of 5 µg/mL. The results demonstrate that anti-CD19 antibody binding density on mouse blood and spleen B220$^{+}$ B cells from TG-1$^{+/-}$ mice is uniform for the antibody isotypes tested and for both blood and spleen B cells.

Figure 1E:
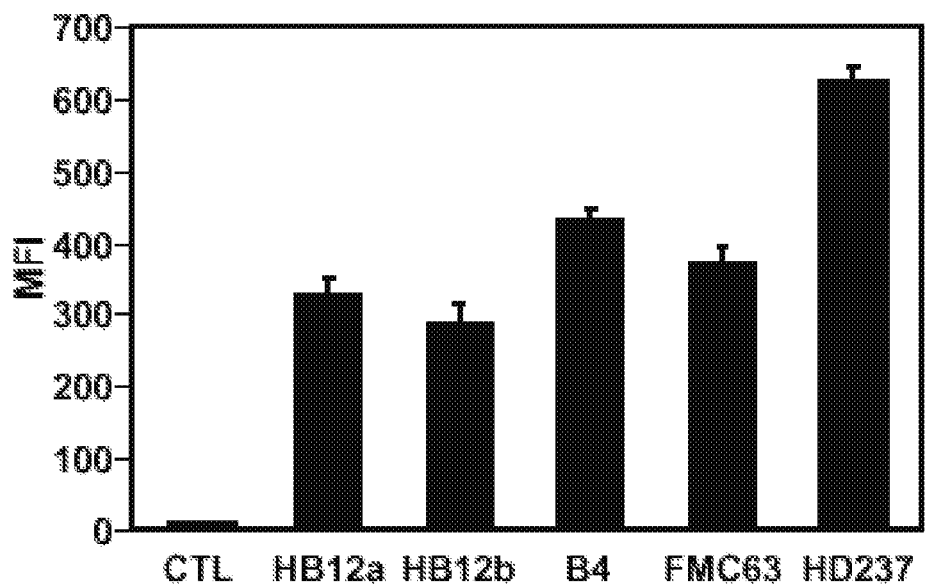

To determine whether mean fluorescence intensities were independent of anti-CD19 antibody isotype, the binding activity of individual anti-CD19 antibodies (at 5 µg/mL) was assessed by staining a mouse pre-B cell line, 300.19, transfected with a hCD19 cDNA using the same anti-mouse Ig secondary antibody. Antibody staining (MFI±SEM) was visualized using mouse Ig-specific PE-conjugated secondary antibody with flow cytometry analysis. The results are shown in FIG. 1E in a histogram of anti-CD19 antibody binding (as shown by staining intensity, y-axis) to hCD19 cDNA-transfected 300.19 cells, for HB12a, HB12b, B4, FMC63, HD237 anti-CD19 antibodies and a control antibody (CTL). Each antibody stained cells with characteristic mean fluorescence intensities that were independent of anti-CD19 antibody isotype, with HB12b showing the lowest levels of staining and HD237 demonstrating the highest. Thus, the results shown demonstrate that 300.19 cells are a model in vitro system for the comparison of the ability of anti-CD19 antibodies to bind CD19 in vitro.

Thus, taken together, the results shown in FIG. 1 demonstrate that hCD19TG mice and the 300.19 cells represent appropriate in vitro and in vivo model systems for assessing the ability of anti-hCD19 antibodies to bind B cells when hCD19 is expressed over a range of densities.

FIGS. 1A-D represent results obtained with ≥3 mice of each genotype.

Example 2

Anti-CD19 Antibody Depletion of B Cells In Vivo

Mouse anti-CD19 antibodies (that bind to human CD19) were assessed for their ability to deplete hCD19TG (TG-1$^{+/-}$) blood, spleen, and lymph node B cells in vivo. Each antibody was given to mice at either 250 or 50 µg/mouse, a single dose about 10 to 50-fold lower than the 375 mg/m$^2$ dose primarily given four times for anti-CD20 therapy in humans (Maloney et al., *J. Clin. Oncol.*, 15:3266-74 (1997) and McLaughlin et al., 12:1763-9 (1998)).

Figure 2A:
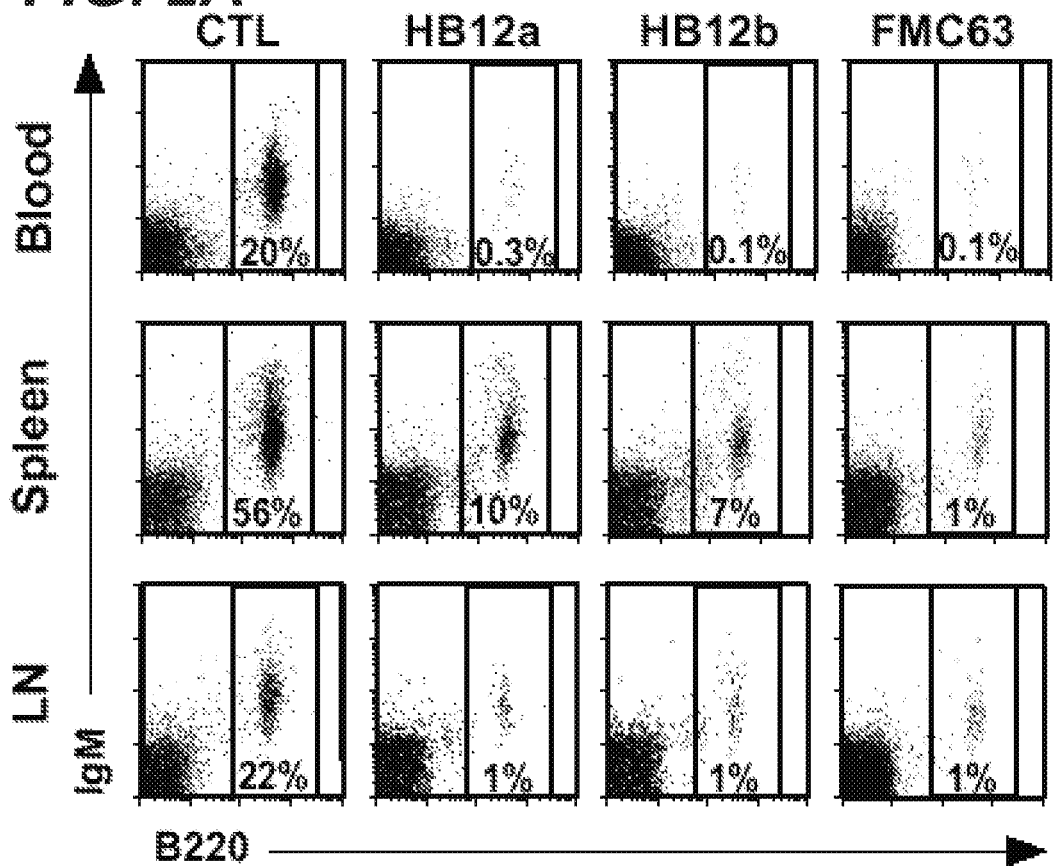

The results are shown in FIG. 2A in a plot of B cell amount 7 days following CD19 or isotype-matched control (CTL) treatment with HB12a, HB12b, or FMC63 anti-CD19 antibodies or a control. Separate plots are provided for lymph nodes, spleen and blood tissues for each anti-CD19 antibody. The percentage of gated lymphocytes depleted at 7 days shown on each plot demonstrates representative B cell depletion from blood, spleen and lymph nodes of TG-1$^{+/-}$ mice as determined by immunofluorescence staining with flow cytometry analysis. FIG. 2B shows mean numbers (±SEM per ml) of B220$^{+}$ blood B cells following treatment with anti-CD19 (closed circles) or isotype-control (open circles) antibodies. The value shown after time 0 represents data obtained at 1 hour. FIG. 2C and FIG. 2D show spleen and lymph node B cell numbers (±SEM), respectively, after treatment of TG-1$^{+/-}$ mice with anti-CD19 (filled bars) or control (open bars) antibody at the indicated doses. In FIGS. 2B-D, significant differences between mean results for anti-CD19 or isotype-control antibody treated mice (≥3 mice per data point) are indicated; *$p<0.05$, **$p<0.01$, in comparison to controls.

Each antibody depleted the majority of circulating B cells within one hour of treatment (FIG. 2B), with potent depleting effects on spleen and lymph node B cell frequencies (FIG. 2A) and numbers (FIGS. 2C-D) by day seven. The HB12a antibody depleted 98% of blood B cells and 90-95% of splenic and lymph node B cells by day seven. Similarly, the HB12b, B4, FMC63, and HD237 antibodies depleted 99%, 96%, 99%, and 97% of blood B cells, respectively. The HB12b, B4, FMC63, and HD237 antibodies depleted 88-93%, 64-85%, 72-95%, and 88-90% of splenic and lymph node B cells, respectively. The few remaining peripheral B cells primarily represented phenotypically immature cells that were potential emigrants from the bone marrow. None of the CD19 antibodies had significant effects when given to WT mice, and isotype-matched control antibodies given under identical conditions did not affect B cell numbers (FIGS. 2A-D). Thus, anti-hCD19 antibodies effectively depleted B cells from the circulation, spleen and lymph nodes of hCD19TG mice by day seven. A summary of B cell depletion in TG-1$^{+/-}$ mice is provided in Table 1.

TABLE 1

| Tissue | B subset[a] | Control mAb[b] | CD19 | % |
|---|---|---|---|---|
| BM: | B220$^+$ | 3.41 ± 0.5 | 0.82 ± 0.13 | 76** |
| | Pro-B | 0.75 ± 0.1 | 0.97 ± 0.22 | 0 |
| | Pre-B | 1.74 ± 0.5 | 0.10 ± 0.01 | 94** |
| | immature | 0.70 ± 0.1 | 0.04 ± 0.01 | 93** |
| | mature | 0.86 ± 0.1 | 0.004 ± 0.0 | 99** |
| Blood: | B220$^+$ | 0.82 ± 0.1 | 0.004 ± 0.0 | 99** |
| Spleen: | B220$^+$ | 25.2 ± 2.2 | 1.7 ± 0.2 | 93** |
| LN: | B220$^+$ | 0.89 ± 0.1 | 0.06 ± 0.01 | 93** |
| Peritoneum: | B220$^+$ | 1.16 ± 0.1 | 0.37 ± 0.03 | 68** |
| | B1a | 0.86 ± 0.1 | 0.31 ± 0.06 | 61** |
| | B2 | 0.34 ± 0.0 | 0.08 ± 0.02 | 73** |

[a]B cell subsets were: bone marrow (BM) pro-B (CD43$^+$IgM$^-$B220$^{lo}$), pre-B (CD43$^-$IgM$^-$B220$^{lo}$), immature B (IgM$^+$B220$^{lo}$) mature B (IgM$^+$B220$^{hi}$); peritoneal B1a (CD5$^+$B220$^{lo}$), B2 (CD5$^-$B220$^{hi}$).
[b]Values (±SEM) indicate cell numbers (×10$^{-6}$) present in mice seven days after antibody treatment (250 µg). BM values are for bilateral femurs. Blood numbers are per/ml. LN numbers are for bilateral inguinal and axillary nodes. Mouse numbers are indicated in parentheses. Significant differences between means are indicated;
*p < 0.05,
**p < 0.01.

[b]Values (±SEM) indicate cell numbers (×10$^{-6}$) present in mice seven days after antibody treatment (250 µg). BM values are for bilateral femurs. Blood numbers are per/ml. LN numbers are for bilateral inguinal and axillary nodes. Mouse numbers are indicated in parentheses. Significant differences between means are indicated; *p<0.05, **p<0.01.

Depletion of Bone Marrow B Cells

Known anti-CD19 antibodies were tested in hCD19TG mice to determine whether such antibodies were effective in depleting B cells from various bodily fluids and tissues. The assays described herein can be used to determine whether other anti-CD19 antibodies, for example, anti-CD19 antibodies that bind to specific portions of the human CD19 antigen, will effectively deplete B cells. The results using anti-CD19 antibodies identified as capable of depleting B cells can be correlated to use in humans. Antibodies with properties of the identified antibodies can be used in the compositions and methods of the invention for the treatment of B cell malignancies in humans. FIGS. 3A-3F depict bone marrow B cell depletion following CD19 antibody treatment.

Figure 3A:
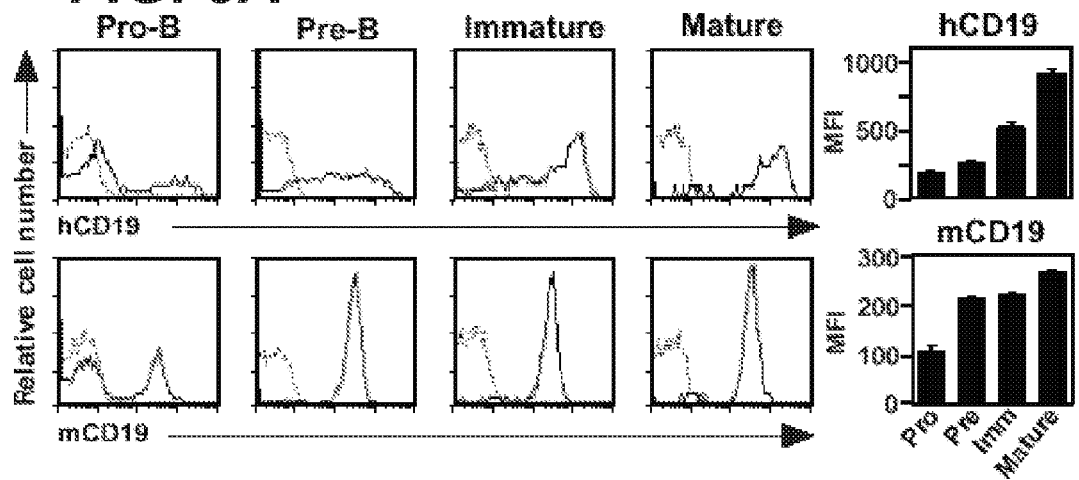

FIG. 3A shows graphs of the fluorescence intensity (x-axis) versus the relative B cell number (y-axis) for hCD19 and mCD19 expression by TG-1$^{+/-}$ bone marrow B cell subpopulations assessed by four-color immunofluorescence staining with flow cytometry analysis of cells with the forward- and side-scatter properties of lymphocytes. Pro-B cells were defined as CD43$^+$IgM$^-$B220$^{lo}$, pre-B cells were CD43$^-$IgM$^-$B220$^{lo}$, immature B cells were IgM$^+$B220$^{lo}$ and mature B cells were IgM$^+$B220$^{hi}$. Bar graphs (right) show relative mean MFI (±SEM) values for CD19 expression by each B cell subset (≥3 mice/data point). As in hCD19TG mice (FIG. 1A), CD19 expression is heterogeneous in humans as B cells mature and exit the bone marrow. Only a small fraction of pro-B cells (20% CD43$^{hi}$IgM$^-$B220$^{lo}$) expressed hCD19 in TG-1$^{+/-}$ mice, while most pre-B cells were hCD19$^+$ and the majority of mature B cells in the bone marrow expressed hCD19 at relatively high levels. Half of pro-B cells (55%, IgM$^-$ B220$^+$) expressed mCD19 in TG-1$^{+/-}$ mice, while mCD19 was expression by the majority of pre-B cells and mature B cells in the bone marrow at relatively high levels.

Figure 3B:
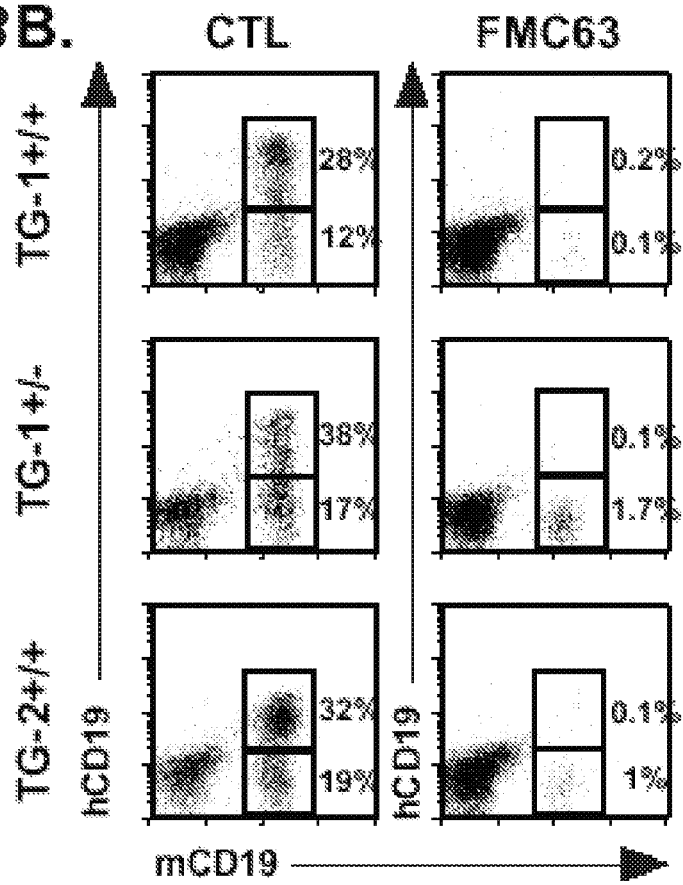

FIG. 3B shows depletion of hCD19 cells in hCD19TG mice seven days following FMC63 or isotype-matched control antibody (250 µg) treatment assessed by two-color immunofluorescence staining with flow cytometry analysis. Numbers represent the relative frequency of cells within the indicated gates. Results represent those obtained with three littermate pairs of each mouse genotype. Following CD19 antibody treatment, the vast majority of hCD19$^+$ cells in the bone marrow of TG-1$^{+/+}$, TG-1$^{+/-}$ and TG-2$^{+/+}$ mice were depleted by the FMC63 antibody given at 250 µg/mouse.

FIG. 3C shows representative B220$^+$ B cell depletion seven days following anti-CD19 or isotype-matched control antibody (250 µg) treatment of TG-1$^{+/-}$ mice. Bar graph values represent the total number (±SEM) of B220$^+$ cells within the bilateral femurs of antibody treated mice. Significant differences between sample means (≥3 mice per group) are indicated; *p<0.05, **p<0.01. Unexpectedly, a large fraction of mCD19$^+$ pre-B cells that expressed hCD19 at low to undetectable levels were also depleted from the bone marrow. Consistent with this, the FMC63, HB12a, HB12b, B4 and HD237 antibodies depleted the majority of bone marrow B220$^+$ cells.

Figure 3E:
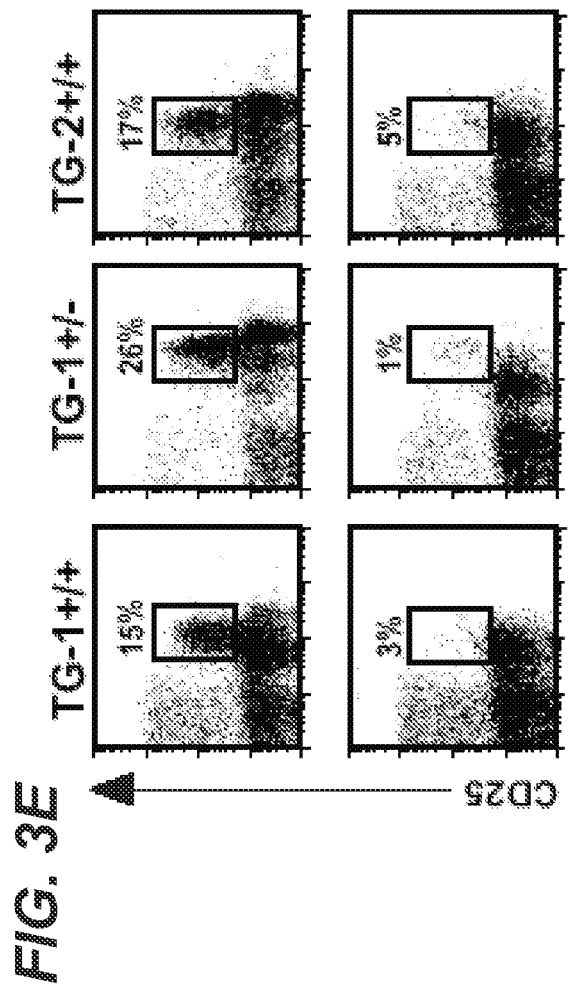
Figure 3F:
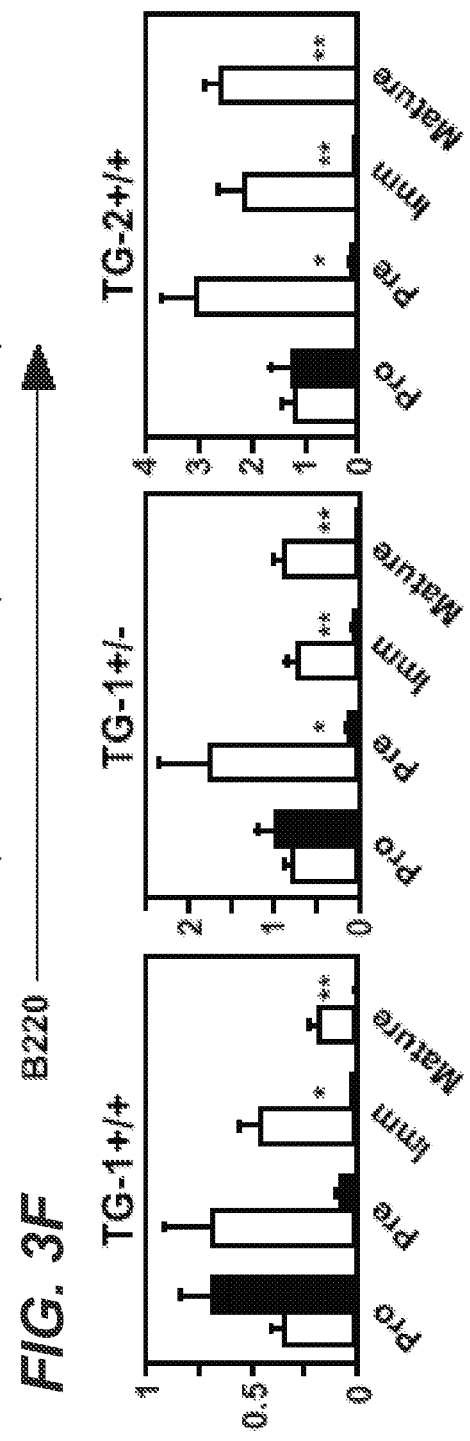

FIG. 3D shows representative bone marrow B cell subset depletion seven days following FMC63 or isotype-matched control antibody (250 µg) treatment of TG-1$^{+/-}$ mice as assessed by three-color immunofluorescence staining IgM$^-$ B220$^{lo}$ pro-/pre-B cells were further subdivided based on CD43 expression (lower panels). FIG. 3E shows representative depletion or CD25$^+$B220$^{lo}$ pre-B cells of bone marrow seven days following FMC63 or isotype-matched control antibody (250 µg) treatment of hCD19TG mouse lines as assessed by two-color immunofluorescence staining Results are from experiments carried out on different days so the gates were not identical. When the individual bone marrow subpopulations were analyzed, the majority of CD43$^{hi}$IgM$^-$B220$^{lo}$ pro-B cells (FIG. 3D) were not affected by FMC63 antibody treatment in TG-1$^{+/+}$, TG-1$^{+/-}$ or TG-2$^{+/+}$ mice, while the majority of CD25$^+$CD43$^{lo}$IgM$^-$B220$^{lo}$ pre-B cells (FIG. 3E) were depleted. FIG. 3F shows bar graphs indicating numbers (±SEM) of pro-B, pre-B, immature, and mature B cells within bilateral femurs seven days following FMC63 (closed bars) or control (open bars) antibody treatment of ≤3 littermate pairs. The results demonstrate that the majority of immature and mature B cells were also depleted from the bone marrow of TG-1$^{+/+}$, TG-1$^{+/-}$ and TG-2$^{+/+}$ mice. Thus, most hCD19$^+$ cells were depleted from the bone marrow by CD19 antibody treatment, including pre-B cells that expressed hCD19 at low levels.

Depletion of Peritoneal B Cells

Figure 4C:
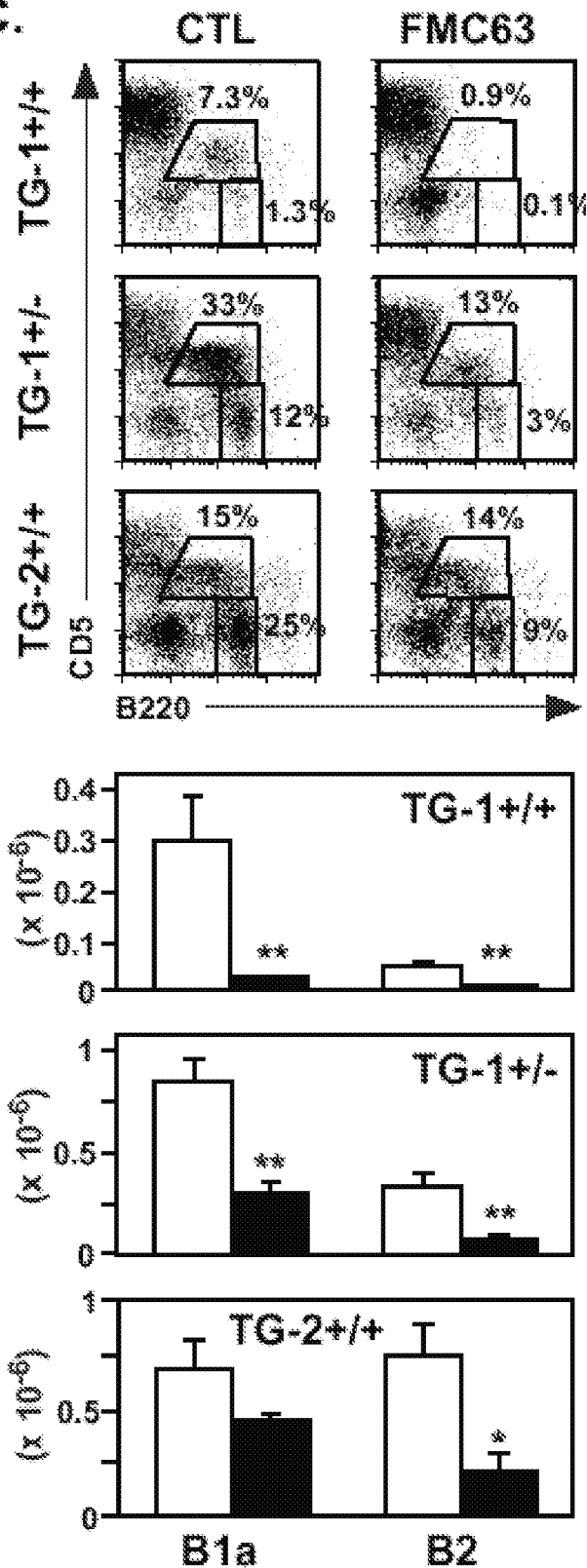

Peritoneal cavity B cells in TG-1$^{+/-}$ mice express hCD19 at higher levels than other tissue B cells (FIG. 1A and FIG. 1C), primarily due to the presence of CD5$^+$IgM$^{hi}$B220$^{lo}$ B1 cells that expressed hCD19 at approximately 25% higher densities than the CD5$^-$IgM$^{lo}$B220$^{hi}$ subset of conventional (B2) B cells (FIG. 4A). FIGS. 4B-4C demonstrate that peritoneal cavity B cells are sensitive to anti-CD19 antibody treatment.

FIG. 4A shows plots of human and mouse CD19 expression (x-axis) versus the relative number of peritoneal cavity CD5$^+$B220$^+$ B 1a and CD5$^-$B220$^{hi}$ B2 (conventional) B cells (y-axis). Single-cell suspensions of peritoneal cavity lymphocytes were examined by three-color immunofluorescence staining with flow cytometry analysis. Bar graphs represent mean MFI (±SEM) values for CD19 expression by 3 littermate pairs of TG-1$^{+/-}$ mice.

FIG. 4B shows depletion of peritoneal cavity B220 cells from TG-1$^{+/-}$ mice treated with CD19 (HB12a, HB12b, and FMC63 at 250 µg; B4 and HD237 at 50 µg) antibodies or control antibody (250 µg). Numbers represent the relative frequencies of B220+ cells within the indicated gates on day seven. Bar graph values represent the total number (±SEM) of B220+ cells within the peritoneum of antibody treated mice (≥3 mice per group). Significant differences between sample means are indicated; *p<0.05, **p<0.01. The results demonstrate that anti-CD19 antibody treatment at 250 µg/mouse depleted a significant portion of peritoneal B220+ B cells by day seven. The results shown in FIG. 4B are in part explained by the depletion of both B1 and conventional B2 cells. When hCD19 was expressed at the highest densities in TG-1+/+ mice, the majority of B1 and B2 cells were depleted. However, CD19-mediated depletion of B1 and B2 cells was less efficient in TG-1+/− and TG-2+/+ mice where hCD19 levels were lower. Thus, CD19 antibody treatment depleted peritoneal B1 and B2 cells depending on their density of CD19 expression as assessed using mean fluorescence intensity, although peritoneal B cells were more resistant to anti-CD19 antibody-mediated depletion than spleen and lymph node B cells.

FIG. 4C shows representative depletion of CD5+B220+ B1a and CD5−B220$^{hi}$ B2 B cells seven days following anti-CD19 antibody or control antibody treatment of hCD19TG mice. Numbers represent the relative frequencies of each B cell subset within the indicated gates. Bar graph values represent the total number (±SEM) of each cell subset within the peritoneum of antibody treated mice (≥3 mice per group). Significant differences between sample means are indicated; *p<0.05, **p<0.01.

Distinct Anti-CD19 Antibodies Mediate B Cell Clearance

In order to determine whether HB12a and HB12b anti-CD19 antibodies are distinct from known anti-CD19 antibodies, the amino acid sequence of each anti-CD19 antibody variable region used herein was analyzed (FIGS. 5A and 5B, 6A and 6B, 7A and 7B).

FIG. 5A depicts the nucleotide (SEQ ID NO:1) and predicted amino acid (SEQ ID NO:2) sequences for heavy chain $V_H$-D-$J_H$ junctional sequences of the HB12a anti-CD19 antibody. Sequences that overlap with the 5' PCR primer are indicated by double underlining and may vary from the actual DNA sequence since redundant primers were used. Approximate junctional borders between V, D, and J sequences are designated in the sequences by vertical bars O. Nucleotides in lower case letters indicate either nucleotide additions at junctional borders or potential sites for somatic hypermutation. The amino-terminal residue of the antibody (E) is marked as residue 1.

FIG. 5B depicts the nucleotide (SEQ ID NO:3) and predicted amino acid (SEQ ID NO:4) sequences for heavy chain $V_H$-D-$J_H$ junctional sequences of the HB12b anti-CD19 antibody. Sequences that overlap with the 5' PCR primer are indicated by double underlining and may vary from the actual DNA sequence since redundant primers were used. Approximate junctional borders between V, D, and J sequences are designated in the sequences by vertical bars O. Nucleotides in lower case letters indicate either nucleotide additions at junctional borders or potential sites for somatic hypermutation. The amino-terminal residue of the antibody (E) is marked as residue 1.

FIG. 6A depicts the nucleotide (SEQ ID NO:15) and predicted amino acid sequence (SEQ ID NO:16) sequences for light chain Vκ-Jκ junctional sequences of the HB12a anti-CD19 antibody. FIG. 6B depicts the nucleotide (SEQ ID NO:17) and predicted amino acid (SEQ ID NO:18) sequences for the light chain V-J junctional sequences of the HB12b anti-CD19 antibody. The amino-terminal amino acid of the mature secreted protein deduced by amino acid sequence analysis is numbered as number 1. Sequences that overlap with the 3' PCR primer are indicated by double underlining. Predicted junctional borders for the V-J-C regions are indicated (/) with J region nucleotides representing potential sites for somatic hypermutation in bold.

FIGS. 7A and 7B depict the amino acid sequence alignment of published mouse anti-CD19 antibodies. FIG. 7A shows a sequence alignment for heavy chain $V_H$-D-$J_H$ junctional sequences including a consensus sequence (SEQ ID NO:5), HB12a (SEQ ID NO:2), 4G7 (SEQ ID NO:6), HB12b (SEQ ID NO:4), HD37 (SEQ ID NO:7), B43 (SEQ ID NO:8), and FMC63 (SEQ ID NO:9). Amino acid numbering and designation of the origins of the coding sequences for each antibody V, D and J region are according to conventional methods (Kabat et al., Sequences of Proteins of Immunological Interest., U.S. Government Printing Office, Bethesda, Md. (1991)) where amino acid positions 1-94 and complementarity-determining regions CDR1 and 2 are encoded by a $V_H$ gene. A dash indicates a gap inserted in the sequence to maximize alignment of similar amino acid sequences. A dot indicates identity between each anti-CD19 antibody and the consensus amino acid sequence for all antibodies. CDR regions are highlighted for clarity. FIG. 7B shows light chain Vκ amino acid sequence analysis of anti-CD19 antibodies. Consensus sequence (SEQ ID NO:10), HB12a (SEQ ID NO:16); HB12b (SEQ ID NO:18); HD37 (SEQ ID NO:11), B43 (SEQ ID NO:12), FMC63 (SEQ ID NO:13), and 4G7 (SEQ ID NO:14) are aligned. Amino acid numbering and designation of the origins of the coding sequence for each anti-CD19 antibody is according to conventional methods (Kabat et al., (1991) Sequences of Proteins of Immunological Interest., U.S. Government Printing Office, Bethesda, Md.). The amino acid following the predicted signal sequence cleavage site is numbered 1. A dash indicates a gap inserted in the sequence to maximize alignment of similar amino acid sequences. CDR regions are highlighted (boxed) for clarity.

Since each anti-CD19 antibody examined in this study depleted significant numbers of B cells in vivo, the amino acid sequence of each anti-CD19 antibody variable region was assessed to determine whether these antibodies differ in sequence and potentially bind to different CD19 epitopes. Antibodies bind target antigens through molecular interactions that are mediated by specific amino acids within the variable regions of each antibody molecule. Thus, complex interactions between protein antigens and the antibodies that bind to specific epitopes on these antigens are almost unique to each antibody and its specific amino acid sequence. This level of complexity in antigen and antibody interactions is a reflection of a diverse antibody repertoire to most protein antigens. While antibody interactions with target antigens are primarily mediated by amino acids within complementarity-determining regions (CDR) of antibody molecules, framework amino acids are also critical to antigen-binding activity. Thus, structurally similar antibodies are likely to bind to the same antigens or region of a target molecule, while structurally dissimilar antibodies with different V and CDR regions are likely to interact with different regions of antigens through different molecular interactions.

Since antibodies that interact with and bind to the same molecular region (or epitope) of a target antigen are structurally similar by definition, the amino acid sequences of HB12a, HB12b, FMC63 and other published anti-CD19 antibodies were compared including the HD37 (Kipriyanov et al., J. Immunol. Methods, 196:51-62 (1996); Le Gall et al., FEBS Letters, 453:164-168 (1999)), 2G7 (Meeker et al., Hybridoma, 3:305-320 (1984); Brandl et al., Exp. Hematol., 27:1264-1270 (1999)), and B43 (Bejcek et al., Cancer Res., 55:2346-2351 (1995)) antibodies. The heavy chains of the anti-CD19 antibodies were generated through different combinations of V(D)J gene segments with the V regions derived from the V1S39, V1S56, V1S136, or V2S 1 gene segments, D regions derived from FL16.1 gene segments, and J regions derived from either J2 or J4 gene segments (Table 2). The published heavy and light chain variable regions of the B43 and HD37 antibodies were virtually identical in amino acid sequence (FIGS. 7A-B). This level of conservation reflects the fact that each of these antibodies is also remarkably similar at the nucleotide level, having identical $V_H(D)J_H$ and $V_LJ_L$ junctions, with most differences accounted for by the use of redundant primers to PCR amplify each cDNA sequence. This indicates that the HD37 and B43 and antibodies share a common, if not identical, origin and therefore bind to identical epitopes on the CD19 protein. The HB12a and 4G7 antibodies were also distinct from other anti-CD19 antibodies. Although the heavy chain regions of the HB12a and 4G7 antibodies were similar and are likely to have derived from the same germline $V_H(D)J_H$ gene segments, different junctional borders were used for D-$J_H$ assembly (FIG. 7A). The HB12b antibody utilized a distinct $V_H$ gene segment (Table 2) and had distinctly different CDR3 sequences (FIG. 7A) from the other anti-CD19 antibodies. The FMC63 antibody also had a very distinct amino acid sequence from the other anti-CD19 antibodies.

TABLE 2

| | Heavy Chain | | | | Light Chain | | |
|---|---|---|---|---|---|---|---|
| | $V^a$ | D | J | Accession #[b] | V | J | Accession # |
| HB12a | V1S136 (12, 8) | FL16.1 | J2 | | V1-133*01 | J2*01 J4* | |
| HB12b | V1S56 (27, 14) | FL16.1 | J2 | | V3-2*01 | 01 | |
| 4G7 | V1S136 (10, 8) | FL16.1 | J2 | AJ555622 | V2-137 | J5 | AJ555479 |
| B43 | V1S39 (37, 17) | FL16.1 | J4 | S78322 | V3-4 | J1 | S78338 |
| HD37 | V1S39 (34, 16) | FL16.1 | J4 | X99230 | V3-4 | J1 | X99232 |
| FMC63 | V2S1 (20, 16) | FL16.1 | J4 | Y14283 | V10-96 | J2 | Y14284 |

N.D., not determined.
[a]Numbers in parenthesis indicate the number of nucleotide differences between the CD19 antibody encoding gene and the most homologous germline sequence identified in current databases, excluding regions overlapping with PCR primers.
[b]GENBANK ® accession numbers for gene sequences.

As shown in FIG. 7B, the HB12a, HB12b, FMC63, 4G7, and HD37/B43 antibodies each utilize distinct light chain genes (FIG. 7B). Light chains were generated from multiple V and J gene segments. The lack of homogeneity among these six anti-CD19 antibodies H and L chain sequences suggests that these antibodies bind to several distinct sites on human CD19. A comparison of amino acid sequences of paired heavy and light chains further indicates that most of these anti-CD19 antibodies are structurally distinct and will therefore bind human CD19 through different molecular interactions. Thus, the ability of anti-CD19 antibodies to deplete B cells in vivo is not restricted to a limited number of antibodies that bind CD19 at identical sites, but is a general property of anti-CD19 antibodies as a class.

CD19 Density Influences the Effectiveness of CD19 Antibody-Induced B Cell Depletion To determine whether an anti-CD19 antibody's ability to deplete B cells is dependent on CD19 density, the HB12b and FMC63 anti-CD19 antibodies were administered to mice having varying levels of CD19 expression. The results demonstrate that human CD19 density on B cells and antibody isotype can influence the depletion of B cells in the presence of an anti-CD19 antibody. The same assay can be used to determine whether other anti-CD19 antibodies can effectively deplete B cells and the results can be correlated to treatment of human patients with varying levels of CD19 expression. Thus, the methods for examining CD19 presence and density in human subjects described herein can be used to identify patients or patient populations for which certain anti-CD19 antibodies can deplete B cells and/or to determine suitable dosages.

The results presented above indicate that although all five anti-CD19 antibodies tested were similarly effective in TG-1$^{+/-}$ mice when used at 250 or 50 μg, the extent of B cell depletion for B cells from blood bone marrow and spleen appeared to correlate with antibody isotype, IgG2a>IgG1>IgG2b (FIGS. 2A-2D). Therefore, the effectiveness of the HB12b (IgG1) and FMC63 (IgG2a) antibodies was compared in homozygous TG-1$^{+/+}$, heterozygous TG-1$^{+/-}$ and homozygous TG-2$^{+/+}$ mice that express CD19 at different densities (FIGS. 1A-E).

To determine whether CD19 density influences the effectiveness of anti-CD19 antibody-induced B cell depletion representative blood and spleen B cell depletion was examined in hCD19TG mice after HB12b (FIG. 8A) or FMC63 (FIG. 8B) antibody treatment (7 days, 250 μg/mouse). Numbers indicate the percentage of gated B220$^+$ lymphocytes. Bar graphs indicate numbers (±SEM) of blood (per mL) or spleen (total number) B cells following treatment with anti-CD19 antibodies (closed bars) or isotype-control (open bars) antibodies. Significant differences between mean results for anti-CD19 antibody or isotype-control antibody treated mice (≥3 mice per data point) are indicated; *p<0.05, **p<0.01.

The results presented in FIGS. 8A-8D demonstrate that CD19 density influences the efficiency of B cell depletion by anti-CD19 antibodies in vivo. Low-level CD19 expression in TG-2 mice had a marked influence on circulating or tissue B cell depletion by the HB12b antibody on day seven (FIG. 8A). Differences in CD19 expression by TG-1$^{+/+}$, TG-1$^{+/-}$ and TG-2$^{+/+}$ mice also influenced circulating and tissue B cell depletion by the FMC63 antibody but did not significantly alter circulating B cell depletion (FIG. 8B).

To further verify that CD19 density is an important factor in CD19 mAb-mediated B cell depletion, the relative depletion rates of CD19TG-1$^{+/+}$ and CD19TG-2$^{+/+}$ B cells were compared directly. Splenocytes from CD19TG-1$^{+/+}$ and CD19TG-2$^{+/+}$ mice were differentially labeled with CFSE by labeling unfractionated splenocytes from hCD19TG-1$^{+/+}$ and hCD19TG-2$^{+/+}$ mice were labeled with 0.1 and 0.01 μM Vybrant™ CFDA SE (CFSE; Molecular Probes), respectively, according to the manufacture's instructions. The relative frequency of B220$^+$ cells among CFSE-labeled splenocytes was determined by immunofluorescence staining with flow cytometry analysis. Subsequently, equal numbers of CFSE-labeled B220$^+$ hCD19TG-1$^{+/+}$ and hCD19TG-2$^{+/+}$ splenocytes ($2.5 \times 10^5$) were injected into the peritoneal cavity of three wild type B6 mice. After 1 hour, the mice were given either FMC63 or control mAb (250 μg, i.p.). After 24 hours, the labeled lymphocytes were recovered with the relative frequencies of CFSE-labeled B220$^+$ and B220$^-$ cells assessed by flow cytometry. The gates in each histogram in FIG. 8C indicate the frequencies of B220$^+$ cells within the CD19TG-1 (CFSE$^{high}$) and CD19TG-2$^{+/+}$ (CFSE$^{low}$) splenocyte populations. The bar graph indicates the number of CFSE labeled cell population present in anti-CD19 mAb treated mice relative to control mAb-treated mice. Results represent hCD19TG-1$^{+/+}$ splenocytes (filled bars) and hCD19TG-2$^{+/+}$ splenocytes (open bars) transferred into ≥3 wild type recipient mice, with significant differences between sample means (±SEM) indicated; **$p<0.01$.

B cell clearance was assessed 24 hours after anti-CD19 or control mAb treatment of individual mice. CD19TG-1$^{+/+}$ B220$^+$ B cells were depleted at significantly faster rates ($p<0.01$) than CD19TG-2$^{+/+}$ B cells in anti-CD19 mAb-treated mice compared with control mAb-treated mice (FIG. 8C). Furthermore, the relative frequency of CD19TG-1$^{+/+}$ B220$^+$ B cells to CD19TG-2$^{+/+}$ B220$^+$ B cells in anti-CD19 mAb treated mice was significantly lower ($p<0.01$) than the ratio of CD19TG-1$^{+/+}$ B220$^+$ B cells to CD19TG-2$^{+/+}$ B220$^+$ B cells in control mAb treated mice. Likewise, the numbers of CD19TG-1$^{+/+}$ and CD19TG-2$^{+/+}$ CFSE-labeled B220$^-$ cells in anti-CD19 or control mAb mice were also comparable. Thus, CD19TG-1$^{+/+}$ B cells that express high density CD19 were depleted at a faster rate than CD19TG-2$^{+/+}$ B cells that express CD19 at a low density.

FIG. 8D shows fluorescence intensity of B220$^+$ cells stained with CD19 (thick lines), CD20 (thin lines) or isotype-matched control (CTL, dashed lines) antibodies (5 μg/mL), with antibody staining visualized using isotype-specific, PE-conjugated secondary antibody with flow cytometry analysis. Results represent those obtained in 4 experiments. The results show the relative anti-hCD19 and anti-mCD20 antibody binding densities on spleen B220$^+$ B cells from TG-1$^{+/-}$ mice. The density of anti-mCD20 antibody binding was 10-64% as high as anti-CD19 antibody binding irrespective of which antibody isotype was used for each antibody (FIG. 8D). Although mCD20 expression was generally lower than hCD19 expression, the levels of hCD19 expression in TG-1+/− mice are still comparable to levels of hCD19 expression found on human B cells (FIG. 1B). Thus, anti-CD19 antibodies effectively depleted TG-2$^{+/+}$ B cells that expressed hCD19 at relatively low densities (FIG. 1B), although high level CD19 expression by TG-1$^{+/+}$ and TG-1$^{+/-}$ B cells obfuscated the relative differences in effectiveness of IgG2a and IgG1 antibodies. Although there is a direct inverse correlation between numbers of B cells and density of hCD19 expression in TG-1 and TG-2 transgenic mice, density of hCD19 is an important factor contributing to the depletion of B cells. Anti-CD19 antibody levels were saturated when administered at 250 μg/mouse (see, also, saturating levels in FIG. 12). Thus, free anti-CD19 antibody levels were in excess regardless of B cell number.

Example 3

Tissue B Cell Depletion is FcγR-Dependent

The following assays were used to determine whether B cell depletion by an anti-CD19 antibody was dependent on FcγR expression. Through a process of interbreeding hCD19tg with mice lacking expression of certain FcγR, mice were generated that expressed hCD19 and lacked expression of certain FcγR. Such mice were used in assays to assess the ability of anti-CD19 antibodies to deplete B cells through pathways that involve FcγR expression, e.g., ADCC. Thus, anti-CD19 antibodies identified in these assays can be used to engineer chimeric, human or humanized anti-CD19 antibodies using the techniques described above. Such antibodies can in turn be used in the compositions and methods of the invention for the treatment of B cell malignanices in humans.

The innate immune system mediates B cell depletion following anti-CD20 antibody treatment through FcγR-dependent processes. Mouse effector cells express four different FcγR classes for IgG, the high-affinity FcγRI (CD64), and the low-affinity FcγRII (CD32), FcγRIII (CD16), and FcγRIV molecules. FcγRI, FcγRIII and FcγRIV are hetero-oligomeric complexes in which the respective ligand-binding a chains associate with a common γ chain (FcRγ). FcRγ chain expression is required for FcγR assembly and for FcγR triggering of effector functions, including phagocytosis by macrophages. Since FcRγ$^{-/-}$ mice lack high-affinity FcγRI (CD64) and low-affinity FcγRIII (CD16) and FcγRIV molecules, FcRγ$^{-/-}$ mice expressing hCD19 were used to assess the role of FcγR in tissue B cell depletion following anti-CD19 antibody treatment. FIG. 9A shows representative blood and spleen B cell depletion seven days after anti-CD19 or isotype-control antibody treatment of FcRγ$^{+/-}$ or FcRγ$^{-/-}$ littermates. Numbers indicate the percentage of B220$^+$ lymphocytes within the indicated gates. FIG. 9B shows blood and tissue B cell depletion seven days after antibody treatment of FcRγ$^{-/-}$ littermates on day zero. For blood, the value shown after time zero represents data obtained at 1 hour. Bar graphs represent mean B220$^+$ B cell numbers (±SEM) after anti-CD19 (filled bars) or isotype-control (open bars) antibody treatment of mice (≥3 mice per group). Significant differences between mean results for anti-CD19 or isotype-control antibody treated mice are indicated; *$p<0.05$, **$p<0.01$. The results presented in FIGS. 9A and 9B demonstrate that B cell depletion following anti-CD19 antibody treatment is FcRγ-dependent. There were no significant changes in numbers of bone marrow, blood, spleen, lymph node and peritoneal cavity B cells in FcRγ$^{-/-}$ mice following FMC63 antibody treatment when compared with FcRγ$^{-/-}$ littermates treated with a control IgG2a antibody. By contrast, anti-CD19 antibody treatment depleted most B cells in FcRγ$^{+/-}$ littermates. Thus, anti-CD19 antibody treatment primarily depletes blood and tissue B cells through pathways that require FcγRI and FcγRIII expression.

FIG. 9C shows representative B cell numbers in monocyte-depleted hCD19TG-1$^{+/-}$ mice. Mice were treated with clodronate-liposomes on day −2, 1 and 4, and given FMC63 (n=9), isotype control (n=6), or CD20 (n=3) mAb (250 μg) on day 0. Mice treated with PBS-liposomes and FMC63 anti-CD19 antibody (n=3) served as controls. Representative blood and spleen B cell depletion is shown 7 days after antibody treatment with the percentage of lymphocytes within the indicated gates indicated.

FIG. 9D shows blood and tissue B cell depletion 7 days after antibody treatment as in (C). Bar graphs represent mean B220$^+$ B cell numbers (±SEM) after antibody treatment of mice (≥3 mice per group). For blood, values indicate numbers of circulating B cells in PBS-treated mice with FMC63 anti-CD19 antibody (closed triangles), or monocyte-depleted mice treated with control antibody (open circles), CD20 antibody (closed squares), or FMC63 anti-CD19 antibody (closed circles). Significant differences between mean results for isotype-control mAb-treated mice and other groups are indicated; *p<0.05, **p<0.01.

The results presented in FIG. 9 show B cell depletion following anti-CD19 antibody treatment is FcRγ and monocyte-dependent. Mice rendered macrophage-deficient by treatment with liposome-encapsulated clodronate did not significantly deplete circulating B cells 1 day after FMC63, anti-CD20 (MB20-11) or control anti-CD19 antibody treatment, while FMC63 antibody treatment eliminated circulating B cells in mice treated with PBS-loaded liposomes (FIGS. 9C-D). After 4-7 days, circulating B cell numbers were significantly depleted by both FMC63 and anti-CD20 antibody treatment, with anti-CD19 antibody treatment having more dramatic effects on B cell numbers in clodronate-treated mice. Similarly, anti-CD19 and anti-CD20 antibody treatment decreased bone marrow $B220^+$ cell numbers by 55% in clodronate-treated mice on day 7 relative to control antibody treated littermates, while anti-CD19 antibody treatment decreased bone marrow $B220^+$ cell numbers by 88% in PBS-treated mice. Anti-CD19 antibody treatment decreased spleen B cell numbers by 52% in clodronate-treated mice on day 7 relative to control antibody treated littermates, while anti-CD20 antibody depleted B cells minimally, and anti-CD19 antibody treatment decreased spleen B cell numbers by 89% in PBS-treated mice. Both anti-CD19 and anti-CD20 antibody treatment decreased lymph node B cell numbers by 48-53% in clodronate-treated mice on day seven relative to control antibody treated littermates, while anti-CD19 antibody treatment decreased lymph node B cell numbers by 93% in PBS-treated mice. In blood, spleen and lymph nodes, anti-CD19 antibody treatment was significantly less effective in clodronate-treated mice than in PBS-treated littermates (p<0.01). These findings implicate macrophages as major effector cells for depletion of $CD19^+$ and $CD20^+$ B cells in vivo, and indicate that anti-CD19 antibody therapy may be more effective than anti-CD20 antibody therapy when monocyte numbers or function are reduced.

Example 4

Anti-CD19 Antibody-Induced B Cell Depletion is Durable

In order to assess the efficacy and duration of B cell depletion, the hCD19TG mice were administered a single low dose 250 µg injection of anti-CD19 antibody. FIGS. 10A-10C demonstrate duration and dose response of B cell depletion following anti-CD19 antibody treatment. FIG. 10A shows numbers of blood $B220^+$ B cells and Thy-$1^+$ T cells following FMC63 or isotype-control antibody treatment of TG-$1^{+/-}$ mice on day zero. Values represent mean (±SEM) results from six mice in each group. The results demonstrate that circulating B cells were depleted for 13 weeks with a gradual recovery of blood-borne B cells over the ensuing 13 weeks. Thy-$1^+$ T cell representation was not altered as a result of anti-CD19 treatment.

FIGS. 10B-10C show representative tissue B cell depletion in the mice shown in FIG. 10A at 11, 16, and 30 weeks following antibody treatment. Numbers indicate the percentage of $B220^+$ lymphocytes within the indicated gates. The results in FIG. 10B show that the bone marrow, blood, spleen, lymph node, and peritoneal cavity were essentially devoid of B cells 11 weeks after antibody treatment (significant differences between sample means are indicated; *p<0.05, **p<0.01). After the first appearance of circulating B cells, it took >10 additional weeks for circulating B cell numbers to reach the normal range. By week 16 post-antibody treatment, blood, spleen, LN and PL B cell numbers had begun to recover while the BM B cell compartment was not significantly different from untreated controls as shown in FIG. 10C. By week 30, all tissues were repopulated with B cells at levels comparable to those in normal controls.

FIG. 10D shows anti-CD19 antibody dose responses for blood, bone marrow and spleen B cell depletion. Mice were treated with anti-CD19 antibodies on day zero with tissue B cells representation assessed on day seven. Results represent those obtained with three mice in each group for each antibody dose. Control antibody doses were 250 µg. Significant differences between sample means are indicated; *p<0.05, **p<0.01. A single FMC63 antibody dose as low as 2 µg/mouse depleted significant numbers of circulating B cells, while 10 µg the HB12b antibody was required to significantly reduce circulating B cell numbers (FIG. 10D). Significant depletion of bone marrow and spleen B cells by day seven required 5-fold higher antibody doses of 10-50 µg/mouse. Thus, CD19 antibody treatment at relatively low doses can deplete the majority of circulating and tissue B cells for significant periods of time.

CD19 Persists on the B Cell Surface after Administration of Anti-CD19 Antibody

Whether CD19 internalization influenced B cell depletion in vivo was assessed by comparing cell-surface CD19 expression following HB12a, HB12b and FMC63 antibody treatment (250 µg).

FIGS. 11A-11C show cell surface CD19 expression and B cell clearance in TG-$1^{+/-}$ mice treated with HB12a (FIG. 11A), HB12b (FIG. 11B), FMC63 (FIG. 11C) or isotype-matched control antibody (250 µg) in vivo. At time zero (prior to anti-CD19 administration), and at 1, 4, and 24 hours post-antibody administration, spleen B cells were harvested and assessed for CD19 (thick line) and control (thin line) antibody binding by treating cells with isotype-specific secondary antibody in vitro with flow cytometry analysis. Isolated B cells were also treated in vitro with saturating concentrations of each CD19 antibody plus isotype-specific secondary antibody in vitro with flow cytometry analysis to visualize total cell surface CD19 expression. Each time point represents results with one mouse. The results presented in FIGS. 11A-11C demonstrate that cell surface CD19 is not eliminated from the cell surface following antibody binding in vivo and show that the majority of spleen B cells expressed uniform high levels of cell surface hCD19 for up to 24 hours after antibody treatment although a subset of B cells expressed reduced levels of hCD19 at 1 hour following FMC63 antibody treatment (FIG. 11C). The results shown in FIGS. 11A-11C also demonstrate that the amount of CD19 on the surface of B cells is constant, indicating that the capability of the B cells to mediate ADCC is maintained.

The results demonstrate that CD19 surprisingly exhibited lower levels of internalization than expected following administration of anti-CD19 antibodies. In particular, the results demonstrate that CD19 unexpectedly persists on the cell surface following binding of an anti-CD19 antibody, thus, the B cell remains accessible to the ADCC activity. These results demonstrate, in part, why the anti-CD19 antibodies and treatment regimens of the invention are efficacious in treating B cell malignancies.

FIGS. 12A-12C document the extent of B cell depletion and the ability of anti-hCD19 antibodies to bind hCD19 and thus inhibit the binding of other anti-hCD19 antibodies. The results in FIG. 12A demonstrate that a single administration of FMC63 (250 µg) to TG-$1^{+/-}$ mice results in significant depletion of both blood and spleen B cells within 1 hour of antibody administration. In this experiment, blood and spleen cells were harvested and assessed for B cell frequencies prior to anti-CD19 antibody administration or at various times thereafter (1, 4, or 24 hours). Blood samples were stained with anti-Thy1.2 and anti-B220 to identify B cells in the lower right quadrant. Spleen cells were stained with anti-IgM and anti-B220 antibodies to identify B cells within the indicated gate. Each time point represents results with one mouse. Unexpectedly, blood B cells were cleared more rapidly than splenic B cells.

The B cell depletion described in FIG. 12A suggested that the administered antibody rapidly saturated available antibody-binding sites on hCD19 within 1 hour of administration. To confirm this observation, mice were treated with either FMC63 (hCD19 binding antibody) or isotype-control antibody. At various time thereafter blood and spleen B cells were stained with the fluorochrome-conjugated B4 antibody to identify unoccupied antibody binding sites on the surface of mCD19$^+$ or mCD20$^+$ B cells. The frequencies of cells within the upper and lower-right quadrants are indicated. Each time point represents results obtained from one mouse. The results indicate FMC63 treatment resulted in a progressive depletion of hCD19 bearing cells over the course of the experiment with blood B cells being depleted more rapidly than spleen. Those B cells remaining at each time point could be identified by their expression of mCD19 or mCD20, but were not stained by B4 suggesting that the administered FMC63 was bound to the remaining B cells. These finding confirm the ability of FMC63 to bind and deplete B cells in vivo. Moreover, FMC63 prevents B4 binding suggesting that these antibodies recognize overlapping epitopes on hCD19. The results in FIG. 12C confirm that HB12b antibody treatment (250 µg) also saturates antibody-binding sites on hCD19 within 1 hour of administration and results in the depleting of hCD19 positive B cells. Unexpectedly, the HB12b antibody did not completely inhibit binding of the B4 antibody suggesting that unlike FMC63, HB12b recognizes an epitope on hCD19 that is distinct from that recognized by B4. The results shown in FIGS. 12B-12C demonstrate that most anti-CD19 antibodies inhibit the binding of most other anti-CD19 antibodies, indicating that most anti-CD19 antibodies bind to similar, the same, or overlapping regions or epitopes on the CD19 protein. Alternatively, these observations may also result from the relatively small size of the CD19 extracellular domain compared with the size of antibody molecules.

Example 5

Anti-CD19 Antibody Treatment Abrogates Humoral Immunity and Autoimmunity

The assays described in this example can be used to determine whether an anti-CD19 antibody is capable of eliminating or attenuating immune responses. Anti-CD19 antibodies identified in these assays can be used to engineer chimeric, human or humanized anti-CD19 antibodies using the techniques described above. Such antibodies can in turn be used in the compositions and methods of the invention for the treatment of B cell malignancies in humans.

The effect of anti-CD19 antibody-induced B cell depletion on serum antibody levels was assessed by giving hCD19TG$^{+/-}$ mice a single injection of anti-CD19 antibody. FIG. 13A shows CD19 antibody treatment reduces serum immunoglobulin levels in TG-1$^{+/-}$ mice. Two-month-old littermates were treated with a single injection of FMC63 (closed circles) or control (open circles) antibody (250 µg) on day 0. Antibody levels were determined by ELISA, with mean values (±SEM) shown for each group of ≥5 mice. Differences between CD19 or control mAb-treated mice were significant; *p<0.05, p<0.01. The results show that after 1 to 2 weeks, serum IgM, IgG2b, IgG3, and IgA antibody levels were significantly reduced, and remained reduced for at least 10 weeks (FIG. 13A**). IgG1 and IgG2a serum levels were significantly below normal at 6 and 4 weeks post-treatment.

Since hCD19TG$^{+/-}$ mice produce detectable autoantibodies after 2 mos of age (Sato et al., *J. Immunol.*, 157:4371 (1996)), serum autoantibody binding to ssDNA, dsDNA and histones was assessed. FIG. 13B shows anti-CD19 antibody treatment reduces autoantibody anti-dsDNA, anti-ssDNA and anti-histone autoantibody levels after anti-CD19 antibody treatment. The results show that anti-CD19 antibody treatment significantly reduced serum IgM autoantibody levels after 2 weeks and prevented the generation of isotype-switched IgG autoantibodies for up to 10 weeks (FIG. 13B). Thus, B cell depletion substantially reduced acute and long-term antibody responses and attenuated class-switching of normal and pathogenic immune responses.

Figure 14C:
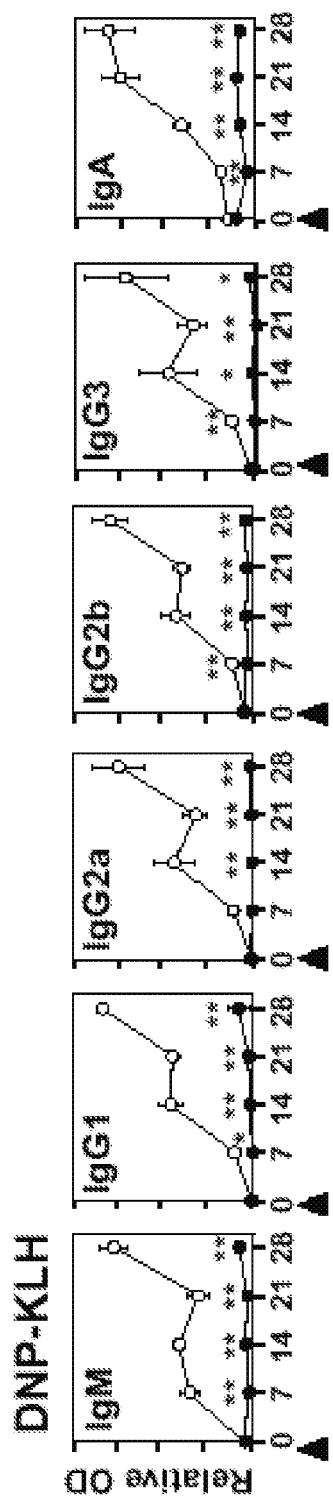
Figure 14D:
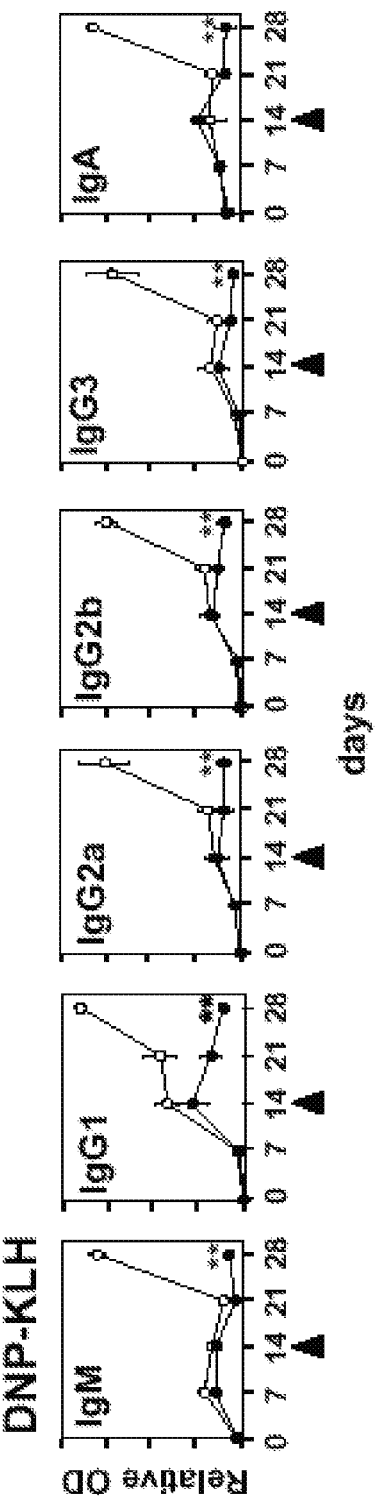

The influence of B cell depletion on T cell-independent type 1 (TI-1) and type 2 (TI-2) antibody responses was assessed by immunizing hCD19TG$^{+/-}$ mice with TNP-LPS or DNP-Ficoll (at day zero), 7 days after anti-CD19 antibody (FMC63) or control antibody treatment. Significant hapten-specific IgM, IgG, and IgA antibody responses were not observed in anti-CD19 antibody-treated mice immunized with either antigen (FIGS. 14A and 14B). Antibody responses to the T cell-dependent (TD) Ag, DNP-KLH, were also assessed using mice treated with anti-CD19 antibody 7 days before immunization (FIG. 14B). FIG. 14C shows that DNP-KLH immunized mice treated with anti-CD19 antibody showed reduced humoral immunity. Littermates were treated with FMC63 (closed circles) or control (open circles) antibody (250 µg) seven days before primary immunizations on day zero, with serum obtained on the indicated day. For DNP-KLH immunizations, all mice were challenged with 100 µg of DNP-KLH on day 21. All values are mean (±SEM) ELISA OD units obtained using sera from five mice of each group. Differences between anti-CD19 or control antibody-treated mice were significant; *p<0.05,  p<0.01. The results show that control antibody-treated littermates generated primary IgM antibody responses 7 days after DNP-KLH immunization and secondary responses after antigen challenge on day 21 (FIG. 14C). However, significant hapten-specific IgM, IgG or IgA antibody responses were not detected in CD19 mAb-treated mice immunized or re-challenged with antigen. To assess the effect of B cell depletion on secondary antibody responses, mice were also immunized with DNP-KLH and treated with anti-CD19 antibody 14 days later (arrows) (FIG. 14D**). By day 21, serum IgM, IgG, and IgA anti-DNP antibody responses had decreased in CD19 mAb-treated mice to levels below those of immunized mice treated with control mAb. However, re-challenge of control mAb-treated mice with DNP-KLH on day 21 induced significant secondary antibody responses, while CD19 mAb-treated mice did not produce anti-DNP antibodies after DNP-KLH rechallenge. Thus, CD19 mAb-induced B cell depletion substantially reduced both primary and secondary antibody responses and prevented class-switching during humoral immune responses.

Example 6

Anti-CD19 Antibody Treatment in Conjunction with Anti-CD20 Antibody Treatment The assay described herein can be used to determine whether other combination or conjugate therapies, e.g., anti- CD19 antibodies in combination with chemotherapy, toxin therapy or radiotherapy, have beneficial effects, such as an additive or more that additive depletion of B cells. The results of combination therapies tested in animal models can be correlated to humans by means well-known in the art.

Anti-CD20 antibodies are effective in depleting human and mouse B cells in vivo. Therefore, the benefit of simultaneous treatment with anti-CD19 (FMC63) and anti-CD20 (MB20-11) antibodies was assessed to determine whether this enhanced B cell depletion. Mice were treated with suboptimal 2 μg doses of each antibody individually, or a combination of both antibodies at 1 μg, or with combined 2 μg doses. FIG. 15 shows the results of TG-1$^{+/-}$ mice treated with control (250 μg), FMC63 (CD19, 2 μg), MB20-11 (CD20, 2 μg), FMC63+MB20-11 (1 μg each), or FMC63+MB20-11 (2 μg each) antibodies on day zero. Blood B cell numbers were measured at time zero, one hour, and on days one, four and seven. Tissue B cell numbers were determined on day seven. Values represent means (±SEM) from groups of three mice. The results shown in FIG. 15 demonstrate that simultaneous anti-CD19 and anti-CD20 antibody treatments are beneficial. B cell depletion in mice treated with a combination of both antibodies at 1 μg was intermediate or similar to depletion observed following treatment of mice with 2 μg of each individual antibody (FIG. 15). However, the simultaneous treatment of mice with both antibodies at 2 μg lead to significantly more B cell depletion than was observed with either antibody alone. Thus, combined anti-CD19 and anti-CD20 antibody therapies had beneficial effects that enhanced B cell depletion. This likely results from the accumulation of more therapeutically effective antibody molecules on the surface of individual B cells.

Example 7

Subcutaneous (S.C.) Anti-CD19 Antibody Administration is Therapeutically Effective The assay described herein can be used to determine whether a subcutaneous route of administration of an anti-CD19 antibody can effectively deplete B cells. The results of the efficacy of different delivery routes tested in animal models can be correlated to humans by means well-known in the art.

Since anti-CD19 antibody given i.v. effectively depletes circulating and tissue B cells, it was assessed whether anti-CD19 antibody given s.c. or i.p. depleted B cells to an equivalent extent. Wild-type mice were treated with the FMC63 antibody at 250 μg either subcutaneous (s.c.), intraperitoneal (i.p.) or i.v. Values represent mean (±SEM) blood (per ml), bone marrow, spleen, lymph node, and peritoneal cavity B220+ B cell numbers on day seven (n>3) as assessed by flow cytometry. Significant differences between mean results for each group of mice are indicated; *p<0.05, p<0.01 in comparison to the control. The results in FIG. 16 demonstrate that subcutaneous (s.c.), intraperitoneal (i.p.) and i.v. administration of CD19 antibody effectively depletes circulating and tissue B cells in vivo. The vast majority of circulating and tissue B cells were depleted in mice given anti-CD19 antibodies as 250 μg doses either i.v., i.p., or s.c. (FIG. 16). Unexpectedly, giving anti-CD19 antibody i.p. did not deplete peritoneal B cells significantly better than i.v. treatment. Accordingly, an anti-CD19 antibody can be used to effectively deplete both circulating and tissue B cells when given as ≤64 mg s.c. injections. Since anti-CD19 antibodies are effective down to 10 μg doses i.v. (FIG. 10D**) even lower s.c. antibody doses are likely to be effective.

Example 8

Anti-CD19 Antibody Treatment Abrogates Tumor Growth In Vivo

Figure 17:
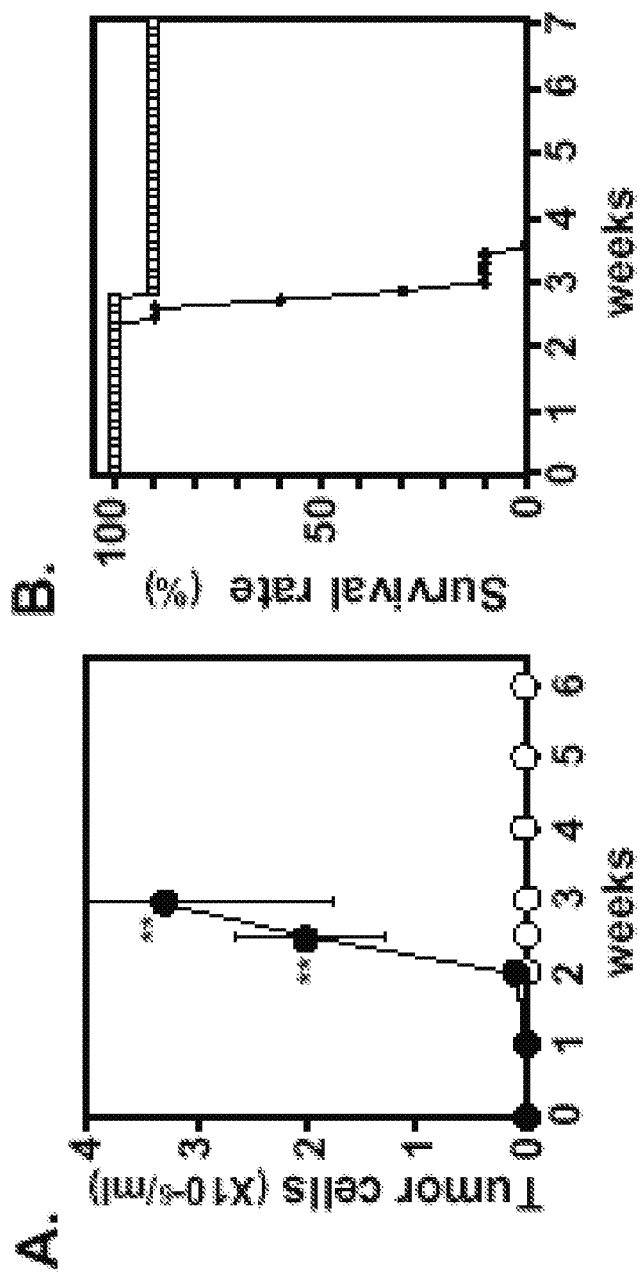

Burkitt's lymphoma, a B cell malignancy in humans, is characterized by translocations of the c-myc proto-oncogene to Ig gene promoter regions, leading to aberrant c-Myc overexpression. Similarly, Eμ-cMyc transgenic (cMycTG) mice, in which the c-myc proto-oncogene is under the control of the Ig heavy chain enhancer, develop aggressive B cell-derived lymphomas at an early age, have about 90% mortality rate by 20 weeks of age, and have a median age of survival at about 12 weeks (Harris et al., *J. Exp. Med.* 167:353 (1988) and Adams et al., *Nature* 318:533 (1985)). Tumors from c-MycTG mice are not restricted to a specific B cell developmental stage, but predominantly present with Ig gene rearrangements and phenotypes characteristic of pre-B or immature B cells (Adams et al., *Nature* 318:533 (1985)). To assess the efficacy of CD19-directed immunotherapy in vivo, hCD19TG-1$^{+/+}$ and cMycTG mice were crossed to generate hCD19TG-1$^{+/-}$ cMycTG$^{+/-}$ mice that developed aggressive B cell-derived lymphomas at an early age. Tumor cells derived from one mouse were isolated, expanded in vitro, and characterized phenotypically to be hCD19$^+$ and mouse CD19$^+$ CD20$^-$ CD43$^-$ IgM$^+$ IgD$^-$ B220$^+$ lymphoblasts, which are typical of the pre-B/immature B cell tumors that develop in c-mycTG$^{+/-}$ mice (Harris et al., *J. Exp. Med.* 167:353 (1988) and Adams et al., *Nature* 318:533 (1985)). Tumor cells ($10^5$) from hCD19TG-1$^{+/-}$ mycTG mice were transplanted i.v. into 20 Rag$^{-/-}$ mice on day 0. Equal numbers of randomly selected mice were treated with FMC63 (filled circles) or control (open circles) antibody (250 μg) on days 1 and 7. FIG. 17A shows the numbers of circulating tumor cells (±SEM) quantified by flow cytometry over a 6 week period and FIG. 17B shows mouse percent survival over a 7 week period. Each value indicates the percentage of viable mice on each day they were examined. The results in FIG. 17 demonstrate that anti-CD19 antibody treatment prevents hCD19$^+$ lymphoma growth in vivo. Transplantation of these tumor cells into twenty Rag$^{-/-}$ mice resulted in the appearance of circulating mouse CD19$^+$ and B220$^+$ lymphoblasts by 2 weeks in ten randomly selected recipients that were treated with a control mAb, with death by 3.5 weeks. By contrast, treating ten mice with anti-CD19 antibody (day 1 and 7) following tumor transplantation prevented the appearance of circulating tumor cells in all 10 recipients for up to 7 weeks. One anti-CD19 antibody-treated mouse died during blood harvest, but never displayed circulating tumor cells. Thus, anti-CD19 antibody treatment may offer an effective therapy for treating patients with B cell lineage malignancies, especially those with tumors that do not express CD20 or express CD20 at low levels.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A pharmaceutical composition comprising a monoclonal chimerized, human or humanized anti CD19 antibody comprising the sequences as set out as amino acids 33 to 37, amino acids 51 to 68 and amino acids 101 to 114 of SEQ ID NO:4 and the sequences as set out as amino acids 44 to 58, amino acids 74 to 80 and amino acids 113-121 of SEQ ID NO:18; that (a) is of the IgG1 or IgG3 human isotype, or (b) mediates human antibody-dependent cellular cytotoxicity (ADCC), in a pharmaceutically acceptable carrier, and wherein one amino acid substitution is introduced into one or more of the sequences selected from the group consisting of amino acids 33 to 37 of SEQ ID NO:4, amino acids 51 to 68 of SEQ ID NO:4, amino acids 101 to 114 of SEQ ID NO:4, amino acids 44 to 58 of SEQ ID NO:18, amino acids 74 to 80 of SEQ ID NO:18, and amino acids 113-121 of SEQ ID NO:18.

2. The pharmaceutical composition of claim 1, wherein a therapeutically effective amount of the monoclonal chimerized anti-CD19 antibody of the IgG1 or IgG3 human isotype for treating B cell malignancy is less than about 1 mg/kg of patient body weight.

3. The pharmaceutical composition of claim 1, wherein a therapeutically effective amount of the monoclonal chimerized anti-CD19 antibody of the IgG1 or IgG3 human isotype for treating B cell malignancy is greater than about 2 mg/kg of patient body weight.

4. The composition of claim 1, wherein the anti-CD 19 antibody that mediates ADCC is of the IgG1, IgG2, IgG3, or IgG4 human isotype.

5. The pharmaceutical composition of claim 1, wherein the anti-CD19 antibody has a half-life in a subject of at least 4 to 7 days.

6. The pharmaceutical composition of claim 1, wherein the anti-CD19 antibody is detectably labeled, is a naked antibody, is conjugated to a therapeutic compound, is conjugated to a cytotoxic agent, or is conjugated to a diagnostic agent.

7. The pharmaceutical composition of claim 1, wherein the anti-CD19 antibody is bispecific.

8. The pharmaceutical composition of claim 7, wherein the bispecific anti-CD19 antibody has specificity for binding leukocyte effector cells.

9. The pharmaceutical composition of claim 1, wherein the ADCC function of the anti-CD 19 antibody is assessed by measuring the ability of the anti-CD 19 antibody to mediate target cell lysis by leukocyte effector cells in vitro.

10. The pharmaceutical composition of claim 1, wherein the anti-CD19 antibody comprises a heavy chain consisting of a sequence having at least 90% identity to SEQ ID NO:4.

11. The pharmaceutical composition of claim 1, wherein the anti-CD19 antibody comprises the light chain consisting of a sequence having at least 95% amino acid sequence identity to SEQ ID NO:18.

12. A method of treating a B cell malignancy in a human patient comprising;
    administering a pharmaceutical composition according to claim 1.

13. The method accordingly to claim 12, wherein the anti-CD 19 antibody comprises a heavy chain consisting of a sequence having at least 90% identity to SEQ ID NO:4.

14. The method accordingly to claim 12, wherein the antibody comprises the light chain consisting of a sequence having at least 95% identity to SEQ ID NO:18.

15. The method accordingly to claim 12, wherein the antibody is able to deplete circulating B cells.

16. The method accordingly to claim 12, wherein the antibody is able to deplete bone marrow B cells.

17. The method accordingly to claim 12, wherein the B cell malignancy is acute lymphoblastic leukaemia, mantle cell lymphoma, pre-B cell acute lymphoblastic leukaemia, or precursor B cell lymphoblastic lymphoma.

18. The method accordingly to claim 12, wherein the anti-CD19 antibody that mediates ADCC is of the IgG1, IgG2, IgG3, or IgG4 human isotype.

19. The method accordingly to claim 12, wherein the B cell malignancy is treated prior to the administration of the anti-CD19 antibody.

20. The method accordingly to claim 12, wherein the B cell malignancy is treated with a therapy other than an anti-CD19 antibody therapy subsequent to the administration of the anti-CD19 antibody.

21. The method accordingly to claim 12, wherein the treatment for the malignancy is chemotherapy, radioimmunotherapy, toxin therapy, prodrug-activating enzyme therapy, antibody therapy, monocyte or macrophage enhancing therapy, immunoregulatory therapy, tumor neovasculature (statin) therapy, calicheamicin therapy, surgical therapy, or any combination thereof.

* * * * *

UNITED STATES PATENT AND TRADEMARK OFFICE
CERTIFICATE OF CORRECTION

PATENT NO. : 9,260,530 B2
APPLICATION NO. : 13/957055
DATED : February 16, 2016
INVENTOR(S) : Thomas F. Tedder et al.

It is certified that error appears in the above-identified patent and that said Letters Patent is hereby corrected as shown below:

In the Specification

Column 1, Line 28:
Insert the subheading:
--STATEMENT OF GOVERNMENT INTEREST--

And replace the following paragraph:
[[This invention was made in part with government support under grant numbers CA1776, CA105001, and CA96547 awarded by the National Cancer Institute of the National Institutes of Health and under grant number AI56363 awarded by the National Institute of Allergy and Infectious Disease of the National Institutes of Heath. The United States Government has certain rights in the invention.]]

With the following paragraph:
--This invention was made with government support under grant numbers AI056363, CA096547, CA105001, CA081776, awarded by the National Institutes of Health. The government has certain rights in the invention.--

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 21

<210> SEQ ID NO 1
<211> LENGTH: 373
<212> TYPE: DNA
<213> ORGANISM: Murine
<220> FEATURE:
<223> OTHER INFORMATION: mouse anti-(human)CD19 antibody HB12a Heavy
      chain VH-D-JH junctional sequence

<400> SEQUENCE: 1

```
gaattcgagg tgcagctgca ggagtctgga cctgagctgg taaagcctgg ggcttcagtg      60
aagatgtcct gcaaggcttc tggatacaca ttcactagct atgttatgca ctgggtgaag     120
cagaagcctg gcagggcct tgagtggatt ggatatttta atccttacaa tgatggtact      180
gattactatg agaagttcaa aggcaaggcc acactgactt cagacaaatc ctccagcaca     240
gcctacatgg cgctcagcag cctgacctct gaggactctg cggtctatta ctgtgcaaga     300
gggacctatt actacggtag tagctacccc tttgactact ggggccaagg caccactctc     360
acagtctcct cag                                                        373
```

<210> SEQ ID NO 2
<211> LENGTH: 124
<212> TYPE: PRT
<213> ORGANISM: Murine
<220> FEATURE:
<223> OTHER INFORMATION: mouse anti-(human)CD19 antibody HB12a Heavy
      chain VH-D-JH junctional sequence

<400> SEQUENCE: 2

```
Glu Phe Glu Val Gln Leu Gln Glu Ser Gly Pro Glu Leu Val Lys Pro
 1               5                  10                  15

Gly Ala Ser Val Lys Met Ser Cys Lys Ala Ser Gly Tyr Thr Phe Thr
            20                  25                  30

Ser Tyr Val Met His Trp Val Lys Gln Lys Pro Gly Gln Gly Leu Glu
        35                  40                  45

Trp Ile Gly Tyr Phe Asn Pro Tyr Asn Asp Gly Thr Asp Tyr Tyr Glu
    50                  55                  60

Lys Phe Lys Gly Lys Ala Thr Leu Thr Ser Asp Lys Ser Ser Ser Thr
65                  70                  75                  80

Ala Tyr Met Ala Leu Ser Ser Leu Thr Ser Glu Asp Ser Ala Val Tyr
                85                  90                  95

Tyr Cys Ala Arg Gly Thr Tyr Tyr Tyr Gly Ser Ser Tyr Pro Phe Asp
            100                 105                 110

Tyr Trp Gly Gln Gly Thr Thr Leu Thr Val Ser Ser
        115                 120
```

<210> SEQ ID NO 3
<211> LENGTH: 370
<212> TYPE: DNA
<213> ORGANISM: Murine
<220> FEATURE:
<223> OTHER INFORMATION: mouse anti-(human)CD19 antibody HB12b Heavy
      chain VH-D-JH junctional sequence

<400> SEQUENCE: 3

```
gaattcgagg tgcagctgca ggagtctgga cctgagctgg tgaagcctgg ggcctcagtg      60
aagatttcct gcaaagcttc tggctacgca ttcagtagct cttggatgaa ctgggtgata     120
cagaggcctg gacagggtct tgagtggatt ggacggattt atcctggaga tggagatact     180
```

```
aactacaatg ggaagttcaa gggcaaggcc acactgactg cagacaaatc ctccagtaca    240
gcctacatgc agctcagcag cctgacctct gtggactctg cggtctattt ctgtgcaaga    300
tcaggattta ttactacggt tttagacttt gactactggg gccacggcac cactctcaca    360
gtctcctcag                                                           370
```

```
<210> SEQ ID NO 4
<211> LENGTH: 123
<212> TYPE: PRT
<213> ORGANISM: Murine
<220> FEATURE:
<223> OTHER INFORMATION: mouse anti-(human)CD19 antibody HB12b Heavy
      chain VH-D-JH junctional sequence

<400> SEQUENCE: 4
```

Glu Phe Glu Val Gln Leu Gln Glu Ser Gly Pro Glu Leu Val Lys Pro
1               5                   10                  15

Gly Ala Ser Val Lys Ile Ser Cys Lys Ala Ser Gly Tyr Ala Phe Ser
            20                  25                  30

Ser Ser Trp Met Asn Trp Val Ile Gln Arg Pro Gly Gln Gly Leu Glu
        35                  40                  45

Trp Ile Gly Arg Ile Tyr Pro Gly Asp Gly Asp Thr Asn Tyr Asn Gly
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Val Asp Ser Ala Val Tyr
                85                  90                  95

Phe Cys Ala Arg Ser Gly Phe Ile Thr Thr Val Leu Asp Phe Asp Tyr
            100                 105                 110

Trp Gly His Gly Thr Thr Leu Thr Val Ser Ser
        115                 120

```
<210> SEQ ID NO 5
<211> LENGTH: 124
<212> TYPE: PRT
<213> ORGANISM: Artificial Sequence
<220> FEATURE:
<223> OTHER INFORMATION: Consensus sequence of mouse anti-(human)CD19
      antibody heavy chain junction VH-D-JH

<400> SEQUENCE: 5
```

Glu Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Asp Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Ala Leu Ser Ser Leu Thr Ser Glu Asp Ser Ala Val Tyr Tyr Cys
                85                  90                  95

Ala Arg Gly Thr Tyr Tyr Tyr Gly Ser Ser Tyr Tyr Pro Phe Asp
            100                 105                 110

Tyr Trp Gly Gln Gly Thr Thr Leu Thr Val Ser Ser
        115                 120

```
<210> SEQ ID NO 6
<211> LENGTH: 121
<212> TYPE: PRT
<213> ORGANISM: Murine
<220> FEATURE:
<223> OTHER INFORMATION: mouse anti-(human)CD19 antibody 4G7 heavy chain
      junction VH-D-JH

<400> SEQUENCE: 6

Glu Val Gln Leu Gln Gln Ser Gly Pro Glu Leu Ile Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
 65                  70                  75                  80

Met Ala Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
                100                 105                 110

Gln Gly Thr Thr Leu Thr Val Ser Ser
        115                 120

<210> SEQ ID NO 7
<211> LENGTH: 124
<212> TYPE: PRT
<213> ORGANISM: Murine
<220> FEATURE:
<223> OTHER INFORMATION: mouse anti-(human)CD19 antibody HD37 heavy
      chain junction VH-D-JH

<400> SEQUENCE: 7

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Ser Val Thr Val Ser Ser
        115                 120

<210> SEQ ID NO 8
<211> LENGTH: 124
<212> TYPE: PRT
<213> ORGANISM: Murine
<220> FEATURE:
<223> OTHER INFORMATION: mouse anti-(human)CD19 antibody B43 heavy chain
      junction VH-D-JH

<400> SEQUENCE: 8
```

```
Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 9
<211> LENGTH: 121
<212> TYPE: PRT
<213> ORGANISM: Murine
<220> FEATURE:
<223> OTHER INFORMATION: mouse anti-(human)CD19 antibody FMC63 heavy
      chain junction VH-D-JH

<400> SEQUENCE: 9

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Asp Thr Thr Tyr Tyr Asn Ser Ala Leu
        50                  55                  60

Lys Ser Arg Leu Thr Ile Ile Lys Asp Asn Ser Lys Ser Gln Val Phe
65                  70                  75                  80

Leu Lys Met Asn Ser Leu Gln Thr Asp Asp Thr Ala Ile Tyr Tyr Cys
                85                  90                  95

Ala Lys His Tyr Tyr Tyr Gly Gly Ser Tyr Ala Met Asp Tyr Trp Gly
            100                 105                 110

Gln Gly Thr Ser Val Thr Val Ser Ser
        115                 120
```

<210> SEQ ID NO 10
<211> LENGTH: 114
<212> TYPE: PRT
<213> ORGANISM: Artificial Sequence
<220> FEATURE:
<223> OTHER INFORMATION: consensus sequence of mouse anti-(human)CD19
      antibody light chain V-kappa

<400> SEQUENCE: 10

```
Asp Ile Val Met Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asn
                20                  25                  30

Gly Asp Ser Tyr Leu Asn Trp Tyr Gln Gln Arg Pro Gly Gln Pro Pro
            35                  40                  45
```

```
Lys Leu Leu Ile Tyr Asp Ala Ser Asn Leu Val Ser Gly Val Pro Asp
            50                  55                  60

Arg Phe Ser Gly Ser Gly Ser Gly Thr Asp Phe Thr Leu Asn Ile His
 65                  70                  75                  80

Pro Val Glu Lys Glu Asp Ala Ala Thr Tyr Tyr Cys Gln Gln Ser Thr
                85                  90                  95

Glu Asp Pro Tyr Thr Phe Gly Gly Gly Thr Lys Leu Glu Ile Lys Arg
            100                 105                 110

Ala Asp

<210> SEQ ID NO 11
<211> LENGTH: 112
<212> TYPE: PRT
<213> ORGANISM: Murine
<220> FEATURE:
<223> OTHER INFORMATION: mouse anti-(human)CD19 antibody HD37 light
      chain V-kappa

<400> SEQUENCE: 11

Asp Ile Leu Leu Thr Gln Thr Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
            50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

<210> SEQ ID NO 12
<211> LENGTH: 114
<212> TYPE: PRT
<213> ORGANISM: Murine
<220> FEATURE:
<223> OTHER INFORMATION: mouse anti-(human)CD19 antibody B43 light chain
      V-kappa

<400> SEQUENCE: 12

Glu Leu Val Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
            50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110
```

Arg Ser

<210> SEQ ID NO 13
<211> LENGTH: 107
<212> TYPE: PRT
<213> ORGANISM: Murine
<220> FEATURE:
<223> OTHER INFORMATION: mouse anti-(human)CD19 antibody FMC63 light
      chain V-kappa

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 14
<211> LENGTH: 115
<212> TYPE: PRT
<213> ORGANISM: Murine
<220> FEATURE:
<223> OTHER INFORMATION: mouse anti-(human)CD19 antibody 4G7 light chain
      V-kappa

<400> SEQUENCE: 14

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp
        115

<210> SEQ ID NO 15
<211> LENGTH: 494
<212> TYPE: DNA
<213> ORGANISM: Murine
<220> FEATURE:
<221> NAME/KEY: CDS
<222> LOCATION: (57)...(494)
<223> OTHER INFORMATION: mouse anti-(human)CD19 antibody HB12a light
      chain

<400> SEQUENCE: 15

```
catggactga aggagtagaa aactgatcac tctcctatgt ttatttcctc aaaatg atg      59
                                                                 Met
                                                                  1 agt cct gcc cag ttc ctg ttt ctg tta gtg ctc tgg att cag gaa acc       107
Ser Pro Ala Gln Phe Leu Phe Leu Leu Val Leu Trp Ile Gln Glu Thr
          5                  10                  15 aac ggt gat gtt ggg atg acc cag act cca ctc act ttg tcg gtc acc       155
Asn Gly Asp Val Gly Met Thr Gln Thr Pro Leu Thr Leu Ser Val Thr
         20                  25                  30 att gga caa cca gcc tct ttc tct tgc aag tca agt cag agc ctc tta       203
Ile Gly Gln Pro Ala Ser Phe Ser Cys Lys Ser Ser Gln Ser Leu Leu
     35                  40                  45 tat agt aat gga aaa acc tat ttg aat tgg tta tta cag agg cca ggc       251
Tyr Ser Asn Gly Lys Thr Tyr Leu Asn Trp Leu Leu Gln Arg Pro Gly
 50                  55                  60                  65 cag tct cca aag cgc cta atc cat ctg gtg tct aaa ctg gac tct gga       299
Gln Ser Pro Lys Arg Leu Ile His Leu Val Ser Lys Leu Asp Ser Gly
                 70                  75                  80 gtc cct gac agg ttc act ggc agt gga tca gga aca gat ttt aca ctg       347
Val Pro Asp Arg Phe Thr Gly Ser Gly Ser Gly Thr Asp Phe Thr Leu
             85                  90                  95 aaa atc ggc aga gtg gag gct gag gat ttg gga gtt tat tac tgc gtg       395
Lys Ile Gly Arg Val Glu Ala Glu Asp Leu Gly Val Tyr Tyr Cys Val
        100                 105                 110 caa ggt aca cat ttt ccg tac acg ttc gga ggg ggg acc aaa cta gaa       443
Gln Gly Thr His Phe Pro Tyr Thr Phe Gly Gly Gly Thr Lys Leu Glu
    115                 120                 125 ata aaa cgg gct gat gct gca cca act gta tcc atc ttc cca cca tcc       491
Ile Lys Arg Ala Asp Ala Ala Pro Thr Val Ser Ile Phe Pro Pro Ser
130                 135                 140                 145 agt                                                                   494
Ser
```

<210> SEQ ID NO 16
<211> LENGTH: 146
<212> TYPE: PRT
<213> ORGANISM: Murine
<220> FEATURE:
<223> OTHER INFORMATION: predicted mouse anti-(human)CD19 antibody HB12a light chain

<400> SEQUENCE: 16

```
Met Ser Pro Ala Gln Phe Leu Phe Leu Leu Val Leu Trp Ile Gln Glu
  1               5                  10                  15

Thr Asn Gly Asp Val Gly Met Thr Gln Thr Pro Leu Thr Leu Ser Val
             20                  25                  30

Thr Ile Gly Gln Pro Ala Ser Phe Ser Cys Lys Ser Ser Gln Ser Leu
         35                  40                  45

Leu Tyr Ser Asn Gly Lys Thr Tyr Leu Asn Trp Leu Leu Gln Arg Pro
     50                  55                  60

Gly Gln Ser Pro Lys Arg Leu Ile His Leu Val Ser Lys Leu Asp Ser
 65                  70                  75                  80

Gly Val Pro Asp Arg Phe Thr Gly Ser Gly Ser Gly Thr Asp Phe Thr
                 85                  90                  95

Leu Lys Ile Gly Arg Val Glu Ala Glu Asp Leu Gly Val Tyr Tyr Cys
            100                 105                 110

Val Gln Gly Thr His Phe Pro Tyr Thr Phe Gly Gly Gly Thr Lys Leu
```

```
                  115                 120                 125
Glu Ile Lys Arg Ala Asp Ala Ala Pro Thr Val Ser Ile Phe Pro Pro
        130                 135                 140

Ser Ser
145

<210> SEQ ID NO 17
<211> LENGTH: 485
<212> TYPE: DNA
<213> ORGANISM: Murine
<220> FEATURE:
<221> NAME/KEY: CDS
<222> LOCATION: (48)...(485)
<223> OTHER INFORMATION: mouse anti-(human)CD19 antibody HB12b light
      chain

<400> SEQUENCE: 17
catggactga aggagtagaa aagcattctc tcttccagtt ctcagag atg gag aaa        56
                                                    Met Glu Lys
                                                      1 gac aca ctc ctg cta tgg gtc ctg ctt ctc tgg gtt cca ggt tcc aca       104
Asp Thr Leu Leu Leu Trp Val Leu Leu Leu Trp Val Pro Gly Ser Thr
  5                  10                  15 ggt gac att gtg ctg acg cag tct cca acc tct ttg gct gtg tct cta       152
Gly Asp Ile Val Leu Thr Gln Ser Pro Thr Ser Leu Ala Val Ser Leu
 20                  25                  30                  35 ggg cag agg gcc acc atc tcc tgc aga gcc agc gaa agt gtt gat act       200
Gly Gln Arg Ala Thr Ile Ser Cys Arg Ala Ser Glu Ser Val Asp Thr
                 40                  45                  50 ttt ggc att agt ttt atg aac tgg ttc caa cag aaa cca gga cag cca       248
Phe Gly Ile Ser Phe Met Asn Trp Phe Gln Gln Lys Pro Gly Gln Pro
             55                  60                  65 ccc aaa ctc ctc atc cat gct gca tcc aat caa gga tcc ggg gtc cct       296
Pro Lys Leu Leu Ile His Ala Ala Ser Asn Gln Gly Ser Gly Val Pro
         70                  75                  80 gcc agg ttt agt ggt agt ggg tct ggg acg gac ttc agc ctc aac atc       344
Ala Arg Phe Ser Gly Ser Gly Ser Gly Thr Asp Phe Ser Leu Asn Ile
     85                  90                  95 cat cct atg gag gag gat gat agt gca atg tat ttc tgt cag caa agt       392
His Pro Met Glu Glu Asp Asp Ser Ala Met Tyr Phe Cys Gln Gln Ser
100                 105                 110                 115 aag gag gtt cca ttc acg ttc ggc tcg ggg aca aag ttg gaa ata aaa       440
Lys Glu Val Pro Phe Thr Phe Gly Ser Gly Thr Lys Leu Glu Ile Lys
                120                 125                 130 cgg gct gat gct gca cca act gta tcc atc ttc cca cca tcc agt           485
Arg Ala Asp Ala Ala Pro Thr Val Ser Ile Phe Pro Pro Ser Ser
            135                 140                 145

<210> SEQ ID NO 18
<211> LENGTH: 146
<212> TYPE: PRT
<213> ORGANISM: Murine
<220> FEATURE:
<223> OTHER INFORMATION: mouse anti-(human)CD19 antibody HB12b light
      chain

<400> SEQUENCE: 18

Met Glu Lys Asp Thr Leu Leu Leu Trp Val Leu Leu Leu Trp Val Pro
  1                   5                  10                  15

Gly Ser Thr Gly Asp Ile Val Leu Thr Gln Ser Pro Thr Ser Leu Ala
                 20                  25                  30

Val Ser Leu Gly Gln Arg Ala Thr Ile Ser Cys Arg Ala Ser Glu Ser
```

```
                35                  40                  45
Val Asp Thr Phe Gly Ile Ser Phe Met Asn Trp Phe Gln Gln Lys Pro
    50                  55                  60

Gly Gln Pro Pro Lys Leu Leu Ile His Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Ser Ala Met Tyr Phe Cys
            100                 105                 110

Gln Gln Ser Lys Glu Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser
145

<210> SEQ ID NO 19
<211> LENGTH: 31
<212> TYPE: DNA
<213> ORGANISM: Artificial Sequence
<220> FEATURE:
<223> OTHER INFORMATION: promiscuous sense 5' VH primer(MsVHE)

<400> SEQUENCE: 19
gggaattcga ggtgcagctg caggagtctg g                                  31

<210> SEQ ID NO 20
<211> LENGTH: 31
<212> TYPE: DNA
<213> ORGANISM: Artificial Sequence
<220> FEATURE:
<223> OTHER INFORMATION: antisense primer complementary to the C coding
      region (primer C 1)

<400> SEQUENCE: 20
gagttccagg tcactgtcac tggctcaggg a                                  31

<210> SEQ ID NO 21
<211> LENGTH: 27
<212> TYPE: DNA
<213> ORGANISM: Artificial Sequence
<220> FEATURE:
<223> OTHER INFORMATION: constant region specific antisense 3' primer

<400> SEQUENCE: 21
gactgaggca cctccagatg ttaactg                                       27
```